United States Patent
Zhang et al.

(10) Patent No.: US 11,958,903 B2
(45) Date of Patent: Apr. 16, 2024

(54) SINGLE-DOMAIN ANTIBODIES AGAINST LAG-3 AND USES THEREOF

(71) Applicant: NANJING LEGEND BIOTECH CO., LTD., Jiangsu (CN)

(72) Inventors: Wang Zhang, Nanjing (CN); Shuai Yang, Nanjing (CN); Shu Wu, Nanjing (CN); Chuan-Chu Chou, Westfield, NJ (US)

(73) Assignee: Nanjing Legend Biotech Co., Ltd., Nanjing (CN)

( * ) Notice: Subject to any disclaimer, the term of this patent is extended or adjusted under 35 U.S.C. 154(b) by 692 days.

(21) Appl. No.: 17/043,054

(22) PCT Filed: Mar. 29, 2019

(86) PCT No.: PCT/CN2019/080528
§ 371 (c)(1),
(2) Date: Dec. 15, 2020

(87) PCT Pub. No.: WO2019/185040
PCT Pub. Date: Oct. 3, 2019

(65) Prior Publication Data
US 2021/0017279 A1    Jan. 21, 2021

(51) Int. Cl.
*C07K 16/28* (2006.01)
*A61P 35/00* (2006.01)
*A61K 39/00* (2006.01)

(52) U.S. Cl.
CPC .......... *C07K 16/2803* (2013.01); *A61P 35/00* (2018.01); *C07K 16/2818* (2013.01); *A61K 2039/505* (2013.01); *C07K 2317/24* (2013.01); *C07K 2317/31* (2013.01); *C07K 2317/33* (2013.01); *C07K 2317/569* (2013.01); *C07K 2317/92* (2013.01)

(58) Field of Classification Search
CPC ............ C07K 16/2803; C07K 2317/31; C07K 2317/569; A61P 35/00; A61K 2039/505
See application file for complete search history.

(56) References Cited

U.S. PATENT DOCUMENTS

| | | |
|---|---|---|
| 3,773,919 A | 11/1973 | Boswell et al. |
| RE30,985 E | 6/1982 | Cartaya |
| 4,419,446 A | 12/1983 | Howley et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 5,122,469 A | 6/1992 | Mather et al. |
| 5,229,275 A | 7/1993 | Goroff |
| 5,264,365 A | 11/1993 | Georgiou et al. |
| 5,500,362 A | 3/1996 | Robinson et al. |
| 5,508,192 A | 4/1996 | Georgiou et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrenbaeck et al. |
| 5,569,825 A | 10/1996 | Lonberg et al. |
| 5,573,905 A | 11/1996 | Lerner et al. |
| 5,591,669 A | 1/1997 | Krimpenfort et al. |
| 5,624,821 A | 4/1997 | Winter et al. |
| 5,625,126 A | 4/1997 | Lonberg et al. |
| 5,633,425 A | 5/1997 | Lonberg et al. |
| 5,639,635 A | 6/1997 | Joly et al. |
| 5,641,870 A | 6/1997 | Rinderknecht et al. |
| 5,648,237 A | 7/1997 | Carter |
| 5,648,260 A | 7/1997 | Winter et al. |
| 5,661,016 A | 8/1997 | Lonberg et al. |
| 5,731,168 A | 3/1998 | Carter et al. |
| 5,750,373 A | 5/1998 | Garrard et al. |
| 5,770,429 A | 6/1998 | Lonberg et al. |
| 5,821,337 A | 10/1998 | Carter et al. |
| 5,840,523 A | 11/1998 | Simmons et al. |
| 6,027,888 A | 2/2000 | Georgiou et al. |
| 6,075,181 A | 6/2000 | Kucherlapati et al. |
| 6,083,715 A | 7/2000 | Georgiou et al. |
| 6,150,584 A | 11/2000 | Kucherlapati et al. |
| 6,194,551 B1 | 2/2001 | Idusogie et al. |
| 6,602,684 B1 | 8/2003 | Umana et al. |

(Continued)

FOREIGN PATENT DOCUMENTS

| | | |
|---|---|---|
| CN | 104479015 | 4/2015 |
| EP | 0404097 | 12/1990 |

(Continued)

OTHER PUBLICATIONS

Muyldermans S. Nanobodies: natural single-domain antibodies. Annu Rev Biochem. 2013;82:775-97. doi: 10.1146/annurev-biochem-063011-092449. Epub Mar. 13, 2013. (Year: 2013).*
Arora SP, Mahalingam D. Immunotherapy in colorectal cancer: for the select few or all? J Gastrointest Oncol. Feb. 2018;9(1):170-179. (Year: 2018).*
Almagro JC, Fransson J. Humanization of antibodies. Front Biosci. Jan. 1, 2008;13:1619-33. (Year: 2008).*
Edwards et al. The remarkable flexibility of the human antibody repertoire; isolation of over one thousand different antibodies to a single protein, BLyS. J Mol Biol Nov. 14, 2003;334(1):103-18. (Year: 2003).*
Kussie et al. A single engineered amino acid substitution changes antibody fine specificity.J Immunol. Jan. 1, 1994;152(1):146-52. (Year: 1994).*

(Continued)

*Primary Examiner* — Aurora M Fontainhas
*Assistant Examiner* — Jennifer A Benavides
(74) *Attorney, Agent, or Firm* — Fish & Richardson P.C.

(57) ABSTRACT

The present application provides anti-LAG-3 constructs comprising a single-domain antibody (sdAb) that specifically recognizes LAG-3. Also provided are methods of making and using these constructs.

23 Claims, 12 Drawing Sheets

Specification includes a Sequence Listing.

(56) References Cited

U.S. PATENT DOCUMENTS

| | | |
|---|---|---|
| 6,737,056 B1 | 5/2004 | Presta |
| 6,982,321 B2 | 1/2006 | Winter |
| 7,041,870 B2 | 5/2006 | Tomizuka et al. |
| 7,087,409 B2 | 8/2006 | Barbas, III et al. |
| 7,189,826 B2 | 3/2007 | Rodman |
| 7,332,581 B2 | 2/2008 | Presta |
| 7,371,826 B2 | 5/2008 | Presta |
| 7,371,849 B2 | 5/2008 | Honda et al. |
| 7,521,541 B2 | 4/2009 | Eigenbrot et al. |
| 7,527,791 B2 | 5/2009 | Adams et al. |
| 8,502,014 B2 | 8/2013 | Grosveld |
| 8,507,748 B2 | 8/2013 | Grosveld |
| 8,754,287 B2 | 6/2014 | MacDonald et al. |
| 8,883,150 B2 | 11/2014 | Craig et al. |
| 8,921,522 B2 | 12/2014 | Grosveld et al. |
| 8,921,524 B2 | 12/2014 | Grosveld et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0079574 A1 | 4/2005 | Bond |
| 2005/0119455 A1 | 6/2005 | Fuh et al. |
| 2005/0123546 A1 | 6/2005 | Umana et al. |
| 2005/0266000 A1 | 12/2005 | Bond et al. |
| 2006/0025576 A1 | 2/2006 | Miller et al. |
| 2007/0061900 A1 | 3/2007 | Murphy et al. |
| 2007/0117126 A1 | 5/2007 | Sidhu et al. |
| 2007/0160598 A1 | 7/2007 | Dennis et al. |
| 2007/0178552 A1 | 8/2007 | Arathoon et al. |
| 2007/0237764 A1 | 10/2007 | Birtalan et al. |
| 2007/0292936 A1 | 12/2007 | Barthelemy et al. |
| 2009/0002360 A1 | 1/2009 | Chen et al. |
| 2009/0307787 A1 | 12/2009 | Grosveld et al. |
| 2010/0122358 A1 | 5/2010 | Bruggemann et al. |
| 2011/0028695 A1 | 2/2011 | Revets et al. |
| 2011/0118444 A1 | 5/2011 | Grosveld et al. |
| 2011/0287009 A1 | 11/2011 | Scheer et al. |
| 2013/0323235 A1 | 12/2013 | Craig et al. |
| 2013/0344057 A1 | 12/2013 | Grosveld et al. |
| 2014/0033335 A1 | 1/2014 | Grosveld |
| 2014/0037616 A1 | 2/2014 | Grosveld |
| 2014/0356908 A1 | 12/2014 | Grosveld et al. |
| 2015/0259420 A1* | 9/2015 | Triebel .......... A61P 17/00 435/69.6 |
| 2015/0289489 A1 | 10/2015 | MacDonald et al. |

FOREIGN PATENT DOCUMENTS

| | | |
|---|---|---|
| EP | 0368684 | 3/1994 |
| EP | 3740510 | 11/2020 |
| JP | 2017-516489 | 6/2017 |
| JP | 2017-532059 | 11/2017 |
| TW | 201726740 | 8/2017 |
| WO | WO 1987/000195 | 1/1987 |
| WO | WO 1990/003430 | 4/1990 |
| WO | WO 1991/010741 | 7/1991 |
| WO | WO 1993/008829 | 5/1993 |
| WO | WO 1993/011161 | 6/1993 |
| WO | WO 1994/004678 | 3/1994 |
| WO | WO 1994/011026 | 5/1994 |
| WO | WO 1994/029351 | 12/1994 |
| WO | WO 1996/027011 | 9/1996 |
| WO | WO 1996/033735 | 10/1996 |
| WO | WO 1996/034096 | 10/1996 |
| WO | WO 1996/034103 | 10/1996 |
| WO | WO 1997/017852 | 5/1997 |
| WO | WO 1997/030087 | 8/1997 |
| WO | WO 1997/049805 | 12/1997 |
| WO | WO 1998/022141 | 5/1998 |
| WO | WO 1998/024893 | 6/1998 |
| WO | WO 1998/050431 | 11/1998 |
| WO | WO 1998/058964 | 12/1998 |
| WO | WO 1999/022764 | 5/1999 |
| WO | WO 1999/037681 | 7/1999 |
| WO | WO 1999/051642 | 10/1999 |
| WO | WO 2000/027435 | 5/2000 |
| WO | WO 2000/043507 | 7/2000 |
| WO | WO 2000/061739 | 10/2000 |
| WO | WO 2001/029246 | 4/2001 |
| WO | WO 2001/077137 | 10/2001 |
| WO | WO 2001/090190 | 11/2001 |
| WO | WO 2002/031140 | 4/2002 |
| WO | WO 2002/085945 | 10/2002 |
| WO | WO 2003/011878 | 2/2003 |
| WO | WO 2003/014161 | 2/2003 |
| WO | WO 2003/035694 | 5/2003 |
| WO | WO 2004/042072 | 5/2004 |
| WO | WO 2004/049794 | 6/2004 |
| WO | WO 2004/056312 | 7/2004 |
| WO | WO 2004/092219 | 10/2004 |
| WO | WO 2003/025020 | 12/2004 |
| WO | WO 2005/035586 | 4/2005 |
| WO | WO 2005/035778 | 4/2005 |
| WO | WO 2005/053742 | 6/2005 |
| WO | WO 2003/084570 | 8/2005 |
| WO | WO 2003/085107 | 8/2005 |
| WO | WO 2003/085119 | 8/2005 |
| WO | WO 2005/100402 | 10/2005 |
| WO | WO 2006/003388 | 1/2006 |
| WO | WO 2006/008548 | 1/2006 |
| WO | WO 2006/029879 | 3/2006 |
| WO | WO 2006/030220 | 3/2006 |
| WO | WO 2007/112940 | 10/2007 |
| WO | WO 2008/077546 | 7/2008 |
| WO | WO 2009/089004 | 7/2009 |
| WO | WO 2013/110531 | 8/2013 |
| WO | WO 2015/116539 | 8/2015 |
| WO | WO 2016/028672 | 2/2016 |
| WO | 2016/200782 A1 | 12/2016 |
| WO | WO 2017/015560 | 1/2017 |
| WO | WO 2017/025498 | 2/2017 |
| WO | 2017/059387 A1 | 4/2017 |
| WO | 2017/087589 A2 | 5/2017 |
| WO | 2017/087901 A2 | 5/2017 |
| WO | WO 2017/198212 | 11/2017 |
| WO | WO 2018/014855 | 1/2018 |
| WO | WO 2018/068695 | 4/2018 |

OTHER PUBLICATIONS

Chen et al. Enhancement and destruction of antibody function by somatic mutation: unequal occurrence is controlled by V gene combinatorial associations.EMBO J. Jun. 15, 1995; 14(12): 2784-94. (Year: 1995).*
Koenig et al. Mutational landscape of antibody variable domains reveals a switch modulating the interdomain conformational dynamics and antigen binding. PNAS Jan. 24, 2017 114(4)E486-E495;firstpublished Jan. 5, 2017. (Year: 2017).*
EP Supplementary European Search Report, dated Dec. 8, 2021 in counterpart EP Application No. 19776254.
European search opinion, dated Dec. 16, 2021 in counterpart EP Application No. 19776254.
Almagro, "Humanization of antibodies," Frontiers in Bioscience: a Journal and Virtual Library, Jan. 2008, 13(5):1619-1633.
Arié et al., "Chaperone function of FkpA, a heat shock prolyl isomerase, in the periplasm of *Escherichia coli*.," Molecular Microbiology, Jan. 2001, 39(1):199-210.
Armour et al., "Recombinant human IgG molecules lacking Fcγ receptor I binding and monocyte triggering activities," European Journal of Immunology, Aug. 1999, 29(8):2613-2624.
Baca et al., "Antibody humanization using monovalent phage display," Journal of Biological Chemistry, Apr. 1997, 272(16):10678-10684.
Bachmann, "Derivation And Genotypes of Some Mutant Derivatives of *Escherichia coli* K-12," in *Escherichia coli* and *Salmonella typhimurium* Cellular and Molecular Biology, Neidhardt et al., (eds)., Jun. 1987, pp. 1190-1219.

(56) References Cited

OTHER PUBLICATIONS

Barbas et al., "In vitro evolution of a neutralizing human antibody to human immunodeficiency virus type 1 to enhance affinity and broaden strain cross-reactivity," Proceedings of the National Academy of Sciences, Apr. 1994, 91(9):3809-3813.
Barnes et al., "Methods for growth of cultured cells in serum-free medium," Analytical Biochemistry, Mar. 1980, 102(2):255-270.
Bass et al., "Hormone phage: an enrichment method for variant proteins with altered binding properties, " Proteins, Sep. 1990, 8(4):309-314.
Bothmann et al. "The periplasmic *Escherichia coli* peptidylprolyl cis, trans-isomerase FkpA: I. Increased functional expression of antibody fragments with and without cis-prolines," Journal of Biological Chemistry, Jun. 2000, 275(22):17100-17105.
Brennan et al., "Preparation of bispecific antibodies by chemical recombination of monoclonal immunoglobulin G1 fragments," Science, Jul. 1985, 229(4708):81-83.
Brüggemann et al., "Comparison of the effector functions of human immunoglobulins using a matched set of chimeric antibodies," The Journal of Experimental Medicine, Nov. 1987, 166(5):1351-1361.
Capel et al., "Heterogeneity of human IgG Fc receptors," ImmunoMethods, Feb. 1994, 4(1):25-34.
Carter et al., "High level *Escherichia coli* expression and production of a bivalent humanized antibody fragment," Bio/technology, Feb. 1992, 10(2):163-167.
Carter et al., "Humanization of an anti-p185HER2 antibody for human cancer therapy," Proceedings of the National Academy of Sciences USA, May 1992, 89(10):4285-4289.
Chen et al., "A large human domain antibody library combining heavy and light chain CDR3 diversity," Molecular Immunology, Jan. 2010, 47(4):912-921.
Chen et al., "Chaperone activity of DsbC," Journal of Biological Chemistry, Jul. 1999, 274(28):19601-19605.
Chothia et al., "Canonical structures for the hypervariable regions of immunoglobulins," Journal of Molecular Biology, Aug. 1987, 196(4):901-917.
Chowdhury, "Engineering Hot Spots for Affinity Enhancement of Antibodies," Methods Mol. Biol., 2008, 207:179-196.
Clackson et al., "Making antibody fragments using phage display libraries," Nature, Aug. 1991, 352(6336):624-628.
Clynes et al., "Fc receptors are required in passive and active immunity to melanoma," Proceedings of the National Academy of Sciences, Jan. 1998, 95(2):652-656.
Conrath et al., "Camel single-domain antibodies as modular building units in bispecific and bivalent antibody constructs" Journal of Biological Chemistry, Mar. 2001, 276(10):7346-7350.
Cragg et al., "Antibody specificity controls in vivo effector mechanisms of anti-CD20 reagents," Blood, Apr. 2004, 103(7):2738-2743.
Cragg et al., "Complement-mediated lysis by anti-CD20 mAb correlates with segregation into lipid rafts," Blood, Feb. 2003, 101(3):1045-1052.
Cunningham et al., "High-resolution epitope mapping of hGH-receptor interactions by alanine-scanning mutagenesis" Science, Jun. 1989, 244(4908):1081-1085.
Daëron, "Fc receptor biology," Annual Review of Immunology, Apr. 1997, 15(1):203-234.
Dall'Acqua et al., "Antibody humanization by framework shuffling," Methods, May 2005, 36(1):43-60.
Davies et al., "'Camelising' human antibody fragments: NMR studies on VH domains," FEBS Letters, Feb. 1994, 339(3):285-290.
Davies et al., "Single antibody domains as small recognition units: design and in vitro antigen selection of camelized, human VH domains with improved protein stability," Protein Engineering, Design and Selection, Jun. 1996, 9(6):531-537.
Duncan et al., "The binding site for C1q on IgG," Nature, Apr. 21, 1988, 332(6166):738-740.
Fellouse et al., "Synthetic antibodies from a four-amino-acid code: a dominant role for tyrosine in antigen recognition," Proceedings of the National Academy of Sciences, Aug. 2004, 101(34):12467-12472.

Fishwild et al., "High-avidity human IgGK monoclonal antibodies from a novel strain of minilocus transgenic mice," Nature Biotechnology, Jul. 1996, 14(7):845-851.
Gazzano-Santoro et al., "A non-radioactive complement-dependent cytotoxicity assay for anti-CD20 monoclonal antibody," Journal of Immunological Methods, Mar. 1997, 202(2):163-171.
Geering et al., "Synthetic immunology: modulating the human immune system," Trends in Biotechnology, Feb. 2015, 33(2):65-79.
GenBank Accession No. P18627.5, "RecName: Full=Lymphocyte activation gene 3 protein; Short=LAG-3; AltName: CD_antigen= CD223; Contains: RecName: Full=Secreted lymphocyte activation gene 3 protein; Short=sLAG-3; Flags: Precursor," dated Sep. 18, 2019, 8 pages.
Ghetie et al. "Increasing the serum persistence of an IgG fragment by random mutagenesis," Nature biotechnology, Jul. 1997, 15(7):637-640.
Ghetie et al., "FcRn: the MHC class I-related receptor that is more than an IgG transporter," Immunology Today, Dec. 1997, 18(12):592-598.
Graham et al., "Characteristics of a human cell line transformed by DNA from human adenovirus type 5," Journal of General Virology, Jul. 1977, 36(1):59-72.
Greenberg et al., "A new antigen receptor gene family that undergoes rearrangement and extensive somatic diversification in sharks," Nature, Mar. 1995, 374(6518):168-173.
Griffiths et al., "Human anti-self antibodies with high specificity from phage display libraries," The EMBO Journal, Feb. 1993, 12(2):725-734.
Gruber et al., "Efficient tumor cell lysis mediated by a bispecific single chain antibody expressed in *Escherichia coli*," The Journal of Immunology, Jun. 1994, 152(11):5368-5374 (abstract only).
Guss et al., Structure of the IgG-binding regions of streptococcal protein G, The EMBO Journal, Jul. 1986, 5(7):1567-1575.
Ham et al., "[5] Media and growth requirements," Methods in Enzymology, Jan. 1979, 58:44-93.
Hamers-Casterman et al., "Naturally occurring antibodies devoid of light chains," Nature, Jun. 1993, 363(6428):446-448.
Hara et al., "Overproduction of penicillin-binding protein 7 suppresses thermosensitive growth defect at low osmolarity due to an spr mutation of *Escherichia coli*.," Microbial Drug Resistance, Jan. 1996, 2(1):63-72.
Harris, "Production of humanized monoclonal antibodies for in vivo imaging and therapy," Biochem. Soc. Trans. Jul. 1995, 23(4):1035-1038.
Hassanzadeh et al., "Nanobodies and their potential applications," Nanomedicine, Jun. 2013, 8(6):1013-1026.
Hawkins et al., "Selection of phage antibodies by binding affinity: mimicking affinity maturation," Journal of Molecular Biology, Aug. 1992, 226(3):889-896.
Hellstrom et al., "Antitumor effects of L6, an IgG2a antibody that reacts with most human carcinomas," Proceedings of the National Academy of Sciences, Sep. 1986, 83(18):7059-7063.
Hellstrom et al., "Strong antitumor activities of IgG3 antibodies to a human melanoma-associated ganglioside," Proceedings of the National Academy of Sciences, Mar. 1985, 82(5):1499-502.
Hinton et al., "Engineered human IgG antibodies with longer serum half-lives in primates," The Journal of Biological Chemistry, Dec. 2003, 279(8):6213-6216.
Holliger et al., ""Diabodies": small bivalent and bispecific antibody fragments," Proc. Natl. Acad. Sci. USA, Jul. 15, 1993, 90(14):6444-6448.
Holt et al., "Domain antibodies: proteins for therapy," Trends in Biotechnology, Nov. 2003, 21(11):848-490.
Hongo et al., "Development and Characterization of Murine Monoclonal Antibodies to the Latency-Associated Peptide of Transforming Growth Factor β1," Hybridoma, Jun. 1995, 14(3):253-260.
Hoogenboom et al., "By-passing immunisation. Human antibodies from synthetic repertoires of germline VH gene segments rearranged in vitro," J. Mol. Biol., Sep. 20, 1992, 227(2):381-388.
Hoogenboom, "Overview of Antibody Phage-Display Technology and Its Applications," Methods in Molecular Biology: Antibody Phage Display, 2001, 178:1-37.

(56) References Cited

OTHER PUBLICATIONS

Hurle et al., "Protein Engineering Techniques for Antibody Humanization," Curr. Op. Biotech., Aug. 1994, 5:428-433.

Idusogie et al., "Mapping of the C1q binding site on rituxan, a chimeric antibody with a human IgG1 Fc," J. Immunol., Apr. 15, 2000, 164(8):4178-4184.

International Preliminary Report on Patentability in International Appln. No. PCT/CN2019/080528, dated Oct. 15, 2020, 7 pages.

International Search Report and Written Opinion in International Appln. No. PCT/CN2019/080528, dated Jul. 2, 2019, 6 pages.

Jakobovits et al., "Germ-line transmission and expression of a human-derived yeast artificial chromosome," Nature, Mar. 18, 1993, 362(6417):255-258.

Jakobovits et al., "Analysis of homozygous mutant chimeric mice: deletion of the immunoglobulin heavy-chain joining region blocks B-cell development and antibody production," Proc. Natl. Acad. Sci. USA, Mar. 15, 1993, 90(6):2551-2555.

Janssens et al., "Generation of heavy-chain-only antibodies in mice," Proc. Natl. Acad. Sci. USA., Oct. 10, 2006, 103(41):15130-151355.

Johnson et al., "Human antibody engineering," Current Opinion in Structural Biology, Aug. 1993, 3(4):564-571.

Jones et al., "Replacing the complementarity-determining regions in a human antibody with those from a mouse," Nature, May 29, 1986, 321:522-525.

Jones, "Analysis of polypeptides and proteins," Advanced Drug Delivery Reviews, Jan.-Apr. 1993, 10(1):29-90.

Kam et al., "Carbon nanotubes as multifunctional biological transporters and near-infrared agents for selective cancer cell destruction," Proc. Natl. Acad. Sci. USA, Aug. 8, 2005, 102(33):11600-11605.

Kanda et al., "Comparison of cell lines for stable production of fucose-negative antibodies with enhanced ADCC†," Biotechnology and Bioengineering, Jul. 5, 2006, 94(4):680-688.

Kashmiri et al., "SDR grafting—a new approach to antibody humanization, " Methods, May 2005, 36(1):25-34.

Kim et al., "Localization of the site of the murine IgG1 molecule that is involved in binding to the murine intestinal Fc receptor," Eur. J. Immunol., 1994, 24(10):2429-2434.

Klimka et al., "Human anti-CD30 recombinant antibodies by guided phage antibody selection using cell panning," Br. J. Cancer, 2000, 83:252-260.

Lauwereys et al., "Potent enzyme inhibitors derived from dromedary heavy-chain antibodies," EMBO J., Jul. 1998, 17(13):3512-3520.

Lee et al., "Bivalent antibody phage display mimics natural immunoglobulin," J. Immunol. Methods, Jan. 2004, 284(1-2):119-132.

Lee et al., "High-affinity Human Antibodies from Phage-displayed Synthetic Fab Libraries with a Single Framework Scaffold," J. Mol. Biol., Jul. 2004, 340(5):1073-1093.

Li et al., "Human antibodies for immunotherapy development generated via a human B cell hybridoma technology," Proc. Natl. Acad. Sci. USA, Feb. 2006, 103:3557-3562.

Nguyen et al., "Clinical blockade of PD1 and LAG3 potential mechanisms of action", Nature Reviews Immunology, Dec. 2014, 15(1):45-56.

Lonberg et al., "Antigen-specific human antibodies from mice comprising four distinct genetic modifications," Nature, Apr. 1994, 368: 856-859.

Lonberg, "Human antibodies from transgenic animals," Nat. Biotech., Sep. 2005, 23(9):1117-1125.

Marks et al., "By—passing Immunization: building high affinity human antibodies by chain shuffling," Bio/technolog, Jul. 1992, 10(7):779-783.

Marks et al., "By-passing immunization: Human antibodies from V-gene libraries displayed on phage," J. Mol. Biol., Dec. 1991, 222(3):581-597.

Mather, "Establishment and characterization of two distinct mouse testicular epithelial cell lines," Biol. Reprod., Aug. 1980, 23(1):243-251.

Morrison et al., "Chimeric human antibody molecules: mouse antigen-binding domains with human constant region domains.," Proc. Natl. Acad. Sci. USA, Nov. 1984, 81(21):6851-6855.

Pardon et al., "A general protocol for the generation of Nanobodies for structural biology," Nature Protocol, 2014; 9(3):674-693.

Petkova et al., "Enhanced half-life of genetically engineered human IgG1 antibodies in a humanized FcRn mouse model: potential application in humorally mediated autoimmune disease, " International Immunology, Dec. 2006, 18(12):1759-1769.

Pluckthun, "Mono- and Bivalent Antibody Fragments Produced in *Escherichia coli*: Engineering, Folding and Antigen Binding," Immunol. Revs., 1992, 130:151-188.

Queen et al., "A humanized antibody that binds to the interleukin 2 receptor.," Proc. Nat'l Acad. Sci. USA, Dec. 1989, 86(24):10029-10033.

Ramm et al., "The Periplasmic *Escherichia coli* Peptidylprolyl cis, trans-Isomerase FkpA," J. Biol. Chem., Jun. 2000, 275(22):17106-17113.

Riechmann et al., "Single domain antibodies: comparison of camel VH and camelised human VH domains," J. Immunol. Meth., Dec. 1999, 231(1-2):25-38.

Rosok et al., "A Combinatorial Library Strategy for the Rapid Humanization of Anticarcinoma BR96 Fab," J. Biol. Chem., Sep. 1996, 271(37):22611-22618.

Huang et al., "LAG3 and PD1 co-inhibitory molecules collaborate to limit CD8+ T cell signaling and dampen antitumor immunity in a murine ovarian cancer model," Oncotarget, Sep. 2015, 6(29):27359-27377.

Shields et al., "High Resolution Mapping of the Binding Site on Human IgG1 for FcγRI, FcγRII, FcγRIII, and FcRn and Design of IgG1 Variants with Improved Binding to the FcγR," J. Biol. Chem., Mar. 2001, 276(9):6591-6604.

Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," J. Biol. Chem., Jan. 2003, 278(5):3466-3473.

Sidhu et al., "Phage-displayed Antibody Libraries of Synthetic Heavy Chain Complementarity Determining Regions," J. Mol. Biol., Apr. 2004, 338(2):299-310.

Siebenlist et al., "*E. coli* RNA polymerase interacts homologously with two different promoters," Cell, Jun. 1980, 20(2):269-281.

Streltsov, "Structure of a shark IgNAR antibody variable domain and modeling of an early-developmental isotype, " Protein Sci., Jan. 2009, 14(11):2901-2909.

Thomas, "Of ITAMs and ITIMs: turning on and off the B cell antigen receptor," J. Exp. Med., Jun. 1995, 181(6):1953-1956.

Transue et al., "Camel single-domain antibody inhibits enzyme by mimicking carbohydrate substrate," Proteins, Sep. 1998, 32(4):515-522.

Traunecker et al., "Bispecific single chain molecules (Janusins) target cytotoxic lymphocytes on HIV infected cells," EMBO J., Dec. 1991, 10(12):3655-3659.

Turnis et al., "Combinatorial Immunotherapy: PD-1 may not be LAG-ing behind any more," Oncoimmunology, Oct. 2012, 1(7):1172-1174.

Urlaub et al., "Isolation of Chinese hamster cell mutants deficient in dihydrofolate reductase activity," Proc. Natl. Acad. Sci. USA, Jul. 1980, 77(7):4216-4220.

Vaswani et al., "Humanized antibodies as potential therapeutic drugs," Ann. Allergy Asthma Immunol., Aug. 1998, 81(2):105-115.

Vivier et al., "Immunoreceptor tyrosine-based inhibition motifs," Immunol. Today, Jun. 1997, 18(6):286-291.

Vollmers et al., "The "early birds": natural IgM antibodies and immune surveillance," Histology and Histopathology, 2005, 20(3):927-937.

Waterhouse et al., "Combinatorial infection and in vivo recombination: a strategy for making large phage antibody repertoires," Nucleic Acids Research, May 11, 1993, 21(9):2265-2266.

Winter et al., "Making Antibodies by Phage Display Technology," Annual Review of Immunology, 1994, 12:433-455.

Zhu et al., "Remodeling domain interfaces to enhance heterodimer formation," Protein Science, Apr. 1997, 6(4):781-788.

(56) References Cited

OTHER PUBLICATIONS

Long et al., "The promising immune checkpoint LAG-3: from tumor microenvironment to cancer immunotherapy," Genes & Cancer, May 2018, 9(5-6):176-189.
EP Office Action in European Appln. No. 19776254.5, dated Dec. 21, 2023, 8 pages.

* cited by examiner

SINGLE-DOMAIN ANTIBODIES AGAINST LAG-3 AND USES THEREOF

CROSS REFERENCE TO RELATED APPLICATIONS

This application is a § 371 National Phase of PCT/CN2019/080528 filed Mar. 29, 2019 and published as WO Publication No. WO 2019/185040 on Oct. 3, 2019 and which claims the priority benefit of International Patent Application No. PCT/CN2018/081356, filed Mar. 30, 2018, the disclosure of which is incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 761422001442SEQLIST.txt, date recorded: Mar. 19, 2019, size: 514 KB).

FIELD OF THE INVENTION

The present invention relates to constructs comprising a single-domain antibody (sdAb) that specifically recognize LAG-3, and methods of making and using thereof.

BACKGROUND OF THE INVENTION

Lymphocyte-activation protein 3 (LAG-3), comprised of 503 amino acids, belongs to the Ig superfamily and contains 4 extracellular Ig-like domains, designated D1 to D4. LAG3 is closely related to CD4. LAG-3 is a cell surface protein expressed on activated T cells, NK cells, B cells, and plasmacytoid dendritic cells, and plays a role in the function of these lymphocyte subsets that is important but not completely understood. The LAG-3 protein negatively regulates cellular proliferation, activation, and homeostasis of T cells. LAG-3 also helps maintain $CD8^+$ T cells in a tolerogenic state. The interaction between LAG-3 and its major ligand, Class II MHC, is thought to play a role in modulating dendritic cell functions. Recent preclinical studies have documented a role for LAG-3 in CD8 T cell exhaustion, and blockade of the LAG-3/Class II MHC interaction using LAG-3 blocking antibodies or LAG-3-Ig fusion proteins is being evaluated in a number of clinical trials in cancer patients.

Programmed Cell Death Receptor 1 (PD-1) is another inhibitory immune checkpoint molecule with important negative regulation on T cell functions. T-cell responses can be attenuated by PD-1 signaling when PD-1 binds to Programmed Cell Death Ligand 1 (PD-L1) and/or Programmed Cell Death Ligand 2 (PD-L2), which regulate T-cell receptor (TCR) signaling. Blockade of the PD-1/PD-L1 axis using antibodies targeting either PD-1 or PD-L1 has been shown to promote tumor-specific T cell immunity with significant clinical benefits to cancer patients. However, there are still huge unmet clinical needs due to resistance or relapse upon PD-1/PD-L1 blockade.

The disclosures of all publications, patents, patent applications and published patent applications referred to herein are hereby incorporated herein by reference in their entirety.

BRIEF SUMMARY OF THE INVENTION

The present invention relates to anti-LAG-3 constructs comprising an sdAb that specifically recognizes LAG-3 (hereinafter referred to as "anti-LAG-3 sdAb"), such as anti-LAG-3 sdAb, anti-LAG-3 HCAb (e.g., anti-LAG-3 sdAb-Fc fusion protein comprising an anti-LAG-3 sdAb fused to a crystalline fragment (Fc) of human immunoglobulin G (IgG), and multispecific (such as bispecific) antigen binding proteins comprising an anti-LAG-3 sdAb fused to, for example, other sdAbs, a full-length four-chain antibody or antigen binding fragments thereof (e.g., Fab or scFv), and methods of making and using thereof.

One aspect of the present application provides an isolated anti-LAG-3 construct comprising a single-domain antibody (sdAb) specifically recognizing LAG-3, wherein the sdAb comprises a CDR1 comprising the amino acid sequence of any one of SEQ ID NOs: 39-76, or a variant thereof comprising up to about 3 amino acid substitutions; a CDR2 comprising the amino acid sequence of any one of SEQ ID NOs: 115-152, or a variant thereof comprising up to about 3 amino acid substitutions; and a CDR3 comprising the amino acid sequence of any one of SEQ ID NOs: 191-228, or a variant thereof comprising up to about 3 amino acid substitutions. In some embodiments, the isolated anti-LAG-3 construct comprises an sdAb specifically recognizing LAG-3, wherein the sdAb comprises a CDR1 comprising the amino acid sequence of any one of SEQ ID NOs: 39-76; a CDR2 comprising the amino acid sequence of any one of SEQ ID NOs: 115-152; and a CDR3 comprising the amino acid sequence of any one of SEQ ID NOs: 191-228; or a variant thereof comprising up to about 3 amino acid substitutions in the CDR regions.

In some embodiments according to any one of the isolated anti-LAG-3 constructs described above, the sdAb specifically recognizing LAG-3 comprises any one of the following:

(1) a CDR1 comprising the amino acid sequence of SEQ ID NO: 39, or a variant thereof comprising up to about 3 amino acid substitutions; a CDR2 comprising the amino acid sequence of SEQ ID NO: 115, or a variant thereof comprising up to about 3 amino acid substitutions; and a CDR3 comprising the amino acid sequence of SEQ ID NO: 191, or a variant thereof comprising up to about 3 amino acid substitutions;

(2) a CDR1 comprising the amino acid sequence of SEQ ID NO: 40, or a variant thereof comprising up to about 3 amino acid substitutions; a CDR2 comprising the amino acid sequence of SEQ ID NO: 116, or a variant thereof comprising up to about 3 amino acid substitutions; and a CDR3 comprising the amino acid sequence of SEQ ID NO: 192, or a variant thereof comprising up to about 3 amino acid substitutions;

(3) a CDR1 comprising the amino acid sequence of SEQ ID NO: 41, or a variant thereof comprising up to about 3 amino acid substitutions; a CDR2 comprising the amino acid sequence of SEQ ID NO: 117, or a variant thereof comprising up to about 3 amino acid substitutions; and a CDR3 comprising the amino acid sequence of SEQ ID NO: 193, or a variant thereof comprising up to about 3 amino acid substitutions;

(4) a CDR1 comprising the amino acid sequence of SEQ ID NO: 42, or a variant thereof comprising up to about 3 amino acid substitutions; a CDR2 comprising the amino acid sequence of SEQ ID NO: 118, or a variant thereof comprising up to about 3 amino acid substitutions; and a CDR3 comprising the amino acid sequence of SEQ ID NO: 194, or a variant thereof comprising up to about 3 amino acid substitutions;

(5) a CDR1 comprising the amino acid sequence of SEQ ID NO: 43, or a variant thereof comprising up to about 3 amino acid substitutions; a CDR2 comprising the amino acid sequence of SEQ ID NO: 119, or a variant thereof comprising up to about 3 amino acid substitutions; and a CDR3 comprising the amino acid sequence of SEQ ID NO: 195, or a variant thereof comprising up to about 3amino acid substitutions;

(6) a CDR1 comprising the amino acid sequence of SEQ ID NO: 44, or a variant thereof comprising up to about 3 amino acid substitutions; a CDR2 comprising the amino acid sequence of SEQ ID NO: 120, or a variant thereof comprising up to about 3 amino acid substitutions; and a CDR3 comprising the amino acid sequence of SEQ ID NO: 196, or a variant thereof comprising up to about 3 amino acid substitutions;

(7) a CDR1 comprising the amino acid sequence of SEQ ID NO: 45, or a variant thereof comprising up to about 3 amino acid substitutions; a CDR2 comprising the amino acid sequence of SEQ ID NO: 121, or a variant thereof comprising up to about 3 amino acid substitutions; and a CDR3 comprising the amino acid sequence of SEQ ID NO: 197, or a variant thereof comprising up to about 3 amino acid substitutions;

(8) a CDR1 comprising the amino acid sequence of SEQ ID NO: 46, or a variant thereof comprising up to about 3 amino acid substitutions; a CDR2 comprising the amino acid sequence of SEQ ID NO: 122, or a variant thereof comprising up to about 3 amino acid substitutions; and a CDR3 comprising the amino acid sequence of SEQ ID NO: 198, or a variant thereof comprising up to about 3 amino acid substitutions;

(9) a CDR1 comprising the amino acid sequence of SEQ ID NO: 54, or a variant thereof comprising up to about 3 amino acid substitutions; a CDR2 comprising the amino acid sequence of SEQ ID NO: 130, or a variant thereof comprising up to about 3 amino acid substitutions; and a CDR3 comprising the amino acid sequence of SEQ ID NO: 206, or a variant thereof comprising up to about 3 amino acid substitutions;

(10) a CDR1 comprising the amino acid sequence of SEQ ID NO: 61, or a variant thereof comprising up to about 3 amino acid substitutions; a CDR2 comprising the amino acid sequence of SEQ ID NO: 137, or a variant thereof comprising up to about 3 amino acid substitutions; and a CDR3 comprising the amino acid sequence of SEQ ID NO: 213, or a variant thereof comprising up to about 3 amino acid substitutions;

(11) a CDR1 comprising the amino acid sequence of SEQ ID NO: 70, or a variant thereof comprising up to about 3 amino acid substitutions; a CDR2 comprising the amino acid sequence of SEQ ID NO: 146, or a variant thereof comprising up to about 3 amino acid substitutions; and a CDR3 comprising the amino acid sequence of SEQ ID NO: 222, or a variant thereof comprising up to about 3 amino acid substitutions;

(12) a CDR1 comprising the amino acid sequence of SEQ ID NO: 72, or a variant thereof comprising up to about 3 amino acid substitutions; a CDR2 comprising the amino acid sequence of SEQ ID NO: 148, or a variant thereof comprising up to about 3 amino acid substitutions; and a CDR3 comprising the amino acid sequence of SEQ ID NO: 224, or a variant thereof comprising up to about 3 amino acid substitutions; or

(13) a CDR1 comprising the amino acid sequence of SEQ ID NO: 73, or a variant thereof comprising up to about 3 amino acid substitutions; a CDR2 comprising the amino acid sequence of SEQ ID NO: 149, or a variant thereof comprising up to about 3 amino acid substitutions; and a CDR3 comprising the amino acid sequence of SEQ ID NO: 225, or a variant thereof comprising up to about 3 amino acid substitutions.

In some embodiments according to any one of the isolated anti-LAG-3 constructs described above, the sdAb specifically recognizing LAG-3 comprises a CDR1 comprising the amino acid sequence of SEQ ID NO: 39; a CDR2 comprising the amino acid sequence of SEQ ID NO: 115; and a CDR3 comprising the amino acid sequence of SEQ ID NO: 191. In some embodiments, the sdAb specifically recognizing LAG-3 comprises a CDR1 comprising the amino acid sequence of SEQ ID NO: 40; a CDR2 comprising the amino acid sequence of SEQ ID NO: 116; and a CDR3 comprising the amino acid sequence of SEQ ID NO: 192. In some embodiments, the sdAb specifically recognizing LAG-3 comprises a CDR1 comprising the amino acid sequence of SEQ ID NO: 41; a CDR2 comprising the amino acid sequence of SEQ ID NO: 117; and a CDR3 comprising the amino acid sequence of SEQ ID NO: 193. In some embodiments, the sdAb specifically recognizing LAG-3 comprises a CDR1 comprising the amino acid sequence of SEQ ID NO: 42; a CDR2 comprising the amino acid sequence of SEQ ID NO: 118; and a CDR3 comprising the amino acid sequence of SEQ ID NO: 194. In some embodiments, the sdAb specifically recognizing LAG-3 comprises a CDR1 comprising the amino acid sequence of SEQ ID NO: 43; a CDR2 comprising the amino acid sequence of SEQ ID NO: 119; and a CDR3 comprising the amino acid sequence of SEQ ID NO: 195. In some embodiments, the sdAb specifically recognizing LAG-3 comprises a CDR1 comprising the amino acid sequence of SEQ ID NO: 44; a CDR2 comprising the amino acid sequence of SEQ ID NO: 120; and a CDR3 comprising the amino acid sequence of SEQ ID NO: 196. In some embodiments, the sdAb specifically recognizing LAG-3 comprises a CDR1 comprising the amino acid sequence of SEQ ID NO: 45; a CDR2 comprising the amino acid sequence of SEQ ID NO: 121; and a CDR3 comprising the amino acid sequence of SEQ ID NO: 197. In some embodiments, the sdAb specifically recognizing LAG-3 comprises a CDR1 comprising the amino acid sequence of SEQ ID NO: 46; a CDR2 comprising the amino acid sequence of SEQ ID NO: 122; and a CDR3 comprising the amino acid sequence of SEQ ID NO: 198. In some embodiments, the sdAb specifically recognizing LAG-3 comprises a CDR1 comprising the amino acid sequence of SEQ ID NO: 54; a CDR2 comprising the amino acid sequence of SEQ ID NO: 130; and a CDR3 comprising the amino acid sequence of SEQ ID NO: 206. In some embodiments, the sdAb specifically recognizing LAG-3 comprises a CDR1 comprising the amino acid sequence of SEQ ID NO: 61; a CDR2 comprising the amino acid sequence of SEQ ID NO: 137; and a CDR3 comprising the amino acid sequence of SEQ ID NO: 213. In some embodiments, the sdAb specifically recognizing LAG-3 comprises a CDR1 comprising the amino acid sequence of SEQ ID NO: 70; a CDR2 comprising the amino acid sequence of SEQ ID NO: 146; and a CDR3 comprising the amino acid sequence of SEQ ID NO: 222. In some embodiments, the sdAb specifically recognizing LAG-3 comprises a CDR1 comprising the amino acid sequence of SEQ ID NO: 72; a CDR2 comprising the amino acid sequence of SEQ ID NO: 148; and a CDR3 comprising the amino acid sequence of SEQ ID NO: 224. In some embodiments, the sdAb specifically recognizing LAG-3 comprises a CDR1 comprising the amino acid sequence of SEQ ID NO: 73; a CDR2 comprising the amino acid sequence of SEQ ID NO: 149; and a CDR3 comprising the amino acid sequence of SEQ ID NO: 225.

In some embodiments, there is provided an isolated anti-LAG-3 construct comprising an sdAb specifically recognizing LAG-3, wherein the sdAb comprises CDR1, CDR2, and CDR3 of any one of SEQ ID NOs: 274-311.

In some embodiments according to any one of the isolated anti-LAG-3 constructs described above, the sdAb comprises $V_HH$ domain comprising: (1) an FR1 comprising the amino acid sequence of any one of SEQ ID NOs: 1-38, or a variant thereof comprising up to about 3 amino acid substitutions; (2) an FR2 comprising the amino acid sequence of any one of SEQ ID NOs: 77-114, or a variant thereof comprising up to about 3 amino acid substitutions; (3) an FR3 comprising the amino acid sequence of any one of SEQ ID NOs: 153-190, or a variant thereof comprising up to about 3 amino acid substitutions; and/or (4) an FR4 comprising the amino acid sequence of any one of SEQ ID NOs: 229-266, or a variant thereof comprising up to about 3 amino acid substitutions.

In some embodiments according to any one of the isolated anti-LAG-3 constructs described above, the sdAb comprises a $V_HH$ domain comprising the amino acid sequence having at least about 80% sequence identify to any one of SEQ ID NOs: 274-311. In some embodiments, the sdAb comprises a $V_HH$ domain comprising the amino acid sequence of any one of SEQ ID NOs: 274-311, or a variant thereof comprising up to about 3 amino acid substitutions in the $V_HH$ domain. In some embodiments, the sdAb comprises a $V_HH$ domain comprising the amino acid sequence of any one of SEQ ID NOs: 274-311.

In some embodiments according to any one of the isolated anti-LAG-3 constructs described above, the $K_D$ of the binding between the sdAb and LAG-3 is about $10^{-7}$ M to about $10^{-12}$ M. In some embodiments, the $K_D$ of the binding between the sdAb and LAG-3 is about $10^{-9}$ M to about $10^{-11}$ M.

In some embodiments according to any one of the isolated anti-LAG-3 constructs described above, the sdAb cross-reacts with a LAG-3 from a non-human mammal. In some embodiments, the sdAb specifically recognizing LAG-3 is camelid, chimeric, human, partially humanized, or fully humanized.

In some embodiments according to any one of the isolated anti-LAG-3 constructs described above, the isolated anti-LAG-3 construct is a heavy chain-only antibody (HCAb) comprising the sdAb specifically recognizing LAG-3 fused to an Fc fragment. In some embodiments, the HCAb is monomeric or dimeric. In some embodiments, the Fc fragment is a human IgG1 (hIgG1) Fc, effectorless (inert) hIgG1 Fc, hIgG4 Fc, or hIgG4 Fc (S228P). In some embodiments, the sdAb is fused to the Fc fragment via a peptide linker. In some embodiments, the peptide linker comprises the amino acid sequence of any one of SEQ ID NOs: 352-353 and 366-372. In some embodiments, the HCAb comprises the amino acid sequence of any one of SEQ ID NOs: 312-349.

In some embodiments according to any one of the isolated anti-LAG-3 constructs described above, the anti-LAG-3 construct comprises: (a) a first antigen binding portion comprising the sdAb specifically recognizing LAG-3; and (b) a second antigen binding portion that specifically recognizes a second epitope. In some embodiments, the second antigen binding portion comprises a full-length antibody, a Fab, a Fab', a (Fab')$_2$, an Fv, a single chain Fv (scFv), an scFv-scFv, a minibody, a diabody, or a second sdAb. In some embodiments, the anti-LAG-3 construct is multispecific (such as bispecific). In some embodiments, the first antigen binding portion and the second antigen binding portion are fused to each other via a peptide linker. In some embodiments, the peptide linker comprises the amino acid sequence of any one of SEQ ID NOs: 352-353 and 366-372. In some embodiments, the N-terminus or the C-terminus of the anti-LAG-3 sdAb is fused to a peptide sequence. In some embodiments, the peptide sequence comprises the amino acid sequence of any one of SEQ ID NOs: 352-353 and 366-372. In some embodiments, the second antigen binding portion comprises a full-length antibody consisting of two heavy chains and two light chains. In some embodiments, the Fc fragment of the full-length antibody is human IgG1 (hIgG1) Fc, effectorless hIgG1 Fc, hIgG4 Fc, or hIgG4 Fc (S228P). In some embodiments, the N-terminus of the sdAb specifically recognizing LAG-3 is fused to the C-terminus of a heavy chain of the full-length antibody. In some embodiments, the C-terminus of the sdAb specifically recognizing LAG-3 is fused to the N-terminus of a heavy chain of the full-length antibody. In some embodiments, the N-terminus of the sdAb specifically recognizing LAG-3 is fused to the C-terminus of a light chain of the full-length antibody. In some embodiments, the C-terminus of the sdAb specifically recognizing LAG-3 is fused to the N-terminus of a light chain of the full-length antibody. In some embodiments, the second antigen binding portion specifically recognizes an immune checkpoint molecule selected from the group consisting of PD-1, 4-1BB, PD-L1, TIM-3, TIGIT, CTLA-4, VISTA, B7-1, B7-H3, CD47, OX40 and GITR. In some embodiments, the second antigen binding portion specifically recognizes PD-1. In some embodiments, the second antigen binding portion comprises HC-CDR1, HC-CDR2, and HC-CDR3 of a heavy chain comprising the amino acid sequence of SEQ ID NO: 356, and LC-CDR1, LC-CDR2, and LC-CDR3 of a light chain comprising the amino acid sequence of SEQ ID NO: 357. In some embodiments, the second antigen binding portion comprises HC-CDR1, HC-CDR2, and HC-CDR3 of a heavy chain comprising the amino acid sequence of SEQ ID NO: 373 and LC-CDR1, LC-CDR2, and LC-CDR3 of a light chain comprising the amino acid sequence of SEQ ID NO: 374. In some embodiments, the second antigen binding portion is a full-length antibody comprising a heavy chain comprising the amino acid sequence of SEQ ID NO: 356, and a light chain comprising the amino acid sequence of SEQ ID NO: 357. In some embodiments, the second antigen binding portion is a full-length antibody comprising a heavy chain comprising the amino acid sequence of SEQ ID NO: 373, and a light chain comprising the amino acid sequence of SEQ ID NO: 374.

Further provided is an isolated anti-LAG-3 construct that specifically binds to LAG-3 competitively with any one of the isolated anti-LAG-3 constructs described above.

Further provided is a pharmaceutical composition comprising any one of the isolated anti-LAG-3 constructs described above, and a pharmaceutically acceptable carrier.

Another aspect of the present application provides a method of treating an individual having a LAG-3-related disease, comprising administering to the individual an effective amount of any one of the pharmaceutical compositions described above. In some embodiments, the LAG-3-related disease is cancer. In some embodiments, the cancer is colon cancer. In some embodiments, the individual is a human.

Further provided is an isolated nucleic acid encoding any one of the isolated anti-LAG-3 constructs described above, a vector comprising the isolated nucleic acid, or an isolated host cell comprising the isolated nucleic acid or the vector. In some embodiments, there is provided a method of producing any one of isolated anti-LAG-3 constructs described above, comprising culturing a host cell comprising any one of the isolated nucleic acids or vectors described above, or culturing any one of the isolated host cells described above, under conditions effective to express the encoded anti-LAG-3 construct; and obtaining the expressed anti-LAG-3 construct from the host cell.

Also provided are compositions, kits and articles of manufacture comprising the any one of the anti-LAG-3 constructs described herein.

$V_HH-C_L$; (2) $V_L-V_H-V_HH-C_H1-C_H2-C_H3$; (3) $V_L-V_H-V_HH-C_H1-C_H2-C_H3$; and (4) $V_HH-C_L$, wherein $V_H$ and $V_L$ of polypeptide chains (2) and (3) each forms an scFv that specifically binds a copy of the second epitope, and each $V_HH$ specifically binds a copy of the first epitope (LAG-3). In alternative formats, the C-terminus of the scFv may be fused to the N-terminus of the chain in the Fab-like fragment comprising $V_HH-C_L$; and/or the scFv domain can comprise from the N-terminus to the C-terminus: $V_H-V_L$. Additionally, to expand specificity, the two scFvs can specifically bind different epitopes, and/or the $V_HH$ fragments can specifically bind different epitopes (e.g., different epitopes from LAG-3).

Figure 17A:
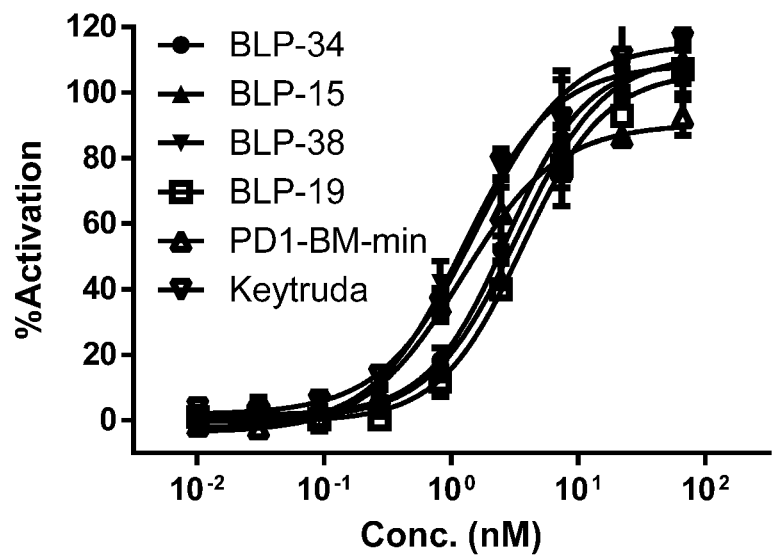
Figure 17B:
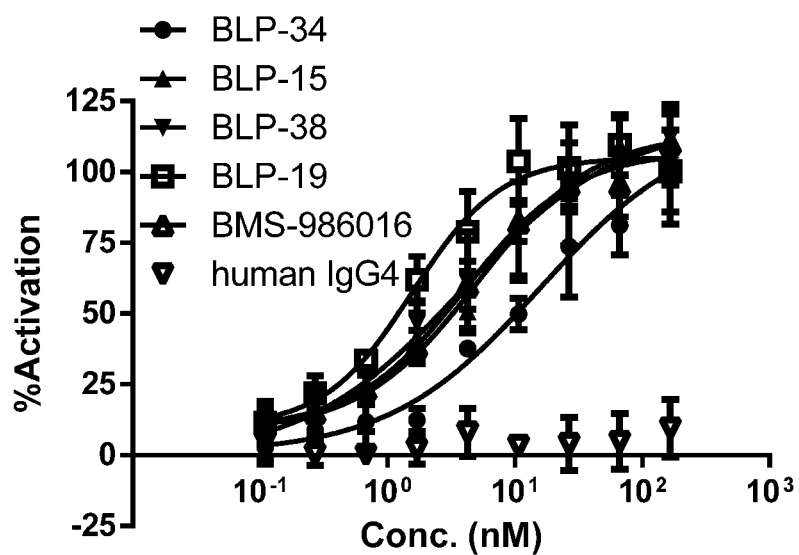

FIGS. 17A-17B depict in vitro activities of PD-1×LAG-3 BABPs in a PD-1 cell based reporter assay (FIG. 17A) and a LAG-3 blockade reporter assay (FIG. 17B). Pembrolizumab and PD1-BM-min were used as controls for PD-1 cell based reporter assay and BMS-986016 was used as a control for LAG-3 blockade reporter assay.

Figure 18A:
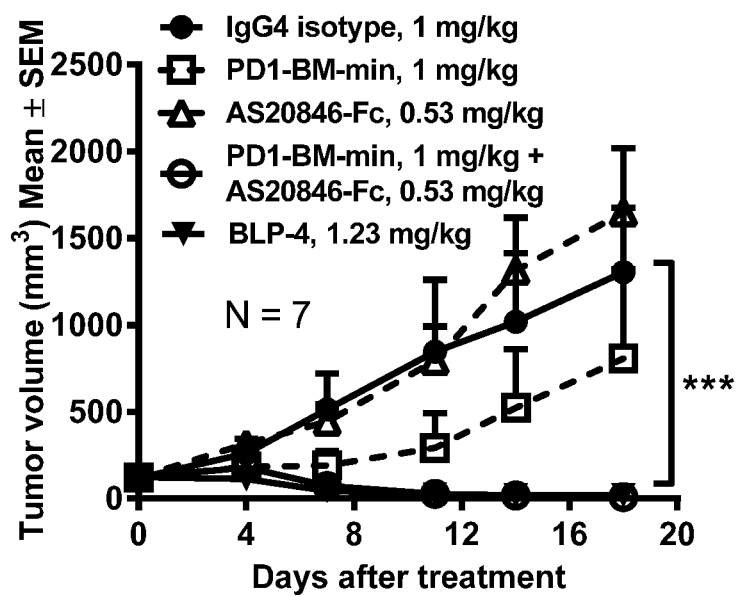
Figure 18B:
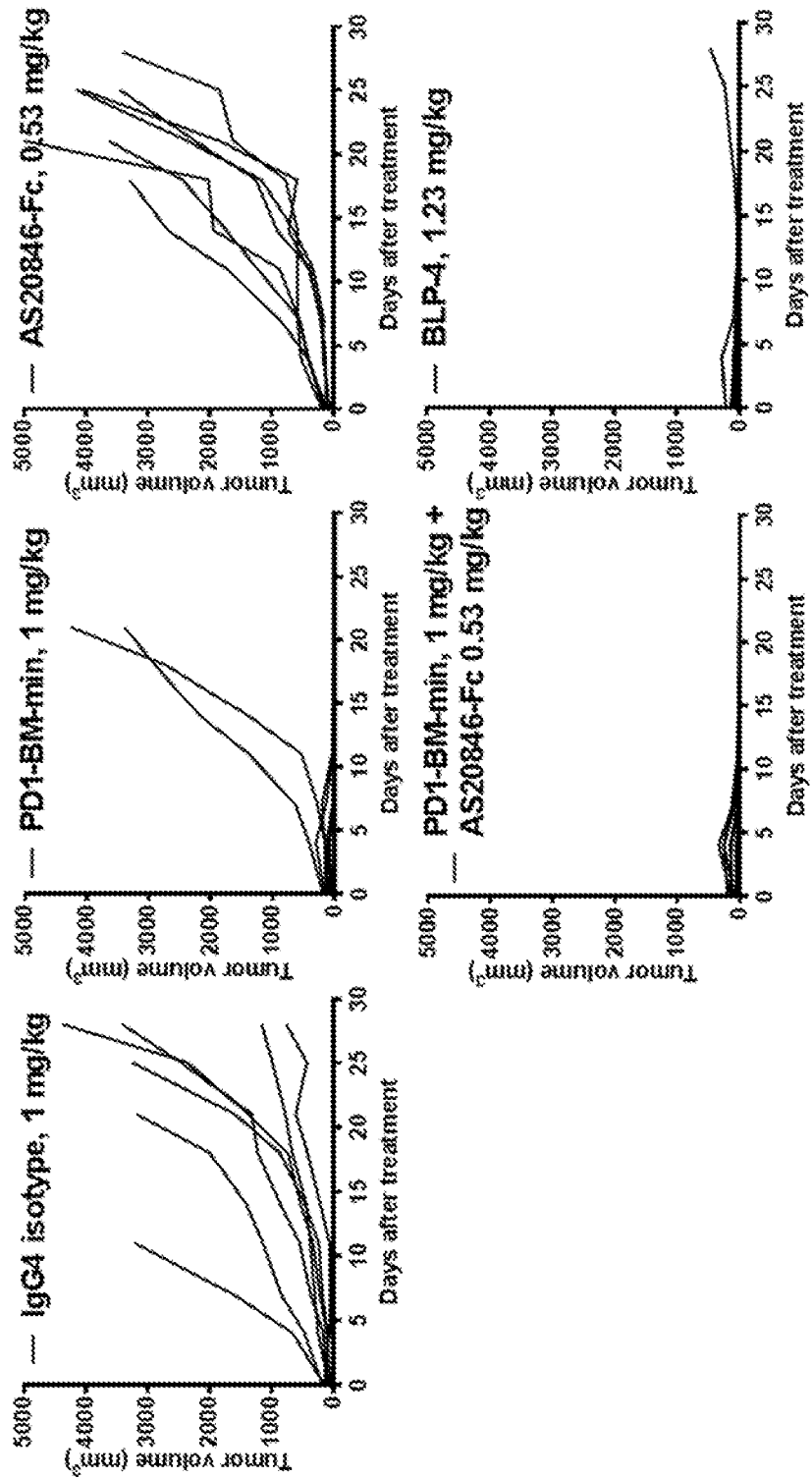

FIGS. 18A-18B depict in vivo efficacy of PD-1×LAG-3 BLP-4 in C57BL/6 human PD-1/LAG-3 double knock-in mice bearing MC38 tumor, as compared to parental elements of BLP-4 (i.e., PD1-BM-min and AS20846-Fc) and combination thereof. FIG. 18A shows average tumor volume in each treatment group. FIG. 18B shows spider plots of tumor volume of each animal IgG4 was used as a negative control.

DETAILED DESCRIPTION OF THE INVENTION

The present invention provides novel single-domain antibodies (sdAbs) specifically recognizing LAG-3 (i.e., anti-LAG-3 sdAb), and constructs comprising the anti-LAG-3 sdAbs. The anti-LAG3 sdAbs described herein have strong binding affinity and are capable of cross-reacting with LAG-3 of a non-human mammal, such as a cynomolgus monkey. The anti-LAG3 constructs described herein are useful for treating LAG-3-related diseases such as cancer.

Accordingly, one aspect of the present application provides an isolated anti-LAG-3 construct comprising an sdAb specifically recognizing LAG-3. The isolated anti-LAG-3 construct can be, for example, an anti-LAG-3 sdAb (e.g., camelid or humanized), a polypeptide comprising a plurality of anti-LAG-3 sdAbs fused together, an anti-LAG-3 sdAb-Fc fusion protein comprising an anti-LAG-3 sdAb fused to an Fc fragment (e.g., a human IgG1 Fc, effectorless IgG1 Fc, IgG2 Fc, or IgG4 Fc), or a multispecific antigen binding protein ("MABP") comprising an anti-LAG-3 sdAb fused to a full-length antibody (such as anti-PD-1 antibody) or an antigen binding fragment thereof. The anti-LAG-3 construct can be monospecific or multispecific (such as bispecific), monovalent or multivalent (such as bivalent).

Also provided are compositions (such as pharmaceutical compositions), kits and articles of manufacture comprising the anti-LAG-3 constructs described herein, methods of making thereof, and methods of treating LAG-3-related disease (such as cancer) using the anti-LAG-3 constructs described herein.

I. Definitions

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the invention contemplate any one or more of these aspects of treatment.

The term "prevent," and similar words such as "prevented," "preventing" etc., indicate an approach for preventing, inhibiting, or reducing the likelihood of the recurrence of, a disease or condition, e.g., cancer. It also refers to delaying the recurrence of a disease or condition or delaying the recurrence of the symptoms of a disease or condition. As used herein, "prevention" and similar words also includes reducing the intensity, effect, symptoms and/or burden of a disease or condition prior to recurrence of the disease or condition.

As used herein, "delaying" the development of cancer means to defer, hinder, slow, retard, stabilize, and/or postpone development of the disease. This delay can be of varying lengths of time, depending on the history of the disease and/or individual being treated. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

The term "effective amount" used herein refers to an amount of an agent or a combination of agents, sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

As used herein, an "individual" or a "subject" refers to a mammal, including, but not limited to, human, bovine, horse, feline, canine, rodent, or primate. In some embodiments, the individual is a human.

The term "antibody" is used in its broadest sense and encompasses various antibody structures, including but not limited to monoclonal antibodies, polyclonal antibodies, multispecific antibodies (e.g., bispecific antibodies), full-length antibodies and antigen-binding fragments thereof, so long as they exhibit the desired antigen-binding activity. The term "antibody" includes conventional 4-chain antibodies, single-domain antibodies, and antigen-binding fragments thereof.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen-binding sites, while IgA antibodies comprise from 2-5 of the basic 4-chain units which can polymerize to form polyvalent assemblages in combination with the J chain. In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, β, ε, γ and μ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1 and IgA2.

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

The term "single-domain antibody" or "sdAb" refers to a single antigen-binding polypeptide having three complementary determining regions (CDRs). The sdAb alone is capable of binding to the antigen without pairing with a corresponding CDR-containing polypeptide. In some cases, single-domain antibodies are engineered from camelid HCAbs, and their heavy chain variable domains are referred herein as "$V_H$Hs" (Variable domain of the heavy chain of the Heavy chain antibody). Camelid sdAb is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic $V_H$H has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

An "isolated" antibody (or construct) is one that has been identified, separated and/or recovered from a component of its production environment (e.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator; or (3) to homogeneity by SDS-PAGE under non-reducing or reducing conditions using Coomassie Blue or, preferably, silver stain. Isolated antibody (or construct) includes the antibody in situ within recombinant cells since at least one component of the antibody's natural environment will not be present. Ordinarily, however, an isolated polypeptide, antibody, or construct will be prepared by at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. Heavy-chain only antibodies from the Camelid species have a single heavy chain variable region, which is referred to as "$V_H$H". $V_H$H is thus a special type of $V_H$.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called complementary determining regions (CDRs) or hypervariable regions (HVRs) both in the heavy chain and light chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies (see Kabat et al., *Sequences of*

*Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature,* 256:495-97 (1975); Hongo et al., *Hybridoma,* 14 (3): 253-260 (1995), Harlow et al., *Antibodies: A Laboratory Manual,* (Cold Spring Harbor Laboratory Press, 2$^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The terms "full-length antibody", "intact antibody", or "whole antibody" are used interchangeably to refer to an antibody in its substantially intact form, as opposed to an antibody fragment. Specifically, full-length 4-chain antibodies include those with heavy and light chains including an Fc region. Full-length heavy-chain only antibodies include the heavy chain variable domain (such as V$_H$H) and an Fc region. The constant domains may be native sequence constant domains (e.g., human native sequence constant domains) or amino acid sequence variants thereof. In some cases, the intact antibody may have one or more effector functions.

An "antibody fragment" or "antigen-binding fragment" comprises a portion of an intact antibody, preferably the antigen binding and/or the variable region of the intact antibody. Examples of antibody fragments include, but are not limited to Fab, Fab', F(ab')$_2$ and Fv fragments; diabodies; linear antibodies (see U.S. Pat. No. 5,641,870, Example 2; Zapata et al., *Protein Eng.* 8(10): 1057-1062 (1995)); single-chain antibody (scFv) molecules; single-domain antibodies (such as V$_H$H), and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable domain of the H chain (V$_H$), and the first constant domain of one heavy chain (C$_H$1). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy-terminus of the C$_H$1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "constant domain" refers to the portion of an immunoglobulin molecule having a more conserved amino acid sequence relative to the other portion of the immunoglobulin, the variable domain, which contains the antigen-binding site. The constant domain contains the C$_H$1, C$_H$2 and C$_H$3 domains (collectively, C$_H$) of the heavy chain and the CHL (or C$_L$) domain of the light chain.

The "light chains" of antibodies (immunoglobulins) from any mammalian species can be assigned to one of two clearly distinct types, called kappa ("κ") and lambda ("λ"), based on the amino acid sequences of their constant domains.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the V$_H$ and V$_L$ antibody domains connected into a single polypeptide chain. Preferably, the scFv polypeptide further comprises a polypeptide linker between the V$_H$ and V$_L$ domains which enables the scFv to form the desired structure for antigen binding. For a review of the scFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing sFv fragments (see preceding paragraph) with short linkers (about 5-10 residues) between the V$_H$ and V$_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., Proc. Natl. Acad. Sci. USA 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). "Humanized antibody" is used as a subset of "chimeric antibodies".

"Humanized" forms of non-human (e.g., llama or camelid) antibodies are chimeric antibodies that contain minimal sequence derived from non-human immunoglobulin. In some embodiments, a humanized antibody is a human immunoglobulin (recipient antibody) in which residues from an CDR (hereinafter defined) of the recipient are replaced by residues from an CDR of a non-human species (donor antibody) such as mouse, rat, rabbit, camel, llama, alpaca, or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227: 381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, single-domain antibodies comprise three HVRs (or CDRs): HVR1 (or CDR1), HVR2 (or CDR2), and HVR3 (or CDR3). HVR3 (or CDR3) displays the most diversity of the three HVRs, and is believed to play a unique role in conferring fine specificity to antibodies. See, e.g., Hamers-Casterman et al., Nature 363:446-448 (1993); Sheriff et al., Nature Struct. Biol. 3:733-736 (1996).

The term "Complementarity Determining Region" or "CDR" are used to refer to hypervariable regions as defined by the Kabat system. See Kabat et al., Sequences of Proteins of Immunological Interest, 5th Ed. Public Health Service, National Institutes of Health, Bethesda, Md. (1991).

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below in Table 1.

TABLE 1

HVR delineations.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The amino acid residues of a single-domain antibody (such as $V_HH$) are numbered according to the general numbering for $V_H$ domains given by Kabat et al. ("Sequence of proteins of immunological interest", US Public Health Services, NIH Bethesda, Md., Publication No. 91), as applied to $V_H H$ domains from Camelids in the article of Riechmann and Muyldermans, J. Immunol. Methods 2000 Jun. 23; 240 (1-2): 185-195. According to this numbering, FR1 of a $V_H H$ comprises the amino acid residues at positions 1-30, CDR1 of a $V_H H$ comprises the amino acid residues at positions 31-35, FR2 of a $V_H H$ comprises the amino acids at positions 36-49, CDR2 of a $V_H H$ comprises the amino acid residues at positions 50-65, FR3 of a $V_H H$ comprises the amino acid residues at positions 66-94, CDR3 of a $V_H H$ comprises the amino acid residues at positions 95-102, and FR4 of a $V_H H$ comprises the amino acid residues at positions 103-113. In this respect, it should be noted that—as is well known in the art for $V_H$ domains and for $V_H H$ domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering).

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest,* 5th Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "affinity-matured" antibody is one with one or more alterations in one or more CDRs thereof that result in an improvement in the affinity of the antibody for antigen, compared to a parent antibody that does not possess those alteration(s). In some embodiments, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by $V_H$- and $V_L$-domain shuffling. Random mutagenesis of CDR and/or framework residues is described by, for example: Barbas et al. *Proc Nat. Acad. Sci.* USA 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As used herein, the term "specifically binds," "specifically recognizes," or is "specific for" refers to measurable and reproducible interactions such as binding between a target and an antigen binding protein (such as an sdAb), which is determinative of the presence of the target in the presence of a heterogeneous population of molecules including biological molecules. For example, an antigen binding protein (such as an sdAb) that specifically binds a target (which can be an epitope) is an antigen binding protein (such as an sdAb) that binds this target with greater affinity, avidity, more readily, and/or with greater duration than it binds other targets. In some embodiments, the extent of binding of an antigen binding protein (such as an sdAb) to an unrelated target is less than about 10% of the binding of the antigen binding protein (such as an sdAb) to the target as measured, e.g., by a radioimmunoassay (RIA). In some embodiments, an antigen binding protein (such as an sdAb) that specifically binds a target has a dissociation constant ($K_D$) of $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. In some embodiments, an antigen binding protein specifically binds an epitope on a protein that is conserved among the protein from different species. In some embodiments, specific binding can include, but does not require exclusive binding. Binding specificity of the antibody or antigen-binding domain can be determined experimentally by methods known in the art. Such methods comprise, but are not limited to Western blots, ELISA-, RIA-, ECL-, IRMA-, EIA-, BIACORE™-tests and peptide scans.

The term "specificity" refers to selective recognition of an antigen binding protein (such as an sdAb) for a particular epitope of an antigen. Natural antibodies, for example, are monospecific. The term "multispecific" as used herein denotes that an antigen binding protein has polyepitopic specificity (i.e., is capable of specifically binding to two, three, or more, different epitopes on one biological molecule or is capable of specifically binding to epitopes on two, three, or more, different biological molecules). "Bispecific" as used herein denotes that an antigen binding protein has two different antigen-binding specificities. Unless otherwise indicated, the order in which the antigens bound by a bispecific antibody listed is arbitrary. That is, for example, the terms "anti-LAG-3/PD-1," "anti-PD-1/LAG-3," "LAG-3×PD-1" and "PD-1×LAG-3" may be used interchangeably to refer to bispecific antibodies that specifically bind to both LAG-3 and PD-1. The term "monospecific" as used herein denotes an antigen binding protein that has one or more binding sites each of which bind the same epitope of the same antigen.

The term "valent" as used herein denotes the presence of a specified number of binding sites in an antigen binding protein. A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein.

"Antibody effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptors); and B cell activation. "Reduced or minimized" antibody effector function means that which is reduced by at least 50% (alternatively 60%, 65%, 70%, 75%, 80%, 85%, 90%, 95%, 96%, 97%, 98%, 99%) from the wild type or unmodified antibody. The determination of antibody effector function is readily determinable and measurable by one of ordinary skill in the art. In a preferred embodiment, the antibody effector functions of complement binding, complement dependent cytotoxicity and antibody dependent cytotoxicity are affected. In some embodiments, effector function is eliminated through a mutation in the constant region that eliminated glycosylation, e.g., "effectorless mutation." In one aspect, the effectorless mutation is an N297A or DANA mutation (D265A+N297A) in the $C_H2$ region. Shields et al., *J. Biol. Chem.* 276 (9): 6591-6604 (2001). Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., *E. coli.*) or in which result in an altered glycosylation pattern that is ineffective or less effective at promoting effector function (e.g., Shinkawa et al., *J. Biol. Chem.* 278(5): 3466-3473 (2003).

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 2 on page 464 of Ravetch and Kinet, *Annu. Rev. Immunol.* 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998).

The term "Fc region" or "fragment crystallizable region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Fc receptor" or "FcR" describes a receptor that binds the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See M. Daeron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9(2): 6591-6604 (2001).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202: 163 (1996), may be performed. Antibody variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair. Binding affinity can be indicated by $K_d$, $K_{off}$, $K_{on}$, or $K_a$. The term "$K_{off}$", as used herein, is intended to refer to the off rate constant for dissociation of an antibody (or antigen-binding domain) from the antibody/antigen complex, as determined from a kinetic selection set up, expressed in units of $s^{-1}$. The term "$K_{on}$", as used herein, is intended to refer to the on rate constant for association of an antibody (or antigen-binding domain) to the antigen to form the antibody/antigen complex, expressed in units of $M^{-1}s^{-1}$. The term equilibrium dissociation constant "$K_D$" or "$K_d$", as used herein, refers to the dissociation constant of a particular antibody-antigen interaction, and describes the concentration of antigen required to occupy one half of all of the antibody-binding domains present in a solution of antibody molecules at equilibrium, and is equal to $K_{off}/K_{on}$, expressed in units of M. The measurement of $K_d$ presupposes that all binding agents are in solution. In the case where the antibody is tethered to a cell wall, e.g., in a yeast expression system, the corresponding equilibrium rate constant is expressed as EC50, which gives a good approximation of $K_d$. The affinity constant, $K_a$, is the inverse of the dissociation constant, $K_d$, expressed in units of $M^{-1}$. The dissociation constant ($K_D$ or $K_d$) is used as an indicator showing affinity of antibodies to antigens. For example, easy analysis is possible by the Scatchard method using antibodies marked with a variety of marker agents, as well as by using BIACORE™ X (made by Amersham Biosciences), which is an over-the-counter, measuring kit, or similar kit, according to the user's manual and experiment operation method attached with the kit. The $K_D$ value that can be derived using these methods is expressed in units of M (Mols). An antibody or antigen-binding fragment thereof that specifically binds to a target may have a dissociation constant ($K_d$) of, for example, $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M.

Half maximal inhibitory concentration ($IC_{50}$) is a measure of the effectiveness of a substance (such as an antibody) in inhibiting a specific biological or biochemical function. It indicates how much of a particular drug or other substance (inhibitor, such as an antibody) is needed to inhibit a given biological process by half. The values are typically expressed as molar concentration. $IC_{50}$ is comparable to an "$EC_{50}$" for agonist drug or other substance (such as an antibody). $EC_{50}$ also represents the plasma concentration required for obtaining 50% of a maximum effect in vivo. As used herein, an "$IC_{50}$" is used to indicate the effective concentration of an antibody needed to neutralize 50% of the antigen bioactivity in vitro. $IC_{50}$ or $EC_{50}$ can be measured by bioassays such as inhibition of ligand binding by FACS analysis (competition binding assay), cell based cytokine release assay, or amplified luminescent proximity homogeneous assay (AlphaLISA).

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An "isolated" nucleic acid molecule encoding a construct, antibody, or antigen-binding fragment thereof described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "pharmaceutical formulation" of "pharmaceutical composition" refers to a preparation that is in such form as to permit the biological activity of the active ingredient to be effective, and that contains no additional components that are unacceptably toxic to a subject to which the formulation would be administered. Such formulations are sterile. A "sterile" formulation is aseptic or free from all living microorganisms and their spores.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Anti-LAG-3 Constructs

One aspect of the present application provides isolated anti-LAG-3 constructs comprising a single-domain antibody (sdAb) that specifically recognizes LAG-3 (i.e., "anti-LAG-3 sdAb"). In some embodiments, the anti-LAG-3 construct is an anti-LAG-3 sdAb, a fusion protein, or an antigen-binding fragment thereof, which specifically binds to LAG-3 and antagonizes its ability to bind MHC class II molecules and/or mediate T cell exhaustion.

(I) Anti-LAG-3 Single-Domain Antibodies

The isolated anti-LAG-3 constructs described herein comprise an anti-LAG-3 sdAb. In some embodiments, the anti-LAG-3 sdAb specifically recognizes human LAG-3. The complete amino acid sequence of an exemplary human LAG-3 comprises or consists of the amino acid sequence of SEQ ID NO: 350. In some embodiments, the anti-LAG-3 sdAb specifically recognizes an epitope within human LAG-3. In some embodiments, the anti-LAG-3 sdAb specifically recognizes the extracellular domain of human LAG-3. The amino acid sequence of the extracellular domain of an exemplary human LAG-3 comprises or consists of the amino acid sequence of SEQ ID NO: 351. In some embodiments, the anti-LAG-3 sdAb cross-reacts with a LAG-3 from a non-human mammal. In some embodiments, the anti-LAG-3 sdAb cross-reacts with LAG-3 from a non-human primate, such as cynomolgus monkey.

In some embodiments, the anti-LAG-3 sdAb cross-reacts with at least one interspecies variant of the LAG-3 protein. In some embodiments, for example, the LAG-3 protein (or fragments thereof) is human LAG-3 and the interspecies variant of the LAG-3 protein (or fragments thereof) is a cynomolgus monkey variant thereof. Cross-reactivity of the anti-LAG-3 sdAbs or constructs thereof may facilitate clinical development of the anti-LAG-3 constructs, for example, by allowing more accurate and responsive dosing in animal studies.

In some embodiments, there is provided an anti-LAG-3 sdAb comprising a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, the anti-LAG-3 sdAb comprises a CDR3 comprising the amino acid sequence of any one of SEQ ID NOs: 191-228, and the amino acid substitutions are in CDR1 and/or CDR2. Thus, in some embodiments, there is provided an anti-LAG-3 sdAb comprising a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of any one of SEQ ID NOs: 39-76; a CDR2 comprising the amino acid sequence of any one of SEQ ID NOs: 115-152; and a CDR3 comprising the amino acid sequence of any one of SEQ ID NOs: 191-228; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of any one of SEQ ID NOs: 39-76; a CDR2 comprising the amino acid sequence of any one of SEQ ID NOs: 115-152; and a CDR3 comprising the amino acid sequence of any one of SEQ ID NOs: 191-228; or a variant thereof comprising up to about 3 (such as about any of 1, 2, or 3) amino acid substitutions in the CDR regions, wherein the amino acid substitutions are in CDR1 and/or CDR2. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of any one of SEQ ID NOs: 39-76; a CDR2 comprising the amino acid sequence of any one of SEQ ID NOs: 115-152; and a CDR3 comprising the amino acid sequence of any one of SEQ ID NOs: 191-228. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

The sequences of the CDRs noted herein are provided in Table 11. The CDRs can be combined in any combinations to generate a number of anti-LAG-3 sdAbs. A skilled person in the art would readily appreciate that antibody constructs comprising CDRs or variable domain sequences derived from the antibodies described herein, but wherein the CDRs or variable domain sequences are predicted using algorithms other than the Kabat system are within the scope of the present invention.

In some embodiments, there is provided an anti-LAG-3 sdAb comprising a CDR1 comprising the amino acid sequence of SEQ ID NO: 39, or a variant thereof comprising up to about 3 (such as about any of 1, 2, or 3) amino acid substitutions; a CDR2 comprising the amino acid sequence of SEQ ID NO: 115, or a variant thereof comprising up to about 3 (such as about any of 1, 2, or 3) amino acid substitutions; and a CDR3 comprising the amino acid sequence of SEQ ID NO: 191, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 39; a CDR2 comprising the amino acid sequence of SEQ ID NO: 115; and a CDR3 comprising the amino acid sequence of SEQ ID NO: 191; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 39; a CDR2 comprising the amino acid sequence of SEQ ID NO: 115; and a CDR3 comprising the amino acid sequence of SEQ ID NO: 191. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 40, or a variant thereof comprising up to about 3 (such as about any of 1, 2, or 3) amino acid substitutions; a CDR2 comprising the amino acid sequence of SEQ ID NO: 116, or a variant thereof comprising up to about 3 (such as about any of 1, 2, or 3) amino acid substitutions; and a CDR3 comprising the amino acid sequence of SEQ ID NO: 192, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 40; a CDR2 comprising the amino acid sequence of SEQ ID NO: 116; and a CDR3 comprising the amino acid sequence of SEQ ID NO: 192; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 40; a CDR2 comprising the amino acid sequence of SEQ ID NO: 116; and a CDR3 comprising the amino acid sequence of SEQ ID NO: 192. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 41, or a variant thereof comprising up to about 3 (such as about any of 1, 2, or 3) amino acid substitutions; a CDR2 comprising the amino acid sequence of SEQ ID NO: 117, or a variant thereof comprising up to about 3 (such as about any of 1, 2, or 3) amino acid substitutions; and a CDR3 comprising the amino acid sequence of SEQ ID NO: 193, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 41; a CDR2 comprising the amino acid sequence of SEQ ID NO: 117; and a CDR3 comprising the amino acid sequence of SEQ ID NO: 193; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 41; a CDR2 comprising the amino acid sequence of SEQ ID NO: 117; and a CDR3 comprising the amino acid sequence of SEQ ID NO: 193. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 42, or a variant thereof comprising up to about 3 (such as about any of 1, 2, or 3) amino acid substitutions; a CDR2 comprising the amino acid sequence of SEQ ID NO: 118, or a variant thereof comprising up to about 3 (such as about any of 1, 2, or 3) amino acid substitutions; and a CDR3 comprising the amino acid sequence of SEQ ID NO: 194, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 42; a CDR2 comprising the amino acid sequence of SEQ ID NO: 118; and a CDR3 comprising the amino acid sequence of SEQ ID NO: 194; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 42; a CDR2 comprising the amino acid sequence of SEQ ID NO: 118; and a CDR3 comprising the amino acid sequence of SEQ ID NO: 194. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 43, or a variant thereof comprising up to about 3 (such as about any of 1, 2, or 3) amino acid substitutions; a CDR2 comprising the amino acid sequence of SEQ ID NO: 119, or a variant thereof comprising up to about 3 (such as about any of 1, 2, or 3) amino acid substitutions; and a CDR3 comprising the amino acid sequence of SEQ ID NO: 195, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 43; a CDR2 comprising the amino acid sequence of SEQ ID NO: 119; and a CDR3 comprising the amino acid sequence of SEQ ID NO: 195; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 43; a CDR2 comprising the amino acid sequence of SEQ ID NO: 119; and a CDR3 comprising the amino acid sequence of SEQ ID NO: 195. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 44, or a variant thereof comprising up to about 3 (such as about any of 1, 2, or 3) amino acid substitutions; a CDR2 comprising the amino acid sequence of SEQ ID NO: 120, or a variant thereof comprising up to about 3 (such as about any of 1, 2, or 3) amino acid substitutions; and a CDR3 comprising the amino acid sequence of SEQ ID NO: 196, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 44; a CDR2 comprising the amino acid sequence of SEQ ID NO: 120; and a CDR3 comprising the amino acid sequence of SEQ ID NO: 196; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 44; a CDR2 comprising the amino acid sequence of SEQ ID NO: 120; and a CDR3 comprising the amino acid sequence of SEQ ID NO: 196. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 45, or a variant thereof comprising up to about 3 (such as about any of 1, 2, or 3) amino acid substitutions; a CDR2 comprising the amino acid sequence of SEQ ID NO: 121, or a variant thereof comprising up to about 3 (such as about any of 1, 2, or 3) amino acid substitutions; and a CDR3 comprising the amino acid sequence of SEQ ID NO: 197, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 45; a CDR2 comprising the amino acid sequence of SEQ ID NO: 121; and a CDR3 comprising the amino acid sequence of SEQ ID NO: 197; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 45; a CDR2 comprising the amino acid sequence of SEQ ID NO: 121; and a CDR3 comprising the amino acid sequence of SEQ ID NO: 197. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 46, or a variant thereof comprising up to about 3 (such as about any of 1, 2, or 3) amino acid substitutions; a CDR2 comprising the amino acid sequence of SEQ ID NO: 122, or a variant thereof comprising up to about 3 (such as about any of 1, 2, or 3) amino acid substitutions; and a CDR3 comprising the amino acid sequence of SEQ ID NO: 198, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 46; a CDR2 comprising the amino acid sequence of SEQ ID NO: 122; and a CDR3 comprising the amino acid sequence of SEQ ID NO: 198; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 46; a CDR2 comprising the amino acid sequence of SEQ ID NO: 122; and a CDR3 comprising the amino acid sequence of SEQ ID NO: 198. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 54, or a variant thereof comprising up to about 3 (such as about any of 1, 2, or 3) amino acid substitutions; a CDR2 comprising the amino acid sequence of SEQ ID NO: 130, or a variant thereof comprising up to about 3 (such as about any of 1, 2, or 3) amino acid substitutions; and a CDR3 comprising the amino acid sequence of SEQ ID NO: 206, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 54; a CDR2 comprising the amino acid sequence of SEQ ID NO: 130; and a CDR3 comprising the amino acid sequence of SEQ ID NO: 206; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 54; a CDR2 comprising the amino acid sequence of SEQ ID NO: 130; and a CDR3 comprising the amino acid sequence of SEQ ID NO: 206. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 61, or a variant thereof comprising up to about 3 (such as about any of 1, 2, or 3) amino acid substitutions; a CDR2 comprising the amino acid sequence of SEQ ID NO: 137, or a variant thereof comprising up to about 3 (such as about any of 1, 2, or 3) amino acid substitutions; and a CDR3 comprising the amino acid sequence of SEQ ID NO: 213, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 61; a CDR2 comprising the amino acid sequence of SEQ ID NO: 137; and a CDR3 comprising the amino acid sequence of SEQ ID NO: 213; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 61; a CDR2 comprising the amino acid sequence of SEQ ID NO: 137; and a CDR3 comprising the amino acid sequence of SEQ ID NO: 213. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 70, or a variant thereof comprising up to about 3 (such as about any of 1, 2, or 3) amino acid substitutions; a CDR2 comprising the amino acid sequence of SEQ ID NO: 146, or a variant thereof comprising up to about 3 (such as about any of 1, 2, or 3) amino acid substitutions; and a CDR3 comprising the amino acid sequence of SEQ ID NO: 222, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 70; a CDR2 comprising the amino acid sequence of SEQ ID NO: 146; and a CDR3 comprising the amino acid sequence of SEQ ID NO: 222; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 70; a CDR2 comprising the amino acid sequence of SEQ ID NO: 146; and a CDR3 comprising the amino acid sequence of SEQ ID NO: 222. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 72, or a variant thereof comprising up to about 3 (such as about any of 1, 2, or 3) amino acid substitutions; a CDR2 comprising the amino acid sequence of SEQ ID NO: 148, or a variant thereof comprising up to about 3 (such as about any of 1, 2, or 3) amino acid substitutions; and a CDR3 comprising the amino acid sequence of SEQ ID NO: 224, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 72; a CDR2 comprising the amino acid sequence of SEQ ID NO: 148; and a CDR3 comprising the amino acid sequence of SEQ ID NO: 224; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 72; a CDR2 comprising the amino acid sequence of SEQ ID NO: 148; and a CDR3 comprising the amino acid sequence of SEQ ID NO: 224. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 73, or a variant thereof comprising up to about 3 (such as about any of 1, 2, or 3) amino acid substitutions; a CDR2 comprising the amino acid sequence of SEQ ID NO: 149, or a variant thereof comprising up to about 3 (such as about any of 1, 2, or 3) amino acid substitutions; and a CDR3 comprising the amino acid sequence of SEQ ID NO: 225, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 73; a CDR2 comprising the amino acid sequence of SEQ ID NO: 149; and a CDR3 comprising the amino acid sequence of SEQ ID NO: 225; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 73; a CDR2 comprising the amino acid sequence of SEQ ID NO: 149; and a CDR3 comprising the amino acid sequence of SEQ ID NO: 225. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 53, or a variant thereof comprising up to about 3 (such as about any of 1, 2, or 3) amino acid substitutions; a CDR2 comprising the amino acid sequence of SEQ ID NO: 129, or a variant thereof comprising up to about 3 (such as about any of 1, 2, or 3) amino acid substitutions; and a CDR3 comprising the amino acid sequence of SEQ ID NO: 205, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 60, or a variant thereof comprising up to about 3 (such as about any of 1, 2, or 3) amino acid substitutions; a CDR2 comprising the amino acid sequence of SEQ ID NO: 136, or a variant thereof comprising up to about 3 (such as about any of 1, 2, or 3) amino acid substitutions; and a CDR3 comprising the amino acid sequence of SEQ ID NO: 212, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 69, or a variant thereof comprising up to about 3 (such as about any of 1, 2, or 3) amino acid substitutions; a CDR2 comprising the amino acid sequence of SEQ ID NO: 145, or a variant thereof comprising up to about 3 (such as about any of 1, 2, or 3) amino acid substitutions; and a CDR3 comprising the amino acid sequence of SEQ ID NO: 221, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a CDR1 comprising the amino acid sequence of SEQ ID NO: 71, or a variant thereof comprising up to about 3 (such as about any of 1, 2, or 3) amino acid substitutions; a CDR2 comprising the amino acid sequence of SEQ ID NO: 147, or a variant thereof comprising up to about 3 (such as about any of 1, 2, or 3) amino acid substitutions; and a CDR3 comprising the amino acid sequence of SEQ ID NO: 223, or a variant thereof comprising up to about 3 (such as about any of 1, 2, or 3) amino acid substitutions. In some embodiments, there is provided an anti-LAG-3 sdAb comprising a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223; or a variant thereof comprising up to about 3 (such as about any of 1, 2, or 3) amino acid substitutions in the CDR regions. In some embodiments, the amino acid substitutions are in CDR1 and/or CDR2. In some embodiments, there is provided an anti-LAG-3 sdAb comprising a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a $V_HH$ domain comprising the amino acid sequence of any one of SEQ ID NOs: 39-76, the amino acid sequence of any one of SEQ ID NOs: 115-152, and the amino acid sequence of any one of SEQ ID NOs: 191-228. In some embodiments, there is provided an anti-LAG-3 sdAb comprising a $V_HH$ domain comprising the sequences of SEQ ID NOs: 39, 115 and 191. In some embodiments, there is provided an anti-LAG-3 sdAb comprising a $V_HH$ domain comprising the sequences of SEQ ID NOs: 40, 116 and 192. In some embodiments, there is provided an anti-LAG-3 sdAb comprising a $V_HH$ domain comprising the sequences of SEQ ID NOs: 41, 117 and 193. In some embodiments, there is provided an anti-LAG-3 sdAb comprising a $V_HH$ domain comprising the sequences of SEQ ID NOs: 42, 118 and 194. In some embodiments, there is provided an anti-LAG-3 sdAb comprising a $V_HH$ domain comprising the sequences of SEQ ID NOs: 43, 119 and 195. In some embodiments, there is provided an anti-LAG-3 sdAb comprising a $V_HH$ domain comprising the sequences of SEQ ID NOs: 44, 120 and 196. In some embodiments, there is provided an anti-LAG-3 sdAb comprising a $V_HH$ domain comprising the sequences of SEQ ID NOs: 45, 121 and 197. In some embodiments, there is provided an anti-LAG-3 sdAb comprising a $V_HH$ domain comprising the sequences of SEQ ID NOs: 46, 122 and 198. In some embodiments, there is provided an anti-LAG-3 sdAb comprising a $V_HH$ domain comprising the sequences of SEQ ID NOs: 54, 130 and 206. In some embodiments, there is provided an anti-LAG-3 sdAb comprising a $V_HH$ domain comprising the sequence of SEQ ID NO: 61, 137, 213. In some embodiments, there is provided an anti-LAG-3 sdAb comprising a $V_HH$ domain comprising the sequences of SEQ ID NOs: 70, 146 and 222. In some embodiments, there is provided an anti-LAG-3 sdAb comprising a $V_HH$ domain comprising the sequences of SEQ ID NOs: 72, 148 and 224. In some embodiments, there is provided an anti-LAG-3 sdAb comprising a $V_HH$ domain comprising the sequences of SEQ ID NOs: 73, 149 and 225. In some embodiments, there is provided an anti-LAG-3 sdAb comprising a $V_HH$ domain comprising the sequences of SEQ ID NOs: 53, 129 and 205. In some embodiments, there is provided an anti-LAG-3 sdAb comprising a $V_HH$ domain comprising the sequences of SEQ ID NOs: 60, 136 and 212. In some embodiments, there is provided an anti-LAG-3 sdAb comprising a $V_HH$ domain comprising the sequences of SEQ ID NOs: 69, 145 and 221. In some embodiments, there is provided an anti-LAG-3 sdAb comprising a $V_HH$ domain comprising the sequences of SEQ ID NOs: 71, 147 and 223. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, there is provided an anti-LAG-3 sdAb comprising a $V_HH$ comprising one, two or three CDRs of the amino acid sequence of SEQ ID NO: 274. In some embodiments, there is provided an anti-LAG-3 sdAb comprising a $V_HH$ comprising one, two or three CDRs of the amino acid sequence of SEQ ID NO: 275. In some embodiments, there is provided an anti-LAG-3 sdAb comprising a $V_HH$ comprising one, two or three CDRs of the amino acid sequence of SEQ ID NO: 276. In some embodiments, there is provided an anti-LAG-3 sdAb comprising a $V_HH$ comprising one, two or three CDRs of the amino acid sequence of SEQ ID NO: 277. In some embodiments, there is provided an anti-LAG-3 sdAb comprising a $V_HH$ comprising one, two or three CDRs of the amino acid sequence of SEQ ID NO: 278. In some embodiments, there is provided an anti-LAG-3 sdAb comprising a $V_HH$ comprising one, two or three CDRs of the amino acid sequence of SEQ ID NO: 279. In some embodiments, there is provided an anti-LAG-3 sdAb comprising a $V_HH$ comprising one, two or three CDRs of the amino acid sequence of SEQ ID NO: 280. In some embodiments, there is provided an anti-LAG-3 sdAb comprising a $V_HH$ comprising one, two or three CDRs of the amino acid sequence of SEQ ID NO: 281. In some embodiments, there is provided an anti-LAG-3 sdAb comprising a $V_HH$ comprising one, two or three CDRs of the amino acid sequence of SEQ ID NO: 282. In some embodiments, there is provided an anti-LAG-3 sdAb comprising a $V_HH$ comprising one, two or three CDRs of the amino acid sequence of SEQ ID NO: 289. In some embodiments, there is provided an anti-LAG-3 sdAb comprising a $V_HH$ comprising one, two or three CDRs of the amino acid sequence of SEQ ID NO: 296. In some embodiments, there is provided an anti-LAG-3 sdAb comprising a $V_HH$ comprising one, two or three CDRs of the amino acid sequence of SEQ ID NO: 305. In some embodiments, there is provided an anti-LAG-3 sdAb comprising a $V_HH$ comprising one, two or three CDRs of the amino acid sequence of SEQ ID NO: 307. In some embodiments, there is provided an anti-LAG-3 sdAb comprising a $V_HH$ comprising one, two or three CDRs of the amino acid sequence of SEQ ID NO: 308. In some embodiments, there is provided an anti-LAG-3 sdAb comprising a $V_HH$ comprising one, two or three CDRs of the amino acid sequence of SEQ ID NO: 288. In some embodiments, there is provided an anti-LAG-3 sdAb comprising a $V_HH$ comprising one, two or three CDRs of the amino acid sequence of SEQ ID NO: 295. In some embodiments, there is provided an anti-LAG-3 sdAb comprising a $V_HH$ comprising one, two or three CDRs of the amino acid sequence of SEQ ID NO: 304. In some embodiments, there is provided an anti-LAG-3 sdAb comprising a $V_HH$ comprising one, two or three CDRs of the amino acid sequence of SEQ ID NO: 306. In some embodiments, there is provided an anti-LAG-3 sdAb comprising a WA comprising CDR1, CDR2, and CDR3 of the amino acid sequence of any one of SEQ ID NOs: 274-306. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

The anti-LAG-3 sdAbs described herein may comprise any suitable sequences for the FR region. In some embodiments, the anti-LAG-3 sdAb comprises a FR1 comprising the amino acid sequence of any one of SEQ ID NOs: 1-38, or a variant thereof comprising up to about 3 (such as about any one of 1, 2, 3, or more) amino acid substitutions. In some embodiments, the anti-LAG-3 sdAb comprises a FR2 comprising the amino acid sequence of any one of SEQ ID NOs: 77-114, or a variant thereof comprising up to about 3 (such as about any one of 1, 2, 3, or more) amino acid substitutions. In some embodiments, the anti-LAG-3 sdAb comprises a FR3 comprising the amino acid sequence of any one of SEQ ID NOs: 153-190, or a variant thereof comprising up to about 3 (such as about any one of 1, 2, 3, or more) amino acid substitutions. In some embodiments, the anti-LAG-3 sdAb comprises a FR4 comprising the amino acid sequence of any one of SEQ ID NOs: 229-266, or a variant thereof comprising up to about 3 (such as about any one of 1, 2, 3, or more) amino acid substitutions. In some embodiments, the anti-LAG-3 sdAb comprises a FR1, a FR2, a FR3, and a FR4 of any one of the anti-LAG-3 sdAbs of Table 11.

In some embodiments, there is provided an anti-LAG-3 sdAb comprising a $V_HH$ domain comprising the amino acid sequence of any one of SEQ ID NOs: 274-311, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs: 289-324. In some embodiments, there is provided an anti-LAG-3 sdAb comprising a $V_HH$ domain comprising the amino acid sequence of any one of SEQ ID NOs: 274-311, or a variant thereof comprising up to about 10 (such as about any of 1, 2, 3, 4, 5, 6, 7, 8, 9, or 10) amino acid substitutions in the $V_HH$ domain. In some embodiments, the anti-LAG-3 sdAb comprising the $V_HH$ domain comprising the amino acid sequence of any one of SEQ ID NOs: 274-311, or a variant thereof comprising up to about 3 (such as about any one of 1, 2, or 3) amino acid substitutions in the CDR1, and/or the CDR2, and/or the CDR3. In some embodiments, the anti-LAG-3 sdAb comprising the $V_HH$ domain comprising the amino acid sequence of any one of SEQ ID NOs: 274-311, or a variant thereof comprising up to about 3 (such as about any one of 1, 2, or 3) amino acid substitutions are in the FR1, and/or the FR2, and/or the FR3, and/or the FR4. In some embodiments, the anti-LAG-3 sdAb comprising the WA domain comprising the amino acid sequence of any one of SEQ ID NOs: 274-311, or a variant thereof comprising amino acid substitutions in both CDRs and FRs. In some embodiments, there is provided an anti-LAG-3 sdAb comprising a $V_HH$ domain comprising the amino acid sequence of any one of SEQ ID NOs: 274-311. In some embodiments, there is provided an anti-LAG-3 sdAb comprising the amino acid sequence of any one of SEQ ID NOs: 274-311. In some embodiments, the $K_D$ of the binding between the anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the anti-LAG-3 sdAb is camelid, chimeric, human, partially humanized, or fully humanized.

In some embodiments, the anti-LAG-3 sdAb comprises a $V_HH$ domain comprising the amino acid sequence of SEQ ID NO: 288, or a variant thereof having at least about 80% (such as at least about any of 80%, 85%, 90%, 91%, 92%, 93%, 94%, 95%, 96%, 97%, 98%, or 99%) sequence identify to SEQ ID NO: 288. In some embodiments, the anti-LAG-3 sdAb comprises one or more amino acid substitutions selected from the group consisting of: (1) at amino acid position 11 (e.g., S or L); (2) at amino acid position 14 (e.g., A or P); (3) at amino acid position 44 (e.g., E or G); (4) at amino acid position 45 (e.g., R or L); (5) at amino acid position 49 (e.g., A or S); (6) at amino acid position 71 (e.g., K or R); (7) at amino acid position 74 (e.g., A or S); (8) at amino acid position 83 (e.g., D or N); (9) at amino acid position 86 (e.g., R or K); (10) at amino acid position 87 (e.g., A or P); (11) at amino acid position 92 (e.g., M or V); (12) at amino acid position 119 (e.g., Q or L); wherein the amino acid positions are based on SEQ ID NO: 288.

In some embodiments, the anti-LAG-3 sdAb comprises a $V_HH$ domain comprising the amino acid sequence of SEQ ID NO: 295, or a variant thereof having at least about 80% (such as at least about any of 80%, 85%, 90%, 91%, 92%, 93%, 94%, 95%, 96%, 97%, 98%, or 99%) sequence identify to SEQ ID NO: 295. In some embodiments, the anti-LAG-3 sdAb comprises one or more amino acid substitutions selected from the group consisting of: (1) at amino acid position 1 (e.g., Q or E); (2) at amino acid position 5 (e.g., A or V); (3) at amino acid position 11 (e.g., S or L); (4) at amino acid position 14 (e.g., A or P); (5) at amino acid position 44 (e.g., E or G); (6) at amino acid position 45 (e.g., R or L); (7) at amino acid position 71 (e.g., K or R); (8) at amino acid position 74 (e.g., A or S); (9) at amino acid position 86 (e.g., R or K); (10) at amino acid position 87 (e.g., A or P); (11) at amino acid position 92 (e.g., M or V); or (12) at amino acid position 117 (e.g., Q or L); wherein the amino acid positions are based on SEQ ID NO: 295.

In some embodiments, the anti-LAG-3 sdAb comprises a $V_HH$ domain comprising the amino acid sequence of SEQ ID NO: 304, or a variant thereof having at least about 80% (such as at least about any of 80%, 85%, 90%, 91%, 92%, 93%, 94%, 95%, 96%, 97%, 98%, or 99%) sequence identify to SEQ ID NO: 304. In some embodiments, the anti-LAG-3 sdAb comprises one or more amino acid substitutions selected from the group consisting of: (1) at amino acid position 1 (e.g., Q or E); (2) at amino acid position 3 (e.g., Q or H); (3) at amino acid position 5 (e.g., M or V); (4) at amino acid position 11 (e.g., S or L); (5) at amino acid position 14 (e.g., V or P); (6) at amino acid position 44 (e.g., E or G); (7) at amino acid position 45 (e.g., R or L); (8) at amino acid position 49 (e.g., A or S); (8) at amino acid position 71 (e.g., K or R); (9) at amino acid position 74 (e.g., A or S); (10) at amino acid position 86 (e.g., R or K); (11) at amino acid position 87 (e.g., A or P); (12) at amino acid position 92 (e.g., M or V); (13) at amino acid position 94 (e.g., F or Y); or (14) at amino acid position 117 (e.g., Q, L, or I); wherein the amino acid positions are based on SEQ ID NO: 304.

In some embodiments, the anti-LAG-3 sdAb comprises a Vali domain comprising the amino acid sequence of SEQ ID NO: 306, or a variant thereof having at least about 80% (such as at least about any of 80%, 85%, 90%, 91%, 92%, 93%, 94%, 95%, 96%, 97%, 98%, or 99%) sequence identify to SEQ ID NO: 306. In some embodiments, the anti-LAG-3 sdAb comprises one or more amino acid substitutions selected from the group consisting of: (1) at amino acid position 5 (e.g., A or V); (2) at amino acid position 11 (e.g., S or L); (3) at amino acid position 14 (e.g., A or P); (4) at amino acid position 44 (e.g., E or G); (5) at amino acid position 45 (e.g., R or L); (6) at amino acid position 49 (e.g., A or S); (7) at amino acid position 71 (e.g., K or R); (8) at amino acid position 74 (e.g., A or S); (9) at amino acid position 86 (e.g., R or S); (10) at amino acid position 87 (e.g., A or P); (11) at amino acid position 92 (e.g., M or V); or (12) at amino acid position 121 (e.g., Q or L); wherein the amino acid positions are based on SEQ ID NO: 306.

In some embodiments, there is provided an anti-LAG-3 sdAb or anti-LAG-3 construct comprising an anti-LAG-3 sdAb that specifically binds to LAG-3 competitively with any one of the anti-LAG-3 sdAbs described herein. In some embodiments, competitive binding may be determined using an ELISA assay. In some embodiments, there is provided an anti-LAG-3 sdAb (or an anti-LAG-3 construct comprising an anti-LAG-3 sdAb) that specifically binds to LAG-3 competitively with an anti-LAG-3 sdAb comprising the amino acid sequence of any one of SEQ ID NOs: 274-311. In some embodiments, there is provided an anti-LAG-3 sdAb (or an anti-LAG-3 construct comprising an anti-LAG-3 sdAb) that specifically binds to LAG-3 competitively with an anti-LAG-3 sdAb comprising a CDR1 comprising the amino acid sequence of any one of SEQ ID NOs: 39-76; a CDR2 comprising the amino acid sequence of any one of SEQ ID NOs: 115-152; and a CDR3 comprising the amino acid sequence of any one of SEQ ID NOs: 191-228. In some embodiments, there is provided an anti-LAG-3 sdAb (or an anti-LAG-3 construct comprising an anti-LAG-3 sdAb) that specifically binds to LAG-3 competitively with any one of the anti-LAG-3 sdAbs of Table 11. In some embodiments, the $K_D$ of the binding between the competing anti-LAG-3 sdAb and LAG-3 is about $10^{-7}$ M to about $10^{-12}$ M (such as about $10^{-8}$ M to about $10^{-12}$ M, or about $10^{-9}$ M to about $10^{-11}$ M). In some embodiments, the anti-LAG-3 sdAb cross-reacts with a LAG-3 from a non-human mammal. In some embodiments, the competing anti-LAG-3 sdAb is camelid, chimeric, human, partially humanized, or fully humanized.

Single-Domain Antibodies

In some embodiments, the anti-LAG-3 construct is a single-domain antibody. Exemplary sdAbs include, but are not limited to, heavy chain variable domains from heavy-chain only antibodies (e.g., $V_H$H (Variable domain of the heavy chain of the Heavy chain antibody) in Camelidae or $V_{NAR}$ (Variable domain of the shark New Antigen Receptor) in cartilaginous fish), binding molecules naturally devoid of light chains, single domains (such as $V_H$ or $V_L$) derived from conventional 4-chain antibodies, humanized heavy-chain only antibodies, human single-domain antibodies produced by transgenic mice or rats expressing human heavy chain segments, and engineered domains and single domain scaffolds other than those derived from antibodies. The sdAbs may be derived from any species including, but not limited to mouse, rat, human, camel, llama, lamprey, fish, shark, goat, rabbit, and bovine. sdAbs contemplated herein also include naturally occurring sdAb molecules from species other than Camelidae and sharks.

In some embodiments, the sdAb is derived from a naturally occurring single-domain antigen binding molecule known as heavy chain antibody devoid of light chains (also referred herein as "heavy chain-only antibodies", or "HCAb"). Such single domain molecules are disclosed in WO 94/04678 and Hamers-Casterman, C. et al. (1993) *Nature* 363:446-448, for example. For clarity reasons, the variable domain derived from a heavy chain molecule naturally devoid of light chain is known herein as a $V_H$H to distinguish it from the conventional VD of four chain immunoglobulins. Such a $V_H$H molecule can be derived from antibodies raised in Camelidae species, for example, camel, llama, vicuna, dromedary, alpaca and guanaco. Other species besides Camelidae may produce heavy chain molecules naturally devoid of light chain, and such $V_H$Hs are within the scope of the present application.

In some embodiments, the sdAb is derived from a variable region of the immunoglobulin found in cartilaginous fish. For example, the sdAb can be derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) *Protein Sci.* 14:2901-2909.

In some embodiments, the sdAb is recombinant, CDR-grafted, humanized, camelized, de-immunized and/or in vitro generated (e.g., selected by phage display). In some embodiments, the amino acid sequence of the framework regions may be altered by "camelization" of specific amino acid residues in the framework regions. Camelization refers to the replacing or substitution of one or more amino acid residues in the amino acid sequence of a (naturally occurring) $V_H$ domain from a conventional 4-chain antibody by one or more of the amino acid residues that occur at the corresponding position(s) in a $V_H$H domain of a heavy chain antibody. This can be performed in a manner known per se, which will be clear to the skilled person, for example on the basis of the further description herein. Such "camelizing" substitutions are preferably inserted at amino acid positions that form and/or are present at the $V_H$-$V_L$ interface, and/or at the so-called Camelidae hallmark residues, as defined herein (see for example WO 94/04678, Davies and Riechmann FEBS Letters 339: 285-290, 1994; Davies and Riechmann Protein Engineering 9 (6): 531-537, 1996; Riechmann J. Mol. Biol. 259: 957-969, 1996; and Riechmann and Muyldermans J. Immunol. Meth. 231: 25-38, 1999).

In some embodiments, the sdAb is a human sdAb produced by transgenic mice or rats expressing human heavy chain segments. See, e.g., US20090307787A1, U.S. Pat. No. 8,754,287, US20150289489A1, US20100122358A1, and WO2004049794. In some embodiments, the sdAb is affinity-matured.

In some embodiments, naturally occurring $V_H$H domains against a particular antigen or target, can be obtained from (naïve or immune) libraries of Camelid $V_H$H sequences. Such methods may or may not involve screening such a library using said antigen or target, or at least one part, fragment, antigenic determinant or epitope thereof using one or more screening techniques known per se. Such libraries and techniques are for example described in WO 99/37681, WO 01/90190, WO 03/025020 and WO 03/035694. Alternatively, improved synthetic or semi-synthetic libraries derived from (naïve or immune) $V_H$H libraries may be used, such as $V_H$H libraries obtained from (naïve or immune) $V_H$H libraries by techniques such as random mutagenesis and/or CDR shuffling, as for example described in WO 00/43507.

In some embodiments, the sdAbs are generated from conventional 4-chain antibodies. See, for example, EP 0 368 684, Ward et al. (Nature 1989 Oct. 12; 341 (6242): 544-6), Holt et al., Trends Biotechnol., 2003, 21(11):484-490; WO 06/030220; and WO 06/003388.

Because of the unique properties of sdAbs, using $V_H$H domains as single antigen-binding proteins or as antigen-binding domains (i.e. as part of a larger protein or polypeptide) offers a number of significant advantages over the conventional $V_H$ and $V_L$, scFv and conventional antibody fragments (such as Fab or (Fab')$_2$): 1) only a single domain is required to bind an antigen with high affinity, so there is no need to have a second domain, nor to assure that these two domains are present in the correct spatial conformation and configuration (e.g. no need to pair the heavy chain and light chain during folding, no need to use a specially designed linker such as for scFv); 2) $V_HH$ domains and other sdAbs can be expressed from a single gene and require no post-translational folding or modifications; 3) $V_HH$ domains and other sdAbs can be easily engineered into multivalent and/or multispecific formats (such as those described in the present application); 4) $V_HH$ domains and other sdAbs are highly soluble and do not have a tendency to aggregate (as with the mouse-derived "dAbs" described by Ward et al., Nature. 1989 Oct. 12; 341(6242):544-6); 5) $V_HH$ domains and other sdAbs are highly stable against heat, pH, proteases and other denaturing agents or conditions; 6) $V_HH$ domains and other sdAbs are easy and relatively cheap to prepare (even on a large production scale), such as using microbial fermentation, because there is no need to use mammalian expression systems (required by production of, for example, conventional antibody fragments); 7) $V_HH$ domains and other sdAbs are relatively small (approximately 15 kDa, or 10 times smaller than a conventional IgG) compared to conventional 4-chain antibodies and antigen-binding fragments thereof, thus have high(er) tissue penetration ability, such as for solid tumors and other dense tissues; and 8) $V_HH$ domains and other sdAbs can exhibit so-called "cavity-binding properties" (due to their extended CDR3 loop compared to that of conventional $V_H$ domains) and can therefore access targets and epitopes not accessible to conventional 4-chain antibodies and antigen-binding fragments thereof, for example, it has been shown that $V_HH$ domains and other sdAbs can inhibit enzymes (see for example WO1997049805; Transue et al., Proteins. 1998 Sep. 1; 32(4):515-22; Lauwereys et al., EMBO J. 1998 July 1; 17(13):3512-20).

LAG-3

Lymphocyte-activation protein 3 (LAG-3), comprised of 503 amino acids, belongs to the Ig superfamily and contains 4 extracellular Ig-like domains, designated D1 to D4. LAG-3 is a cell surface protein expressed on activated T cells, NK cells, B cells, and plasmacytoid dendritic cells, and plays a role in the function of these lymphocyte subsets that is important but not completely understood.

The terms "lymphocyte-activation protein 3", "LAG-3", "LAG-3 antigen", and "LAG-3 epitope" are used interchangeably, and include variants, isoforms, species homologs of human LAG-3, and analogs having at least one common epitope with LAG-3.

An exemplary amino acid sequence of human LAG-3 is disclosed at Genbank Accession Number P18627. In some embodiments, a human LAG-3 may be at least about 90%, 95%, 96%, 97%, 98%, or 99% identical in amino acid sequence to the human LAG-3 of Genbank Accession Number P18627. In some embodiments, a human LAG-3 sequence has no more than about 10 amino acid differences from the human LAG-3 of Genbank Accession Number P18627. In some embodiments, the human LAG-3 may display no more than 5, 4, 3, 2, or 1 amino acid difference from the human LAG-3 of Genbank Accession Number P18627. In some embodiments, a human LAG-3 sequence may differ from the human LAG-3 of Genbank Accession Number P18627 by having, for example, conserved mutations or mutations in non-conserved regions and the LAG-3 has substantially the same biological function as the human LAG-3 of Genbank Accession Number P18627.

In some embodiments, the anti-LAG-3 sdAb described herein specifically recognizes a LAG-3 polypeptide having at least about 90% amino acid sequence identity to the human LAG-3 of Genbank Accession Number P18627. In some embodiments, the anti-LAG-3 sdAb described herein specifically recognizes a LAG-3 polypeptide comprising an amino acid sequence of SEQ ID NO: 350 or 351.

In some embodiments, the anti-LAG-3 sdAb may cross-react with LAG-3 from species other than human, or other proteins which are structurally related to human LAG-3 (e.g., human LAG-3 homologs). In some embodiments, the anti-LAG-3 sdAb is completely specific for human LAG-3 and not exhibit species or other types of cross-reactivity. In some embodiments, the anti-LAG-3 sdAb specifically recognizes a soluble isoform of human LAG-3. In some embodiments, the anti-LAG-3 sdAb specifically recognizes a membrane-bound isoform of human LAG-3 (e.g., SEQ ID NO: 350).

In some embodiments, the anti-LAG-3 sdAb described herein specifically recognizes the extracellular domain (ECD) of LAG-3. In some embodiments, the anti-LAG-3 sdAb specifically recognizes the N-terminal portion of the LAG-3 ECD. In some embodiments, the anti-LAG-3 sdAb specifically recognizes the C-terminal portion of the LAG-3 ECD. In some embodiments, the anti-LAG-3 sdAb specifically recognizes the middle portion of the LAG-3 ECD. In some embodiments, the ECD of LAG-3 specifically recognized by the anti-LAG-3 sdAb is at least about 95%, 96%, 97%, 98%, or 99% identical in amino acid sequence to the ECD of the human LAG-3 of Genbank Accession Number P18627. In some embodiments, the ECD of LAG-3 specifically recognized by the anti-LAG-3 sdAb is 100% identical in amino acid sequence to the ECD of the human LAG-3 of Genbank Accession Number P18627. In some embodiments, the anti-LAG-3 sdAb specifically recognizes a LAG-3 polypeptide comprising an amino acid sequence of SEQ ID NO: 351.

Antibody Affinity

Binding specificity of the antibody or antigen-binding domain can be determined experimentally by methods known in the art. Such methods comprise, but are not limited to Western blots, ELISA-, RIA-, ECL-, IRMA-, EIA-, BIACORE™-tests and peptide scans.

In some embodiments, the $K_D$ of the binding between the anti-LAG-3 sdAb and LAG-3 is about $10^{-7}$ M to about $10^{-12}$ M, about $10^{-7}$ M to about $10^{-8}$ M, about $10^{-8}$ M to about $10^{-9}$ M, about $10^{-9}$ M to about $10^{-10}$ M, about $10^{-10}$ M to about $10^{-11}$ M, about $10^{-11}$ M to about $10^{-12}$ M, about $10^{-7}$ M to about $10^{-12}$ M, about $10^{-8}$ M to about $10^{-12}$ M, about $10^{-9}$ M to about $10^{-12}$ M, about $10^{-10}$ M to about $10^{-12}$ M, about $10^{-7}$ M to about $10^{-11}$ M, about $10^{-8}$ M to about $10^{-11}$ M, about $10^{-9}$ M to about $10^{-11}$ M, about $10^{-7}$ M to about $10^{-10}$ M, about $10^{-8}$ M to about $10^{-10}$ M, or about $10^{-7}$ M to about $10^{-9}$ M. In some embodiments, the $K_d$ of the binding between the anti-LAG-3 sdAb and LAG-3 is stronger than about any one of $10^{-7}$ M, $10^{-8}$ M, $10^{-9}$ M, $10^{-10}$ M, $10^{-11}$ M, or $10^{-12}$ M. In some embodiments, the LAG-3 is human LAG-3. In some embodiments, the LAG-3 is cynomolgus monkey LAG-3. In some embodiments, the LAG-3 is the extracellular domain of LAG-3.

In some embodiments, the $K_{on}$ of the binding between the anti-LAG-3 sdAb and LAG-3 is about $10^3$ M$^{-1}$s$^{-1}$ to about $10^8$ M$^{-1}$s$^{-1}$, about $10^3$ M$^{-1}$s$^{-1}$ to about $10^4$ M$^{-1}$s$^{-1}$, about $10^4$ M$^{-1}$s$^{-1}$ to about $10^5$ M$^{-1}$s$^{-1}$, about $10^5$ M$^{-1}$s$^{-1}$ to about $10^6$ $M^{-1}s^{-1}$, about $10^6$ $M^{-1}s^{-1}$ to about $10^7$ $M^{-1}s^{-1}$, or about $10^7$ $M^{-1}s^{-1}$ to about $10^8$ $M^{-1}s^{-1}$. In some embodiments, the $K_{on}$ of the binding between the anti-LAG-3 sdAb and LAG-3 is about $10^3$ $M^{-1}s^{-1}$ to about $10^5$ $M^{-1}s^{-1}$, about $10^4$ $M^{-1}s^{-1}$ to about $10^6$ $M^{-1}s^{-1}$, about $10^5$ $M^{-1}s^{-1}$ to about $10^7$ $M^{-1}s^{-1}$, about $10^6$ $M^{-1}s^{-1}$ to about $10^8$ $M^{-1}s^{-1}$, about $10^4$ $M^{-1}s^{-1}$ to about $10^7$ $M^{-1}s^{-1}$, or about $10^5$ $M^{-1}s^{-1}$ to about $10^8$ $M^{-1}s^{-1}$. In some embodiments, the $K_{on}$ of the binding between the anti-LAG-3 sdAb and LAG-3 is no more than about any one of $10^3$ $M^{-1}s^{-1}$, $10^4$ $M^{-1}s^{-1}$, $10^5$ $M^{-1}s^{-1}$, $10^6$ $M^{-1}s^{-1}$, $10^7 M^{-1}s^{-1}$ or $10^8 M^{-1}s^{-1}$.

In some embodiments, the $K_{off}$ of the binding between the anti-LAG-3 sdAb and LAG-3 is about 1 $s^{-1}$ to about $10^{-6}$ $s^{-1}$, about 1 $s^{-1}$ to about $10^{-2}$ $s^{-1}$, about $10^{-2}$ $s^{-1}$ to about $10^{-3}$ $s^{-1}$, about $10^{-3}$ $s^{-1}$ to about $10^{-4}$ $s^{-1}$, about $10^{-4}$ $s^{-1}$ to about $10^{-5}$ $s^{-1}$, about $10^{-5}$ $s^{-1}$ to about $10^{-6}$ $s^{-1}$, about 1 $s^{-1}$ to about $10^{-5}$ $s^{-1}$, about $10^{-2}$ $s^{-1}$ to about $10^{-6}$ $s^{-1}$, about $10^{-3}$ $s^{-1}$ to about $10^{-6}$ $s^{-1}$, about $10^{-4}$ $s^{-1}$ to about $10^{-6}$ $s^{-1}$, about $10^{-2}$ $s^{-1}$ to about $10^{-5}$ $s^{-1}$, or about $10^{-3}$ $s^{-1}$ to about $10^{-5}$ $s^{-1}$. In some embodiments, the $K_{off}$ of the binding between the anti-LAG-3 sdAb and LAG-3 is at least about any one of 1 $s^{-1}$, $10^{-2}$ $s^{-1}$, $10^{-3}$ $s^{-1}$, $10^{-4}$ $s^{-1}$, $10^{-5}$ $s^{-1}$ or $10^{-6}$ $s^{-1}$.

In some embodiments, the $EC_{50}$ of the anti-LAG-3 sdAb is less than 10 nM in an amplified luminescent proximity homogeneous assay (AlphaLISA). In some embodiments, the EC50 of the anti-LAG-3 sdAb is less than 500 nM in an inhibition of ligand binding by FACS analysis (competition binding assay), or cell based cytokine release assay. In some embodiments, the EC50 of the anti-LAG-3 sdAb is less than 1 nM (such as about 0.001 nM to about 0.01 nM, about 0.01 nM to about 0.1 nM, about 0.1 nM to about 1 nM, etc.), about 1 nM to about 10 nM, about 1 nM to about 5 nM, about 5 nM to about 10 nM, about 10 nM to about 50 nM, about 50 nM to about 100 nM, about 100 nM to about 200 nM, about 200 nM to about 300 nM, about 300 nM to about 400 nM, or about 400 nM to about 500 nM. In some embodiments, the $EC_{50}$ of the binding between the anti-LAG-3 sdAb and LAG-3 is no more than about any one of 0.1 nM, 1 nM, 5 nM, 10 nM, 50 nM, 10 nM, 100 nM, 200 nM, or 500 nM.

Chimeric or Humanized Antibodies

In some embodiments, the anti-LAG-3 sdAb provided herein is a chimeric antibody. Certain chimeric antibodies are described, e.g., in U.S. Pat. No. 4,816,567; and Morrison et al., *Proc. Natl. Acad. Sci.* USA, 81:6851-6855 (1984)). In some embodiments, a chimeric antibody comprises a non-human variable region (e.g., a variable region derived from a camelid species, such as llama) and a human constant region. In some embodiments, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci.* USA 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci.* USA, 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In some embodiments, the anti-LAG-3 sdAbs are modified, such as humanized, without diminishing the native affinity of the domain for antigen and while reducing its immunogenicity with respect to a heterologous species. For example, the amino acid residues of the antibody variable domain ($V_H$H) of an llama antibody can be determined, and one or more of the Camelid amino acids, for example, in the framework regions, are replaced by their human counterpart as found in the human consensus sequence, without that polypeptide losing its typical character, i.e. the humanization does not significantly affect the antigen binding capacity of the resulting polypeptide. Humanization of Camelid single-domain antibodies requires the introduction and mutagenesis of a limited amount of amino acids in a single polypeptide chain. This is in contrast to humanization of scFv, Fab', (Fab')$_2$ and IgG, which requires the introduction of amino acid changes in two chains, the light and the heavy chain and the preservation of the assembly of both chains.

sdAbs comprising a $V_H$H domain can be humanized to have human-like sequences. In some embodiments, the FR regions of the $V_H$H domain used herein comprise at least about any one of 50%, 60%, 70%, 80%, 90%, 95% or more of amino acid sequence homology to human VH framework regions. One exemplary class of humanized $V_H$H domains is characterized in that the $V_H$Hs carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 and a tryptophan at position 103, according to the Kabat numbering. As such, polypeptides belonging to this class show a high amino acid sequence homology to human VH framework regions and said polypeptides might be administered to a human directly without expectation of an unwanted immune response therefrom, and without the burden of further humanization.

Another exemplary class of humanized Camelid single-domain antibodies has been described in WO 03/035694 and contains hydrophobic FR2 residues typically found in conventional antibodies of human origin or from other species, but compensating this loss in hydrophilicity by the charged arginine residue on position 103 that substitutes the conserved tryptophan residue present in $V_H$ from double-chain antibodies. As such, peptides belonging to these two classes show a high amino acid sequence homology to human $V_H$ framework regions and said peptides might be administered to a human directly without expectation of an unwanted immune response therefrom, and without the burden of further humanization.

Human Antibodies

In some embodiments, the anti-LAG-3 sdAb provided herein is a human antibody (known as human domain antibody, or human DAb). Human antibodies can be produced using various techniques known in the art. Human antibodies are described generally in van Dijk and van de Winkel, *Curr. Opin. Pharmacol.* 5: 368-74 (2001), Lonberg, *Curr. Opin. Immunol.* 20:450-459 (2008), and Chen, *Mol. Immunol.* 47(4):912-21 (2010). Transgenic mice or rats capable of producing fully human single-domain antibodies (or DAb) are known in the art. See, e.g., US20090307787A1, U.S. Pat. No. 8,754,287, US20150289489A1, US20100122358A1, and WO2004049794.

Human antibodies (e.g., human DAbs) may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies (e.g., human DAbs) can also be made by hybridoma-based methods. Human myeloma and mouse-human heteromyeloma cell lines for the production of human monoclonal antibodies have been described (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991)). Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4): 265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies (e.g., human DAbs) may also be generated by isolating Fv clone variable domain sequences selected from human-derived phage display libraries. Such variable domain sequences may then be combined with a desired human constant domain. Techniques for selecting human antibodies from antibody libraries are described below.

One technique for obtaining $V_HH$ sequences directed against a particular antigen or target involves suitably immunizing a transgenic mammal that is capable of expressing heavy chain antibodies (i.e. so as to raise an immune response and/or heavy chain antibodies directed against said antigen or target), obtaining a suitable biological sample from said transgenic mammal that contains (nucleic acid sequences encoding) said $V_HH$ sequences (such as a blood sample, serum sample or sample of B-cells), and then generating $V_HH$ sequences directed against said antigen or target, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssens et al., *Proc. Natl. Acad. Sci. USA*. 2006 October 10; 103(41):15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

Library-Derived Antibodies

Antibodies of the present application may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci.* USA 101(34): 12467-12472 (2004); and Lee et al., *J. Immunol. Methods* 284(1-2): 119-132(2004). Methods for constructing single-domain antibody libraries have been described, for example, see U.S. Pat. No. 7,371,849.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Repertoires of $V_HH$ genes can be similarly cloned by PCR, recombined randomly in phage libraries, and screened for antigen-binding phage. Phage typically display antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Biological Activities

The biological activity of anti-LAG-3 sdAb described herein can be determined by measuring its half maximal effective concentration ($EC_{50}$), which is a measure of the effectiveness of an antibody in binding to its target, or half maximal inhibitory concentration ($IC_{50}$), which is a measure of the effectiveness of an antibody in inhibiting a specific biological or biochemical function (such as inhibiting the binding between LAG-3 and MHC class II molecules). For example, here $EC_{50}$ can be used to indicate the effective concentration of an anti-LAG-3 sdAb needed to bind 50% LAG-3 on cell surface, $IC_{50}$ can be used to indicate the effective concentration of anti-LAG-3 sdAb needed to neutralize 50% of LAG-3 bioactivity in vitro. $EC_{50}$ also represents the plasma concentration required for obtaining 50% of a maximum effect in vivo. $EC_{50}$ or $IC_{50}$ can be measured by assays known in the art, for example, bioassays such as FACS binding analysis, inhibition of ligand binding by FACS analysis (competition binding assay), cell-based cytokine release assay, or amplified luminescent proximity homogeneous assay (AlphaLISA).

For example, the blockade of ligand binding can be studied using flow cytometry (also see Example 1). CHO cells expressing human LAG-3 can be dissociated from adherent culture flasks and mixed with varying concentrations of anti-LAG-3 sdAb for test, and a constant concentration of labeled-MHC class II protein. An anti-LAG-3 antibody positive control can be employed, such as BMS-986016 (Bristol-Myers Squibb). The mixture is equilibrated for 30 minutes at room temperature, washed three times with FACS buffer (PBS containing 1% BSA). Then, an antibody specifically recognizing the labeled MHC class II of constant concentration is added and incubated for 15 minutes at room temperature. Cells are washed with FACS buffer and analyzed by flow cytometry. Data can be analyzed with Prism (GraphPad Software, San Diego, Calif.) using non-linear regression to calculate $IC_{50}$. The results from the competition assay can demonstrate the ability of anti-LAG-3 sdAbs in inhibiting the interaction between MHC class II and LAG-3.

The biological activity of anti-LAG-3 sdAb can be tested using a LAG-3-blockade assay via a luciferase reporter (also see Example 4). LAG-3 blockade reporter assay was performed using Promega LAG-3 blockade reporter assay kit (Promega, Cat #CS194819), according to the vendor's protocol. Briefly, Thaw-and-Use MHC-II APC Cells (including TCR Activating Antigen) can be plated overnight and then incubated with a serial dilution of anti-LAG-3 antibodies or anti-LAG-3 sdAb-Fc fusion proteins, followed by addition of Thaw-and-Use LAG-3 Effector cells. After 6 hours of induction at 37° C. and 5% $CO_2$, BIO-GLO™ Luciferase Assay Reagent can be added, and luminescence can be determined. The results can demonstrate the ability of anti-LAG-3 sdAbs in inhibiting the interaction between MHC class II and LAG-3.

In some embodiments, the anti-LAG-3 sdAb blocks or antagonizes signals transduced by the LAG-3 receptor. In some embodiments, the anti-LAG-3 sdAb can bind to an epitope on LAG-3 so as to inhibit LAG-3 from interacting with MHC class II molecules. In some embodiments, the anti-LAG-3 sdAb can reduce the binding of LAG-3 to MHC class II molecules by at least about any one of 5%, 10%, 20%, 25%, 30%, 40%, 50%, 60%, 70%, 75%, 80%, 90%, 95%, 99% or 99.9%.

(II) Fusion Constructs

The present application further provides anti-LAG-3 fusion constructs comprising any one of the anti-LAG-3 sdAbs described herein and a second polypeptide, such as a second antibody or antigen binding fragment thereof, or an Fc fragment of an immunoglobulin. In some embodiments, the anti-LAG-3 construct comprises two or more polypeptides other than the anti-LAG-3 sdAb. The additional polypeptide(s) may or may not change or otherwise influence the biological properties of the anti-LAG-3 sdAb, and may or may not add further functionality to the anti-LAG-3 sdAb. In some embodiments, the second polypeptide confers one or more desired properties or functionalities to the anti-LAG-3 sdAb.

In some embodiments, the anti-LAG-3 construct comprises a second antibody or antigen binding fragment thereof (such as sdAb, scFv, Fab, full-length antibody, etc.) that specifically recognizes a second epitope. In some embodiments, the second epitope is from LAG-3. In some embodiments, the second epitope is not from LAG-3. In some embodiments, the second antibody specifically recognizes the same epitope on LAG-3 as the anti-LAG-3 sdAb described herein. In some embodiments, the second antibody specifically recognizes a different epitope on LAG-3 as the anti-LAG-3 sdAb described herein.

In some embodiments, there is provided an anti-LAG-3 construct comprising a plurality (such as 2, 3, 4, or more) of anti-LAG-3 sdAbs described herein. In some embodiments, the plurality of the anti-LAG-3 sdAbs are fused to each other via a linker (such as a peptide linker). The plurality of the anti-LAG-3 sdAbs can be the same or different.

In some embodiments, the anti-LAG-3 construct comprises a second polypeptide that enhances the half-life, solubility, and/or absorption, reduces immunogenicity or toxicity, eliminates or attenuates undesirable side effects, confers other advantageous properties to and/or reduces other undesired properties of the anti-LAG-3 construct, compared to the anti-LAG-3 sdAb alone. Some non-limiting examples of such polypeptides include serum proteins, such as human serum albumin (HSA; see e.g. WO 00/27435) or haptenic molecules (e.g. haptens that are recognized by circulating antibodies, see e.g. WO 98/22141). It was shown that linking fragments of immunoglobulins (such as $V_H$ domains) to serum albumin or fragments thereof may increase antibody half-life (see e.g. WO 00/27435 and WO 01/077137). Thus, in some embodiments, the anti-LAG-3 construct comprises an anti-LAG-3 sdAb fused to serum albumin or a fragment thereof, optionally via a suitable linker (such as peptide linker). In some embodiments, the serum albumin comprises at least domain III (see PCT/EP2007/002817). The anti-LAG-3 sdAb-HSA fusion protein can be of any suitable format, such as $(sdAb)_n$-HSA (n is an integer of at least 1), sdAb-HSA-sdAb, etc.

Anti-LAG-3 Heavy Chain-Only Antibody (HCAb)

In some embodiments, the anti-LAG-3 construct is a heavy chain-only antibody (HCAb) comprising an anti-LAG-3 sdAb described herein. In some embodiments, the anti-LAG-3 sdAb is fused to one or more $C_H2$ and/or $C_H3$ domains, e.g., an Fc fragment. In some embodiments, $C_H2$ and/or $C_H3$ domains are derived from human immunoglobulins. In some embodiments, the anti-LAG-3 sdAb is fused to the $C_H2$ and/or $C_H3$ domains via a peptide linker. The $C_H2$ and/or $C_H3$ domains may increase the half-life of the anti-LAG-3 construct in vivo.

Thus, in some embodiments, there is provided an isolated anti-LAG-3 HCAb comprising an anti-LAG-3 sdAb described herein fused to an Fc fragment of an immunoglobulin, such as IgA, IgD, IgE, IgG, or IgM. In some embodiments, the anti-LAG-3 HCAb comprises an Fc fragment of IgG, such as IgG1, IgG2, IgG3, or IgG4. In some embodiments, the Fc fragment is a human Fc, such as human IgG1 (hIgG1) Fc, hIgG2 Fc, or hIgG4 Fc. In some embodiments, the Fc fragment is effectorless, with reduced, minimized, or eliminated antibody effector functions such as ADCC, CDC, and/or ADCP (antibody-dependent cellular phagocytosis). In some embodiments, the effectorless Fc comprises an N297A or DANA mutation (D265A+N297A) in the $C_H2$ region. In some embodiments, the effectorless Fc comprises K322A and L234A/L235A (LALA) mutations. In some embodiments, the Fc fragment is an effectorless IgG1 Fc, such as effectorless hIgG1 Fc. In some embodiments, the Fc fragment is a human IgG4 Fc (S228P). In some embodiments, the anti-LAG-3 HCAb is monomeric. In some embodiments, the anti-LAG-3 HCAb is dimeric. In some embodiments, the anti-LAG-3 HCAb is multispecific and multivalent (such as bispecific and bivalent), e.g., comprising two or more different anti-LAG-3 sdAbs described herein. In some embodiments, the anti-LAG-3 HCAb is monospecific and multivalent (e.g., bivalent), e.g., comprising two or more copies of the same anti-LAG-3 sdAb.

In some embodiments, the anti-LAG-3 sdAb and the Fc fragment are fused to each other via a peptide linker. In some embodiments, the peptide linker is a human IgG1 hinge (SEQ ID NO: 352). In some embodiments, the peptide linker is a mutated human IgG1 hinge (SEQ ID NO: 353). In some embodiments, the peptide linker is a human IgG4 hinge. In some embodiments, the peptide linker is a hIgG2 hinge.

Thus, in some embodiments, there is provided an isolated anti-LAG-3 HCAb comprising an sdAb specifically recognizing LAG-3, wherein the anti-LAG-3 sdAb comprises a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions, and wherein the anti-LAG-3 sdAb is fused to an Fc fragment of an immunoglobulin. In some embodiments, there is provided an anti-LAG-3 HCAb comprising an sdAb specifically recognizing LAG-3, wherein the sdAb comprises: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223, and wherein the anti-LAG-3 sdAb is fused to an Fc fragment of an immunoglobulin. In some embodiments, there is provided an isolated anti-LAG-3 HCAb comprising an sdAb specifically recognizing LAG-3, wherein the sdAb comprises a $V_HH$ domain comprising the amino acid sequence of any one of SEQ ID NOs: 274-311, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs: 274-311, and wherein the anti-LAG-3 sdAb is fused to an Fc fragment of an immunoglobulin. In some embodiments, there is provided an isolated anti-LAG-3 HCAb comprising an sdAb specifically recognizing LAG-3, wherein the sdAb comprises a $V_HH$ domain comprising the amino acid sequence of any one of SEQ ID NOs: 274-311, and wherein the anti-LAG-3 sdAb is fused to an Fc fragment of an immunoglobulin. In some embodiments, the anti-LAG-3 sdAb is fused to the Fc fragment via a peptide linker. In some embodiments, the anti-LAG-3 HCAb is monomeric. In some embodiments, the Fc fragment is a human IgG1 Fc, effectorless human IgG1 Fc, hIgG2 Fc, human IgG4 Fc, or hIgG4 Fc (S228P).

In some embodiments, there is provided an isolated anti-LAG-3 HCAb comprising two sdAbs specifically recognizing LAG-3, wherein each anti-LAG-3 sdAb comprises a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions, and wherein the C-terminus of each anti-LAG-3 sdAb is fused to the N-terminus of an Fc fragment of an immunoglobulin. In some embodiments, there is provided an isolated anti-LAG-3 HCAb comprising two sdAbs specifically recognizing LAG-3, wherein each anti-LAG-3 sdAb comprises: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223, and wherein the C-terminus of each anti-LAG-3 sdAb is fused to the N-terminus of an Fc fragment of an immunoglobulin. In some embodiments, the two anti-LAG-3 sdAbs are the same. In some embodiments, the two anti-LAG-3 sdAbs are different. In some embodiments, the anti-LAG-3 sdAbs are fused to the Fc fragment via a peptide linker. In some embodiments, the Fc fragment is a human IgG1 Fc, effectorless human IgG1 Fc, hIgG2 Fc, human IgG4 Fc, or hIgG4 Fc (S228P).

In some embodiments, there is provided an isolated anti-LAG-3 HCAb comprising the amino acid sequence of any one of SEQ ID NOs: 312-349, or a variant thereof having at least about 80% (such as at least about any of 80%, 85%, 90%, 91%, 92%, 93%, 94%, 95%, 96%, 97%, 98%, or 99%) sequence identify to any one of SEQ ID NOs: 312-349. In some embodiments, there is provided a polypeptide comprising the amino acid sequence of any one of SEQ ID NOs: 312-349.

Also provided are isolated anti-LAG-3 HCAbs that specifically binds to LAG-3 competitively with any one of the isolated anti-LAG-3 HCAbs, anti-LAG-3 sdAbs, or anti-LAG-3 constructs described herein.

Multivalent and/or Multispecific Constructs

The present application provides multivalent and multispecific anti-LAG-3 constructs. Multispecific anti-LAG-3 constructs are also referred herein as "anti-LAG-3 multispecific antigen binding proteins (MABPs)." In some embodiments, the anti-LAG-3 constructs are bispecific, which are also referred herein as "anti-LAG-3 bispecific antigen binding proteins (BABPs)."

In some embodiments, there is provided an isolated anti-LAG-3 construct (e.g., MABP or BABP) comprising: (a) a first antigen binding portion comprising an anti-LAG-3 sdAb comprising a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions, and (b) a second antigen binding portion that specifically binds a second epitope (e.g., immune checkpoint molecule, such as PD-1), wherein the first antigen binding portion and the second antigen binding portion are fused to each other. In some embodiments, there is provided an isolated anti-LAG-3 construct (e.g., MABP or BABP) comprising: (a) a first antigen binding portion comprising an anti-LAG-3 sdAb comprising: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223, and (b) a second antigen binding portion that specifically binds a second epitope (e.g., immune checkpoint molecule, such as PD-1), wherein the first antigen binding portion and the second antigen binding portion are fused to each other. In some embodiments, the second antigen binding portion specifically recognizes an immune checkpoint molecule, such as PD-1, 4-1BB, PD-L1, TIM-3, TIGIT, CTLA-4, VISTA, B7-1, B7-H3, CD47, OX40 or GITR. In some embodiments, the second antigen binding portion comprises a heavy chain comprising the $V_H$ and a light chain comprising the $V_L$. In some embodiments, the first antigen binding portion is fused to the second antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion comprises a Fab or an scFv. In some embodiments, the first antigen binding portion is fused to the second antigen binding portion at the C-terminus of the Fab or scFv. In some embodiments, the second antigen binding portion comprises a full-length 4-chain antibody. In some embodiments, the first antigen binding portion is fused to the second antigen binding portion via a peptide linker. In some embodiments, the peptide linker is no more than about 30 (such as no more than about any one of 25, 20, or 15) amino acids long. In some embodiments, the peptide linker comprises the amino acid sequence of any one of SEQ ID NOs: 352-353 and 366-372. In some embodiments, the N-terminus or the C-terminus of the anti-LAG-3 sdAb is fused to a peptide sequence. In some embodiments, the peptide sequence comprises the amino acid sequence of any one of SEQ ID NOs: 352-353 and 366-372. In some embodiments, the second antigen binding fragment comprises an Fc region, such as an IgG1 Fc, effectorless IgG1 Fc, IgG2 Fc, IgG4 Fc, or IgG4 Fc (S228P).

In some embodiments, the anti-LAG-3 construct is an anti-LAG-3 MABP comprising a second antigen binding portion that specifically recognizes an immune checkpoint molecule. As used herein, the term "immune checkpoint molecules" refer molecules in the immune system that generally act to maintain self-tolerance or modulate the duration and amplitude of physiological immune responses to minimize collateral tissue damage. Immune checkpoint inhibitors can inhibit an immune system checkpoint by stimulating the activity of a stimulatory checkpoint molecule, or inhibiting the activity of an inhibitory checkpoint molecule in the pathway. Stimulatory checkpoint molecules are molecules, such as proteins, that stimulate or positively regulate the immune system. Inhibitory checkpoint molecules are molecules, such as proteins, that inhibit or negatively regulate the immune system. Immune system checkpoint molecules include, but are not limited to, cytotoxic T-lymphocyte antigen 4 (CTLA-4), programmed cell death 1 protein (PD-1), programmed cell death 1 ligand 1 (PD-L1), programmed cell death 1 ligand 2 (PD-L2), lymphocyte activation gene 3 (LAG3), B7-1, B7-H3, T cell membrane protein 3 (TIM3), B- and T-lymphocyte attenuator (BTLA), T cell immunoreceptor with Ig and ITIM domains (TIGIT), V-domain immunoglobulin (Ig)-containing suppressor of T-cell activation (VISTA), tumor necrosis factor receptor superfamily member 4 (TNFRSF4, also known as CD134 or OX40), tumor necrosis factor receptor superfamily member 9 (TNFRSF9, also known as 4-1BB or CD137), cluster of differentiation 47 (CD47 or IAP) and glucocorticoid-induced tumor necrosis factor receptor (GITR). Any of the known antibodies against the immune checkpoint molecules may be used in an anti-LAG-3 MABP.

In some embodiments, there is provided an isolated anti-LAG-3 construct (e.g., MABP or BABP) comprising: (a) a first antigen binding portion comprising an anti-LAG-3 sdAb comprising a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions; and (b) a second antigen binding portion that specifically binds an immune checkpoint molecule (e.g., PD-1), wherein the first antigen binding portion and the second antigen binding portion are fused to each other. In some embodiments, there is provided an isolated anti-LAG-3 construct (e.g., MABP or BABP) comprising: (a) a first antigen binding portion comprising an anti-LAG-3 sdAb comprising: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223, and (b) a second antigen binding portion that specifically binds an immune checkpoint molecule (e.g., PD-1), wherein the first antigen binding portion and the second antigen binding portion are fused to each other. In some embodiments, the second antigen binding portion comprises a heavy chain comprising the $V_H$ and a light chain comprising the $V_L$. In some embodiments, the first antigen binding portion is fused to the second antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion comprises a Fab or an scFv. In some embodiments, the first antigen binding portion is fused to the second antigen binding portion at the C-terminus of the Fab or scFv. In some embodiments, the second antigen binding portion comprises a full-length 4-chain antibody. In some embodiments, the first antigen binding portion is fused to the second antigen binding portion chemically. In some embodiments, the first antigen binding portion is fused to the second antigen binding portion via a peptide linker. In some embodiments, the peptide linker is no more than about 30 (such as no more than about any one of 25, 20, or 15) amino acids long. In some embodiments, the peptide linker comprises the amino acid sequence of any one of SEQ ID NOs: 352-353 and 366-372. In some embodiments, the N-terminus or the C-terminus of the anti-LAG-3 sdAb is fused to a peptide sequence. In some embodiments, the peptide sequence comprises the amino acid sequence of any one of SEQ ID NOs: 352-353 and 366-372. In some embodiments, the second antigen binding fragment comprises an Fc region, such as an IgG1 Fc, effectorless IgG1 Fc, IgG2 Fc, IgG4 Fc, or IgG4 Fc (S228P).

In some embodiments, the isolated anti-LAG-3 construct comprises an anti-LAG-3 sdAb described herein fused to a second antibody or antigen binding fragment thereof. In some embodiments, the anti-LAG-3 construct comprises two or more antibodies or antigen binding fragments thereof fused to the anti-LAG-3 sdAb. In some embodiments, the second antibody specifically recognizes an antigen other than LAG-3, or a second epitope on LAG-3. In some embodiments, the second antibody is a full-length antibody, a Fab, a Fab', a (Fab')$_2$, an Fv, an scFv, an scFv-scFv, a minibody, a diabody, or an sdAb. In some embodiments, the second antibody comprises a heavy chain variable domain ($V_H$) and a light chain variable domain ($V_L$).

In some embodiments, the anti-LAG-3 construct is monospecific. In some embodiments, the anti-LAG-3 construct is multispecific (such as bispecific). Multispecific molecules are molecules that have binding specificities for at least two different epitopes (e.g., bispecific antibodies have binding specificities for two epitopes). Multispecific molecules with more than two valencies and/or specificities are also contemplated. For example, trispecific antibodies can be prepared. Tutt et al. *J. Immunol.* 147: 60 (1991).

In some embodiments, the anti-LAG-3 construct is monovalent. In some embodiments, the anti-LAG-3 construct is multivalent (e.g., bivalent) and monospecific. In some embodiments, the anti-LAG-3 construct comprises an anti-LAG-3 sdAb described herein and a second antibody (such as a full-length antibody, sdAb, or an antigen binding fragment comprising a $V_H$ and a $V_L$) specifically recognizing the same LAG-3 epitope as the anti-LAG-3 sdAb. In some embodiments, the second antibody comprises the same CDRs and/or the same $V_H$H as the anti-LAG-3 sdAb. For example, the anti-LAG-3 construct may comprise two or more anti-LAG-3 sdAbs described herein, wherein the two or more anti-LAG-3 sdAbs are the same. In some embodiments, the two or more anti-LAG-3 sdAbs are fused to each other via a peptide linker. The monospecific or multispecific anti-LAG-3 construct comprising two or more anti-LAG-3 sdAbs may have increase avidity compared to that of a single anti-LAG-3 sdAb described herein.

In some embodiments, the anti-LAG-3 construct is multivalent and multispecific (e.g., bispecific). In some embodiments, the anti-LAG-3 construct comprises an anti-LAG-3 sdAb described herein and a second antibody (such as a full-length antibody, sdAb, or an antigen binding fragment comprising a $V_H$ and a $V_L$) specifically recognizing a second antigen other than LAG-3, or a different LAG-3 epitope from that recognized by the anti-LAG-3 sdAb.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci.* USA, 90:6444-6448 (1993)); and using single-chain Fv (sFv) dimers (see, e.g., Gruber et al., *J. Immunol.,* 152:5368 (1994)); and preparing trispecific antibodies as described, e.g., in Tutt et al. *J. Immunol.* 147: 60 (1991); and creating polypeptides comprising tandem single-domain antibodies (see, e.g., U.S. Patent Application No. 20110028695; and Conrath et al. J. Biol. Chem., 2001; 276(10):7346-50). Engineered antibodies with three or more functional antigen binding sites, including "Octopus antibodies," are also included herein (see, e.g., US 2006/0025576A1).

In some embodiments, there is provided an isolated anti-LAG-3 construct comprising an anti-LAG-3 sdAb described herein fused to a full-length antibody or antigen binding fragment thereof that comprises a $V_H$ and a $V_L$. The full-length antibody or antigen binding fragment recognizes an antigen other than LAG-3, or an epitope from LAG-3 that is different from the epitope recognized by the anti-LAG-3 sdAb, thereby conferring a broadened targeting capability. Due to the small size of the sdAb, in some embodiments, the anti-LAG-3 MABP (e.g., anti-LAG-3 BABPs) described herein can have similar molecular weight and pharmacokinetic properties compared to those of the full-length antibody or antigen binding fragment component. For example, an anti-LAG-3 MABP can be designed by fusing one or more anti-LAG-3 sdAbs to a monoclonal antibody with proven clinical efficacy and safety to provide increased clinical benefits and desirable pharmacokinetic properties without impeding the expressibility of the multispecific construct. In some embodiments, the anti-LAG-3 sdAb is fused to the full-length antibody or antigen binding fragment by a peptide linker.

The anti-LAG-3 MABPs (e.g., anti-LAG-3 BABPs) described herein can be adopted to target a variety of disease-related epitope or antigen combinations besides LAG-3, such as LAG-3 with the combination of immune checkpoint molecules, cell surface antigens (such as tumor antigens), or pro-inflammatory molecules, thereby providing agents that are useful for treating a variety of diseases and conditions, such as cancer. The anti-LAG-3 MABP (e.g., anti-LAG-3 BABPs) can be of any format, such as those disclosed in PCT/CN2017/093644, which is incorporated herein by reference in its entirety.

Thus, in some embodiments, there is provided an isolated anti-LAG-3 construct (e.g., MABP or BABP) comprising: (a) a first antigen binding portion comprising an anti-LAG-3 sdAb comprising a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions, and (b) a second antigen binding portion comprising a $V_H$ and a $V_L$, wherein the $V_H$ and $V_L$ together form an antigen-binding site that specifically binds a second epitope (e.g., immune checkpoint molecule, such as PD-1), wherein the first antigen binding portion and the second antigen binding portion are fused to each other. In some embodiments, there is provided an isolated anti-LAG-3 construct (e.g., MABP or BABP) comprising: (a) a first antigen binding portion comprising an anti-LAG-3 sdAb comprising: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223, and (b) a second antigen binding portion comprising a $V_H$ and a $V_L$, wherein the $V_H$ and $V_L$ together form an antigen-binding site that specifically binds a second epitope (e.g., immune checkpoint molecule, such as PD-1), wherein the first antigen binding portion and the second antigen binding portion are fused to each other. In some embodiments, the second epitope is from an immune checkpoint molecule, such as PD-1, 4-1BB, PD-L1, TIM-3, TIGIT, CTLA-4, VISTA, B7-1, B7-H3, CD47, OX40 or GITR. In some embodiments, the second antigen binding portion comprises a heavy chain comprising the $V_H$ and a light chain comprising the $V_L$. In some embodiments, the first antigen binding portion is fused to the second antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion comprises a Fab or an scFv. In some embodiments, the first antigen binding portion is fused to the second antigen binding portion at the C-terminus of the Fab or scFv. In some embodiments, the second antigen binding portion comprises a full-length 4-chain antibody. In some embodiments, the second antigen binding portion comprises an anti-PD-1 full-length antibody or antigen binding fragment thereof. In some embodiments, the anti-PD-1 full-length antibody or antigen binding fragment thereof (e.g., Fab, scFv) comprises: (i) a $V_H$ comprising HC-CDR1, HC-CDR2, and HC-CDR3 of the amino acid sequence of SEQ ID NO: 356, and a $V_L$ comprising LC-CDR1, LC-CDR2, and LC-CDR3 of the amino acid sequence of SEQ ID NO: 357; or (ii) a $V_H$ comprising HC-CDR1, HC-CDR2, and HC-CDR3 of the amino acid sequence of SEQ ID NO: 373, and a $V_L$ comprising LC-CDR1, LC-CDR2, and LC-CDR3 of the amino acid sequence of SEQ ID NO: 374. In some embodiments, the anti-PD-1 full-length antibody comprises: (i) a heavy chain comprising the amino acid sequence of SEQ ID NO: 356, and a light chain comprising the amino acid sequence of SEQ ID NO: 357; or (ii) a heavy chain comprising the amino acid sequence of SEQ ID NO: 373, and a light chain comprising the amino acid sequence of SEQ ID NO: 374. In some embodiments, the anti-PD-1 full-length antibody is pembrolizumab or PD1-BM-min. In some embodiments, the first antigen binding portion is fused to the second antigen binding portion chemically. In some embodiments, the first antigen binding portion is fused to the second antigen binding portion via a peptide linker. In some embodiments, the peptide linker is no more than about 30 (such as no more than about any one of 25, 20, or 15) amino acids long. In some embodiments, the peptide linker comprises the amino acid sequence of any one of SEQ ID NOs: 352-353 and 366-372. In some embodiments, the N-terminus or the C-terminus of the anti-LAG-3 sdAb is fused to a peptide sequence. In some embodiments, the peptide sequence comprises the amino acid sequence of any one of SEQ ID NOs: 352-353 and 366-372. In some embodiments, the second antigen binding fragment comprises an Fc region, such as an IgG1 Fc, effectorless IgG1 Fc, IgG2 Fc, IgG4 Fc, or IgG4 Fc (S228P).

In some embodiments, the isolated anti-LAG-3 MABP (e.g., BABP) comprises at least two antigen binding portions that can specifically bind at least two different epitopes. Some of the at least two antigen binding portions may be identical, so long as the MABP has binding sites for two different epitopes. The anti-LAG-3 MABPs (e.g., BABPs) can be symmetric or asymmetric. For example, the anti-LAG-3 MABP (e.g., BABP) may comprise one to eight copies of the first antigen binding portion comprising the anti-LAG-3 sdAb described herein, and one or two copies of the second antigen binding portion comprising a $V_H$ and a $V_L$. In some embodiments, the anti-LAG-3 MABP (e.g., BABP) comprises two different antigen binding portions that each comprise a $V_H$ domain and a $V_L$ domain that together form a different antigen binding site. For example, the second antigen binding portion can be a bispecific antibody. In some embodiments, the second antigen binding portion is a monospecific full-length antibody or antigen binding fragment thereof, such as Fab or scFv.

In some embodiments, the anti-LAG-3 MABP (e.g., BABP) comprises any one of 1, 2, 3, 4, 5, 6, 7, 8, or more different antigen binding portions that each comprises an anti-LAG-3 sdAb described herein. In some embodiments, two identical anti-LAG-3 sdAbs are fused to each other, which are further fused to the second antigen binding portion. In some embodiments, two different anti-LAG-3 sdAbs are fused to each other, which are further fused to the second antigen binding portion.

The isolated anti-LAG-3 MABP (e.g., BABP) may have any suitable number of valencies for LAG-3 and/or the second epitope (e.g., PD-1), and any suitable number of specificity. In some embodiments, the anti-LAG-3 MABP (e.g., BABP) is bivalent, trivalent, tetravalent, pentavalent, hexavalent, or of higher valencies for LAG-3. In some embodiments, the anti-LAG-3 MABP (e.g., BABP) is bivalent, trivalent, tetravalent, pentavalent, hexavalent, or of higher valencies for the second epitope (e.g., PD-1). In some embodiments, the anti-LAG-3 MABP is bispecific (e.g., PD-1×LAG-3 BABP). Exemplary BABPs are depicted in FIGS. 7-16. In some embodiments, the MABP is trispecific. In some embodiments, the MABP is tetraspecific. In some embodiments, the MABP has more than four specificities.

In some embodiments, the anti-LAG-3 MABP (e.g., BABP) comprises: (a) one or more copies (such as 2) of a first antigen binding portion comprising an anti-LAG-3 sdAb, and (b) a single copy of a second antigen binding portion comprising a $V_H$ and a $V_L$, wherein the $V_H$ and $V_L$ together form an antigen-binding site that specifically binds a second epitope (e.g., PD-1), wherein each copy of the first antigen binding portion is fused to the second antigen binding portion. In some embodiments, there is provided an anti-LAG-3 MABP (e.g., BABP) comprising: (a) a plurality (such as 2, 3, 4, 5, 6, 7, 8, or more) of identical or different anti-LAG-3 sdAbs, and (b) a plurality (such as 2, 3, 4, 5, 6, or more) of a second antigen binding portion comprising a $V_H$ and a $V_L$, wherein the $V_H$ and $V_L$ together form an antigen-binding site that specifically binds a second epitope (e.g., PD-1), and, wherein the anti-LAG-3 sdAbs are fused to each other, and/or to the second antigen binding portion. In some embodiments, there is provided an anti-LAG-3 MABP (e.g., BABP) comprising: (a) a plurality (such as 2, 3, or 4) of identical or different anti-LAG-3 sdAbs, and (b) two copies of a second antigen binding portion each comprising a $V_H$ and a $V_L$, wherein the $V_H$ and $V_L$ together form an antigen-binding site that specifically binds a second epitope (e.g., PD-1), and wherein the anti-LAG-3 sdAbs are fused to each other, and/or to the second antigen binding portion. In some embodiments, one or more of the anti-LAG-3 sdAb is each further fused to another identical or different anti-LAG-3 sdAb.

In some embodiments, the anti-LAG-3 MABP (e.g., BABP) comprises: (a) a single copy of a first antigen binding portion comprising an anti-LAG-3 sdAb, and (b) two copies of a second antigen binding portion each comprising a $V_H$ and a $V_L$, wherein the $V_H$ and $V_L$ together form an antigen-binding site that specifically binds a second epitope, wherein the first antigen binding portion is fused to one of the two copies of the second antigen binding portion. In some embodiments, the anti-PD-1 MABP (e.g., BABP) comprises: (a) two copies of a first antigen binding portion each comprising an anti-LAG-3 sdAb, (b) two copies of a second antigen binding portion each comprising a $V_H$ and a $V_L$, wherein the $V_H$ and $V_L$ together form an antigen-binding site that specifically binds a second epitope, wherein one copy of the first antigen binding portion is fused to each copy of the second antigen binding portion. In some embodiments, one or more of the anti-LAG-3 sdAbs are each further fused to another identical or different anti-LAG-3 sdAb.

In some embodiments, the anti-LAG-3 construct comprises an anti-LAG-3 sdAb described herein fused to a second antibody, wherein the second antibody is a full-length antibody consisting of two heavy chains and two light chains (such as full-length antibody specifically recognizing PD-1). In some embodiments, the anti-LAG-3 sdAb and the full-length antibody are fused to each other via a linker, such as a peptide linker. In some embodiments, the N-terminus or the C-terminus of the anti-LAG-3 sdAb is fused to a peptide sequence.

Thus, in some embodiments, there is provided an isolated anti-LAG-3 construct comprising an anti-LAG-3 sdAb and a full-length antibody consisting of two heavy chains and two light chains (such as a full-length antibody specifically recognizing PD-1), wherein the anti-LAG-3 sdAb comprises a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions. In some embodiments, there is provided an isolated anti-LAG-3 construct comprising an anti-LAG-3 sdAb and a full-length antibody consisting of two heavy chains and two light chains (such as a full-length antibody specifically recognizing PD-1), wherein the anti-LAG-3 sdAb comprises: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223. In some embodiments, the Fc fragment of the full-length antibody is hIgG1 Fc, effectorless hIgG1 Fc, hIgG2 Fc, hIgG4 Fc, or hIgG4 Fc (S228P). In some embodiments, the full-length antibody is an activator of a stimulatory immune checkpoint molecule. In some embodiments, the full-length antibody is an immune checkpoint inhibitor, such as an inhibitor of TIGIT, TIM-3, CTLA-4, or PD-1. In some embodiments, the full-length antibody is pembrolizumab, PD1-BM-min or nivolumab. In some embodiments, the anti-LAG-3 sdAb and the full-length antibody are fused to each other via a peptide linker. In some embodiments, the peptide linker comprises the amino acid sequence of any one of SEQ ID NOs: 352-353 and 366-372. In some embodiments, the N-terminus or the C-terminus of the anti-LAG-3 sdAb is fused to a peptide sequence. In some embodiments, the peptide sequence comprises the amino acid sequence of any one of SEQ ID NOs: 352-353 and 366-372.

The multispecific anti-LAG3 construct may be of any suitable format. Exemplary bispecific anti-LAG3 constructs are shown in FIGS. 7-16.

In some embodiments, the anti-LAG-3 construct comprises two anti-LAG-3 sdAbs. In some embodiments, the N-terminus of each anti-LAG-3 sdAb is fused to the C-terminus of a heavy chain of the full-length antibody (exemplified as FIG. 8). In some embodiments, the C-terminus of each anti-LAG-3 sdAb is fused to the N-terminus of a heavy chain of the full-length antibody (exemplified as FIG. 7). In some embodiments, the N-terminus of each anti-LAG-3 sdAb is fused to the C-terminus of a light chain of the full-length antibody (exemplified as FIG. 10). In some embodiments, the C-terminus of each anti-LAG-3 sdAb is fused to the N-terminus of a light chain of the full-length antibody (exemplified as FIG. 9). In some embodiments, the C-terminus of each anti-LAG-3 sdAb is fused to the N-terminus of a $C_H2$ domain of the full-length antibody, and the N-terminus of each anti-LAG-3 sdAb is fused to the C-terminus of a $C_H1$ domain of the full-length antibody (exemplified as FIG. 13). In some embodiments, the N-terminus of each anti-LAG-3 sdAb is fused to the C-terminus of an scFv, and the C-terminus of each anti-LAG-3 sdAb is fused to the N-terminus of an $C_H2$ domain of a Fc region (exemplified as FIG. 14).

In some embodiments, the anti-LAG-3 construct comprises four anti-LAG-3 sdAbs. In some embodiments, the C-terminus of a first anti-LAG-3 sdAb is fused to the N-terminus of a heavy chain of the full-length antibody, and the C-terminus of a second anti-LAG-3 sdAb is fused to the N-terminus of a light chain of the full-length antibody (exemplified as FIG. 11). In some embodiments, the C-terminus of a first anti-LAG-3 sdAb is fused to the N-terminus of a heavy chain of the full-length antibody, and the C-terminus of a second anti-LAG-3 sdAb is fused to the N-terminus of the first anti-LAG-3 sdAb (exemplified as FIG. 12). In some embodiments, the N-terminus of a first anti-LAG-3 sdAb is fused to the C-terminus of a $C_H1$ domain of a Fab, and the C-terminus of the first anti-LAG-3 sdAb is fused to the N-terminus of a second $C_H1$ domain; and the N-terminus of a second anti-LAG-3 sdAb is fused to the C-terminus of a $C_L$ domain of a Fab, and the C-terminus of the second anti-LAG-3 sdAb is fused to the N-☐terminus of a second $C_L$ domain (exemplified as FIG. 15). In some embodiments, the N-terminus of a anti-LAG-3 sdAb is fused to the C-terminus of an scFv, and the C-terminus of the first anti-LAG-3 sdAb is fused to the N-terminus of a $C_H1$ domain; and the C-terminus of a second anti-LAG-3 sdAb is fused to the N-terminus of a second $C_L$ domain (exemplified as FIG. 16).

a) Fusion Polypeptides

The first antigen binding portion comprising an anti-LAG-3 sdAb described herein and the second antigen binding portion comprising a $V_H$ and a $V_L$ of the anti-LAG-3 MABP (e.g., BABP) are fused (i.e., covalently linked) to each other. Thus, the anti-LAG-3 MABPs (e.g., BABPs) of the present application comprise one or more fusion polypeptides. Each fusion polypeptide may comprise the first antigen binding portion comprising an anti-LAG-3 sdAb described herein, and a polypeptide from the second antigen binding portion.

The first antigen binding portion comprising an anti-LAG-3 sdAb described herein and the second antigen binding portion comprising a $V_H$ and a $V_L$ may be linked directly by a single chemical bond (such as peptide bond) or via a peptide linker. The first antigen binding portion comprising an anti-LAG-3 sdAb may be fused at either the N-terminus or the C-terminus of any one (including each) polypeptide of the second antigen binding portion, or may be fused at an internal position of any one (including each) polypeptide of the second antigen binding portion, such as at the N-terminus of the Fc region in the heavy chain of the second antigen binding portion. The fusion polypeptides may be obtained either recombinantly or chemically. In some embodiments, the C-terminus of the first antigen binding portion comprising an anti-LAG-3 sdAb is fused to the N-terminus of any (including each) polypeptide of the second antigen binding portion via a chemical bond (such as peptide bond) or a peptide linker. In some embodiments, the N-terminus of the first antigen binding portion comprising an anti-LAG-3 sdAb is fused to the C-terminus of any (including each) polypeptide of the second antigen binding portion via a chemical bond (such as peptide bond) or a peptide linker. In some embodiments, the first antigen binding portion comprising an anti-LAG-3 sdAb is fused to the second antigen binding portion via a chemical bond that is not a peptide bond involving the main chain chemical groups of amino acids.

In some embodiments, the second antigen binding portion comprises a single-chain antibody fragment comprising the $V_H$ and $V_L$. In some embodiments, the second antigen binding portion comprises an scFv. In some embodiments, the anti-LAG-3 MABP (e.g., BABP) comprises a fusion polypeptide comprising in the N-terminus to C-terminus direction: the first antigen binding portion comprising the anti-LAG-3 sdAb described herein, an optional peptide linker, the $V_H$ domain and the $V_L$ domain. In some embodiments, the anti-LAG-3 MABP (e.g., BABP) comprises a fusion polypeptide comprising in the N-terminus to C-terminus direction: the first antigen binding portion comprising the anti-LAG-3 sdAb described herein, an optional peptide linker, the $V_L$ domain and the $V_H$ domain. In some embodiments, the anti-LAG-3 MABP (e.g., BABP) comprises a fusion polypeptide comprising in the N-terminus to C-terminus direction: the $V_H$ domain, the $V_L$ domain, an optional peptide linker, and the first antigen binding portion comprising the anti-LAG-3 sdAb described herein. In some embodiments, anti-LAG-3 MABP (e.g., BABP) comprises a fusion polypeptide comprising in the N-terminus to C-terminus direction: the $V_L$ domain, the $V_H$ domain, an optional peptide linker, and the first antigen binding portion comprising the anti-LAG-3 sdAb described herein.

In some embodiments, the second antigen binding portion comprises a heavy chain comprising the $V_H$ domain, and a light chain comprising the $V_L$ domain. In some embodiments, the heavy chain further comprises one or more heavy chain constant domains, such as $C_H1$, $C_H2$, $C_H3$, and $C_H4$, and/or an antibody hinge region (HR). In some embodiments, the light chain further comprises a light chain constant domain ($C_L$), such as the lambda $C_L$ domain or kappa $C_L$ domain. In some embodiments, the N-terminus of the first antigen binding portion comprising the anti-LAG-3 sdAb described herein is fused to the C-terminus of the heavy chain. In some embodiments, the C-terminus of the first antigen binding portion comprising the anti-LAG-3 sdAb is fused to the N-terminus of the heavy chain. In some embodiments, the N-terminus of the first antigen binding portion comprising the anti-LAG-3 sdAb is fused to the C-terminus of the light chain. In some embodiments, the C-terminus of the first antigen binding portion comprising the anti-LAG-3 sdAb is fused to the N-terminus of the light chain. In some embodiments, the anti-LAG-3 MABP (e.g., BABP) comprises a first polypeptide comprising from the N-terminus to the C-terminus: the heavy chain, an optional peptide linker, and the first antigen binding portion comprising the anti-LAG-3 sdAb and an optional peptide sequence; and a second polypeptide comprising the light chain. In some embodiments, the anti-LAG-3 MABP (e.g., BABP) comprises a first polypeptide comprising from the N-terminus to the C-terminus: the first antigen binding portion comprising an optional peptide sequence and the anti-LAG-3 sdAb, an optional peptide linker, and the heavy chain; and a second polypeptide comprising the light chain. In some embodiments, the anti-LAG-3 MABP (e.g., BABP) comprises a first polypeptide comprising from the N-terminus to the C-terminus: the light chain, an optional peptide linker, and the first antigen binding portion comprising the anti-LAG-3 sdAb and an optional peptide sequence; and a second polypeptide comprising the heavy chain. In some embodiments, the anti-LAG-3 MABP (e.g., BABP) comprises a first polypeptide comprising from the N-terminus to the C-terminus: the first antigen binding portion comprising an optional peptide sequence and the anti-LAG-3 sdAb, an optional peptide linker, and the light chain; and a second polypeptide comprising the heavy chain. In some embodiments, the anti-LAG-3 MABP (e.g., BABP) comprises two identical first polypeptides and two identical second polypeptides described herein.

In some embodiments, the second antigen binding portion comprises a full-length antibody consisting of two heavy chains and two light chains. In some embodiments, the full-length antibody is a full-length monoclonal antibody consisting of two identical heavy chains and two identical light chains. In some embodiments, the anti-LAG-3 MABP (e.g., BABP) comprises two identical first polypeptides each comprising from the N-terminus to the C-terminus the heavy chain, an optional peptide linker, the first antigen binding portion comprising the anti-LAG-3 sdAb and an optional peptide sequence; and two identical second polypeptides each comprising the light chain (e.g., FIG. 8). In some embodiments, the anti-LAG-3 MABP (e.g., BABP) comprises two identical first polypeptides each comprising from the N-terminus to the C-terminus: the first antigen binding portion comprising an optional peptide sequence and the anti-LAG-3 sdAb, an optional peptide linker, and the heavy chain; and two identical second polypeptides each comprising the light chain (e.g., FIG. 7). In some embodiments, the anti-LAG-3 MABP (e.g., BABP) comprises two identical first polypeptides each comprising from the N-terminus to the C-terminus: the light chain, an optional peptide linker, and the first antigen binding portion comprising the anti-LAG-3 sdAb and an optional peptide sequence; and two identical second polypeptides each comprising the heavy chain (e.g., FIG. 10). In some embodiments, the anti-LAG-3 MABP (e.g., BABP) comprises two identical first polypeptides each comprising from the N-terminus to the C-terminus: the first antigen binding portion comprising an optional peptide sequence and the anti-LAG-3 sdAb, an optional peptide linker, and the light chain; and two identical second polypeptides comprising the heavy chain (e.g., FIG. 9).

In some embodiments, the anti-LAG-3 MABP (e.g., BABP) comprises: (a) a full-length antibody consisting of a first and a second heavy chains and a first and a second light chains, wherein the full-length antibody specifically recognizes a first epitope (e.g., PD-1); (b) a first anti-LAG-3 sdAb; (c) a second anti-LAG-3 sdAb; (d) a third anti-LAG-3 sdAb; and (e) a fourth anti-LAG-3 sdAb; wherein the C-terminus of the first anti-LAG-3 sdAb is fused to the N-terminus of the first light chain, wherein the C-terminus of the second anti-LAG-3 sdAb is fused to the N-terminus of the second light chain, wherein the C-terminus of the third anti-LAG-3 sdAb is fused to the N-terminus of the first heavy chain, and wherein the C-terminus of the fourth anti-LAG-3 sdAb is fused to the N-terminus of the second heavy chain. In some embodiments, the four anti-LAG-3 sdAbs are different. In some embodiments, the four anti-LAG-3 sdAbs are identical. In some embodiments, the anti-LAG-3 MABP (e.g., BABP) comprises two identical first polypeptides each comprising from the N-terminus to the C-terminus: an optional peptide sequence, the third or the fourth anti-LAG-3 sdAb, an optional peptide linker, and the heavy chain; and two identical second polypeptides each comprising an optional peptide sequence, the first or the second anti-LAG-3 sdAb, an optional peptide linker, and the light chain. See, for example, FIG. 11.

In some embodiments, the anti-LAG-3 MABP (e.g., BABP) comprises: (a) a full-length antibody consisting of two heavy chains and two light chains, wherein the full-length antibody specifically recognizes a first epitope (e.g., PD-1); (b) a first anti-LAG-3 sdAb; (c) a second anti-LAG-3 sdAb; (d) a third anti-LAG-3 sdAb; and (e) a fourth anti-LAG-3 sdAb; wherein the C-terminus of the first anti-LAG-3 sdAb is fused to the N-terminus of the second anti-LAG-3 sdAb, and the C-terminus of the second anti-LAG-3 sdAb is fused to the N-terminus of one heavy chain, and wherein the C-terminus of the third anti-LAG-3 sdAb is fused to the N-terminus of the fourth anti-LAG-3 sdAb, and the C-terminus of the fourth anti-LAG-3 sdAb is fused to the N-terminus of the other heavy chain. In some embodiments, the four anti-LAG-3 sdAbs are different. In some embodiments, the four anti-LAG-3 sdAbs are identical. In some embodiments, the anti-LAG-3 MABP (e.g., BABP) comprises two identical first polypeptides each comprising from the N-terminus to the C-terminus: an optional peptide sequence, the first or the third anti-LAG-3 sdAb, an optional peptide linker, the second or the fourth anti-LAG-3 sdAb, an optional peptide linker, and the heavy chain; and two identical second polypeptides each comprising the light chain. See, for example, FIG. 12.

In some embodiments, the anti-LAG-3 MABP (e.g., BABP) comprises: (a) a full-length antibody consisting of two heavy chains and two light chains, wherein the full-length antibody specifically recognizes a first epitope (e.g., PD-1); (b) a first anti-LAG-3 sdAb; and (c) a second anti-LAG-3 sdAb, wherein the N-terminus of the first or the second anti-LAG-3 sdAb is fused to the C-terminus of the $C_H1$ region of the heavy chain, and the C-terminus of the first or the second anti-LAG-3 sdAb is fused to the N-terminus of the $C_H2$ region of the heavy chain. In some embodiments, the two anti-LAG-3 sdAbs are identical. In some embodiments, the two anti-LAG-3 sdAbs are different. In some embodiments, the anti-LAG-3 MABP (e.g., BABP) comprises two identical first polypeptides each comprising from the N-terminus to the C-terminus: $V_H$-$C_H1$-an optional peptide linker-anti-LAG-3 sdAb-$C_H2$-$C_H3$; and two identical second polypeptides each comprising the light chain. See, for example, FIG. 13.

In some embodiments, the anti-LAG-3 MABP (e.g., BABP) comprises: (a) a first scFv that specifically recognizes a first epitope (e.g., PD-1); (b) a second scFv that specifically recognizes a second epitope (e.g., PD-1); (c) an Fc region; (d) a first anti-LAG-3 sdAb; and (e) a second anti-LAG-3 sdAb, wherein the N-terminus of each anti-LAG-3 sdAb is fused to the C-terminus of an scFv and the C-terminus of the anti-LAG-3 sdAb is fused to the N-terminus of the Fc region. In some embodiments, the two anti-LAG-3 sdAbs are identical. In some embodiments, the two anti-LAG-3 sdAbs are different. In some embodiments, the two scFvs are identical. In some embodiments, the two scFvs are different. In some embodiments, the anti-LAG-3 MABP (e.g., BABP) comprises two identical polypeptides each comprising from the N-terminus to the C-terminus: scFv-an optional peptide linker-anti-LAG-3 sdAb-$CH_2$-$CH_3$, such as $V_H$-$V_L$-an optional peptide linker-anti-LAG-3 sdAb-$CH_2$—$CH_3$, or $V_L$-$V_H$-an optional peptide linker-anti-LAG-3 sdAb-$C_H2$-$C_H3$. See, for example, FIG. 14.

In some embodiments, the anti-LAG-3 MABP (e.g., BABP) comprises: (a) a first Fab that specifically recognizes a first epitope (e.g., PD-1); (b) a second Fab that specifically recognizes a second epitope (e.g., PD-1); (c) an Fc region; (d) a first Fab-like domain comprising a first anti-LAG-3 sdAb and a second anti-LAG-3 sdAb; (e) a second Fab-like domain comprising a third anti-LAG-3 sdAb and a fourth anti-LAG-3 sdAb, wherein the N-termini of each Fab-like domain are fused to the C-termini of a Fab and one of the two C-termini of the Fab-like domain is fused to the N-terminus of the Fc region. In some embodiments, the four anti-LAG-3 sdAbs are identical. In some embodiments, the four anti-LAG-3 sdAbs are different. In some embodiments, the two Fabs are identical. In some embodiments, the two Fabs are different. In some embodiments, the anti-LAG-3 MABP (e.g., BABP) comprises two identical first polypeptides each comprising from the N-terminus to the C-terminus: $V_H$-$C_H$1-an optional peptide linker-anti-LAG-3 sdAb-$C_H$1-$C_H$2-$C_H$3; and two identical second polypeptides each comprising from the N-terminus to the C-terminus: $V_L$-$C_L$-an optional peptide linker-anti-LAG-3 sdAb-$C_L$. See, for example, FIG. 15.

In some embodiments, the anti-LAG-3 MABP (e.g., BABP) comprises: (a) a first scFv that specifically recognizes a first epitope (e.g., PD-1); (b) a second scFv that specifically recognizes a second epitope (e.g., PD-1); (c) an Fc region; (d) a first Fab-like domain comprising a first anti-LAG-3 sdAb and a second anti-LAG-3 sdAb; (e) a second Fab-like domain comprising a third anti-LAG-3 sdAb and a fourth anti-LAG-3 sdAb, wherein one of the two N-termini of each Fab-like domain is fused to the C-terminus of an scFv and one of the two C-termini of the Fab-like domain is fused to the N-terminus of the Fc region. In some embodiments, the four anti-LAG-3 sdAbs are identical. In some embodiments, the four anti-LAG-3 sdAbs are different. In some embodiments, the two scFvs are identical. In some embodiments, the two scFvs are different. In some embodiments, the anti-LAG-3 MABP (e.g., BABP) comprises two identical first polypeptides each comprising from the N-terminus to the C-terminus: scFv-an optional peptide linker-anti-LAG-3 sdAb-$C_H$1-$C_H$2-$C_H$3; and two identical second polypeptides each comprising from the N-terminus to the C-terminus: anti-LAG-3 sdAb-$C_L$. In some embodiments, the scFv comprises from the N-terminus to the C-terminus: $V_H$-$V_L$ or $V_L$-$V_H$. See, for example, FIG. 16.

The anti-LAG-3 MABPs (e.g., BABPs) described herein may comprise one or more peptide linkers situated between the first antigen binding portion and the second antigen binding portion. In some embodiments, the peptide linker between the heavy chain polypeptide of the second antigen binding portion and the first antigen binding portion is the same as the peptide linker between the light chain polypeptide of the second antigen binding portion and the first antigen binding portion. In some embodiments, the peptide linker between the heavy chain polypeptide of the second antigen binding portion and the first antigen binding portion is different from the peptide linker between the light chain polypeptide of the second antigen binding portion and the first antigen binding portion. In some embodiments, the first antigen binding portion and the second antigen binding portion are directly fused to each other without a peptide linker disposed therebetween. The peptide linker between the two or more anti-LAG-3 sdAbs may be the same as or different from that between the anti-LAG-3 sdAb and the second antigen binding portion. Any of the peptide linkers described below in the "Peptide linkers" section above can be employed in any of the anti-LAG-3 MABPs (e.g., BABPs) described herein.

b) Second Antigen Binding Portion Comprising $V_V$ and $V_L$

The anti-LAG-3 MABPs (e.g., BABPs) comprise at least one second antigen binding portion comprising a $V_H$ and a $V_L$. Such antigen binding portion can be a full-length conventional antibody consisting of two heavy chains and two light chains, or an antigen binding fragment derived therefrom, e.g., Fab, scFv.

In some embodiments, the second antigen binding portion is an antigen binding fragment comprising a heavy chain comprising the $V_H$ domain and a light chain comprising the $V_L$ domain. Exemplary antigen binding fragments contemplated herein include, but are not limited to, Fab, Fab', $F(ab')_2$, and Fv fragments; diabodies; linear antibodies; single-chain antibody molecules (such as scFv); and multispecific antibodies formed from antibody fragments.

In some embodiments, the second antigen binding portion comprises an Fc region, such as a human Fc region. In some embodiments, the Fc region is derived from an IgG molecule, such as any one of the IgG1, IgG2, IgG3, or IgG4 subclass. In some embodiments, the Fc region is capable of mediating an antibody effector function, such as ADCC and/or CDC. For example, antibodies of subclass IgG1, IgG2, and IgG3 with wildtype Fc sequences usually show complement activation including C1q and C3 binding, whereas IgG4 does not activate the complement system and does not bind C1q and/or C3. In some embodiments, the Fc region comprises a modification that reduces binding affinity of the Fc region to an Fc receptor. In some embodiments, the Fc region is an IgG1 Fc. In some embodiments, the IgG1 Fc comprises one or mutations in positions 233-236, such as L234A and/or L235A. In some embodiments, the Fc region is an effectorless IgG1 Fc. In some embodiments, the Fc region is an IgG4 Fc. In some embodiments, the IgG4 Fc comprises a mutation in positions 327, 330 and/or 331. See, for example, Armour K L et al., Eur J. Immunol. 1999; 29: 2613; and Shields R L et al., J. Biol. Chem. 2001; 276: 6591. In some embodiments, the Fc region comprises a P329G mutation. In some embodiments, the Fc region is an IgG4 Fc (S228P). In some embodiments, the Fc region comprises an amino acid sequence of any one of SEQ ID NOs: 363-365.

In some embodiments, the Fc region comprises a modification that promotes heterodimerization of two non-identical heavy chains. Such modified Fc regions may be of particular interest for anti-LAG-3 MABPs (e.g., BABPs) described herein having an asymmetric design. In some embodiments, said modification is a knob-into-hole modification, comprising a knob modification in one of the heavy chains or heavy chain fusion polypeptides and a hole modification in the other one of the two heavy chains or heavy chain fusion polypeptides. In one embodiment, the Fc region comprises a modification within the interface between the two heavy chains in the $C_H3$ domain, wherein i) in the $C_H3$ domain of one heavy chain, an amino acid residue is replaced with an amino acid residue having a larger side chain volume, thereby generating a protuberance ("knob") within the interface in the $C_H3$ domain of one heavy chain which is positionable in a cavity ("hole") within the interface in the $C_H3$ domain of the other heavy chain, and ii) in the $C_H3$ domain of the other heavy chain, an amino acid residue is replaced with an amino acid residue having a smaller side chain volume, thereby generating a cavity ("hole") within the interface in the second $C_H3$ domain within which a protuberance ("knob") within the interface in the first $C_H3$ domain is positionable. Examples of knob-into-hole modifications have been described, for example, in US 2011/0287009, US2007/0178552, WO 96/027011, WO 98/050431, and Zhu et al., 1997, *Protein Science* 6:781-788. Other modifications to the Fc region that promote heterodimerization are also contemplated herein. For example, electrostatic steering effects can be engineered into the Fc region to provide Fc-heterodimeric molecules (see, e.g., US4676980, and Brennan et al., *Science,* 229: 81 (1985)). In some embodiments, the Fc region comprises a modification that inhibits Fab arm exchange. For example, the S228P mutation in IgG4 Fc prevents Fab arm exchange.

In some embodiments, the second antigen binding portion comprises a kappa light chain constant region. In some embodiments, the second antigen binding portion comprises a lambda light chain constant region. In some embodiments, the second antigen binding portion comprises a heavy chain constant region.

In some embodiments, the second antigen binding portion is a full-length antibody consisting of two heavy chains and two light chains. In some embodiments, the second antigen binding portion comprises a monoclonal antibody consisting of two heavy chains and two light chains (also referred herein as "4-chain antibody"). In some embodiments, the second antigen binding portion comprises a multispecific (e.g., bispecific) full-length antibody consisting of two heavy chains and two light chains. In some embodiments, the second antigen binding portion comprises a full-length antibody of human IgG1 subclass, of effectorless hIgG1 subclass, or of human IgG1 subclass with the mutations L234A and L235A. In some embodiments, the second antigen binding portion comprises a full-length antibody of human IgG2 subclass. In some embodiments, the second antigen binding portion comprises a full-length antibody of human IgG3 subclass. In some embodiments, the second antigen binding portion comprises a full-length antibody of human IgG4 subclass or, of human IgG4 subclass with the additional mutation S228P.

Any full-length 4-chain antibody known in the art or antigen binding fragments derived therefrom can be used as the second antigen binding portion of the anti-LAG-3 MABP (e.g. BABP) described herein. Antibodies or antibody fragments with proven clinical efficacy, safety, and pharmacokinetics profile are of particular interest. In some embodiments, the antibody or antibody fragment known in the art is further engineered, such as humanized or mutagenized to select for a variant with a suitable affinity, prior to fusion with the first antigen binding portion to provide the anti-LAG-3 MABP (e.g., BABP). In some embodiments, the second antigen binding portion comprises the $V_H$ and $V_L$ domains of a monoclonal antibody or antibody fragment known in the art, and modified heavy chain constant region and/or light chain constant region. In some embodiments, the second antigen binding portion comprises the monoclonal antibody known in the art and a modified Fc region, such as an IgG4 Fc with an S228P mutation, or an effectorless IgG1 Fc. In some embodiments, the second antigen binding portion comprises a human, humanized, or chimeric full-length antibody or antibody fragments.

c) Exemplary Anti-LAG-3 MABPs

In some embodiments, the anti-LAG-3 construct is an anti-LAG-3 MABP comprising a second antigen binding portion that specifically recognizes PD-1. In some embodiments, the second antigen binding portion comprises an anti-PD-1 sdAb. In some embodiments, the second antigen binding portion comprises a full-length anti-PD-1 antibody consisting of two heavy chains and two light chains.

PD-1 is an inhibitory member of the CD28 receptor family, which also includes CD28, CTLA-4, ICOS and BTLA. PD-1 contains a membrane proximal immunoreceptor tyrosine inhibitory motif (ITIM) and a membrane distal tyrosine-based switch motif (ITSM) (Thomas, M. L. (1995) J Exp Med 181:1953-6; Vivier, E and Dacron, M (1997) Immunol Today 18:286-91). Although structurally similar to CTLA-4, PD-1 lacks the MYPPPY motif that is critical for B7-1 and B7-2 binding.

PD-1 regulates T-cell activation and tolerance, and thus antagonistic anti-PD-1 antibodies can be useful for overcoming tolerance. PD-1 has been defined as a receptor for B7-4. B7-4 can inhibit immune cell activation upon binding to an inhibitory receptor on an immune cell. Engagement of the PD-1/PD-L1 pathway results in inhibition of T-cell effector function, cytokine secretion and proliferation (Turnis et al., OncoImmunology 1(7):1172-1174, 2012). High levels of PD-1 are associated with exhausted or chronically stimulated T cells. Moreover, increased PD-1 expression correlates with reduced survival in cancer patients. Agents for down modulating PD-1, B7-4, and the interaction between B7-4 and PD-1 inhibitory signal in an immune cell can result in enhancement of the immune response.

In some embodiments, there is provided an anti-LAG-3 construct comprising an anti-LAG-3 sdAb described herein fused to an anti-PD-1 sdAb. In some embodiments, the anti-LAG-3 sdAb is fused to the anti-PD-1 sdAb via a linker (such as a peptide linker). In some embodiments, the anti-LAG-3 construct comprises a plurality (such as 2, 3, 4, or more) of anti-LAG-3 sdAbs, which can be the same or different. In some embodiments, the anti-LAG-3 construct comprises a plurality (such as 2, 3, 4, or more) of anti-PD-1 sdAbs, which can be the same or different. The anti-PD-1 sdAb can be derived from any known anti-PD-1 sdAbs, such as those disclosed in PCT/CN2018/071729, the contents of which are incorporated herein by reference in their entirety. The anti-LAG-3 construct can be of any suitable format, for example, from N- to C-terminus: (anti-LAG-3 sdAb)-$L_1$-(anti-PD-1 sdAb) or (anti-PD-1 sdAb)-$L_1$-(anti-LAG-3 sdAb), wherein $L_1$ is a chemical bond or a linker, such as peptide linker.

Exemplary 4-chain anti-PD-1 antibodies that can be used for making multispecific anti-LAG_3 constructs described herein include, but are not limited to, pembrolizumab (e.g., KEYTRUDA®), nivolumab (e.g., OPDIVO®), PD1-BM-min, including biosimilars thereof, derivatives thereof, and antibodies having the same sequences.

In some embodiments, the second antigen binding portion comprises an anti-PD-1 full-length antibody or antigen binding fragment thereof (e.g., Fab, scFv). In some embodiments, the anti-PD-1 full-length antibody or antigen binding fragment thereof (e.g., Fab, scFv) comprises: (i) a $V_H$ comprising HC-CDR1, HC-CDR2, and HC-CDR3 of the amino acid sequence of SEQ ID NO: 356, and a $V_L$ comprising LC-CDR1, LC-CDR2, and LC-CDR3 of the amino acid sequence of SEQ ID NO: 357; or (ii) a $V_H$ comprising HC-CDR1, HC-CDR2, and HC-CDR3 of the amino acid sequence of SEQ ID NO: 373, and a $V_L$ comprising LC-CDR1, LC-CDR2, and LC-CDR3 of the amino acid sequence of SEQ ID NO: 374. In some embodiments, the anti-PD-1 full-length antibody comprises: (i) a heavy chain comprising the amino acid sequence of SEQ ID NO: 356, and a light chain comprising the amino acid sequence of SEQ ID NO: 357; or (ii) a heavy chain comprising the amino acid sequence of SEQ ID NO: 373, and a light chain comprising the amino acid sequence of SEQ ID NO: 374. In some embodiments, the anti-PD-1 full-length antibody is pembrolizumab (e.g., KEYTRUDA®) or PD1-BM-min.

In some embodiments, the anti-LAG-3 MABP (e.g., BABP) comprises (a) a first antigen binding portion comprising an anti-LAG-3 sdAb described herein, and (b) a second antigen binding portion comprising a $V_H$ and a $V_L$, wherein the $V_H$ and $V_L$ together form an antigen-binding site that specifically binds PD-1, wherein the first antigen binding portion and the second antigen binding portion are fused to each other (herein after referred to as "LAG-3×PD-1 MABP" or "LAG-3×PD-1 BABP"). Exemplary anti-LAG-3/PD-1 BABPs are shown in FIGS. 7-14 and Table 7.

In some embodiments, there is provided an anti-LAG-3 BABP comprising: (a) a first polypeptide comprising from N-terminus to C-terminus: anti-LAG-3 sdAb-$V_H$-$C_H1$-$C_H2$-$C_H3$; and (b) a second polypeptide comprising from N-terminus to C-terminus: $V_L$-$C_L$, wherein $V_H$ and $V_L$ forms an antigen binding site that specifically binds a second epitope (e.g., an immune checkpoint molecule, such as PD-1), and wherein the anti-LAG-3 sdAb comprises a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions. In some embodiments, the anti-LAG-3 sdAb comprises: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223. In some embodiments, the anti-LAG-3 sdAb comprises a $V_HH$ domain comprising the amino acid sequence of any one of SEQ ID NO: 274-311. In some embodiments, the anti-LAG-3 sdAb comprises a $V_HH$ domain comprising the amino acid sequence of any one of SEQ ID NO: 288, 295, 304 or 306. In some embodiments, $V_H$ and $V_L$ form an antigen binding site that specifically binds PD-1. In some embodiments, the $V_H$ and $V_L$ domains are derived from pembrolizumab or PD1-BM-min. In some embodiments, the $V_H$ comprises HC-CDR1, HC-CDR2, and HC-CDR3 of the amino acid sequence of SEQ ID NO: 356, and $V_L$ comprises LC-CDR1, LC-CDR2, and LC-CDR3 of the amino acid sequence of SEQ ID NO: 357. In some embodiments, the $V_H$ comprises HC-CDR1, HC-CDR2, and HC-CDR3 of the amino acid sequence of SEQ ID NO: 373, and $V_L$ comprises LC-CDR1, LC-CDR2, and LC-CDR3 of the amino acid sequence of SEQ ID NO: 374. In some embodiments, the $C_H3$ and anti-LAG-3 sdAb are fused to each other via a peptide linker, such as a peptide linker comprising the amino acid sequence of any one of SEQ ID NOs: 352-353 and 366-372. In some embodiments, the N-terminus of the anti-LAG-3 sdAb is fused to a peptide sequence. In some embodiments, the peptide sequence comprises the amino acid sequence of any one of SEQ ID NOs: 352-353 and 366-372. In some embodiments, the $C_H2$ and $C_H3$ domains are derived from IgG1 Fc, effectorless IgG1 Fc, IgG2 Fc, IgG4 Fc, or IgG4 Fc (S228P).

In some embodiments, there is provided an anti-LAG-3 BABP comprising: (a) a first polypeptide comprising from N-terminus to C-terminus: $V_H$-$C_H1$-$C_H2$-$C_H3$-anti-LAG-3 sdAb; and (b) a second polypeptide comprising from N-terminus to C-terminus: $V_L$-$C_L$, wherein $V_H$ and $V_L$ forms an antigen binding site that specifically binds a second epitope (e.g., an immune checkpoint molecule, such as PD-1), and wherein the anti-LAG-3 sdAb comprises a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions. In some embodiments, the anti-LAG-3 sdAb comprises: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223. In some embodiments, the anti-LAG-3 sdAb comprises a $V_HH$ domain comprising the amino acid sequence of any one of SEQ ID NO: 274-311. In some embodiments, the anti-LAG-3 sdAb comprises a $V_HH$ domain comprising the amino acid sequence of any one of SEQ ID NO: 288, 295, 304 or 306. In some embodiments, $V_H$ and $V_L$ form an antigen binding site that specifically binds PD-1. In some embodiments, the $V_H$ and $V_L$ domains are derived from pembrolizumab or PD1-BM-min. In some embodiments, the $V_H$ comprises HC-CDR1, HC-CDR2, and HC-CDR3 of the amino acid sequence of SEQ ID NO: 356, and $V_L$ comprises LC-CDR1, LC-CDR2, and LC-CDR3 of the amino acid sequence of SEQ ID NO: 357. In some embodiments, the $V_H$ comprises HC-CDR1, HC-CDR2, and HC-CDR3 of the amino acid sequence of SEQ ID NO: 373, and $V_L$ comprises LC-CDR1, LC-CDR2, and LC-CDR3 of the amino acid sequence of SEQ ID NO: 374. In some embodiments, the $C_H3$ and anti-LAG-3 sdAb are fused to each other via a peptide linker, such as a peptide linker comprising the amino acid sequence of any one of SEQ ID NOs: 352-353 and 366-372. In some embodiments, the C-terminus of the anti-LAG-3 sdAb is fused to a peptide sequence. In some embodiments, the peptide sequence comprises the amino acid sequence of any one of SEQ ID NOs: 352-353 and 366-372. In some embodiments, the $C_H2$ and $C_H3$ domains are derived from IgG1 Fc, effectorless IgG1 Fc, IgG2 Fc, IgG4 Fc, or IgG4 Fc (S228P).

In some embodiments, there is provided an anti-LAG-3 BABP comprising: (a) a first polypeptide comprising from N-terminus to C-terminus: $V_H$-$C_H1$-$C_H2$-$C_H3$; and (b) a second polypeptide comprising from N-terminus to C-terminus: anti-LAG-3 sdAb-$V_L$-$C_L$, wherein $V_H$ and $V_L$ forms an antigen binding site that specifically binds a second epitope (e.g., an immune checkpoint molecule, such as PD-1), and wherein the anti-LAG-3 sdAb comprises a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions. In some embodiments, the anti-LAG-3 sdAb comprises: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223. In some embodiments, the anti-LAG-3 sdAb comprises a $V_HH$ domain comprising the amino acid sequence of any one of SEQ ID NO: 274-311. In some embodiments, the anti-LAG-3 sdAb comprises a $V_HH$ domain comprising the amino acid sequence of any one of SEQ ID NO: 288, 295, 304 or 306. In some embodiments, $V_H$ and $V_L$ form an antigen binding site that specifically binds PD-1. In some embodiments, the $V_H$ and $V_L$ domains are derived from pembrolizumab or PD1-BM-min. In some embodiments, the $V_H$ comprises HC-CDR1, HC-CDR2, and HC-CDR3 of the amino acid sequence of SEQ ID NO: 356, and $V_L$ comprises LC-CDR1, LC-CDR2, and LC-CDR3 of the amino acid sequence of SEQ ID NO: 357. In some embodiments, the $V_H$ comprises HC-CDR1, HC-CDR2, and HC-CDR3 of the amino acid sequence of SEQ ID NO: 373, and $V_L$ comprises LC-CDR1, LC-CDR2, and LC-CDR3 of the amino acid sequence of SEQ ID NO: 374. In some embodiments, the $C_H3$ and anti-LAG-3 sdAb are fused to each other via a peptide linker, such as a peptide linker comprising the amino acid sequence of any one of SEQ ID NOs: 352-353 and 366-372. In some embodiments, the N-terminus of the anti-LAG-3 sdAb is fused to a peptide sequence. In some embodiments, the peptide sequence comprises the amino acid sequence of any one of SEQ ID NOs: 352-353 and 366-372. In some embodiments, the $C_H2$ and $C_H3$ domains are derived from IgG1 Fc, effectorless IgG1 Fc, IgG2 Fc, IgG4 Fc, or IgG4 Fc (S228P).

In some embodiments, there is provided an anti-LAG-3 BABP comprising: (a) a first polypeptide comprising from N-terminus to C-terminus: $V_H$-$C_H1$-$C_H2$-$C_H3$; and (b) a second polypeptide comprising from N-terminus to C-terminus: $V_L$-$C_L$-anti-LAG-3 sdAb, wherein $V_H$ and $V_L$ forms an antigen binding site that specifically binds a second epitope (e.g., an immune checkpoint molecule, such as PD-1), and wherein the anti-LAG-3 sdAb comprises a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions. In some embodiments, the anti-LAG-3 sdAb comprises: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223. In some embodiments, the anti-LAG-3 sdAb comprises a $V_HH$ domain comprising the amino acid sequence of any one of SEQ ID NO: 274-311. In some embodiments, the anti-LAG-3 sdAb comprises a $V_HH$ domain comprising the amino acid sequence of any one of SEQ ID NO: 288, 295, 304 or 306. In some embodiments, $V_H$ and $V_L$ form an antigen binding site that specifically binds PD-1. In some embodiments, the $V_H$ and $V_L$ domains are derived from pembrolizumab or PD1-BM-min. In some embodiments, the $V_H$ comprises HC-CDR1, HC-CDR2, and HC-CDR3 of the amino acid sequence of SEQ ID NO: 356, and $V_L$ comprises LC-CDR1, LC-CDR2, and LC-CDR3 of the amino acid sequence of SEQ ID NO: 357. In some embodiments, the $V_H$ comprises HC-CDR1, HC-CDR2, and HC-CDR3 of the amino acid sequence of SEQ ID NO: 373, and $V_L$ comprises LC-CDR1, LC-CDR2, and LC-CDR3 of the amino acid sequence of SEQ ID NO: 374. In some embodiments, the $C_H3$ and anti-LAG-3 sdAb are fused to each other via a peptide linker, such as a peptide linker comprising the amino acid sequence of any one of SEQ ID NOs: 352-353 and 366-372. In some embodiments, the C-terminus of the anti-LAG-3 sdAb is fused to a peptide sequence. In some embodiments, the peptide sequence comprises the amino acid sequence of any one of SEQ ID NOs: 352-353 and 366-372. In some embodiments, the $C_H2$ and $C_H3$ domains are derived from IgG1 Fc, effectorless IgG1 Fc, IgG2 Fc, IgG4 Fc, or IgG4 Fc (S228P).

In some embodiments, there is provided an anti-LAG-3 BABP comprising: (a) a first polypeptide comprising from N-terminus to C-terminus: $V_H$-$C_H1$-anti-LAG-3 sdAb-$C_H2$-$C_H3$; and (b) a second polypeptide comprising from N-terminus to C-terminus: $V_L$-$C_L$, wherein $V_H$ and $V_L$ forms an antigen binding site that specifically binds a second epitope (e.g., an immune checkpoint molecule, such as PD-1), and wherein the anti-LAG-3 sdAb comprises a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions. In some embodiments, the anti-LAG-3 sdAb comprises: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223. In some embodiments, the anti-LAG-3 sdAb comprises a $V_H H$ domain comprising the amino acid sequence of any one of SEQ ID NO: 274-311. In some embodiments, the anti-LAG-3 sdAb comprises a $V_H H$ domain comprising the amino acid sequence of any one of SEQ ID NO: 288, 295, 304 or 306. In some embodiments, $V_H$ and $V_L$ form an antigen binding site that specifically binds PD-1. In some embodiments, the $V_H$ and $V_L$ domains are derived from pembrolizumab or PD1-BM-min. In some embodiments, the $V_H$ comprises HC-CDR1, HC-CDR2, and HC-CDR3 of the amino acid sequence of SEQ ID NO: 356, and $V_L$ comprises LC-CDR1, LC-CDR2, and LC-CDR3 of the amino acid sequence of SEQ ID NO: 357. In some embodiments, the $V_H$ comprises HC-CDR1, HC-CDR2, and HC-CDR3 of the amino acid sequence of SEQ ID NO: 373, and $V_L$ comprises LC-CDR1, LC-CDR2, and LC-CDR3 of the amino acid sequence of SEQ ID NO: 374. In some embodiments, the $C_H3$ and anti-LAG-3 sdAb are fused to each other via a peptide linker, such as a peptide linker comprising the amino acid sequence of any one of SEQ ID NOs: 352-353 and 366-372. In some embodiments, the $C_H2$ and $C_H3$ domains are derived from IgG1 Fc, effectorless IgG1 Fc, IgG2 Fc, IgG4 Fc, or IgG4 Fc (S228P).

In some embodiments, there is provided an anti-LAG-3 BABP comprising a polypeptide comprising from N-terminus to C-terminus: $V_L$-$V_H$-anti-LAG-3 sdAb-$C_H2$-$C_H3$, wherein the $V_L$ and $V_H$ together forms an scFv that specifically binds a second epitope (e.g., an immune checkpoint molecule, such as PD-1), and wherein the anti-LAG-3 sdAb comprises a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions. In some embodiments, the anti-LAG-3 sdAb comprises: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223. In some embodiments, the anti-LAG-3 sdAb comprises a $V_H H$ domain comprising the amino acid sequence of any one of SEQ ID NO: 274-311. In some embodiments, the anti-LAG-3 sdAb comprises a $V_H H$ domain comprising the amino acid sequence of any one of SEQ ID NO: 288, 295, 304 or 306. In some embodiments, $V_H$ and $V_L$ form an antigen binding site that specifically binds PD-1. In some embodiments, the $V_H$ and $V_L$ domains are derived from pembrolizumab or PD1-BM-min. In some embodiments, the $V_H$ comprises HC-CDR1, HC-CDR2, and HC-CDR3 of the amino acid sequence of SEQ ID NO: 356, and $V_L$ comprises LC-CDR1, LC-CDR2, and LC-CDR3 of the amino acid sequence of SEQ ID NO: 357. In some embodiments, the $V_H$ comprises HC-CDR1, HC-CDR2, and HC-CDR3 of the amino acid sequence of SEQ ID NO: 373, and $V_L$ comprises LC-CDR1, LC-CDR2, and LC-CDR3 of the amino acid sequence of SEQ ID NO: 374. In some embodiments, the $C_H3$ and anti-LAG-3 sdAb are fused to each other via a peptide linker, such as a peptide linker comprising the amino acid sequence of any one of SEQ ID NOs: 352-353 and 366-372. In some embodiments, the $C_H2$ and $C_H3$ domains are derived from IgG1 Fc, effectorless IgG1 Fc, IgG2 Fc, IgG4 Fc, or IgG4 Fc (S228P).

In some embodiments, the anti-LAG-3 construct comprises two identical copies of the first polypeptide and two identical copies of the second polypeptide. In some embodiments, there is provided an anti-LAG-3 construct (e.g., BABP) comprising a first polypeptide comprising the amino acid sequence of SEQ ID NO: 358, and a second polypeptide comprising the amino acid sequence of SEQ ID NO: 359. In some embodiments, there is provided an anti-LAG-3 construct (e.g., BABP) comprising a first polypeptide comprising the amino acid sequence of SEQ ID NO: 360, and a second polypeptide comprising the amino acid sequence of SEQ ID NO: 361. In some embodiments, there is provided an anti-LAG-3 construct (e.g., BABP) comprising a first polypeptide comprising the amino acid sequence of SEQ ID NO: 362, and a second polypeptide comprising the amino acid sequence of SEQ ID NO: 363. In some embodiments, there is provided an anti-LAG-3 construct (e.g., BABP) comprising a first polypeptide comprising the amino acid sequence of SEQ ID NO: 364, and a second polypeptide comprising the amino acid sequence of SEQ ID NO: 365. In some embodiments, there is provided an anti-LAG-3 construct (e.g., BABP) comprising a first polypeptide comprising the amino acid sequence of SEQ ID NO: 375, and a second polypeptide comprising the amino acid sequence of SEQ ID NO: 376. In some embodiments, there is provided an anti-LAG-3 construct (e.g., BABP) comprising a first polypeptide comprising the amino acid sequence of SEQ ID NO: 377, and a second polypeptide comprising the amino acid sequence of SEQ ID NO: 378. In some embodiments, there is provided an anti-LAG-3 construct (e.g., BABP) comprising a first polypeptide comprising the amino acid sequence of SEQ ID NO: 379, and a second polypeptide comprising the amino acid sequence of SEQ ID NO: 380. In some embodiments, there is provided an anti-LAG-3 construct (e.g., BABP) comprising a first polypeptide comprising the amino acid sequence of SEQ ID NO: 381, and a second polypeptide comprising the amino acid sequence of SEQ ID NO: 382. In some embodiments, there is provided an anti-LAG-3 construct (e.g., BABP) comprising a first polypeptide comprising the amino acid sequence of SEQ ID NO: 383, and a second polypeptide comprising the amino acid sequence of SEQ ID NO: 384. In some embodiments, there is provided an anti-LAG-3 construct (e.g., BABP) comprising a first polypeptide comprising the amino acid sequence of SEQ ID NO: 385, and a second polypeptide comprising the amino acid sequence of SEQ ID NO: 386. In some embodiments, there is provided an anti-LAG-3 construct (e.g., BABP) comprising a first polypeptide comprising the amino acid sequence of SEQ ID NO: 387, and a second polypeptide comprising the amino acid sequence of SEQ ID NO: 388. In some embodiments, there is provided an anti-LAG-3 construct (e.g., BABP) comprising a first polypeptide comprising the amino acid sequence of SEQ ID NO: 389, and a second polypeptide comprising the amino acid sequence of SEQ ID NO: 390. In some embodiments, there is provided an anti-LAG-3 construct (e.g., BABP) comprising a first polypeptide comprising the amino acid sequence of SEQ ID NO: 391, and a second polypeptide comprising the amino acid sequence of SEQ ID NO: 392. In some embodiments, there is provided an anti-LAG-3 construct (e.g., BABP) comprising a first polypeptide comprising the amino acid sequence of SEQ ID NO: 393, and a second polypeptide comprising the amino acid sequence of SEQ ID NO: 394. In some embodiments, there is provided an anti-LAG-3 construct (e.g., BABP) comprising a first polypeptide comprising the amino acid sequence of SEQ ID NO: 395, and a second polypeptide comprising the amino acid sequence of SEQ ID NO: 396. In some embodiments, there is provided an anti-LAG-3 construct (e.g., BABP) comprising a first polypeptide comprising the amino acid sequence of SEQ ID NO: 397, and a second polypeptide comprising the amino acid sequence of SEQ ID NO: 398. In some embodiments, there is provided an anti-LAG-3 construct (e.g., BABP) comprising a first polypeptide comprising the amino acid sequence of SEQ ID NO: 399, and a second polypeptide comprising the amino acid sequence of SEQ ID NO: 400. In some embodiments, there is provided an anti-LAG-3 construct (e.g., BABP) comprising a first polypeptide comprising the amino acid sequence of SEQ ID NO: 401, and a second polypeptide comprising the amino acid sequence of SEQ ID NO: 402. In some embodiments, there is provided an anti-LAG-3 construct (e.g., BABP) comprising a first polypeptide comprising the amino acid sequence of SEQ ID NO: 403, and a second polypeptide comprising the amino acid sequence of SEQ ID NO: 404. In some embodiments, there is provided an anti-LAG-3 construct (e.g., BABP) comprising a first polypeptide comprising the amino acid sequence of SEQ ID NO: 405, and a second polypeptide comprising the amino acid sequence of SEQ ID NO: 406. In some embodiments, there is provided an anti-LAG-3 construct (e.g., BABP) comprising a first polypeptide comprising the amino acid sequence of SEQ ID NO: 407, and a second polypeptide comprising the amino acid sequence of SEQ ID NO: 408. In some embodiments, there is provided an anti-LAG-3 construct (e.g., BABP) comprising a first polypeptide comprising the amino acid sequence of SEQ ID NO: 409, and a second polypeptide comprising the amino acid sequence of SEQ ID NO: 410. In some embodiments, there is provided an anti-LAG-3 construct (e.g., BABP) comprising a first polypeptide comprising the amino acid sequence of SEQ ID NO: 411, and a second polypeptide comprising the amino acid sequence of SEQ ID NO: 412. In some embodiments, there is provided an anti-LAG-3 construct (e.g., BABP) comprising a first polypeptide comprising the amino acid sequence of SEQ ID NO: 413, and a second polypeptide comprising the amino acid sequence of SEQ ID NO: 414. In some embodiments, there is provided an anti-LAG-3 construct (e.g., BABP) comprising a first polypeptide comprising the amino acid sequence of SEQ ID NO: 415, and a second polypeptide comprising the amino acid sequence of SEQ ID NO: 416. In some embodiments, there is provided an anti-LAG-3 construct (e.g., BABP) comprising a first polypeptide comprising the amino acid sequence of SEQ ID NO: 417, and a second polypeptide comprising the amino acid sequence of SEQ ID NO: 418. In some embodiments, there is provided an anti-LAG-3 construct (e.g., BABP) comprising a first polypeptide comprising the amino acid sequence of SEQ ID NO: 419, and a second polypeptide comprising the amino acid sequence of SEQ ID NO: 420. In some embodiments, there is provided an anti-LAG-3 construct (e.g., BABP) comprising a first polypeptide comprising the amino acid sequence of SEQ ID NO: 421, and a second polypeptide comprising the amino acid sequence of SEQ ID NO: 422. In some embodiments, there is provided an anti-LAG-3 construct (e.g., BABP) comprising a first polypeptide comprising the amino acid sequence of SEQ ID NO: 423, and a second polypeptide comprising the amino acid sequence of SEQ ID NO: 424. In some embodiments, there is provided an anti-LAG-3 construct (e.g., BABP) comprising a first polypeptide comprising the amino acid sequence of SEQ ID NO: 425, and a second polypeptide comprising the amino acid sequence of SEQ ID NO: 426. In some embodiments, there is provided an anti-LAG-3 construct (e.g., BABP) comprising a first polypeptide comprising the amino acid sequence of SEQ ID NO: 427, and a second polypeptide comprising the amino acid sequence of SEQ ID NO: 428. In some embodiments, there is provided an anti-LAG-3 construct (e.g., BABP) comprising a first polypeptide comprising the amino acid sequence of SEQ ID NO: 429, and a second polypeptide comprising the amino acid sequence of SEQ ID NO: 430. In some embodiments, there is provided an anti-LAG-3 construct (e.g., BABP) comprising a first polypeptide comprising the amino acid sequence of SEQ ID NO: 431, and a second polypeptide comprising the amino acid sequence of SEQ ID NO: 432. In some embodiments, there is provided an anti-LAG-3 construct (e.g., BABP) comprising a first polypeptide comprising the amino acid sequence of SEQ ID NO: 433, and a second polypeptide comprising the amino acid sequence of SEQ ID NO: 434. In some embodiments, there is provided an anti-LAG-3 construct (e.g., BABP) comprising a first polypeptide comprising the amino acid sequence of SEQ ID NO: 435, and a second polypeptide comprising the amino acid sequence of SEQ ID NO: 436. In some embodiments, there is provided an anti-LAG-3 construct (e.g., BABP) comprising a first polypeptide comprising the amino acid sequence of SEQ ID NO: 437, and a second polypeptide comprising the amino acid sequence of SEQ ID NO: 438. In some embodiments, there is provided an anti-LAG-3 construct (e.g., BABP) comprising a first polypeptide comprising the amino acid sequence of SEQ ID NO: 439, and a second polypeptide comprising the amino acid sequence of SEQ ID NO: 440. In some embodiments, there is provided an anti-LAG-3 construct (e.g., BABP) comprising a first polypeptide comprising the amino acid sequence of SEQ ID NO: 441, and a second polypeptide comprising the amino acid sequence of SEQ ID NO: 442. In some embodiments, there is provided an anti-LAG-3 construct (e.g., BABP) comprising a first polypeptide comprising the amino acid sequence of SEQ ID NO: 443, and a second polypeptide comprising the amino acid sequence of SEQ ID NO: 444. In some embodiments, there is provided an anti-LAG-3 construct (e.g., BABP) comprising a first polypeptide comprising the amino acid sequence of SEQ ID NO: 445, and a second polypeptide comprising the amino acid sequence of SEQ ID NO: 446. In some embodiments, there is provided a polypeptide comprising the amino acid sequence of any one of SEQ ID NOs: 358-365 and 375-446.

Peptide Linkers

The various domains and components, such as anti-LAG-3 sdAbs, Fc fragment, the first antigen binding portion, and the second antigen binding portion in the anti-LAG3 construct may be fused to each other via a suitable linker, such as a peptide linker. The length, the degree of flexibility and/or other properties of the peptide linker(s) used in the anti-LAG-3 construct may have some influence on properties, including but not limited to the affinity, specificity or avidity for one or more particular antigens or epitopes. For example, longer peptide linkers may be selected to ensure that two adjacent domains do not sterically interfere with one another. In some embodiment, a peptide linker comprises flexible residues (such as glycine and serine) so that the adjacent domains are free to move relative to each other. For example, a glycine-serine doublet can be a suitable peptide linker.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acid to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a human IgG1 hinge (SEQ ID NO: 352). In some embodiments, the peptide linker is a mutated human IgG1 hinge (SEQ ID NO: 353). In some embodiments, the peptide linker is a human IgG4 hinge. In some embodiments, the peptide linker is a hIgG2 hinge. In some embodiments, the peptide linker is a flexible linker. Exemplary flexible linkers include glycine polymers (G). (SEQ ID NO: 368), glycine-serine polymers (including, for example, (GS)$_n$ (SEQ ID NO: 369), (GSGGS)$_n$ (SEQ ID NO: 370), (GGGS)$_n$ (SEQ ID NO: 371), and (GGGGS)$_n$ (SEQ ID NO: 372), where n is an integer of at least one), glycine-alanine polymers, alanine-serine polymers, and other flexible linkers known in the art. In some embodiments, the peptide linker comprises the amino acid sequence of SEQ ID NO: 366 (GGGGSGGGS) or 367 (GGGGSGGGGSGGGGS).

In some embodiments, the N-terminus or the C-terminus of the anti-LAG-3 sdAb may be fused to a peptide sequence, which may have any of the sequence features described herein for peptide linkers.

(III) Antibody Variants

In some embodiments, amino acid sequence variants of the anti-LAG-3 construct (e.g., anti-LAG-3 sdAb, anti-LAG-3 sdAb-Fc fusion protein (e.g., HCAb), anti-LAG-3 MABP/BABP) provided herein are contemplated. For example, it may be desirable to improve the binding affinity and/or other biological properties of the antibody. Amino acid sequence variants of an antibody may be prepared by introducing appropriate modifications into the nucleic acid sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, Deletion and Variants

In some embodiments, antibody variants having one or more amino acid substitutions are provided. Sites of interest for substitutional mutagenesis include the HVRs (or CDRs) and FRs. Conservative substitutions are shown in Table 2 under the heading of "Preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

Amino acid substitutions

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs. In some embodiments of the variant $V_HH$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In some embodiments, an isolated anti-LAG-3 construct provided herein is altered to increase or decrease the extent to which the construct is glycosylated. Addition or deletion of glycosylation sites to an antibody may be conveniently accomplished by altering the amino acid sequence such that one or more glycosylation sites is created or removed.

Where the anti-LAG-3 construct comprises an Fc region (e.g., anti-LAG-3 sdAb-Fc fusion protein (e.g., HCAb), LAG-3×PD-1 MABP), the carbohydrate attached thereto may be altered. Native antibodies produced by mammalian cells typically comprise a branched, biantennary oligosaccharide that is generally attached by an N-linkage to Asn297 of the $C_H2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-LAG-3 construct of the present application may be made in order to create antibody variants with certain improved properties.

In some embodiments, anti-LAG-3 construct antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Anti-LAG-3 construct variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc region Variants

In some embodiments, one or more amino acid modifications may be introduced into the Fc region of the anti-LAG-3 constructs provided herein (e.g., anti-LAG-3 HCAbs, or anti-LAG-3 MABPs), thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates an anti-PD-1 construct (e.g., anti-LAG-3 HCAb, or anti-LAG-3 MABP) variant that possesses some but not all effector functions, which make it a desirable candidate for applications in which the half-life of the anti-LAG-3 construct in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 2 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci.* USA 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci.* USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, an anti-LAG-3 construct variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

In some embodiments, there is provided an anti-LAG-3 construct (e.g., anti-PD-1 sdAb-Fc fusion protein (e.g., anti-LAG-3 HCAb, or anti-LAG-3 MABP) variant comprising a variant Fc region comprising one or more amino acid substitutions which increase half-life and/or improve binding to the neonatal Fc receptor (FcRn). Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-LAG-3 constructs (e.g., anti-LAG-3 HCAbs or anti-LAG-3 MABPs) comprising any of the Fc variants described herein, or combinations thereof, are contemplated.

d) Cysteine Engineered Antibody Variants

In some embodiments, it may be desirable to create cysteine engineered anti-LAG-3 constructs, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In some embodiments, any one or more of the following residues may be substituted with cysteine: A118 (EU numbering) of the heavy chain; and S400 (EU numbering) of the heavy chain Fc region. Cysteine engineered anti-LAG-3 constructs may be generated as described, e.g., in U.S. Pat. No. 7,521,541.

e) Antibody Derivatives

In some embodiments, an anti-LAG-3 construct provided herein may be further modified to comprise additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In some embodiments, conjugates of an anti-LAG-3 construct and nonproteinaceous moiety that may be selectively heated by exposure to radiation are provided. In some embodiments, the nonproteinaceous moiety is a carbon nanotube (Kam et al., *Proc. Natl. Acad. Sci.* USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

In some embodiments, an anti-LAG-3 construct provided herein (e.g., anti-LAG-3 HCAb, or anti-LAG-3 MABP) may be further modified to comprise one or more biologically active protein, polypeptides or fragments thereof "Bioactive" or "biologically active", as used herein interchangeably, means showing biological activity in the body to carry out a specific function. For example, it may mean the combination with a particular biomolecule such as protein, DNA, etc., and then promotion or inhibition of the activity of such biomolecule. In some embodiments, the bioactive protein or fragments thereof include proteins and polypeptides that are administered to patients as the active drug substance for prevention of or treatment of a disease or condition, as well as proteins and polypeptides that are used for diagnostic purposes, such as enzymes used in diagnostic tests or in vitro assays, as well as proteins and polypeptides that are administered to a patient to prevent a disease such as a vaccine. In some embodiments, the bioactive protein or fragments thereof have immune-stimulatory/immune-regulatory, membrane transport, or enzymatic activities. In some embodiments, the biologically active protein, polypeptides or fragments thereof is an enzyme, a hormone, a growth factor, a cytokine, or a mixture thereof. In some embodiments, the biologically active protein, polypeptides or fragments can specifically recognize a target peptide (such as antigen, or other proteins).

In some embodiments, the bioactive protein or fragments thereof that can be comprised within the anti-LAG-3 construct described herein is a protein-binding protein. In some embodiments, the bioactive protein or fragments thereof that can be comprised within the anti-LAG-3 construct described herein is an antibody mimetics, which are small engineered proteins comprising antigen-binding domains reminiscent of antibodies (Geering and Fussenegger, Trends Biotechnol., 33(2):65-79, 2015). These molecules are derived from existing human scaffold proteins and comprise a single polypeptide. Exemplary antibody mimetics that can be comprised within the anti-LAG-3 construct described herein can be, but are not limited to, a Designed ankyrin repeat protein (DARPin; comprising 3-5 fully synthetic ankyrin repeats flanked by N- and C-terminal Cap domains), an avidity multimer (avimer; a high-affinity protein comprising multiple A domains, each domain with low affinity for a target), or an Anticalin (based on the scaffold of lipocalins, with four accessible loops, the sequence of each can be randomized). In some embodiments, the bioactive protein or fragments thereof that can be comprised within the anti-LAG-3 construct described herein is an Armadillo repeat protein (e.g., β-catenin, α-importin, plakoglobin, adenomatous polyposis coli (APC)), which comprises armadillo repeat units (characteristic, repetitive amino acid sequence of about 40 residues in length). Each Armadillo repeat is composed of a pair of alpha helices that form a hairpin structure. Multiple copies of the repeat form what is known as an alpha solenoid structure. Armadillo repeat proteins are able to bind different types of peptides, relying on a constant way of binding of the peptide backbone without requiring specific conserved side chains or interactions with free N- or C-termini of a peptide. The possibility of recognizing a peptide residue by residue, combined with the intrinsic modularity of a repeat protein, makes the armadillo repeat proteins promising candidates for the design of a generic scaffold for peptide binding.

In some embodiments, the biologically active protein or fragments thereof that can be comprised within the anti-LAG-3 construct described herein is a ligand, such as lymphokines and cellular factors which interact with specific cellular receptor. Lymphokines are low molecular weight proteins which are secreted by T cells when antigens or lectins stimulate T cell growth.

III. Pharmaceutical Compositions

Further provided by the present application are pharmaceutical compositions comprising any one of the anti-LAG-3 constructs described herein (e.g., anti-LAG-3 sdAb, anti-LAG-3 HCAb or anti-LAG-3 MABP), and optionally a pharmaceutically acceptable carrier. Pharmaceutical compositions can be prepared by mixing an anti-LAG-3 construct described herein having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

The pharmaceutical composition is preferably to be stable, in which the anti-LAG-3 construct here essentially retains its physical and chemical stability and integrity upon storage. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month, and/or stable at 2-8° C. for at least 2 years. Where the formulation is to be stored at 30° C., generally the formulation should be stable for at least 2 years at 30° C., and/or stable at 40° C. for at least 6 months. For example, the extent of aggregation during storage can be used as an indicator of protein stability. In some embodiments, the stable formulation of anti-LAG-3 construct described herein may comprise less than about 10% (preferably less than about 5%) of the anti-LAG-3 construct present as an aggregate in the formulation.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers (e.g. sodium chloride), stabilizers, metal complexes (e.g. Zn-protein complexes); chelating agents such as EDTA and/or non-ionic surfactants.

Examples of physiologically acceptable carriers include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counterions such as sodium; metal complexes (e.g. Zn-protein complexes); and/or nonionic surfactants such as TWEEN™, polyethylene glycol (PEG), and PLURONICS™ or polyethylene glycol (PEG).

Buffers are used to control the pH in a range which optimizes the therapeutic effectiveness, especially if stability is pH dependent. Buffers are preferably present at concentrations ranging from about 50 mM to about 250 mM. Suitable buffering agents for use in the present application include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives are added to retard microbial growth, and are typically present in a range from 0.2%-1.0% (w/v). The addition of a preservative may, for example, facilitate the production of a multi-use (multiple-dose) formulation. Suitable preservatives for use in the present application include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1% to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl cellulose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they must be sterile. The pharmaceutical composition may be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intra-arterial, intralesional or intraarticular routes, topical administration, inhalation or by sustained release or extended-release means.

Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The pharmaceutical compositions herein may also contain more than one active compound as necessary for the particular indication being treated, preferably those with complementary activities that do not adversely affect each other. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 18th edition.

In some embodiments, the pharmaceutical composition is contained in a single-use vial, such as a single-use sealed vial. In some embodiments, the pharmaceutical composition is contained in a multi-use vial. In some embodiments, the pharmaceutical composition is contained in bulk in a container. In some embodiments, the pharmaceutical composition is cryopreserved.

IV. Methods of Treating LAG-3-Related Diseases

The anti-LAG-3 constructs (e.g., anti-LAG-3 sdAb, anti-LAG-3 HCAb, or anti-LAG-3 MABP) and compositions (such as pharmaceutical compositions) thereof are useful for a variety of applications, such as in diagnosis, molecular assays, and therapy.

One aspect of the invention provides a method of treating a LAG-3 related disease or a condition in an individual in need thereof, comprising administering to the individual an effective amount of a pharmaceutical composition comprising any one of the anti-LAG-3 constructs described herein. In some embodiments, the LAG-3 related disease is cancer. In some embodiments, the LAG-3-related disease is an immune-related disease. In some embodiments, immune-related disease is associated with a T cell dysfunctional disorder. In some embodiments, the T cell dysfunctional disorder is characterized by T cell anergy or decreased ability to secrete cytokines, proliferate or execute cytolytic activity. In some embodiments, the T cell dysfunctional disorder is characterized by T cell exhaustion. In some embodiments, the T cells are CD4+ and CD8+ T cells. In some embodiments, an anti-LAG-3 construct described herein is used for increasing, enhancing, or stimulating an immune response or function in a subject in need thereof. In some embodiments, the LAG-3-related disease (e.g., cancer, immune-related disease) is partially resistant to immune checkpoint molecule mono-blockade (e.g., partially resistant to anti-PD-1 antibody monotherapy treatment).

In some embodiments, there is provided a method of treating a LAG-3-related disease in an individual, comprising administering to the individual an effective amount of a pharmaceutical composition comprising an isolated anti-LAG-3 construct comprising an anti-LAG-3 sdAb, wherein the anti-LAG-3 sdAb comprises a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions; and a pharmaceutically acceptable carrier. In some embodiments, there is provided a method of treating a LAG-3-related disease in an individual, comprising administering to the individual an effective amount of a pharmaceutical composition comprising an isolated anti-LAG-3 construct comprising an anti-LAG-3 sdAb, wherein the anti-LAG-3 sdAb comprises: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223, and a pharmaceutically acceptable carrier. In some embodiments, the anti-LAG-3 sdAb comprises a $V_H H$ domain comprising the amino acid sequence of any one of SEQ ID NOs: 274-311. In some embodiments, the anti-LAG-3 sdAb comprises a Vali domain comprising the amino acid sequence of any one of SEQ ID NOs: 288, 295, 304, or 306.

In some embodiments, there is provided a method of treating cancer (e.g., colon cancer) in an individual, comprising administering to the individual an effective amount of a pharmaceutical composition comprising an isolated anti-LAG-3 construct comprising an anti-LAG-3 sdAb, wherein the anti-LAG-3 sdAb comprises a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions; and a pharmaceutically acceptable carrier. In some embodiments, there is provided a method of treating cancer (e.g., colon cancer) in an individual, comprising administering to the individual an effective amount of a pharmaceutical composition comprising an isolated anti-LAG-3 construct comprising an anti-LAG-3 sdAb, wherein the anti-LAG-3 sdAb comprises: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223, and a pharmaceutically acceptable carrier. In some embodiments, the anti-LAG-3 sdAb comprises a $V_HH$ domain comprising the amino acid sequence of any one of SEQ ID NOs: 274-311. In some embodiments, the anti-LAG-3 sdAb comprises a $V_HH$ domain comprising the amino acid sequence of any one of SEQ ID NOs: 288, 295, 304, or 306.

In some embodiments, there is provided a method of treating a LAG-3-related disease (e.g., cancer, such as colon cancer) in an individual comprising administering to the individual an effective amount of a pharmaceutical composition comprising an isolated anti-LAG-3 HCAb comprising an sdAb specifically recognizing LAG-3, wherein the anti-LAG-3 sdAb comprises a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions, wherein the anti-LAG-3 sdAb is fused to an Fc fragment of an immunoglobulin; and a pharmaceutically acceptable carrier. In some embodiments, there is provided a method of treating a LAG-3-related disease (e.g., cancer, such as colon cancer) in an individual comprising administering to the individual an effective amount of a pharmaceutical composition comprising an isolated anti-LAG-3 construct comprising an anti-LAG-3 sdAb, wherein the anti-LAG-3 sdAb comprises: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; or (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223, and a pharmaceutically acceptable carrier. In some embodiments, the anti-LAG-3 sdAb comprises a $V_HH$ domain comprising the amino acid sequence of any one of SEQ ID NOs: 274-311. In some embodiments, the anti-LAG-3 sdAb comprises a $V_HH$ domain comprising the amino acid sequence of any one of SEQ ID NOs: 288, 295, 304, or 306. In some embodiments, the anti-LAG-3 sdAb is fused to the Fc fragment via a peptide linker. In some embodiments, the anti-LAG-3 HCAb is monomeric. In some embodiments, the anti-LAG-3 HCAb is dimeric. In some embodiments, the Fc fragment is a human IgG1 Fc, effectorless human IgG1 Fc, hIgG2 Fc, human IgG4 Fc, or hIgG4 Fc (S228P).

In some embodiments, there is provided a method of treating a LAG-3-related disease (e.g., cancer, such as colon cancer) in an individual, comprising administering to the individual an effective amount of a pharmaceutical composition comprising an isolated anti-LAG-3 construct (e.g., MABP or BABP) comprising: (a) a first antigen binding portion comprising an anti-LAG-3 sdAb comprising a CDR1 comprising the amino acid sequence of any one of SEQ ID NOs: 39-76, or a variant thereof comprising up to about 3 (such as about any of 1, 2, or 3) amino acid substitutions; a CDR2 comprising the amino acid sequence of any one of SEQ ID NOs: 115-152, or a variant thereof comprising up to about 3 (such as about any of 1, 2, or 3) amino acid substitutions; and a CDR3 comprising the amino acid sequence of any one of SEQ ID NOs: 191-228, or a variant thereof comprising up to about 3 (such as about any of 1, 2, or 3) amino acid substitutions, and (b) a second antigen binding portion that specifically binds a second epitope (e.g., an immune checkpoint inhibitor, such as PD-1), wherein the first antigen binding portion and the second antigen binding portion are fused to each other; and a pharmaceutically acceptable carrier. In some embodiments, there is provided a method of treating a LAG-3-related disease (e.g., cancer, such as colon cancer) in an individual, comprising administering to the individual an effective amount of a pharmaceutical composition comprising an isolated anti-LAG-3 construct (e.g., MABP or BABP) comprising: (a) a first antigen binding portion comprising an anti-LAG-3 sdAb comprising: (1) a CDR1 comprising the amino acid sequence of SEQ ID NO: 53; a CDR2 comprising the amino acid sequence of SEQ ID NO: 129; and a CDR3 comprising the amino acid sequence of SEQ ID NO: 205; (2) a CDR1 comprising the amino acid sequence of SEQ ID NO: 60; a CDR2 comprising the amino acid sequence of SEQ ID NO: 136; and a CDR3 comprising the amino acid sequence of SEQ ID NO: 212; (3) a CDR1 comprising the amino acid sequence of SEQ ID NO: 69; a CDR2 comprising the amino acid sequence of SEQ ID NO: 145; and a CDR3 comprising the amino acid sequence of SEQ ID NO: 221; (4) a CDR1 comprising the amino acid sequence of SEQ ID NO: 71; a CDR2 comprising the amino acid sequence of SEQ ID NO: 147; and a CDR3 comprising the amino acid sequence of SEQ ID NO: 223, (5) a CDR1 comprising the amino acid sequence of SEQ ID NO: 43; a CDR2 comprising the amino acid sequence of SEQ ID NO: 119; and a CDR3 comprising the amino acid sequence of SEQ ID NO: 195, and (b) a second antigen binding portion that specifically binds a second epitope (e.g., an immune checkpoint inhibitor, such as PD-1), wherein the first antigen binding portion and the second antigen binding portion are fused to each other; and a pharmaceutically acceptable carrier. In some embodiments, the second epitope is from an immune checkpoint molecule, such as PD-1, 4-1BB, PD-L1, TIM-3, TIGIT, CTLA-4, VISTA, B7-1, B7-H3, CD47, OX40 or GITR. In some embodiments, the first antigen binding portion is fused to the second antigen binding portion at the N-terminus of the heavy chain, the N-terminus of the light chain, the N-terminus of the Fc region, the C-terminus of the heavy chain, or the C-terminus of the light chain. In some embodiments, the second antigen binding portion comprises a Fab or an scFv. In some embodiments, the second antigen binding portion comprises a full-length 4-chain antibody consisting of two heavy chains and two light chains. In some embodiments, the second antigen binding portion comprises an anti-PD-1 full-length antibody (e.g., pembrolizumab or PD1-BM-min) or antigen binding fragment thereof. In some embodiments, the anti-PD-1 full-length antibody or antigen binding fragment thereof (e.g., Fab, scFv) comprises a $V_H$ comprising HC-CDR1, HC-CDR2, and HC-CDR3 of the amino acid sequence of SEQ ID NO: 356, and a $V_L$ comprising LC-CDR1, LC-CDR2, and LC-CDR3 of the amino acid sequence of SEQ ID NO: 357. In some embodiments, the $V_H$ comprises HC-CDR1, HC-CDR2, and HC-CDR3 of the amino acid sequence of SEQ ID NO: 373, and $V_L$ comprises LC-CDR1, LC-CDR2, and LC-CDR3 of the amino acid sequence of SEQ ID NO: 374. In some embodiments, the anti-PD-1 full-length antibody comprises a heavy chain comprising the amino acid sequence of SEQ ID NO: 356, and a light chain comprising the amino acid sequence of SEQ ID NO: 357. In some embodiments, the anti-PD-1 full-length antibody comprises a heavy chain comprising the amino acid sequence of SEQ ID NO: 373, and a light chain comprising the amino acid sequence of SEQ ID NO: 374. In some embodiments, the first antigen binding portion is fused to the second antigen binding portion via a peptide linker. In some embodiments, the second antigen binding fragment comprises an Fc region, such as an IgG1 Fc, effectorless IgG1 Fc, IgG2 Fc, IgG4 Fc, or IgG4 Fc (S228P). In some embodiments, the anti-LAG-3 construct comprises a first polypeptide comprising the amino acid sequence of SEQ ID NO: 358, and a second polypeptide comprising the amino acid sequence of SEQ ID NO: 359. In some embodiments, the anti-LAG-3 construct comprises a first polypeptide comprising the amino acid sequence of SEQ ID NO: 362, and a second polypeptide comprising the amino acid sequence of SEQ ID NO: 363. In some embodiments, the anti-LAG-3 construct comprises a first polypeptide comprising the amino acid sequence of SEQ ID NO: 381, and a second polypeptide comprising the amino acid sequence of SEQ ID NO: 382.

In some embodiments, the method of treating cancer has one or more of the following biological activities: (1) killing cancer cells (including bystander killing); (2) inhibiting proliferation of cancer cells; (3) inducing immune response in a tumor; (4) reducing tumor size; (5) alleviating one or more symptoms in an individual having cancer; (6) inhibiting tumor metastasis; (7) prolonging survival; (8) prolonging time to cancer progression; and (9) preventing, inhibiting, or reducing the likelihood of the recurrence of a cancer. In some embodiments, the method of killing cancer cells mediated by the pharmaceutical composition described herein can achieve a tumor cell death rate of at least about any of 40%, 50%, 60%, 70%, 80%, 90%, 95%, or more. In some embodiments, the method of reducing tumor size mediated by the pharmaceutical composition described herein can reduce at least about 10% (including for example at least about any of 20%, 30%, 40%, 60%, 70%, 80%, 90%, or 100%) of the tumor size. In some embodiments, the method of inhibiting tumor metastasis mediated by the pharmaceutical composition described herein can inhibit at least about 10% (including for example at least about any of 20%, 30%, 40%, 60%, 70%, 80%, 90%, or 100%) of the metastasis. In some embodiments, the method of prolonging survival of an individual (such as a human) mediated by the pharmaceutical composition described herein can prolongs the survival of the individual by at least any of 1, 2, 3, 4, 5, 6, 7, 8, 9, 10, 11, 12, 18, or 24 months. In some embodiments, the method of prolonging time to cancer progression mediated by the pharmaceutical composition described herein can prolongs the time to cancer progression by at least any of 1, 2, 3, 4, 5, 6, 7, 8, 9, 10, 11, or 12 weeks. In some embodiments, the method of treating immune-related disease can increase, enhance, or stimulate an immune response or function in a subject. In some embodiments, the immune response or function is increased, enhanced, and/or stimulated by activating effector cells (e.g., T cells, e.g., CD8+ and/or CD4+ T cells), expanding (increasing) an effector cell population, and/or killing target cells (e.g., target tumor cells) in the subject. In some embodiments, the CD4 and/or CD8 T cells in the individual have increased or enhanced priming, activation, proliferation, cytokine release and/or cytolytic activity relative to prior to the administration of the pharmaceutical composition comprising the anti-LAG-3 construct described herein.

The methods described herein are suitable for treating a variety of cancers, including both solid cancer and liquid cancer. The methods are applicable to cancers of all stages, including early stage cancer, non-metastatic cancer, primary cancer, advanced cancer, locally advanced cancer, metastatic cancer, or cancer in remission. The methods described herein may be used as a first therapy, second therapy, third therapy, or combination therapy with other types of cancer therapies known in the art, such as surgery, radiation, chemotherapy, immunotherapy, hormone therapy, or a combination thereof. In some embodiments, the method is used to treat an individual who has previously been treated. In some embodiments, the cancer has been refractory to prior therapy. In some embodiments, the method is used to treat an individual who has not previously been treated. In some embodiments, the cancer is partially resistant to immune checkpoint inhibitor monotherapy (e.g., partially resistant to anti-PD-1 antibody monotherapy treatment).

Dosages and desired drug concentrations of pharmaceutical compositions of the present application may vary depending on the particular use envisioned. The determination of the appropriate dosage or route of administration is well within the skill of an ordinary artisan Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

When in vivo administration of the anti-LAG-3 construct described herein (such as anti-LAG-3 sdAb, anti-LAG-3 HCAb, anti-LAG-3 MABP) are used, normal dosage amounts may vary from about 10 ng/kg up to about 100 mg/kg of mammal body weight depending upon the route of administration. It is within the scope of the present application that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

In some embodiments, the pharmaceutical composition is administered for a single time (e.g. bolus injection). In some embodiments, the pharmaceutical composition is administered for multiple times (such as any of 2, 3, 4, 5, 6, or more times). If multiple administrations, they may be performed by the same or different routes and may take place at the same site or at alternative sites. The pharmaceutical composition may be administered daily to once per year. The interval between administrations can be about any one of 24 h to a year. Intervals can also be irregular (e.g. following tumor progression). In some embodiments, there is no break in the dosing schedule. The optimal dosage and treatment regime for a particular patient can readily be determined by one skilled in the art of medicine by monitoring the patient for signs of disease and adjusting the treatment accordingly.

The pharmaceutical compositions of the present application, including but not limited to reconstituted and liquid formulations, are administered to an individual in need of treatment, preferably a human, in accord with known methods, such as intravenous administration as a bolus or by continuous infusion over a period of time, by intramuscular, intraperitoneal, intracerobrospinal, subcutaneous, intravenous (i.v.), intra-articular, intrasynovial, intrathecal, oral, topical, or inhalation routes. A reconstituted formulation can be prepared by dissolving a lyophilized anti-LAG-3 construct described herein in a diluent such that the protein is dispersed throughout. Exemplary pharmaceutically acceptable (safe and non-toxic for administration to a human) diluents suitable for use in the present application include, but are not limited to, sterile water, bacteriostatic water for injection (BWFI), a pH buffered solution (e.g. phosphate-buffered saline), sterile saline solution, Ringer's solution or dextrose solution, or aqueous solutions of salts and/or buffers.

In some embodiments, the pharmaceutical compositions are administered to the individual by subcutaneous (i.e. beneath the skin) administration. For such purposes, the pharmaceutical compositions may be injected using a syringe. However, other devices for administration of the pharmaceutical compositions are available such as injection devices; injector pens; auto-injector devices, needleless devices; and subcutaneous patch delivery systems. In some embodiments, the pharmaceutical compositions are administered to the individual intravenously. In some embodiments, the pharmaceutical composition is administered to an individual by infusion, such as intravenous infusion. Infusion techniques for immunotherapy are known in the art (see, e.g., Rosenberg et al., New Eng. J. of Med. 319: 1676 (1988)).

V. Methods of Preparation

The anti-LAG-3 construct described herein (such as anti-LAG-3 sdAb, anti-LAG-3 HCAb, anti-LAG-3 MABP) may be prepared using any methods known in the art or as described herein. Also see Examples 1-3. In some embodiments, there is provided a method of producing an anti-LAG-3 construct, comprising: (a) culturing a host cell comprising an isolated nucleic acid or vector encoding the anti-LAG-3 construct described herein under conditions effective to express the encoded anti-LAG-3 construct; and (b) obtaining the expressed anti-LAG-3 construct from said host cell. In some embodiments, the method of step (a) further comprises producing a host cell comprising the isolated nucleic acid or vector encoding the anti-LAG-3 construct described herein.

Methods of preparing sdAbs have been described. See, for example, Els Pardon et al., Nature Protocol, 2014; 9(3): 674. sdAbs (such as $V_HHs$) may be obtained using methods known in the art such as by immunizing a Camelid species (such as camel or llama) and obtaining hybridomas therefrom, or by cloning a library of single-domain antibodies using molecular biology techniques known in the art and subsequent selection by ELISA with individual clones of unselected libraries or by using phage display.

For recombinant production of the sdAbs, the nucleic acids encoding the single-domain antibodies are isolated and inserted into a replicable vector for further cloning (amplification of the DNA) or for expression. DNA encoding the single-domain antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. In some embodiments, the isolated nucleic acid encoding the anti-LAG-3 construct described herein comprises the nucleic acid sequence of any one of SEQ ID NOs: 267-273.

1. Recombinant Production in Prokaryotic Cells
a) Vector Construction

Polynucleic acid sequences encoding the antibodies of the present application can be obtained using standard recombinant techniques. Desired polynucleic acid sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as GEM™-11 may be utilized in making a recombinant vector which can be used to transform susceptible host cells such as E. coli LE392.

The expression vector of the present application may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the present application. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the -galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleic acid sequences have been published, thereby enabling a skilled worker operably to ligate them to cistrons encoding the target light and heavy chains (Siebenlist et al. (1980) *Cell* 20: 269) using linkers or adaptors to supply any required restriction sites.

In one aspect, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In some embodiments of the present application, the signal sequences used in both cistrons of the expression system are STII signal sequences or variants thereof.

In some embodiments, the production of the anti-LAG-3 construct according to the present application can occur in the cytoplasm of the host cell, and therefore does not require the presence of secretion signal sequences within each cistron. In some embodiments, polypeptide components, such as the polypeptide encoding the $V_H$ domain of the second antigen binding portion optionally fused to the first antigen binding portion, and the polypeptide encoding the $V_L$ domain of the second antigen binding portion optionally fused to the first antigen binding portion, are expressed, folded and assembled to form functional antibodies within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun *Gene*, 159:203 (1995).

The present invention provides an expression system in which the quantitative ratio of expressed polypeptide components can be modulated in order to maximize the yield of secreted and properly assembled the antibodies of the present application. Such modulation is accomplished at least in part by simultaneously modulating translational strengths for the polypeptide components. One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleic acid sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

Preferably, a set of vectors is generated with a range of TIR strengths for each cistron therein. This limited set provides a comparison of expression levels of each chain as well as the yield of the desired protein products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the present application.

b) Prokaryotic Host Cells

Prokaryotic host cells suitable for expressing the antibodies of the present application include Archaebacteria and Eubacteria, such as Gram-negative or Gram-positive organisms. Examples of useful bacteria include *Escherichia* (e.g., *E. coli*), *Bacilli*(e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. In some embodiments, gram-negative cells are used. In some embodiments, *E. coli* cells are used as hosts for the invention. Examples of *E. coli* strains include strain W3110 (Bachmann, *Cellular and Molecular Biology,* vol. 2 (Washington, D.C.: American Society for Microbiology, 1987), pp. 1190-1219; ATCC Deposit No. 27,325) and derivatives thereof, including strain 33D3 having genotype W3110 AfhuA (AtonA) ptr3 lac Iq lacL8 AompT A(nmpc-fepE) degP41 kan$^R$ (U.S. Pat. No. 5,639,635). Other strains and derivatives thereof, such as *E. coli* 294 (ATCC 31,446), *E. coli* B, *E. coli* 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., *Proteins,* 8:309-314 (1990). It is generally necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon.

Typically the host cell should secrete minimal amounts of proteolytic enzymes, and additional protease inhibitors may desirably be incorporated in the cell culture.

c) Protein Production

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the antibodies of the present application are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol. The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the present application, protein expression is induced under conditions suitable for the activation of the promoter. In one aspect of the present application, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

The expressed anti-LAG-3 construct of the present application are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Alternatively, protein production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

During the fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the antibodies of the present application, various fermentation conditions can be modified. For example, to improve the proper assembly and folding of the secreted polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance*, 2:63-72 (1996).

*E. coli* strains deficient for proteolytic enzymes and transformed with plasmids overexpressing one or more chaperone proteins may be used as host cells in the expression system encoding the antibodies of the present application.

d) Protein Purification

The anti-LAG-3 construct produced herein are further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In some embodiments, Protein A immobilized on a solid phase is used for immunoaffinity purification of the antibodies comprising an Fc region of the present application. Protein A is a 411(D cell wall protein from *Staphylococcus aureas* which binds with a high affinity to the Fc region of antibodies. Lindmark et al (1983) *J. Immunol. Meth.* 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants. The solid phase is then washed to remove contaminants non-specifically bound to the solid phase. Finally the antibodies of interest are recovered from the solid phase by elution.

2. Recombinant Production in Eukaryotic Cells

For eukaryotic expression, the vector components generally include, but are not limited to, one or more of the following, a signal sequence, an origin of replication, one or more marker genes, and enhancer element, a promoter, and a transcription termination sequence.

a) Signal Sequence Component

A vector for use in a eukaryotic host may also an insert that encodes a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibodies of the present application.

b) Origin of Replication

Generally, the origin of replication component is not needed for mammalian expression vectors (the SV40 origin may typically be used only because it contains the early promoter).

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid encoding the antibodies of the present application, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with the polypeptide encoding-DNA sequences, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

d) Promoter Component

Expression and cloning vectors usually contain a promoter that is recognized by the host organism and is operably linked to the nucleic acid encoding the desired polypeptide sequences. Virtually all eukaryotic genes have an AT-rich region located approximately 25 to 30 based upstream from the site where transcription is initiated. Another sequence found 70 to 80 bases upstream from the start of the transcription of many genes is a CNCAAT region where N may be any nucleotide. At the 3' end of most eukaryotic is an AATAAA sequence that may be the signal for addition of the poly A tail to the 3' end of the coding sequence. All of these sequences may be inserted into eukaryotic expression vectors.

Other promoters suitable for use with prokaryotic hosts include the phoA promoter, -lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibodies.

Polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of a DNA encoding the antibodies of the present application by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (100-270 bp), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the polypeptide encoding sequence, but is preferably located at a site 5' from the promoter.

f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the polypeptide-encoding mRNA. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibodies production and cultured in conventional nutrient media modified as appropriate for inducing promoters, selecting transformants, or amplifying the genes encoding the desired sequences.

h) Culturing the Host Cells

The host cells used to produce the antibodies of the present application may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMY-CIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

i) Protein Purification

When using recombinant techniques, the antibodies can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify the antibodies that are based on human immunoglobulins containing 1, 2, or 4 heavy chains (Lindmark et al., *J. Immunol. Meth.* 62:1-13 (1983)). Protein G is recommended for all mouse isotypes and for human 3 (Guss et al., *EMBO J.* 5:15671575 (1986)). The matrix to which the affinity ligand is attached is most often agarose, but other matrices are available. Mechanically stable matrices such as controlled pore glass or poly(styrene-divinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEP-HAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

3. Polyclonal Antibodies

Polyclonal antibodies are generally raised in animals by multiple subcutaneous (s.c.) or intraperitoneal (i.p.) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the antigen, immunogenic conjugates, or derivatives by combining, e.g., 100 μg or 5 μg or the protein or conjugate (for rabbits or mice, respectively) with 3 volumes of Freund's complete adjuvant and injecting the solution intradermally at multiple sites. One month later, the animals are boosted with ⅕ to 1/10 the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response. Also see Example 1 for immunization in Camels.

4. Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies. For example, the monoclonal antibodies may be made using the hybridoma method first described by Kohler et al., *Nature,* 256:495 (1975), or may be made by recombinant DNA methods (U.S. Pat. No. 4,816,567). In the hybridoma method, a mouse or other appropriate host animal, such as a hamster or a llama, is immunized as hereinabove described to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59-103 (Academic Press, 1986). Also see Example 1 for immunization in Camels.

The immunizing agent will typically include the antigenic protein or a fusion variant thereof. Generally either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice,* Academic Press (1986), pp. 59-103.

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassas, Va. USA. Human myeloma and mouse-human heteromyeloma cell lines also have been described for the production of human monoclonal antibodies (Kozbor, *J. Immunol.,* 133:3001 (1984); Brodeur et al., *Monoclonal Antibody Production Techniques and Applications,* pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.,* 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., Curr. Opinion in Immunol., 5:256-262 (1993) and Plückthun, Immunol. Revs. 130:151-188 (1992).

In a further embodiment, antibodies can be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nucl. Acids Res., 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Nati Acad. Sci. USA, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Also, see, Example 1 for monoclonal sdAb production.

5. Humanized Antibodies

Humanized forms of non-human (e.g., murine) antibodies are chimeric immunoglobulins, immunoglobulin chains or fragments thereof (such as Fv, Fab. Fab', F(ab')$_2$ or other antigen-binding subsequences of antibodies) which contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat, rabbit, camelid, or llama having the desired specificity, affinity, and capacity. In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin, and all or substantially all of the FR regions are those of a human immunoglobulin consensus sequence. In some embodiments, the humanized antibody will comprise at least a portion of an immunoglobulin constant region (Fc), typically that of a human immunoglobulin. See, e.g., Jones et al., Nature, 321: 522-525 (1986); Riechmann et al., Nature, 332: 323-329 (1988); Presta, Curr. Op. Struct. Biol., 2:593-596 (1992).

Methods for humanizing; non-human antibodies are well known in the art. Generally, a humanized antibody has one or more amino acid residues introduced into it from a source which is non-human. These non-human amino acid residues are often referred to as "import" residues, which are typically taken from an "import." variable domain. Humanization can be essentially performed following the method of Winter and co-workers, Jones et al., Nature 321:522-525 (1986); Riechmann et al., Nature 332:323-327 (1988); Verhoeyen et al., Science 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., J. Immunol., 151:2296 (1993); Chothia et al., J. Mol. Biol., 196:901 (1987). Another method uses a particular framework derived from the consensus sequence of all human antibodies of a particular subgroup of light or heavy chains. The same framework may be used for several different humanized antibodies. Carter et Proc. Natl. Acad. Sci. USA, 89:4285 (1992); Presta et al., J. Immunol., 151: 2623 (1993).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

In some embodiments, the sdAbs are modified, such as humanized, without diminishing the native affinity of the domain for antigen and while reducing its immunogenicity with respect to a heterologous species. For example, the amino acid residues of the antibody variable domain ($V_HH$) of an llama antibody can be determined, and one or more of the Camelidae amino acids, for example, in the framework regions, are replaced by their human counterpart as found in the human consensus sequence, without that polypeptide losing its typical character, i.e. the humanization does not significantly affect the antigen binding capacity of the resulting polypeptide. Humanization of Camelidae sdAbs requires the introduction and mutagenesis of a limited amount of amino acids in a single polypeptide chain. This is in contrast to humanization of scFv, Fab', (Fab')$_2$ and IgG, which requires the introduction of amino acid changes in two chains, the light and the heavy chain and the preservation of the assembly of both chains.

6. Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *PNAS USA*, 90:2551 (1993); Jakobovits et al., *Nature*, 362:255-258 (1993); Bruggemann et al., *Year in Immunol.*, 7:33 (1993); U.S. Pat. Nos. 5,545,806, 5,569,825, 5,591,669; 5,545,807; and WO 97/17852. Transgenic mice or rats capable of producing fully human sdAbs are known in the art. See, US20090307787A1, U.S. Pat. No. 8,754,287, US20150289489A1, US20100122358A1, and WO2004049794.

Alternatively. phage display technology can be used to produce human antibodies and antibody fragments in vitro, from immunoglobulin variable (V) domain gene repertoires from unimmunized donors. McCafferty et Nature 348:552-553 (1990); Hoogenboom and Winter, *J. Mol. Biol.* 227: 381 (1991). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Curr. Opin Struct. Biol.*, 3:564-571 (1993). Several sources of V-gene segments can be used for phage display. Clarkson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et at, *J. Mol. Biol.* 222:581-597 (1991), or Griffith et al., *EMBO J.* 12:725-734 (1993). See also, U.S. Pat. Nos. 5,565,332 and 5,573,905.

The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1): 86-95 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016, and Marks et al., Bio/Technology, 10: 779-783 (1992); Lonberg et al., *Nature*, 368: 856-859 (1994); Morrison, *Nature*, 368: 812-813 (1994); Fishwild et al., *Nature Biotechnology*, 14: 845-851 (1996); Neuberger, *Nature Biotechnology*, 14: 826 (1996); Lonberg and Huszar, *Intern. Rev. Immunol.*, 13: 65-93 (1995). For example, in some embodiments, human antibodies (e.g., human DAbs) can be generated by immunization of human HCAb mice. For example, HCAb (e.g., sdAb-Fc fusion proteins) can be produced by immunizing a transgenic mouse in which endogenous murine antibody expression has been eliminated and human transgenes have been introduced. HCAb mice are disclosed in U.S. Pat. Nos. 8,883,150, 8,921,524, 8,921,522, 8,507,748, 8,502,014, US2014/0356908, US2014/0033335, US2014/0037616, US2014/0356908, US2013/0344057, US2013/0323235, US2011/0118444, and US2009/0307787, all of which are incorporated herein by reference for all they disclose regarding heavy chain only antibodies and their production in transgenic mice. The HCAb mice are immunized and the resulting primed spleen cells fused with a murine myeloma cells to form hybridomas. The resultant HCAb can then be made fully human by replacing the murine CH2 and CH3 regions with human sequences.

Finally, human antibodies may also be generated by in vitro activated B cells (see U.S. Pat. Nos. 5,567,610 and 5,229,275) or by using various techniques known in the art, including phage display libraries (Hoogenboom and Winter, *J. Mol. Biol.*, 227:381 (1991); Marks et al., *J. Mol. Biol.*, 222:581 (1991).

VI. Articles of Manufacture and Kits

Further provided are kits and articles of manufacture comprising any of the isolated anti-LAG-3 constructs (such as anti-LAG-3 sdAb, anti-LAG-3 HCAb, anti-LAG-3 MABP), isolated nucleic acids or vectors encoding thereof, or isolated host cells comprising the isolated nucleic acids or vectors encoding the anti-LAG-3 constructs described herein. In some embodiments, a kit is provided which comprises any one of the pharmaceutical compositions described herein and preferably provides instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder (such as cancer) described herein, and may have a sterile access port (for example the container may be an intravenous solution bag or a vial having a stopper pierceable by a hypodermic injection needle). The label or package insert indicates that the composition is used for treating the particular condition in an individual. The label or package insert will further comprise instructions for administering the composition to the individual. The label may indicate directions for reconstitution and/or use. The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical composition and instructions for use, packaged in quantities sufficient for storage and use in pharmacies, for example, hospital pharmacies and compounding pharmacies.

EXAMPLES

The examples below are intended to be purely exemplary of the invention and should therefore not be considered to limit the invention in any way. The following examples and detailed description are offered by way of illustration and not by way of limitation.

Example 1: Generation of Anti-LAG-3 sdAbs

Immunization

Figure 1:
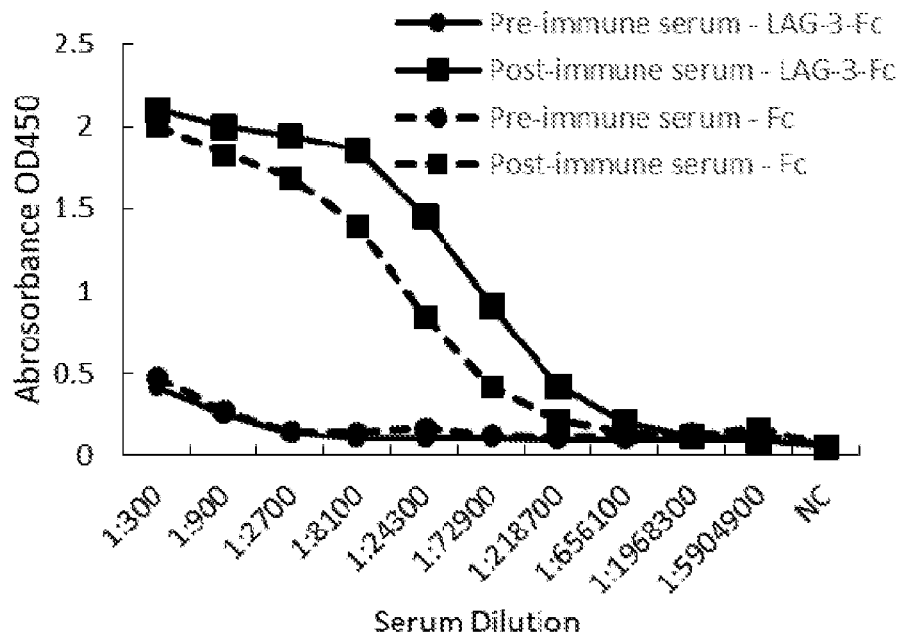
FIG. 1 depicts the evaluation of immune response against LAG3-Fc or Fc alone for pre-immune serum, and post-immune serum after final boost.
Figure 2:
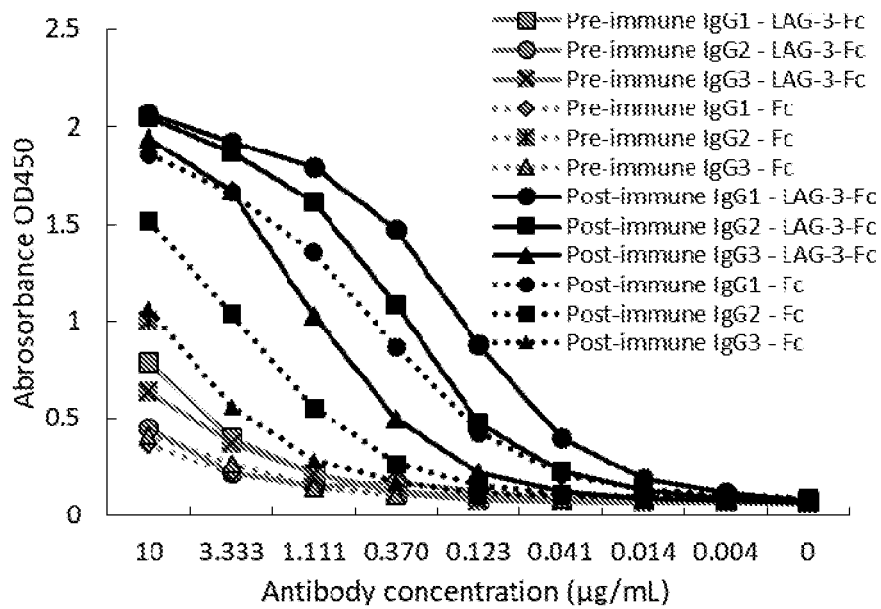
FIG. 2 depicts the evaluation of immune response against LAG3-Fc or Fc alone for regular antibodies (IgG1) and heavy chain antibodies (IgG2 and IgG3) in post-immune serum after final boost. Corresponding immunoglobulin fragments isolated from pre-immune serum were used as controls.

Camels were immunized with recombinant LAG-3-His and LAG-3-Fc (Acrobiosystems and R&D Systems) proteins and CHO-K1 cells expressing human LAG-3 (CHO-huLAG-3 cells), all under current animal welfare regulations. For immunization, the antigen was formulated as an emulsion with CFA (Complete Freund's adjuvant; primary immunization) or IFA (incomplete Freund's adjuvant; boost immunizations). The antigen was administered subcutaneously at the neck. Each animal received 5 injections of 100 µg of LAG-3-His in CFA emulsion, and 5 subsequent injections of LAG-3-Fc in IFA emulsion, at two-week intervals. Subsequently, two boosts with CHO-huLAG-3 cells and two boosts with LAG-3 protein were performed. At various time points during the immunization schedule, 10 mL blood samples were collected from the animals and sera were prepared. The induction of an antigen specific humoral immune response was verified using the serum samples in an ELISA-based assay with immobilized LAG-3-Fc protein or Fc protein as a control (FIG. 1 and FIG. 2). Although antibodies against Fc protein were detected, the observed antibody binding to LAG-3-Fc was even stronger, thereby showing an adequate elicitation of response against LAG-3 protein. In particular, heavy chain immunoglobulins (HCAbs) against LAG-3 protein were detected. Five days after the last immunization, a blood sample of 300 mL was collected from each animal Peripheral blood lymphocytes (PBLs), as the genetic source of the camel HCAbs, were isolated from this 300 mL blood sample using a FICOLL®-Paque gradient (Amersham Biosciences), yielding $1\times10^9$ PBLs.

Library Construction

RNA extracted from PBLs was used as starting material for RT-PCR to amplify sdAb encoding gene fragments. These fragments were cloned into an in-house phagemid vector. The vector coded for a C-terminal His-Tag in frame with the sdAb coding sequence. The library size is around $6\times10^8$ bp. The library phage was prepared according to a standard protocol, filter sterilized, and stored at 4° C. for further use.

Selections and High-Throughput Screening

Selections were carried out with on above libraries using solid panning as well as cell-based panning Only a single round of selection was performed for both conditions. Each selection output was analyzed for enrichment factor (# of phage present in eluate relative to control), as well as diversity and percentage of LAG-3 positive clones (ELISA). Based on these parameters the best selections were chosen for further analysis. To this end, the output from each selection was recloned as a pool into a soluble expression vector for high-throughput screening. The vector coded for a C-terminal His-Tag in frame with the sdAb coding sequence. Colonies were picked and grown in 96 deep well plates (in 1 mL volume); sdAb expression and release into supernatant was induced by adding IPTG and 0.1% Triton to the colonies.

The contents in the supernatant were analyzed for their ability to bind to LAG-3 protein (by ELISA) and LAG-3-expressing CHO-K1 stable cell line (by FACS). The positive binders were sequenced and the unique clones were selected for further characterization.

The unique clones were grown in 2×YT medium; sdAb expression and release into supernatant was induced by adding IPTG to the clones. The supernatants containing unique binders were analyzed for their ability to inhibit the interaction between MHC II and LAG-3. To this end, A375 melanoma cells, which express MHC II, were incubated with the sdAb-containing supernatant and biotinylated LAG-3-Fc, followed by incubation with fluorophore-labelled strepatavidin. A shift in mean fluorescent intensity (MFI) as compared to samples without anti-LAG-3 sdAb blockade represents an inhibition of the MHC II/LAG-3 interaction.

All potential inhibitors were selected for $K_D$ analysis by surface plasmon resonance (SPR) on a BIACORE™ T200 instrument. The dissociation phase was used to calculate the $k_{off}$ values for each individual sdAb.

Example 2: Preparation and in vitro Evaluation of Non-Humanized Anti-LAG-3 sdAb-Fc Fusion Proteins Production of sdAb-Fc Fusion Protein The anti-LAG-3 sdAb-Fc fusion protein constructs were generated by fusion of anti-LAG-3 sdAbs with a human IgG4 Fc region. The IgG4 Fc referred here carries a S228P mutation to prevent arm exchange. Maxipreps of the constructs were prepared for CHO-K1 cell transient expression and purification. The expressed anti-LAG-3 sdAb-Fc fusion proteins were purified by chromatography through a column containing Protein A agarose resins. Protein purity was determined by SEC-HPLC. An anti-LAG-3 monoclonal antibody generated by Bristol-Myers Squibb, BMS-986016, was produced according to the sequence in a published patent (See WO/2015/116539, SEQ ID NOs: 17 and 18; incorporated herein as SEQ ID NOs: 354 and 355 in the present application) on a human IgG4 backbone.

Target Protein Binding and Cross-Species Reaction Test by Surface Plasmon Resonance (SPR)

BIACORE™ T200 instrument was utilized to determine the affinity constant ($K_D$) of each anti-LAG-3 antibody (sdAb-Fc fusion protein or mAb format) by SPR. Briefly, anti-LAG-3 antibody was immobilized on the sensor chip through capture antibody (Jackson ImmunoResearch Cat. No. 115-005-071) at an appropriate density. Human or cynomolgus LAG-3 protein (Acrobiosystem, 772-6BGF2-D5 and 2187-71HF1-DZ, respectively) was injected at no less than 5 different concentrations. The data of dissociation rate constant ($k_{off}$) and association rate constant ($k_{on}$) were obtained using BIACORE™ T200 evaluation software and the affinity constant ($K_D$) were calculated from the ratio of $k_{off}$ to $k_{on}$. The kinetics data of several exemplary anti-LAG-3 antibodies were summarized in Table 2.

TABLE 2

Affinity determination of non-humanized anti-LAG-3 sdAb-Fc fusion proteins against LAG-3

| Target | Construct | $k_{on}$ (1/Ms) | $k_{off}$ (1/s) | $K_D$ (M) |
|---|---|---|---|---|
| Human LAG-3-His | AS20592-Fc | 2.1E+06 | 2.2E−04 | 1.1E−10 |
| | AS20594-Fc | 2.2E+06 | 2.4E−04 | 1.1E−10 |
| | AS20601-Fc | 4.4E+06 | 1.8E−04 | 4.2E−11 |
| | AS20846-Fc | 2.2E+06 | 1.5E−04 | 6.7E−11 |
| | BMS-986016 | 1.9E+06 | 1.1E−03 | 5.9E−10 |
| Cynomolgus LAG-3-Fc | AS20592-Fc | 4.5E+06 | 4.2E−04 | 9.3E−11 |
| | AS20594-Fc | 5.3E+06 | 2.8E−04 | 5.2E−11 |
| | AS20601-Fc | 1.2E+07 | 3.5E−03 | 2.9E−10 |
| | AS20846-Fc | 5.4E+06 | 2.2E−04 | 4.2E−11 |
| | BMS-986016 | 1.1E+07 | 2.0E−02 | 1.7E−09 |

Epitope Binning Test

Figure 3:
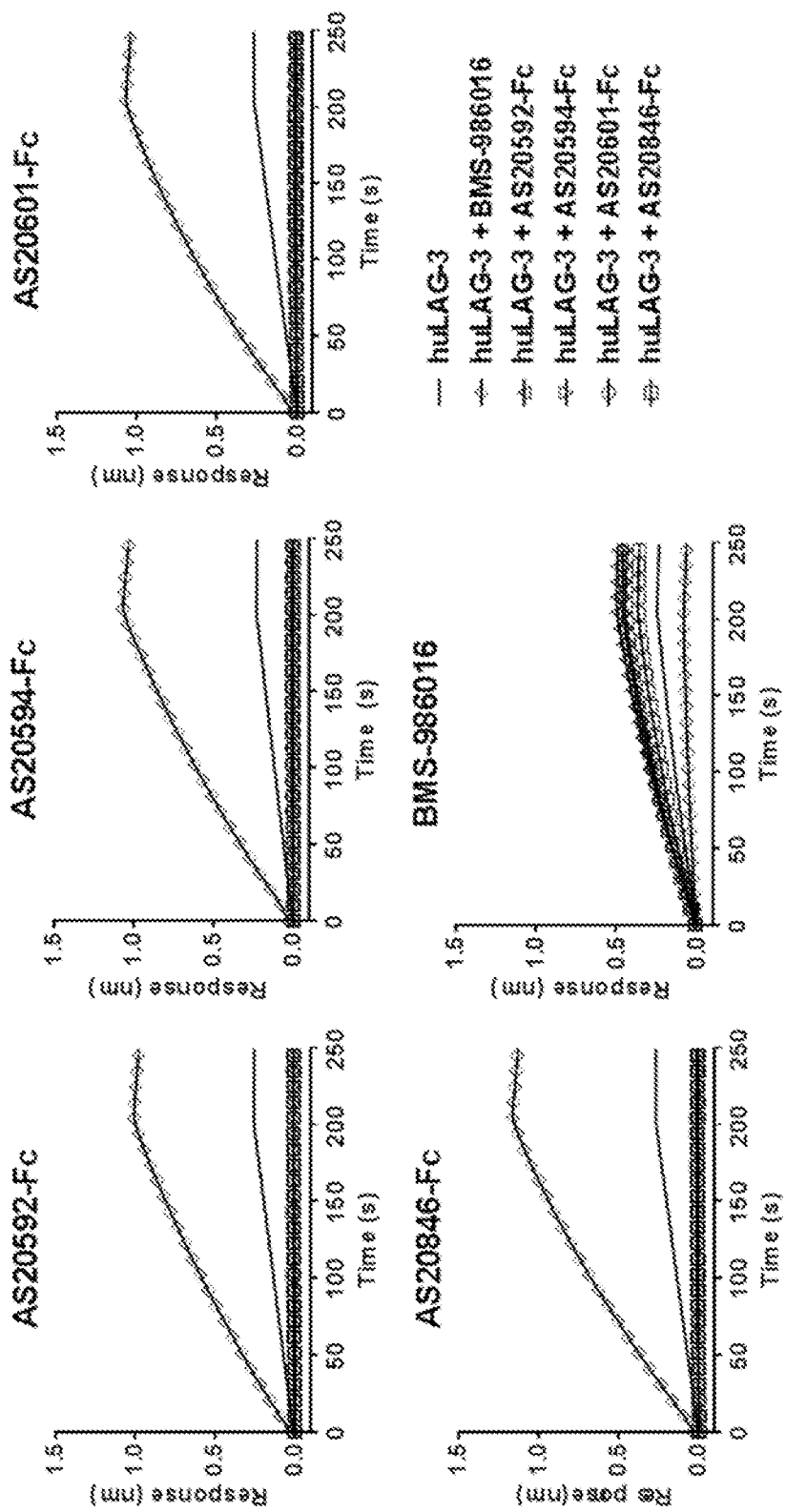
FIG. 3 depicts epitope a binning test for non-humanized anti-LAG-3 sdAb-Fc fusion proteins and the benchmark antibody, BMS-986016.

Epitope binning test was performed on an OCTET® RED96 instrument (ForteBio). All measurements were performed at 30° C. An sdAb-Fc fusion protein of interest was immobilized onto the biosensors using amine coupling method. Human LAG-3 protein was diluted in PBST buffer (1x PBS, pH 7.4, and 0.05% Tween-20) as used as analyte 1. A mixture of human LAG-3 (at the same concentration as in analyte 1) and a second LAG-3 binding entity (which could be a second sdAb-Fc fusion protein or benchmark antibody BMS-986016) was used as analyte 2. The coated biosensors were first dipped into analyte 1, and after regeneration and equilibration, into analyte 2. The sensorgrams of analyte 1 (i.e., curve for human LAG-3 alone) and analyte 2 (i.e., curves for human LAG-3+ second LAG-3 binding entity) were compared to determine binding competition by the sdAb-Fc fusion protein of interest. Binning results are shown in FIG. 3. None of the 4 non-humanized sdAb-Fc fusion proteins tested competes with BMS-986016 for binding to human LAG-3 protein, while the 4 sdAb-Fc fusion proteins compete with one another, indicating that the sdAbs bind against a new epitope on LAG-3 different from the one targeted by the benchmark antibody BMS-986016.

CHO-huLAG-3 Cell Binding and Inhibition of Ligand Binding by FACS Analysis

Figure 4:
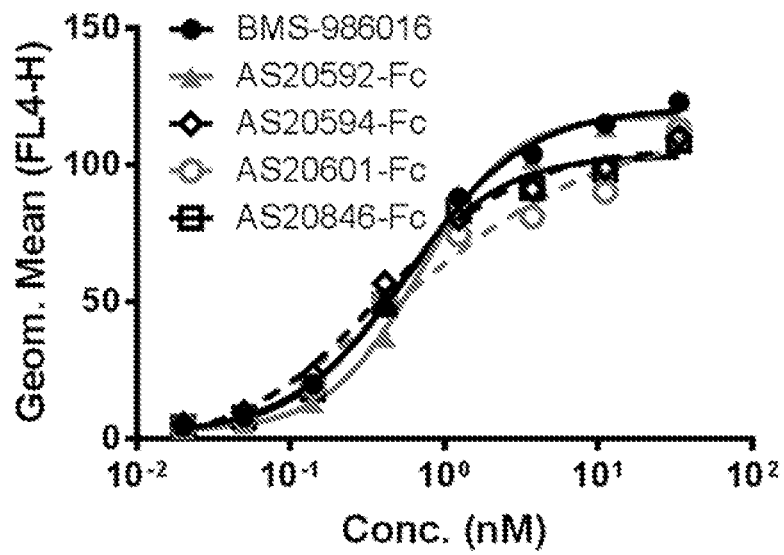
FIG. 4 depicts the binding of non-humanized anti-LAG-3 sdAb-Fc fusion proteins to CHO-K1 cells expressing human LAG-3, tested with FACS. BMS-986016 was used as a positive control.
Figure 5:
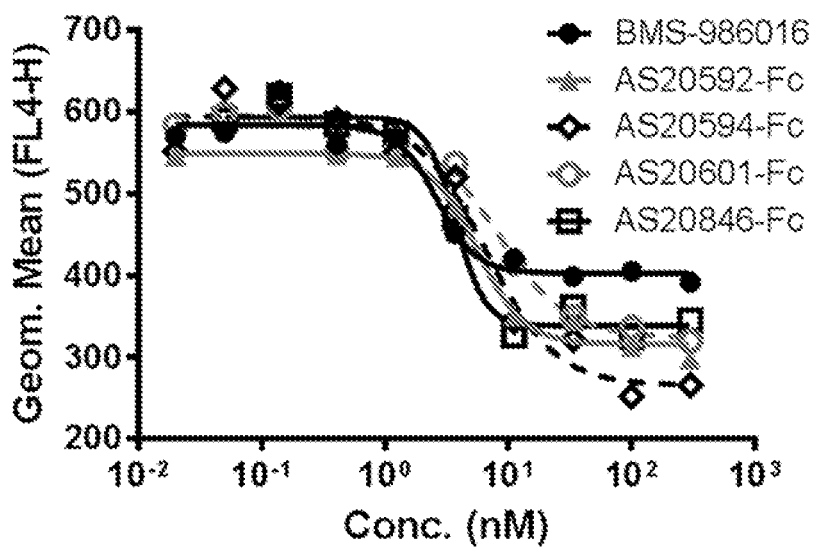
FIG. 5 depicts the blocking of interaction between MHC II and human LAG-3 by non-humanized anti-LAG-3 sdAb-Fc fusion proteins, as measured by flow cytometry. BMS-986016 was used as a positive control.

To determine cell binding $EC_{50}$, CHO-K1 cells expressing human or cynomolgus LAG-3 were harvested and incubated with anti-LAG-3 sdAb-Fc fusion proteins at gradient concentrations, followed by fluorophore-labeled secondary antibodies against human Fc. For blocking assay, anti-LAG-3 sdAb-Fc protein at gradient concentrations and biotinylated LAG-3-Fc protein at a fixed concentration were co-incubated with MHC II-expressing A375 melanoma cells. The binding of LAG-3-Fc to A375 cells was detected with fluorophore-labeled streptavidin. The samples were then analyzed with flow cytometry. The binding and blocking curves were shown in FIG. 4 and FIG. 5, respectively. EC50 of binding and blocking capabilities of the anti-LAG-3 sdAb-Fc fusion proteins were summarized in Table 3. The anti-LAG-3 sdAb-Fc fusion proteins had similar binding capabilities to human LAG-3 expressed on CHO cells, as compared to the positive control BMS-986016. In the cell blocking assay, although EC50 of the blocking curves of all anti-LAG-3 sdAb-Fc fusion proteins are higher than that of BMS-986016, it is notable that their spans of blocking curves are greater than that of BMS-986016, indicating that binding of sdAb-Fc fusion proteins against its specific epitope may block LAG-3's interaction with MHC II more completely than BMS-986016 does.

TABLE 3

Binding and blocking of ligand binding data of non-humanized anti-LAG-3 sdAb-Fc fusion proteins against LAG-3

| | Binding Assay EC50 (nM) | | Blocking Assay (Human) | |
|---|---|---|---|---|
| | Human | Cynomolgus | EC50 (nM) | Span |
| AS20592-Fc | 0.686 | 1.829 | 5.544 | 233.2 |
| AS20594-Fc | 0.390 | 1.024 | 6.584 | 328.2 |
| AS20601-Fc | 0.494 | 1.607 | 7.992 | 260.0 |
| AS20846-Fc | 0.462 | 1.230 | 3.723 | 354.9 |
| BMS-986016 | 0.590 | 17.55 | 2.634 | 181.3 |

Example 3: Humanization, Production and Characterization of Anti-LAG-3 sdAb-Fc Fusion Proteins Humanization of Anti-LAG-3 sdAbs Protein sequences of sdAb AS20592, AS20594, AS20601 and AS20846 were aligned with the 5 closest human germline sequences sharing the highest degree of homology. The best human germline sequences were selected as human acceptors, respectively. Homology models were then constructed. According to the model analysis data, residues potentially critical for antigen binding or antibody scaffold formation were left unaltered while the rest were selected for conversion into human counterparts. Initially a panel of four to six sequence optimized variants was generated (stage 1). These variants were analyzed for a number of parameters and the results obtained were used to design a second set of sdAbs (stage 2). The humanized sdAbs are indicated with "$V_H$" in their names.

Production of Humanized Anti-LAG-3 sdAb-Fc Fusion Proteins

Among humanized variants, AS20592VH10, AS20594VH10, AS20601VH4 and AS20846VH12 were selected for production and characterization according to affinity and small scale production level. The humanized anti-LAG-3 sdAb-Fc fusion protein constructs were generated by fusing humanized anti-LAG-3 sdAbs with the human IgG4 Fc region. Maxipreps of the constructs were prepared for HEK293 cell transient expression and purification. The expressed humanized anti-LAG-3 sdAb-Fc fusion proteins were purified by chromatography through a column containing Protein A agarose resins. Protein purity was determined by SEC-HPLC. Expression results were summarized in Table 4.

TABLE 4

Expression of humanized anti-LAG-3 sdAb-Fc fusion proteins

| Construct | Transient expression (mg/L) | Purity (%) | Endotoxin level (EU/mg) |
| --- | --- | --- | --- |
| AS20592VH10-Fc | 96.0 | 99.56 | 0.3 |
| AS20594VH10-Fc | 18.7 | 97.94 | 0.7 |
| AS20601VH4-Fc | 55.0 | 95.50 | 0.8 |
| AS20846VH12-Fc | 24.8 | 99.00 | 0.8 |

Target Protein binding and Cross-Species Reaction Test by Surface Plasmon Resonance (SPR)

BIACORE™ T200 instrument was utilized to determine affinity constant ($K_D$) of each anti-LAG-3 antibody (sdAb-Fc fusion protein or mAb format) by SPR. Briefly, for measuring the affinity against human LAG-3, anti-LAG-3 antibody was immobilized on the sensor chip through capture antibody (Jackson ImmunoResearch Cat. No. 115-005-071) at an appropriate density. Human LAG-3 protein (Acrobiosystem, 772-6BGF2-D5) was injected at no less than 5 different concentrations. For measuring the affinity against cynomolgus LAG-3, the cynomolgus LAG-3 protein (Acrobiosystem, 2187-71HF1-DZ) was immobilized on the sensor chip at an appropriate density and anti-LAG-3 antibodies were injected at no less than 5 different concentrations. The data of dissociation rate constant ($k_{off}$) and association rate constant ($k_{on}$) were obtained using BIACORE™ T200 evaluation software and the affinity constant ($K_D$) were calculated from the ratio of $k_{off}$ to $k_{on}$. The kinetics data of several exemplary anti-LAG-3 antibodies were summarized in Table 5.

TABLE 5

Affinity determination of humanized anti-LAG-3 sdAb-Fc fusion proteins

| Target | Construct | $k_{on}$ (1/Ms) | $k_{off}$ (1/s) | $K_D$ (M) |
| --- | --- | --- | --- | --- |
| Human LAG-3-His | AS20592VH10-Fc | 1.4E+06 | 6.5E−04 | 4.7E−10 |
| | AS20594VH10-Fc | 1.6E+06 | 7.9E−04 | 4.9E−10 |
| | AS20601VH4-Fc | 3.2E+06 | 3.3E−04 | 1.0E−10 |
| | AS20846VH12-Fc | 1.3E+06 | 6.0E−04 | 4.6E−10 |
| | BMS-986016 | 9.2E+05 | 7.0E−04 | 7.6E−10 |
| Cynomolgus LAG-3-Fc | AS20592VH10-Fc | 3.7E+04 | 1.5E−03 | 3.9E−08 |
| | AS20594VH10-Fc | 6.5E+04 | 3.3E−03 | 5.1E−08 |
| | AS20601VH4-Fc | 9.2E+04 | 7.0E−03 | 7.6E−08 |
| | AS20846VH12-Fc | 3.1E+04 | 1.5E−03 | 4.9E−08 |
| | BMS-986016 | 7.4E+04 | 7.5E−02 | 1.0E−06 |

LAG-3 Blockade Reporter Assay

Figure 6:
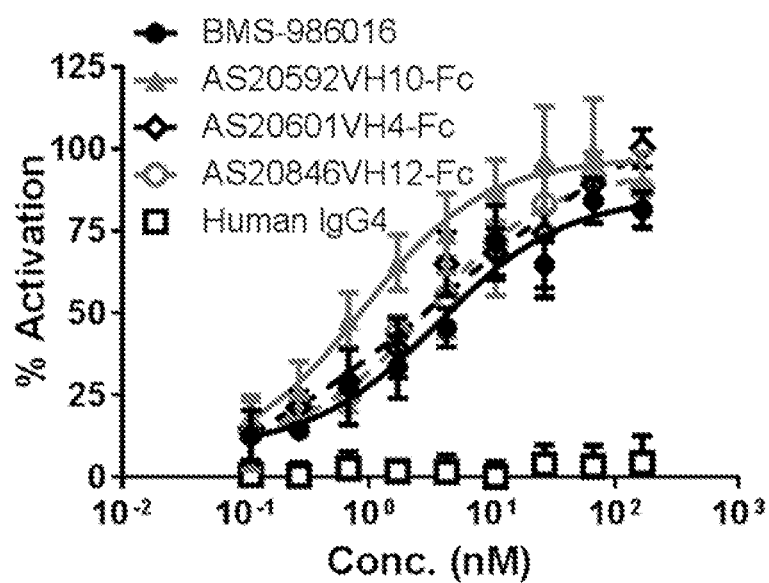
FIG. 6 depicts the in vitro functional blockade of LAG-3 by humanized anti-LAG-3 sdAb-Fc fusion proteins, measured with a reporter assay. BMS-986016 was used as a positive control and human IgG4 isotype control as a negative control.

LAG-3 blockade reporter assay was performed using Promega LAG-3 blockade reporter assay kit (Promega, Cat #CS194819), according to the vendor's protocol. Briefly, Thaw-and-Use MHC-II APC Cells (including TCR Activating Antigen) were plated overnight and then incubated with a serial dilution of anti-LAG-3 antibodies or anti-LAG-3 sdAb-Fc fusion proteins, followed by addition of Thaw-and-Use LAG-3 Effector cells. After 6 hours of induction at 37° C. and 5% $CO_2$, BIO-GLO™ Luciferase Assay Reagent was added, and luminescence was determined. Four-parameter logistic curve analysis was performed with GraphPad Prism 6 software. Data curves are shown in FIG. 6 and summarized in Table 6. AS20592VH10-Fc, AS20601VH4-Fc and AS20846VH12-Fc have comparable or superior functions to BMS-986016 in the LAG-3 blockade reporter assay. Notably, the signal spans, which are indicative of the level of inhibition, of the sdAb-Fc fusion proteins were all greater than that of the benchmark antibody BMS-986016, consistent with the findings in the previously described ligand blocking test.

TABLE 6

LAG-3 blockade reporter assay for humanized anti-LAG-3 sdAb-Fc fusion proteins

| Construct | EC50 (nM) | Signal span (% activation) |
| --- | --- | --- |
| AS20592VH10-Fc | 0.89 | 91.96 |
| AS20601VH4-Fc | 3.98 | 92.66 |
| AS20846VH12-Fc | 3.13 | 83.30 |
| BMS-986016 | 3.82 | 76.84 |

Example 4: Generation and Characterization of PD-1×LAG-3 BABPs

Construction of PD-1×LAG-3 BABPs

This example describes the construction of PD-1×LAG-3 BABPs.

BABPs can be constructed by fusing an anti-LAG-3 sdAb to a full-length antibody, or to a scFv or Fab region derived from the full-length antibody containing an Fc region at the C-terminus, such as anti-PD-1 antibodies, e.g., KEYTRUDA® (Pembrolizumab), OPDIVO® (nivolumab), or PD1-BM-min. The anti-LAG-3 sdAb can be connected to the full-length antibody (or scFv or Fab region derived from the full-length antibody with Fc region at the C-terminus) via a linker (such as 9-amino acid Gly/Ser linker (9GS linker), human IgG1 (hIgG1) hinge, or mutated hIgG1 hinge), or without a linker. In addition, a short peptide sequence can be fused to the N-terminus (see FIGS. 7, 9, 11 and 12) or C-terminus (see FIGS. 8 and 10) of an anti-LAG-3 sdAb. The BABP can be of any one of the configurations exemplified in FIGS. 7-16. For example, anti-LAG-3 sdAb can be fused to at least one of the heavy chains, at least one of the light chains, or both the heavy chains and light chains, via N- or C-terminus (see FIGS. 7-10).

As shown in Table 7 below, exemplary BABPs were generated. The anti-LAG-3 sdAb (AS20592VH10, AS20594VH10, AS20601VH4 or AS20846VH12) were fused to the N-terminus of the heavy chain, the C terminus of the heavy chain, the N-terminus of the light chain, or the C-terminus of the light chain of a full-length anti-PD-1 antibody (Pembrolizumab or PD1-BM-min) via a mutated human IgG1 (hIgG1) hinge as the linker, or without a linker. In some BABP constructs, an additional short peptide was added to the N-termini of the sdAbs.

TABLE 7

Exemplary PD-1 × LAG-3 constructs

Figure 7:
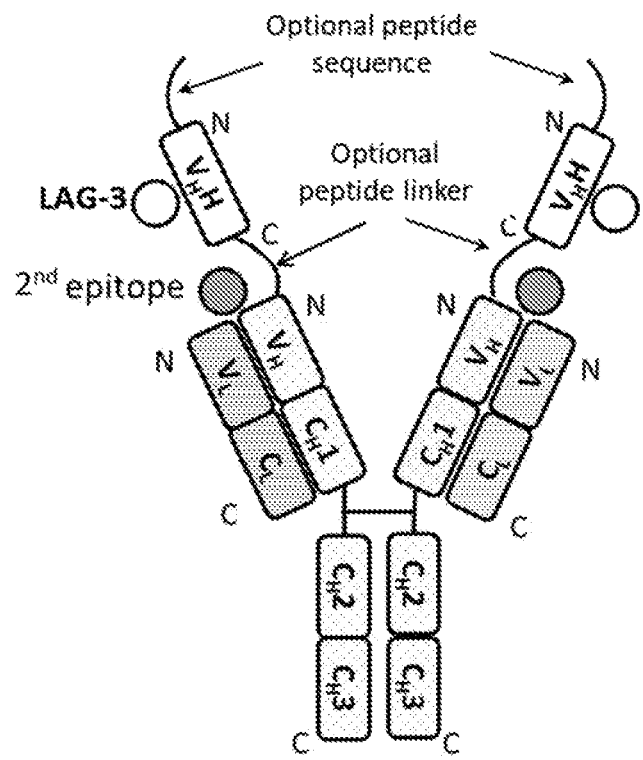
FIG. 7 depicts a schematic structure of an exemplary BABP comprising a monospecific full-length antibody having two identical heavy chains and two identical light chains, and two identical anti-LAG-3 sdAbs, wherein the C-terminus of each anti-LAG-3 sdAb is fused to the N-terminus of one heavy chain via an optional peptide linker. An optional peptide sequence can be fused to the N-terminus of each anti-LAG-3 sdAb. Each of the two anti-LAG-3 sdAbs specifically binds a first epitope (LAG-3). The full-length antibody has two antigen binding sites, each specifically binding a second epitope. For example, the BABP can consist of four polypeptide chains with structures from the N-terminus to the C-terminus as follows: (1) $V_L$-$C_L$; (2) $V_H$H-$V_H$-$C_H$1-$C_H$2-$C_H$3; (3) $V_H$H-$V_H$-$C_H$1-$C_H$2-$C_H$3; and (4) $V_L$-$C_L$, wherein $V_H$ and $V_L$ of polypeptide chains (1) and (2) form an antigen binding site that specifically binds a first copy of the second epitope, $V_H$ and $V_L$ of polypeptide chains (3) and (4) form an antigen binding site that specifically binds a second copy of the second epitope, and each $V_H$H specifically binds a copy of the first epitope (LAG-3). In alternative formats, each anti-LAG-3 sdAb may be omitted, or replaced with two identical or different anti-LAG-3 sdAbs fused to each other. The monospecific full-length antibody may be replaced with a bispecific full-length antibody to further expand binding specificity.
Figure 8:
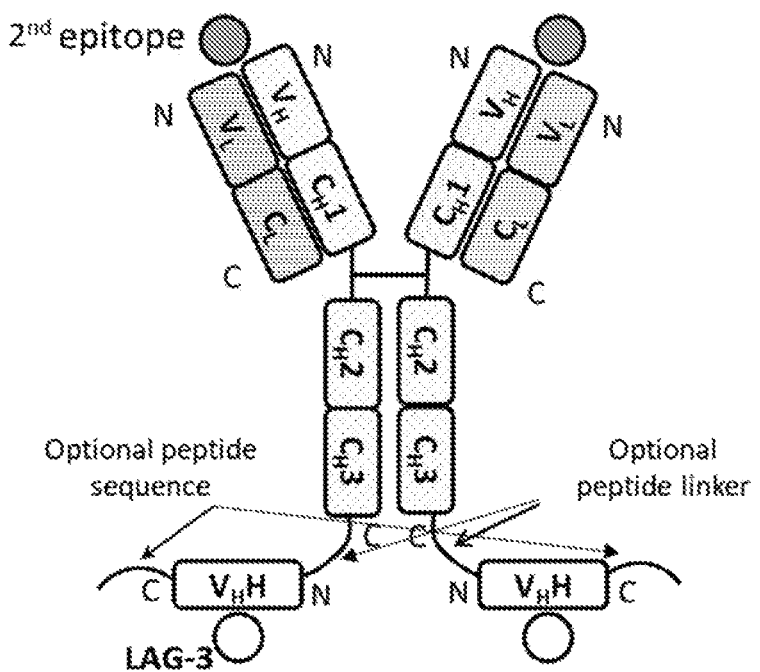
FIG. 8 depicts a schematic structure of an exemplary BABP comprising a monospecific full-length antibody having two identical heavy chains and two identical light chains, and two identical anti-LAG-3 sdAbs, wherein the N-terminus of each anti-LAG-3 sdAb is fused to the C-terminus of one heavy chain via an optional peptide linker. An optional peptide sequence can be fused to the C-terminus of each anti-LAG-3 sdAb. Each of the two anti-LAG-3 sdAbs specifically binds a first epitope (LAG-3). The full-length antibody has two antigen binding sites, each specifically binding a second epitope. For example, the BABP can consist of four polypeptide chains with structures from the N-terminus to the C-terminus as follows: (1) $V_L$-$C_L$; (2) $V_H$-$C_H$1-$C_H$2-$C_H$3-$V_H$H; (3) $V_H$-$C_H$1-$C_H$2-$C_H$3-$V_H$H; and (4) $V_L$-$C_L$, wherein $V_H$ and $V_L$ of polypeptide chains (1) and (2) form an antigen binding site that specifically binds a first copy of the second epitope, $V_H$ and $V_L$ of polypeptide chains (3) and (4) form an antigen binding site that specifically binds a second copy of the second epitope, and each $V_H$H specifically binds a copy of the first epitope (LAG-3). In alternative formats, each anti-LAG-3 sdAb may be omitted, or replaced with two identical or different anti-LAG-3 sdAbs fused to each other. The monospecific full-length antibody may be replaced with a bispecific full-length antibody to further expand binding specificity.
Figure 9:
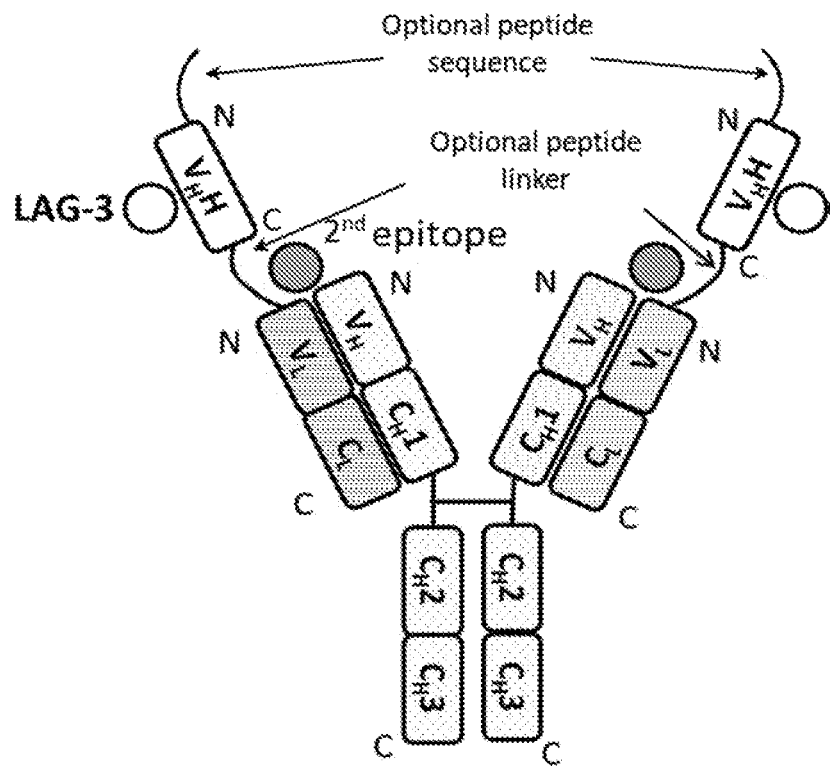
FIG. 9 depicts a schematic structure of an exemplary BABP comprising a monospecific full-length antibody having two identical heavy chains and two identical light chains, and two identical anti-LAG-3 sdAbs, wherein the C-terminus of each anti-LAG-3 sdAb is fused to the N-terminus of one light chain via an optional peptide linker. An optional peptide sequence can be fused to the N-terminus of each anti-LAG-3 sdAb. Each of the two anti-LAG-3 sdAbs specifically binds a first epitope (LAG-3). The full-length antibody has two antigen binding sites, each specifically binding a second epitope. For example, the BABP can consist of four polypeptide chains with structures from the N-terminus to the C-terminus as follows: (1) $V_H$H-$V_L$-$C_L$; (2) $V_H$-$C_H$1-$C_H$2-$C_H$3; (3) $V_H$-$C_H$1-$C_H$2-$C_H$3; and (4) $V_H$H-$V_L$-$C_L$, wherein $V_H$ and $V_L$ of polypeptide chains (1) and (2) form an antigen binding site that specifically binds a first copy of the second epitope, $V_H$ and $V_L$ of polypeptide chains (3) and (4) form an antigen binding site that specifically binds a second copy of the second epitope, and each $V_H$H specifically binds a copy of the first epitope (LAG-3). In alternative formats, each anti-LAG-3 sdAb may be omitted, or replaced with two identical or different anti-LAG-3 sdAbs fused to each other. The monospecific full-length antibody may be replaced with a bispecific full-length antibody to further expand binding specificity.
Figure 10:
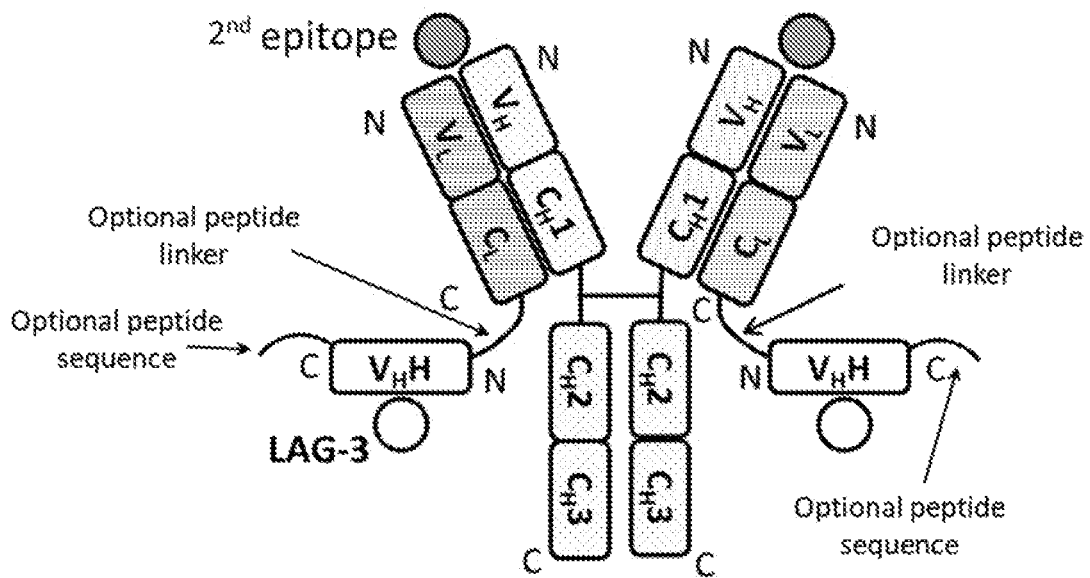
FIG. 10 depicts a schematic structure of an exemplary BABP comprising a monospecific full-length antibody having two identical heavy chains and two identical light chains, and two identical anti-LAG-3 sdAbs, wherein the N-terminus of each anti-LAG-3 sdAb is fused to the C-terminus of one light chain via an optional peptide linker. An optional peptide sequence can be fused to the C-terminus of each anti-LAG-3 sdAb. Each of the two anti-LAG-3 sdAbs specifically binds a first epitope. The full-length antibody has two antigen binding sites, each specifically binding a second epitope. For example, the BABP can consist of four polypeptide chains with structures from the N-terminus to the C-terminus as follows: (1) $V_L$-$C_L$-$V_H$H; (2) $V_H$-$C_H$1-$C_H$2-$C_H$3; (3) $V_H$-$C_H$1-$C_H$2-$C_H$3; and (4) $V_L$-$C_L$-$V_H$H, wherein $V_H$ and $V_L$ of polypeptide chains (1) and (2) form an antigen binding site that specifically binds a first copy of the second epitope, $V_H$ and $V_L$ of polypeptide chains (3) and (4) form an antigen binding site that specifically binds a second copy of the second epitope, and each $V_H$H specifically binds a copy of the first epitope (LAG-3). In alternative formats, each anti-LAG-3 sdAb may be omitted, or replaced with two identical or different anti-LAG-3 sdAbs fused to each other. The monospecific full-length antibody may be replaced with a bispecific full-length antibody to further expand binding specificity.
Figure 11:
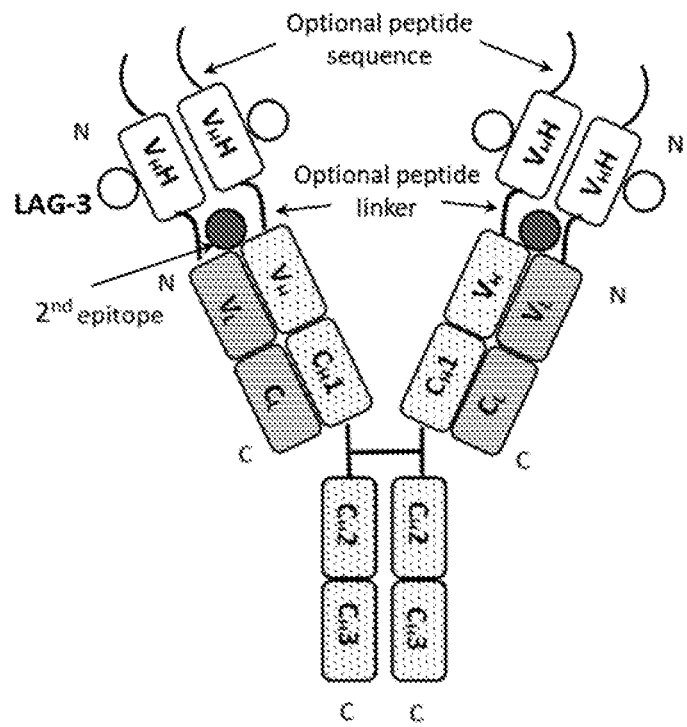
FIG. 11 depicts a schematic structure of an exemplary BABP comprising a monospecific full-length antibody having two identical heavy chains and two identical light chains, and four identical anti-LAG-3 sdAbs, wherein the C-terminus of each anti-LAG-3 sdAb is fused to the N-terminus of a heavy chain or a light chain of the monospecific full-length antibody via an optional peptide linker. An optional peptide sequence can be fused to the N-terminus of each anti-LAG-3 sdAb. Each anti-LAG-3 sdAb specifically binds to a first epitope (LAG-3). The full-length antibody has two antigen binding sites that each specifically binds a second epitope. For example, the BABP can consist of four polypeptide chains with structures from the N-terminus to the C-terminus as follows: (1) $V_HH-V_L-C_L$; (2) $V_HH-V_H-C_H1-C_H2-C_H3$; (3) $V_HH-V_H-C_H1-C_H2-C_H3$; and (4) $V_HH-V_L-C_L$, wherein $V_H$ and $V_L$ of polypeptide chains (1) and (2) form an antigen binding site that specifically binds a first copy of the second epitope, $V_H$ and $V_L$ of polypeptide chains (3) and (4) form an antigen binding site that specifically binds a second copy of the second epitope, and each $V_HH$ specifically binds a copy of the first epitope (LAG-3). In alternative formats, each anti-LAG-3 sdAb may be omitted, or replaced with two identical or different anti-LAG-3 sdAbs fused to each other. The monospecific full-length antibody may be replaced with a bispecific full-length antibody to further expand binding specificity.
Figure 12:
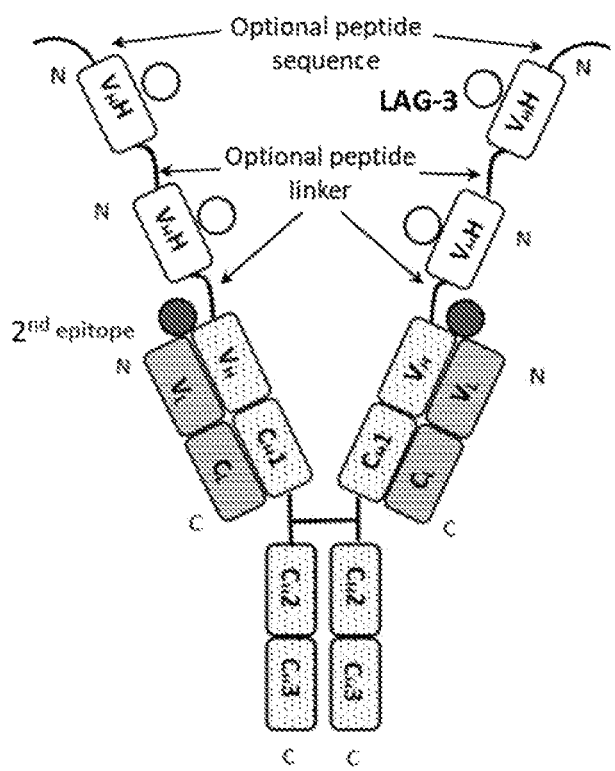
FIG. 12 depicts a schematic structure of an exemplary BABP comprising a monospecific full-length antibody having two identical heavy chains and two identical light chains, and four identical anti-LAG-3 sdAbs, wherein fused to the N-terminus of each heavy chain are two identical anti-LAG-3 sdAbs, the two anti-LAG-3 sdAbs being fused to each other via an optional peptide linker, and the two anti-LAG-3 sdAbs are fused to the N-terminus of each heavy chain via an optional peptide linker. An optional peptide sequence can be fused to the N-terminus of the chimeric heavy chain. Each anti-LAG-3 sdAb specifically binds a first epitope (LAG-3). The full-length antibody has two antigen binding sites that each specifically binds a second epitope. For example, the BABP can consist of four polypeptide chains with structures from the N-terminus to the C-terminus as follows: (1) $V_L-C_L$; (2) $V_HH-V_HH-V_H-C_H1-C_H2-C_H3$; (3) $V_HH-V_HH-V_H-C_H1-C_H2-C_H3$; and (4) $V_L-C_L$, wherein $V_H$ and $V_L$ of polypeptide chains (1) and (2) form an antigen binding site that specifically binds a first copy of the second epitope, $V_H$ and $V_L$ of polypeptide chains (3) and (4) form an antigen binding site that specifically binds a second copy of the second epitope, and each $V_HH$ specifically binds a copy of the first epitope (LAG-3). In alternative formats, each anti-LAG-3 sdAb may be omitted, or replaced with two identical or different anti-LAG-3 sdAbs fused to each other. The monospecific full-length antibody may be replaced with a bispecific full-length antibody to further expand binding specificity.
Figure 13:
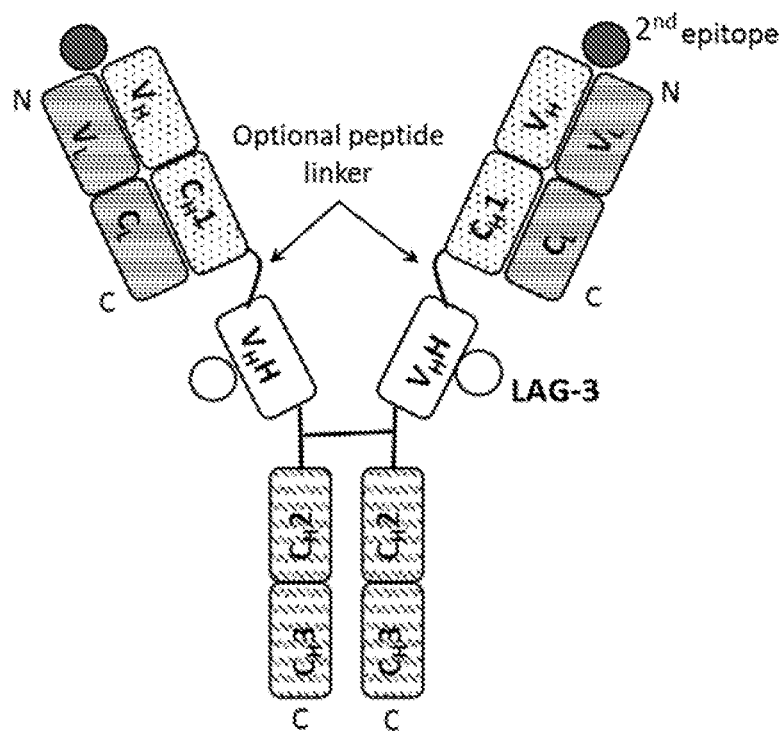
FIG. 13 depicts a schematic structure of an exemplary BABP comprising two identical antigen-binding (Fab) fragments, two identical anti-LAG-3 sdAbs, and an Fc region, wherein the N-terminus of each anti-LAG-3 sdAb is fused to the C-terminus of the $C_H1$ region of the Fab fragment via an optional peptide linker and the C-terminus of each anti-LAG-3 sdAb is fused to the N-terminus of the $C_H2$ region of the Fc region. Each anti-LAG-3 sdAb specifically binds a first epitope (LAG-3). Each Fab fragment specifically binds a second epitope. For example, the BABP can consist of four polypeptide chains with structures from the N-terminus to the C-terminus as follows: (1) $V_L-C_L$; (2) $V_H-C_H1-V_HH-C_H2-C_H3$; (3) $V_H-C_H1-V_HH-C_H2-C_H3$; and (4) $V_L-C_L$, wherein $V_H$ and $V_L$ of polypeptide chains (1) and (2) form an antigen binding site that specifically binds a first copy of the second epitope, $V_H$ and $V_L$ of polypeptide chains (3) and (4) form an antigen binding site that specifically binds a second copy of the second epitope, and each $V_HH$ specifically binds a copy of the first epitope (LAG-3). In alternative formats, each anti-LAG-3 sdAb may be omitted, or replaced with two identical or different anti-LAG-3 sdAbs fused to each other. In alternative formats, to expand specificity, the two Fab fragments can specifically bind different epitopes, and/or the $V_HH$ fragments can specifically bind different epitopes.
Figure 14:
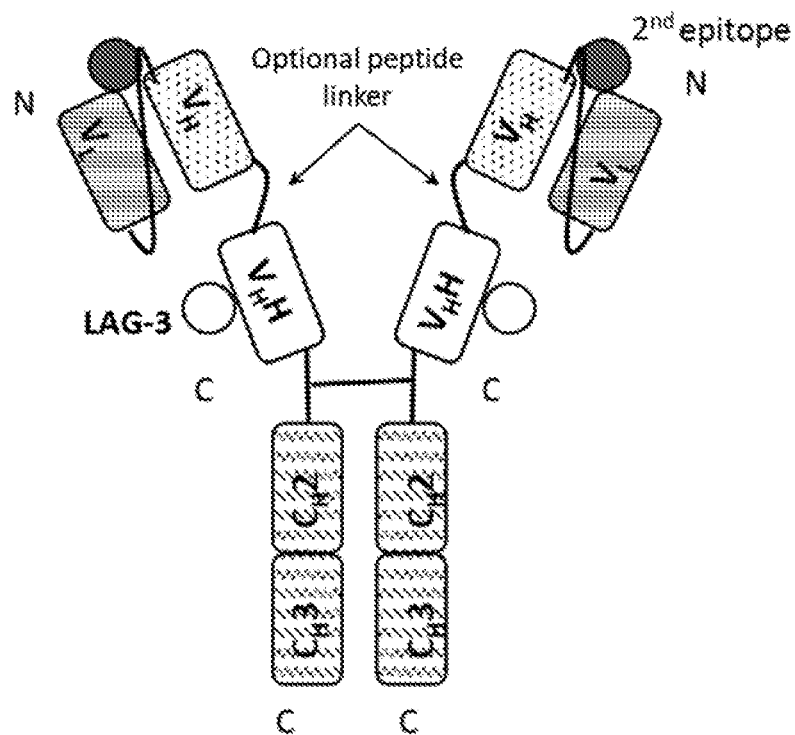
FIG. 14 depicts a schematic structure of an exemplary BABP comprising two identical single chain variable fragments (scFvs), two identical anti-LAG-3 sdAbs, and an Fc region, wherein the N-terminus of each anti-LAG-3 sdAb is fused to the C-terminus of an scFv via an optional peptide linker and the C-terminus of each anti-LAG-3 sdAb is fused to the N-terminus of the Fc region. Each anti-LAG-3 sdAb specifically binds a first epitope (LAG-3). Each scFv specifically binds a second epitope. For example, the BABP can consist of two polypeptide chains each with a structure from the N-terminus to the C-terminus as follows: $V_L-V_H-V_HH-C_H2-C_H3$, wherein $V_H$ and $V_L$ of each polypeptide chain form a scFv domain that specifically binds a copy of the second epitope, and each $V_HH$ specifically binds a copy of the first epitope (LAG-3). In alternative formats, the scFv domain can comprise from the N-terminus to the C-terminus: $V_H-V_L$. In alternative formats, each anti-LAG-3 sdAb may be omitted, or replaced with two identical or different anti-LAG-3 sdAbs fused to each other. Additionally, to expand specificity, the two scFvs can specifically bind different epitopes, and/or the $V_HH$ fragments can specifically bind different epitopes.
Figure 15:
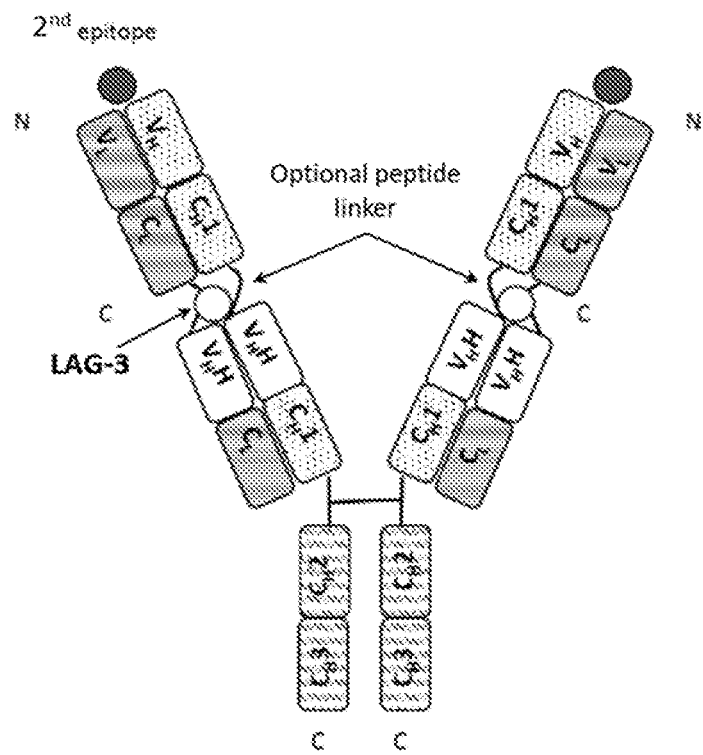
FIG. 15 depicts a schematic structure of an exemplary BABP comprising two identical Fab fragments, two identical Fab-like fragments each comprising two $V_HH$ fragments, and an Fc region. In each Fab-like fragment, the $V_H$ and $V_L$ regions are each replaced by an anti-LAG-3 sdAb. Each Fab-like fragment specifically binds a first epitope (LAG-3). Each Fab fragment specifically binds a second epitope. For example, the BABP can consist of four polypeptide chains with structures from the N-terminus to the C-terminus as follows: (1) $V_L-C_L-V_HH-C_L$; (2) $V_H-C_H1-V_HH-C_H1-C_H2-C_H3$; (3) $V_H-C_H1-V_HH-C_H1-C_H2-C_H3$; and (4) $V_L-C_L-V_HH-C_L$, wherein $V_H$ and $V_L$ of polypeptide chains (1) and (2) forms an antigen binding site that specifically binds a first copy of the second epitope, $V_H$ and $V_L$ of polypeptide chains (3) and (4) forms an antigen binding site that specifically binds a second copy of the second epitope, and each $V_HH$ specifically binds a copy of the first epitope (LAG-3). In alternative formats, to expand specificity, the two Fab fragments can specifically bind different epitopes, and/or the Fab-like fragments can specifically bind different epitopes (e.g., different epitopes from LAG-3).
Figure 16:
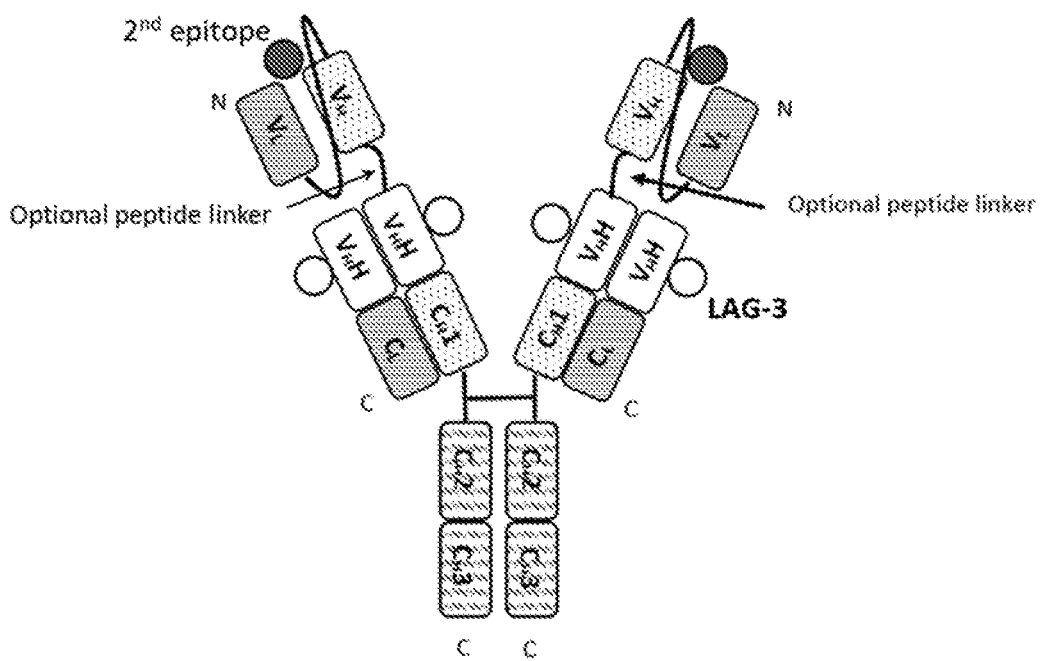
FIG. 16 depicts a schematic structure of an exemplary BABP comprising two identical scFvs, two identical Fab-like fragments each comprising two $V_HH$ fragments, and an Fc region. In each Fab-like fragment, the $V_H$ and $V_L$ regions are each replaced by an anti-LAG-3 sdAb. Each Fab-like fragment specifically binds a first epitope (LAG-3). Each scFv specifically binds a second epitope. For example, the BABP can consist of four polypeptide chains with structures from the N-terminus to the C-terminus as follows: (1)

| BABP | anti-LAG-3 sdAb | anti-PD-1 full-length antibody | Location of sdAb | Fusion format |
|---|---|---|---|---|
| BLP-1 | AS20592 | PD1-BM-min | N-terminus of heavy chain | FIG. 7 |
| BLP-2 | AS20594 | PD1-BM-min | N-terminus of heavy chain | FIG. 7 |
| BLP-3 | AS20601 | PD1-BM-min | N-terminus of heavy chain | FIG. 7 |
| BLP-4 | AS20846 | PD1-BM-min | N-terminus of heavy chain | FIG. 7 |
| BLP-5 | AS20592VH10 | PD1-BM-min | N-terminus of heavy chain | FIG. 7 |
| BLP-6 | AS20592VH10 | PD1-BM-min | C-terminus of heavy chain | FIG. 8 |
| BLP-7 | AS20592VH10 | PD1-BM-min | N-terminus of light chain | FIG. 9 |
| BLP-8 | AS20592VH10 | PD1-BM-min | C-terminus of light chain | FIG. 10 |
| BLP-9 | AS20594VH10 | PD1-BM-min | N-terminus of light chain | FIG. 7 |
| BLP-10 | AS20594VH10 | PD1-BM-min | C-terminus of heavy chain | FIG. 8 |
| BLP-11 | AS20594VH10 | PD1-BM-min | N-terminus of light chain | FIG. 9 |
| BLP-12 | AS20594VH10 | PD1-BM-min | C-terminus of light chain | FIG. 10 |
| BLP-13 | AS20846VH12 | PD1-BM-min | N-terminus of light chain | FIG. 7 |
| BLP-14 | AS20846VH12 | PD1-BM-min | C-terminus of heavy chain | FIG. 8 |
| BLP-15 | AS20846VH12 | PD1-BM-min | N-terminus of light chain | FIG. 9 |
| BLP-16 | AS20846VH12 | PD1-BM-min | C-terminus of light chain | FIG. 10 |
| BLP-17 | AS20601VH4 | PD1-BM-min | N-terminus of heavy chain | FIG. 7 |
| BLP-18 | AS20601VH4 | PD1-BM-min | C-terminus of heavy chain | FIG. 8 |
| BLP-19 | AS20601VH4 | PD1-BM-min | N-terminus of light chain | FIG. 9 |
| BLP-20 | AS20601VH4 | PD1-BM-min | C-terminus of light chain | FIG. 10 |
| BLP-21 | AS20846VH12 | Pembrolizumab | N-terminus of heavy chain | FIG. 7 |
| BLP-22 | AS20846VH12 | Pembrolizumab | N-terminus of light chain | FIG. 9 |
| BLP-23 | AS20601VH4 | Pembrolizumab | N-terminus of heavy chain | FIG. 7 |
| BLP-24 | AS20601VH4 | Pembrolizumab | N-terminus of light chain | FIG. 9 |
| BLP-25 | AS20592VH10 | PD1-BM-min | N-terminus of heavy chain | FIG. 7 |
| BLP-26 | AS20592VH10 | PD1-BM-min | N-terminus of light chain | FIG. 9 |
| BLP-27 | AS20594VH10 | PD1-BM-min | N-terminus of heavy chain | FIG. 7 |
| BLP-28 | AS20594VH10 | PD1-BM-min | N-terminus of light chain | FIG. 9 |
| BLP-29 | AS20846VH12 | PD1-BM-min | N-terminus of heavy chain | FIG. 7 |
| BLP-30 | AS20846VH12 | PD1-BM-min | N-terminus of light chain | FIG. 9 |
| BLP-31 | AS20601VH4 | PD1-BM-min | N-terminus of heavy chain | FIG. 7 |
| BLP-32 | AS20601VH4 | PD1-BM-min | N-terminus of light chain | FIG. 9 |
| BLP-33 | AS20592VH10 | PD1-BM-min | N-terminus of heavy chain | FIG. 7 |
| BLP-34 | AS20592VH10 | PD1-BM-min | N-terminus of light chain | FIG. 9 |
| BLP-35 | AS20594VH10 | PD1-BM-min | N-terminus of heavy chain | FIG. 7 |
| BLP-36 | AS20594VH10 | PD1-BM-min | N-terminus of light chain | FIG. 9 |
| BLP-37 | AS20846VH12 | PD1-BM-min | N-terminus of heavy chain | FIG. 7 |
| BLP-38 | AS20846VH12 | PD1-BM-min | N-terminus of light chain | FIG. 9 |
| BLP-39 | AS20601VH4 | PD1-BM-min | N-terminus of heavy chain | FIG. 7 |
| BLP-40 | AS20601VH4 | PD1-BM-min | N-terminus of light chain | FIG. 9 |

Anti-LAG-3 sdAbs AS20592, AS20594, AS20601 and AS20846 were each fused to heavy chain N-terminus of an anti-PD-1 antibody named PD1-BM-min, to generate PD-1×LAG-3 proof-of-concept (POC) BABPs BLP-1, BLP-2, BLP-3 and BLP-4, respectively, via a mutated human IgG1 (hIgG1) hinge as the linker. The exemplary structures of PD-1×LAG-3 POC BABPs are shown in FIG. 7.

Humanized anti-LAG-3 sdAbs AS20592VH10, AS20594VH10, AS20601VH4 and AS20846VH12 were each fused to the N-terminus of the heavy chain, the C terminus of the heavy chain, the N-terminus of the light chain, or the C-terminus of the light chain of PD1-BM-min to generate PD-1×LAG-3 BABPs, via a mutated human IgG1 (hIgG1) hinge as the linker, or without a linker.

Affinity Determination of PD-1×LAG-3 BABPs

Affinities of the exemplary PD-1×LAG-3 BABPs with human PD-1 or human LAG-3 were assessed as described in Example 3 above. Results are summarized in Table 8.

TABLE 8

Affinity determination of PD-1 × LAG-3 BABPs

| Affinity ($K_D$, M) | Human PD-1 | Human LAG-3 |
|---|---|---|
| Experiment 1 | | |
| BLP-1 | 1.8E−09 | 4.4E−10 |
| BLP-2 | 4.4E−09 | 4.4E−10 |
| BLP-3 | 2.0E−09 | 5.9E−10 |
| BLP-4 | 4.5E−09 | 1.3E−10 |
| PD1-BM-min | 1.4E−09 | / |
| AS20592-Fc | / | 1.1E−10 |
| AS20594-Fc | / | 1.1E−10 |
| AS20601-Fc | / | 4.2E−11 |
| AS20846-Fc | / | 6.7E−11 |
| Experiment 2 | | |
| BLP-34 | 3.1E−09 | 3.7E−09 |
| BLP-15 | 4.4E−09 | 7.6E−10 |
| BLP-38 | 2.5E−09 | 1.7E−09 |
| BLP-19 | 4.0E−09 | 1.4E−09 |
| PD1-BM-min | 2.3E−09 | / |
| AS20592VH10-Fc | / | 4.7E−10 |
| AS20601VH4-Fc | / | 1.0E−10 |
| AS20846VH12-Fc | / | 4.6E−10 |
| BMS-986016 | / | 7.6E−10 |

Target Cell Binding and Ligand Inhibition

The binding affinities of the exemplary PD-1×LAG-3 BABPs to PD-1 or LAG-3 expressed on CHO cells and blockade of ligand binding to the cells (i.e. PD-L1 binding to CHO-PD-1 cells or LAG-3-Fc binding to MHC II-expressing A375 melanoma cells) were assessed as described in Example 3 above. Results are summarized in Table 9.

TABLE 9

Binding and blocking data of PD-1 × LAG-3 BABPs

| EC50 (nM) | PD-1 Binding | PD-1 Blocking | LAG-3 Binding | LAG-3 Blocking |
|---|---|---|---|---|
| Experiment 1 | | | | |
| BLP-1 | 7.906 | 6.658 | 0.883 | 1.797 |
| BLP-2 | 4.292 | 3.196 | 0.360 | 0.825 |
| BLP-3 | 4.64 | 4.376 | 0.194 | 0.922 |
| BLP-4 | 3.512 | 2.578 | 0.543 | 0.778 |
| PD1-BM-min | 2.44 | 1.718 | / | / |
| AS20592-Fc | / | / | 1.244 | 0.781 |
| AS20594-Fc | / | / | 0.304 | 1.058 |
| AS20601-Fc | / | / | 0.229 | 0.844 |
| AS20846-Fc | / | / | 0.342 | 0.802 |
| Experiment 2 | | | | |
| BLP-34 | 12.48 | 13.78 | 3.118 | 37.10 |
| BLP-15 | 13.67 | 18.48 | 10.260 | 29.41 |
| BLP-38 | 8.513 | 12.44 | 4.632 | 17.31 |
| BLP-19 | 14.59 | 21.02 | 13.510 | 44.61 |
| PD1-BM-min | 6.269 | 9.565 | / | / |
| AS20592VH10-Fc | / | / | 10.540 | 47.40 |
| AS20601VH4-Fc | / | / | 14.490 | 49.78 |
| AS20846VH12-Fc | / | / | 12.430 | 48.83 |
| BMS-986016 | / | / | 3.973 | 24.32 |

In vitro Functional Assays

In vitro activities of the exemplary PD-1×LAG-3 BABPs were analyzed by PD-1 cell based reporter assay (FIG. 17A) and LAG-3 blockade reporter assay (Promega, FIG. 17B). Results are summarized in Table 10.

TABLE 10

In vitro functional assays for PD-1 × LAG-3 BABPs

| EC50 (nM) | PD-1 | LAG-3 |
|---|---|---|
| Experiment 1 | | |
| BLP-1 | 7.623 | 4.597 |
| BLP-2 | 5.138 | 2.039 |
| BLP-3 | 5.917 | 1.451 |
| BLP-4 | 5.943 | 1.848 |
| PD1-BM-min | 1.343 | / |
| Pembrolizumab | 1.146 | / |
| AS20592-Fc | / | 2.329 |
| AS20594-Fc | / | 1.667 |
| AS20601-Fc | / | 1.342 |
| AS20846-Fc | / | 1.992 |
| BMS-986016 | / | 3.294 |
| Experiment 2 | | |
| BLP-34 | 2.773 | 15.830 |
| BLP-15 | 3.322 | 5.116 |
| BLP-38 | 1.253 | 3.834 |
| BLP-19 | 3.648 | 1.570 |
| PD1-BM-min | 1.209 | / |
| Pembrolizumab | 1.596 | / |
| AS20592VH10-Fc | / | 0.891 |
| AS20601VH4-Fc | / | 3.979 |
| AS20846VH12-Fc | / | 3.125 |
| BMS-986016 | / | 3.820 |

In vivo Anti-Tumor Efficacy

The in vivo anti-tumor activity of BLP-4 was evaluated in syngeneic MC38 colon cancer model established in C57BL/6 mice having human PD-1 and human LAG-3 double knock-in Animals started to receive treatment with BLP-4, PD-BM-min, AS20846-Fc or combination of PD1-BM-min and AS20846-Fc when the tumor size reached around 120 mm$^3$. IgG4 was used as a negative control. Although PD-1 blockade was effective in this model, PD1-BM-min alone at tested dosage failed to delay the tumor growth in 2 out of 7 mice. In contrast, treatment with BLP-4, as well as the combination of PD1-BM-min and AS20846-Fc fusion protein, induced tumor regression in all 7 mice, showing superior efficacy to PD-1 blockade alone (FIGS. 18A and 18B).

SEQUENCE LISTING

TABLE 11

Anti-LAG-3 sdAb SEQ ID NOs

| | SEQ ID NO: FR1 | | SEQ ID NO: CDR1 | | SEQ ID NO: FR2 | | SEQ ID NO: CDR2 | SEQ ID NO: FR3 | SEQ ID NO: CDR3 | SEQ ID NO: FR4 |
|---|---|---|---|---|---|---|---|---|---|---|
| AS20410 | 1 | QVQLAESGGGSVHAGGSLRLSCVVS | 39 | EYTFSSDSMG | 77 | WFRQAPGKEREGVA | 115 | AIDSDGSTSYAGSVKG | 153 RFTISKDNAENTLYLQMNSLKPEDTAMYYCAT | 191 SPLWLLSRLDPADFEY | 229 WGQGTQVTVSS |
| AS20592 | 2 | EVQLVESGGGSVQAGGSLRLSCAAS | 40 | GYMSSYC MG | 78 | WFRQAPGKEREGVA | 116 | AIDSDGGTSYADSVKG | 154 RFTISKDNAKNTLYLQMDSLKPEDTAMYYCAA | 192 DFCWVDEDRHLYEYNS | 230 WGQGTQVTVSS |
| AS20594 | 3 | QVQLAESGGGSVQAGGSLRLSCAAS | 41 | GYTISSYC MG | 79 | WFRQAPGKEREGVA | 117 | AIDSDGSTSYADSVKG | 155 RFTISKDNAKNTLYLQMNSLKPEDTAMYYCAA | 193 DFCWVDDFYEYNY | 231 WGQGTQVTVSS |

TABLE 11-continued

Anti-LAG-3 sdAb SEQ ID NOs

| | SEQ ID NO:FR1 | | SEQ ID NO:CDR1 | | SEQ ID NO:FR2 | | SEQ ID NO:CDR2 | | SEQ ID NO:FR3 | | SEQ ID NO:CDR3 | | SEQ ID NO:FR4 |
|---|---|---|---|---|---|---|---|---|---|---|---|---|---|
| AS20601 | 4 | EVQLAESGGGSVQAGGGSLRLSCAAS | 42 | GYTYGGYCMG | 80 | WFRQAPGKEREGVA | 118 | TINSDGSTNYADSVKG | 156 | RFTISKDNAKNTLYLQMNSLSPEDTAMYYCAV | 194 | DLAPCWVAGPIEAADFGY | 233 | WGQGTQVTVSS |
| AS20846 | 5 | QVHLMESGGGSVQVGGSLRLSCAAS | 43 | GYTVSSYCMG | 81 | WFRQAPGKEREGVA | 119 | AIDSDGSVSYADSVKG | 157 | RFTISKDNAKNTLYLQMNSLKPEDTAMYFCAA | 195 | DLCWVDQDQGEYNT | 233 | WGQGTQVTVSS |
| AS20916 | 6 | EVQLVESGGGLVQAGGSLRLSCTAS | 44 | GLTFDDYAMG | 82 | WFRQAPGKEREGVS | 120 | CISWSGGSTYYTDSVKG | 158 | RFTISRDNAKNTLYLQMNSLKPEDTAMYYCAA | 196 | DLFCPPPDDTTGWGMDPPEHNY | 234 | WGQGTQVTVSS |
| AS21317 | 7 | QVQLVESGGGSVQAGGSLRLSCAAS | 45 | GYTLSSYCMG | 83 | WFRQAPGKEREGVA | 121 | AIDSDGSTSYADSVKG | 159 | RFTISKDNAKNTLFLQMNGLKPEDTAVYYCAP | 197 | LCWVDYPLPSGPY | 235 | WGQGTQVTVSS |
| AS20592M6 | 8 | EVQLVESGGGSVQAGGSLRLSCAAS | 46 | GYIISSYCMG | 84 | WFRQAPGKEREGVA | 122 | AIDSSGGTSYADSVKG | 160 | RFTISKDNAKNTLYLQMDSLKPEDTAMYYCAA | 198 | DFCWVDEDRHLYEYQS | 236 | WGQGTQVTVSS |
| AS20592VH4 | 9 | EVQLVESGGGLVQPGGSLRLSCAAS | 47 | GYIISSYCMG | 85 | WFRQAPGKGLEGVS | 123 | AIDSDGGTSYADSVKG | 161 | RFTISRDNSKNTLYLQMNSLRAEDTAVYYCAA | 199 | DFCWVDEDRHLYEYNS | 237 | WGQGTLVTVSS |
| AS20592VH5 | 10 | EVQLVESGGGLVQPGGSLRLSCAAS | 48 | GYIISSYCMG | 86 | WFRQAPGKGLEGVA | 124 | AIDSDGGTSYADSVKG | 162 | RFTISRDNSKNTLYLQMNSLRAEDTAVYYCAA | 200 | DFCWVDEDRHLYEYNS | 238 | WGQGTLVTVSS |
| AS20592VH6 | 11 | EVQLVESGGGLVQPGGSLRLSCAAS | 49 | GYIISSYCMG | 87 | WFRQAPGKGLEGVA | 125 | AIDSDGGTSYADSVKG | 163 | RFTISRDNSKNTLYLQMNSLRAEDTAMYYCAA | 201 | DFCWVDEDRHLYEYNS | 239 | WGQGTLVTVSS |
| AS20592VH7 | 12 | EVQLVESGGGLVQPGGSLRLSCAAS | 50 | GYIISSYCMG | 88 | WFRQAPGKGREGVA | 126 | AIDSDGGTSYADSVKG | 164 | RFTISRDNSKNTLYLQMNSLRAEDTAMYYCAA | 202 | DFCWVDEDRHLYEYNS | 240 | WGQGTLVTVSS |
| AS20592VH8 | 13 | EVQLVESGGGLVQPGGSLRLSCAAS | 51 | GYIISSYCMG | 89 | WFRQAPGKEREGVA | 127 | AIDSDGGTSYADSVKG | 165 | RFTISRDNSKNTLYLQMNSLRAEDTAMYYCAA | 203 | DFCWVDEDRHLYEYNS | 241 | WGQGTLVTVSS |
| AS20592VH9 | 14 | EVQLVESGGGLVQPGGSLRLSCAAS | 52 | GYIISSYCMG | 90 | WFRQAPGKEREGVA | 128 | AIDSDGGTSYADSVKG | 166 | RFTISKDNSKNTLYLQMNSLRAEDTAMYYCAA | 204 | DFCWVDEDRHLYEYNS | 242 | WGQGTLVTVSS |
| AS20592VH10 | 15 | EVQLVESGGGLVQPGGSLRLSCAAS | 53 | GYIISSYCMG | 91 | WFRQAPGKGLEGVA | 129 | AIDSDGGTSYADSVKG | 167 | RFTISKDNSKNTLYLQMNSLRAEDTAMYYCAA | 205 | DFCWVDEDRHLYEYNS | 243 | WGQGTLVTVSS |
| AS20592VH10M1 | 16 | EVQLVESGGGLV | 54 | GYIISSYC | 92 | WFRQAPGK | 130 | AIDSSGGTSYA | 168 | RFTISKDNSKNTLYL | 206 | DFCWVDEDRH | 244 | WGQGTLVTVSS |

TABLE 11-continued

Anti-LAG-3 sdAb SEQ ID NOs

| | SEQ ID NO:FR1 | | SEQ ID NO:CDR1 | | SEQ ID NO:FR2 | | SEQ ID NO:CDR2 | | SEQ ID NO:FR3 | | SEQ ID NO:CDR3 | | SEQ ID NO:FR4 |
|---|---|---|---|---|---|---|---|---|---|---|---|---|---|
| | | QPGGSL RLSCAA S | | MG | | GLEG VA | | DSVKG | | QMNSLRA EDTAMYY CAA | | LYEYN S | |
| AS20594VH5 | 17 | EVQLVE SGGGLV QPGGSL RLSCAA S | 55 | GYTI SSYC MG | 93 | WFRQ APGK GLEG VA | 131 | AIDSD GSTSY ADSVK G | 169 | RFTISRDN SKNTLYL QMNSLRA EDTAVYY CAA | 207 | DFCWV DDFYE YNY | 245 | WGQGT LVTVSS |
| AS20594VH6 | 18 | EVQLVE SGGGLV QPGGSL RLSCAA S | 56 | GYTI SSYC MG | 94 | WFRQ APGK GLEG VA | 132 | AIDSD GSTSY ADSVK G | 170 | RFTISRDN SKNTLYL QMNSLRA EDTAMYY CAA | 208 | DFCWV DDFYE YNY | 246 | WGQGT LVTVSS |
| AS20594VH7 | 19 | EVQLVE SGGGLV QPGGSL RLSCAA S | 57 | GYTI SSYC MG | 95 | WFRQ APGK GREG VA | 133 | AIDSD GSTSY ADSVK G | 171 | RFTISRDN SKNTLYL QMNSLRA EDTAMYY CAA | 209 | DFCWV DDFYE YNY | 247 | WGQGT LVTVSS |
| AS20594VH8 | 20 | EVQLVE SGGGLV QPGGSL RLSCAA S | 58 | GYTI SSYC MG | 96 | WFRQ APGK EREG VA | 134 | AIDSD GSTSY ADSVK G | 172 | RFTISRDN SKNTLYL QMNSLRA EDTAMYY CAA | 210 | DFCWV DDFYE YNY | 248 | WGQGT LVTVSS |
| AS20594VH9 | 21 | EVQLVE SGGGLV QPGGSL RLSCAA S | 59 | GYTI SSYC MG | 97 | WFRQ APGK EREG VA | 135 | AIDSD GSTSY ADSVK G | 173 | RFTISKDN SKNTLYL QMNSLRA EDTAMYY CAA | 211 | DFCWV DDFYE YNY | 249 | WGQGT LVTVSS |
| AS20594VH10 | 22 | EVQLVE SGGGLV QPGGSL RLSCAA S | 60 | GYTI SSYC MG | 98 | WFRQ APGK GLEG VA | 136 | AIDSD GSTSY ADSVK G | 174 | RFTISKDN SKNTLYL QMNSLRA EDTAVYY CAA | 212 | DFCWV DDFYE YNY | 250 | WGQGT LVTVSS |
| AS20594VH10M1 | 23 | EVQLVE SGGGLV QPGGSL RLSCAA S | 61 | GYTI SSYC MG | 99 | WFRQ APGK GLEG VA | 137 | AIDSSG STSYA DSVKG | 175 | RFTISKDN SKNTLYL QMNSLRA EDTAVYY CAA | 213 | DFCWV DDFYE YNY | 251 | WGQGT LVTVSS |
| AS20846VH4 | 24 | EVQLVE SGGGLV QPGGSL RLSCAA S | 62 | GYT VSSY CMG | 100 | WFRQ APGK GLEG VS | 138 | AIDSD GSVSY ADSVK G | 176 | RFTISRDN SKNTLYL QMNSLRA EDTAVYY CAA | 214 | DLCW VDQDQ GEYNT | 252 | WGQGT LVTVSS |
| AS20846VH5 | 25 | EVQLVE SGGGLV QPGGSL RLSCAA S | 63 | GYT VSSY CMG | 101 | WFRQ APGK GLEG VS | 139 | AIDSD GSVSY ADSVK G | 177 | RFTISRDN SKNTLYL QMNSLRA EDTAVYF CAA | 215 | DLCW VDQDQ GEYNT | 253 | WGQGT LVTVSS |
| AS20846VH6 | 26 | EVQLVE SGGGLV QPGGSL RLSCAA S | 64 | GYT VSSY CMG | 102 | WFRQ APGK GLEG VA | 140 | AIDSD GSVSY ADSVK G | 178 | RFTISRDN SKNTLYL QMNSLRA EDTAVYF CAA | 216 | DLCW VDQDQ GEYNT | 254 | WGQGT LVTVSS |
| AS20846VH7 | 27 | EVQLVE SGGGLV QPGGSL RLSCAA S | 65 | GYT VSSY CMG | 103 | WFRQ APGK GLEG VA | 141 | AIDSD GSVSY ADSVK G | 179 | RFTISRDN SKNTLYL QMNSLRA EDTAMYF CAA | 217 | DLCW VDQDQ GEYNT | 255 | WGQGT LVTVSS |
| AS20846VH8 | 28 | EVQLVE SGGGLV QPGGSL | 66 | GYT VSSY CMG | 104 | WFRQ APGK GREG | 142 | AIDSD GSVSY ADSVK | 180 | RFTISRDN SKNTLYL QMNSLRA | 218 | DLCW VDQDQ GEYNT | 256 | WGQGT LVTVSS |

TABLE 11-continued

Anti-LAG-3 sdAb SEQ ID NOs

| | SEQ ID NO:FR1 | SEQ ID NO:CDR1 | SEQ ID NO: FR2 | SEQ ID NO:CDR2 | SEQ ID NO:FR3 | SEQ ID NO:CDR3 | SEQ ID NO:FR4 |
|---|---|---|---|---|---|---|---|
| | RLSCAA S | | VA | G | EDTAMYF CAA | | |
| AS20846VH9 | 29 EVQLVE SGGGLV QPGGSL RLSCAA S | 67 GYT VSSY CMG | 105 WFRQ APGK EREG VA | 143 AIDSD GSVSY ADSVK G | 181 RFTISRDN SKNTLYL QMNSLRA EDTAMYF CAA | 219 DLCW VDQDQ GEYNT | 257 WGQGT LVTVSS |
| AS20846VH10 | 30 EVQLVE SGGGLV QPGGSL RLSCAA S | 68 GYT VSSY CMG | 106 WFRQ APGK EREG VA | 144 AIDSD GSVSY ADSVK G | 182 RFTISKDN SKNTLYL QMNSLRA EDTAMYF CAA | 220 DLCW VDQDQ GEYNT | 258 WGQGT LVTVSS |
| AS20846VH12 | 31 EVQLVE SGGGLV QPGGSL RLSCAA S | 69 GYT VSSY CMG | 107 WFRQ APGK GREG VS | 145 AIDSD GSVSY ADSVK G | 183 RFTISKDN SKNTLYL QMNSLRA EDTAVYF CAA | 221 DLCW VDQDQ GEYNT | 259 WGQGT LVTVSS |
| AS20846VH12M1 | 32 EVQLVE SGGGLV QPGGSL RLSCAA S | 70 GYT VSSY CMG | 108 WFRQ APGK GREG VS | 146 AIDSSG SVSYA DSVKG | 184 RFTISKDN SKNTLYL QMNSLRA EDTAVYF CAA | 222 DLCW VDQDQ GEYNT | 260 WGQGT LVTVSS |
| AS20601VH4 | 33 EVQLVE SGGGLV QPGGSL RLSCAA S | 71 GYT YGG YCM G | 109 WFRQ APGK GLEG VS | 147 TINSD GSTNY ADSVK G | 185 RFTISRDN SKNTLYL QMNSLRA EDTAVYY CAV | 223 DLAPC WVAG PIEAA DFGY | 261 WGQGT LVTVSS |
| AS20601VH4.M6 | 34 EVQLVE SGGGLV QPGGSL RLSCAA S | 72 GYT YGG YCM G | 110 WFRQ APGK GLEG VS | 148 TIASEG STNYA DSVKG | 186 RFTISRDN SKNTLYL QMNSLRA EDTAVYY CAV | 224 DLAPC WVAG PIEAA DFGY | 262 WGQGT LVTVSS |
| AS20601VH4.M7 | 35 EVQLVE SGGGLV QPGGSL RLSCAA S | 73 GYT YGG YCM G | 111 WFRQ APGK GLEG VS | 149 TIASSG STNYA DSVKG | 187 RFTISRDN SKNTLYL QMNSLRA EDTAVYY CAV | 225 DLAPC WVAG PIEAA DFGY | 263 WGQGT LVTVSS |
| AS20601VH11 | 36 EVQLVE SGGGLV QPGGSL RLSCAA S | 74 GYT YGG YCM G | 112 WFRQ APGK GREG VS | 150 TINSD GSTNY ADSVK G | 188 RFTISRDN AKNTLYL QMNSLRP EDTAVYY CAV | 226 DLAPC WVAG PIEAA DFGY | 264 WGQGT LVTVSS |
| AS20601VH11.M6 | 37 EVQLVE SGGGLV QPGGSL RLSCAA S | 75 GYT YGG YCM G | 113 WFRQ APGK GREG VS | 151 TIASEG STNYA DSVKG | 189 RFTISRDN AKNTLYL QMNSLRP EDTAVYY CAV | 227 DLAPC WVAG PIEAA DFGY | 265 WGQGT LVTVSS |
| AS20601VH11.M7 | 38 EVQLVE SGGGLV QPGGSL RLSCAA S | 76 GYT YGG YCM G | 114 WFRQ APGK GREG VS | 152 TIASSG STNYA DSVKG | 190 RFTISRDN AKNTLYL QMNSLRP EDTAVYY CAV | 228 DLAPC WVAG PIEAA DFGY | 266 WGQGT LVTVSS |

(AS20410 sdAb nucleic acid sequence) SEQ ID NO: 267

CAGGTGCAACTGGCGGAGTCTGGGGGAGGCTCGGTGCATGCTGGAGGGTCTCTGAGACTCT

CCTGTGTAGTTTCTGAATATACCTTCAGTAGTGATTCTATGGGCTGGTTCCGCCAGGCTCCAG

GGAAGGAGCGCGAGGGGGTCGCAGCTATTGATAGTGATGGTAGCACAAGCTACGCAGGCTC

CGTGAAGGGGCGATTCACCATCTCCAAAGACAACGCCGAGAACACTCTGTATCTGCAAATG

AACAGCCTGAAACCTGAGGACACTGCCATGTACTACTGTGCGACAAGCCCTCTGTGGCTGCT

ATCCAGGCTCGACCCAGCTGACTTTGAATACTGGGGCCAGGGGACCCAGGTCACCGTCTCCT

CA (AS20592 sdAb nucleic acid sequence)

SEQ ID NO: 268

GAGGTGCAACTGGTGGAGTCTGGGGGAGGCTCGGTGCAGGCTGGAGGGTCTCTGAGACTCT

CCTGTGCAGCCTCTGGATACATCATCAGTAGCTACTGCATGGGCTGGTTCCGCCAGGCTCCA

GGGAAGGAGCGCGAGGGGGTCGCAGCTATTGATAGTGATGGTGGCACAAGCTACGCAGACT

CCGTGAAGGGCCGATTCACCATCTCCAAAGACAACGCCAAGAACACTCTGTATCTGCAAATG

GACAGCCTGAAACCTGAGGACACTGCCATGTACTACTGTGCGGCAGATTTTTGTTGGGTAGA

TGAGGATCGCCACCTCTATGAGTATAACTCCTGGGGCCAGGGGACCCAGGTCACCGTCTCCT

CA (AS20594 sdAb nucleic acid sequence)

SEQ ID NO: 269

CAGGTGCAGCTGGCGGAGTCTGGGGGAGGCTCGGTGCAGGCTGGAGGGTCTCTGAGACTCT

CCTGTGCAGCCTCTGGATACACCATCAGTAGCTACTGCATGGGCTGGTTCCGCCAGGCTCCA

GGGAAGGAGCGCGAGGGGGTCGCAGCTATTGATAGTGATGGTAGCACAAGCTACGCAGACT

CCGTGAAGGGCCGATTCACCATCTCCAAAGACAACGCCAAGAACACTCTGTATCTGCAAATG

AACAGCCTGAAACCTGAGGACACTGCCATGTACTACTGTGCGGCAGATTTTTGTTGGGTGGA

CGACTTCTATGAGTATAACTACTGGGGCCAGGGGACCCAGGTCACCGTCTCCTCA (AS20601 sdAb nucleic acid sequence)

SEQ ID NO: 270

GAGGTGCAACTGGCGGAGTCTGGGGGAGGCTCGGTGCAGGCTGGAGGGTCTCTGAGACTCT

CCTGTGCAGCCTCTGGATACACCTACGGTGGCTACTGCATGGGCTGGTTCCGCCAGGCTCCA

GGGAAGGAGCGCGAGGGGGTCGCAACTATTAATAGTGATGGTAGCACAAACTACGCAGACT

CCGTGAAGGGCCGATTCACCATCTCCAAAGACAACGCCAAGAACACTCTGTATCTGCAAATG

AACAGCCTGAGCCCTGAGGACACTGCCATGTACTACTGCGCGGTGGATCTCGCCCCATGTTG

GGTAGCTGGTCCCATCGAGGCCGCTGACTTTGGTTACTGGGGCCAGGGGACCCAGGTCACCG

TCTCCTCA (AS20846 sdAb nucleic acid sequence)

SEQ ID NO: 271

CAGGTGCACCTGATGGAGTCTGGGGGAGGCTCGGTGCAGGTTGGAGGGTCTCTGAGACTCTC

CTGTGCAGCCTCTGGATACACCGTCAGTAGCTACTGCATGGGCTGGTTCCGCCAGGCTCCAG

GGAAGGAGCGCGAGGGGGTCGCAGCTATTGATAGTGATGGTAGCGTAAGTTATGCAGACTC

CGTGAAGGGCCGATTCACCATCTCCAAAGACAACGCCAAGAACACTCTGTATCTGCAAATG

AACAGCCTGAAACCTGAGGACACTGCCATGTACTTCTGTGCGGCAGATCTTTGCTGGGTGGA

CCAGGACCAGGGAGAATATAACACCTGGGGCCAGGGGACCCAGGTCACCGTCTCCTCA (AS20916 sdAb nucleic acid sequence)

SEQ ID NO: 272

GAGGTGCAGCTGGTGGAGTCTGGGGGAGGCTTGGTGCAGGCAGGGGGGTCTCTGAGACTCT

CCTGTACAGCCTCTGGATTGACTTTTGATGATTATGCCATGGGCTGGTTCCGCCAGGCTCCAG

GGAAGGAGCGCGAGGGGGTCTCATGTATTAGCTGGAGTGGTGGTAGCACATACTATACCGA

CTCCGTGAAGGGCCGATTCACCATCTCCAGAGACAACGCCAAGAACACGCTGTATCTGCAA

ATGAACAGCCTGAAACCTGAGGACACGGCCATGTATTACTGTGCGGCAGATTTGTTCTGTCC

-continued

CCCACCTGATGATACTACGGGTTGGGGTATGGACCCTCCCGAGCATAACTACTGGGGCCAGG

GGACCCAGGTCACCGTCTCCTCA (AS21317 sdAb nucleic acid sequence)
SEQ ID NO: 273
CAGGTTCAGCTGGTGGAGTCTGGGGGAGGCTCGGTGCAGGCTGGAGGGTCTCTGAGACTTTC

CTGTGCAGCCTCTGGATACACCTTGAGTAGCTACTGCATGGGCTGGTTCCGCCAGGCTCCAG

GGAAGGAGCGCGAGGGGGTCGCAGCTATTGATAGTGATGGTAGCACAAGCTACGCAGACTC

CGTGAAGGGCCGATTCACCATCTCCAAAGACAACGCCAAGAACACTCTGTTTCTGCAAATGA

ACGGCCTGAAACCTGAGGACACTGCGGTGTACTACTGTGCTCCACTATGCTGGGTTGATTAC

CCATTGCCGTCGGGCCCATACTGGGGCCAGGGGACCCAGGTCACCGTCTCCTCA (AS20410 sdAb amino acid sequence; CDRs are underlined)
SEQ ID NO: 274
QVQLAESGGGSVHAGGSLRLSCVVS<u>EYTFSSDSMG</u>WFRQAPGKEREGVA<u>AIDSDGSTSYAGSVK</u>

<u>GRFTISKDNAENTLYLQMNSLKPEDTAMYYCATSPLWLLSRLDPADFEY</u>WGQGTQVTVSS (AS20592 sdAb amino acid sequence; CDRs are underlined)
SEQ ID NO: 275
EVQLVESGGGSVQAGGSLRLSCAAS<u>GYIISSYCMG</u>WFRQAPGKEREGVA<u>AIDSDGGTSYADSVK</u>

<u>GRFTISKDNAKNTLYLQMDSLKPEDTAMYYCAADFCWVDEDRHLYEYNSW</u>GQGTQVTVSS (AS20594 sdAb amino acid sequence; CDRs are underlined)
SEQ ID NO: 276
QVQLAESGGGSVQAGGSLRLSCAAS<u>GYTISSYCMG</u>WFRQAPGKEREGVA<u>AIDSDGSTSYADSVK</u>

<u>GRFTISKDNAKNTLYLQMNSLKPEDTAMYYCAADFCWVDDFYEYNYW</u>GQGTQVTVSS (AS20601 sdAb amino acid sequence; CDRs are underlined)
SEQ ID NO: 277
EVQLAESGGGSVQAGGSLRLSCAAS<u>GYTYGGYCMG</u>WFRQAPGKEREGVA<u>TINSDGSTNYADSV</u>

<u>KGRFTISKDNAKNTLYLQMNSLSPEDTAMYYCAVDLAPCWVAGPIEAADFGY</u>WGQGTQVTVSS (AS20846 sdAb amino acid sequence; CDRs are underlined)
SEQ ID NO: 278
QVHLMESGGGSVQVGGSLRLSCAAS<u>GYTVSSYCMG</u>WFRQAPGKEREGVA<u>AIDSDGSVSYADSV</u>

<u>KGRFTISKDNAKNTLYLQMNSLKPEDTAMYFCAADLCWVDQDQGEYNTW</u>GQGTQVTVSS (AS20916 sdAb amino acid sequence; CDRs are underlined)
SEQ ID NO: 279
EVQLVESGGGLVQAGGSLRLSCTAS<u>GLTFDDYAMG</u>WFRQAPGKEREGVS<u>CISWSGGSTYYTDS</u>

<u>VKGRFTISRDNAKNTLYLQMNSLKPEDTAMYYCAADLFCPPPDDTTGWGMDPPEHNY</u>WGQGT

QVTVSS (AS21317 sdAb amino acid sequence; CDRs are underlined)
SEQ ID NO: 280
QVQLVESGGGSVQAGGSLRLSCAAS<u>GYTLSSYCMG</u>WFRQAPGKEREGVA<u>AIDSDGSTSYADSV</u>

<u>KGRFTISKDNAKNTLFLQMNGLKPEDTAVYYCAPLCWVDYPLPSGPY</u>WGQGTQVTVSS (AS20592M6 sdAb amino acid sequence; CDRs are underlined)
SEQ ID NO: 281
EVQLVESGGGSVQAGGSLRLSCAAS<u>GYIISSYCMG</u>WFRQAPGKEREGVA<u>AIDSSGGTSYADSVK</u>

<u>GRFTISKDNAKNTLYLQMDSLKPEDTAMYYCAADFCWVDEDRHLYEYQSW</u>GQGTQVTVSS (AS20592VH4 sdAb amino acid sequence; CDRs are underlined)
SEQ ID NO: 282
EVQLVESGGGLVQPGGSLRLSCAAS<u>GYIISSYCMG</u>WFRQAPGKGLEGVS<u>AIDSDGGTSYADSVK</u>

<u>GRFTISRDNSKNTLYLQMNSLRAEDTAVYYCAADFCWVDEDRHLYEYNSW</u>GQGTLVTVSS (AS20592VH5 sdAb amino acid sequence; CDRs are underlined)
SEQ ID NO: 283
EVQLVESGGGLVQPGGSLRLSCAAS<u>GYIISSYCMG</u>WFRQAPGKGLEGVA<u>AIDSDGGTSYADSVK</u>

<u>GRFTISRDNSKNTLYLQMNSLRAEDTAVYYCAADFCWVDEDRHLYEYNSW</u>GQGTLVTVSS (AS20592VH6 sdAb amino acid sequence; CDRs are underlined)

```
                                                SEQ ID NO: 284
EVQLVESGGGLVQPGGSLRLSCAASGYIISSYCMGWFRQAPGKGLEGVAAIDSDGGTSYADSVK

GRFTISRDNSKNTLYLQMNSLRAEDTAMYYCAADFCWVDEDRHLYEYNSWGQGTLVTVSS (AS20592VH7 sdAb amino acid sequence; CDRs are underlined)
                                                SEQ ID NO: 285
EVQLVESGGGLVQPGGSLRLSCAASGYIISSYCMGWFRQAPGKGREGVAAIDSDGGTSYADSVK

GRFTISRDNSKNTLYLQMNSLRAEDTAMYYCAADFCWVDEDRHLYEYNSWGQGTLVTVSS (AS20592VH8 sdAb amino acid sequence; CDRs are underlined)
                                                SEQ ID NO: 286
EVQLVESGGGLVQPGGSLRLSCAASGYIISSYCMGWFRQAPGKEREGVAAIDSDGGTSYADSVK

GRFTISRDNSKNTLYLQMNSLRAEDTAMYYCAADFCWVDEDRHLYEYNSWGQGTLVTVSS (AS20592VH9 sdAb amino acid sequence; CDRs are underlined)
                                                SEQ ID NO: 287
EVQLVESGGGLVQPGGSLRLSCAASGYIISSYCMGWFRQAPGKEREGVAAIDSDGGTSYADSVK

GRFTISKDNSKNTLYLQMNSLRAEDTAMYYCAADFCWVDEDRHLYEYNSWGQGTLVTVSS (AS20592VH10 sdAb amino acid sequence; CDRs are underlined)
                                                SEQ ID NO: 288
EVQLVESGGGLVQPGGSLRLSCAASGYIISSYCMGWFRQAPGKGLEGVAAIDSDGGTSYADSVK

GRFTISKDNSKNTLYLQMNSLRAEDTAMYYCAADFCWVDEDRHLYEYNSWGQGTLVTVSS (AS20592VH10M1 sdAb amino acid sequence; CDRs are underlined)
                                                SEQ ID NO: 289
EVQLVESGGGLVQPGGSLRLSCAASGYIISSYCMGWFRQAPGKGLEGVAAIDSSGGTSYADSVK

GRFTISKDNSKNTLYLQMNSLRAEDTAMYYCAADFCWVDEDRHLYEYNSWGQGTLVTVSS (AS20594VH5 sdAb amino acid sequence; CDRs are underlined)
                                                SEQ ID NO: 290
EVQLVESGGGLVQPGGSLRLSCAASGYTISSYCMGWFRQAPGKGLEGVAAIDSDGSTSYADSVK

GRFTISRDNSKNTLYLQMNSLRAEDTAVYYCAADFCWVDDFYEYNYWGQGTLVTVSS (AS20594VH6 sdAb amino acid sequence; CDRs are underlined)
                                                SEQ ID NO: 291
EVQLVESGGGLVQPGGSLRLSCAASGYTISSYCMGWFRQAPGKGLEGVAAIDSDGSTSYADSVK

GRFTISRDNSKNTLYLQMNSLRAEDTAMYYCAADFCWVDDFYEYNYWGQGTLVTVSS (AS20594VH7 sdAb amino acid sequence; CDRs are underlined)
                                                SEQ ID NO: 292
EVQLVESGGGLVQPGGSLRLSCAASGYTISSYCMGWFRQAPGKGREGVAAIDSDGSTSYADSVK

GRFTISRDNSKNTLYLQMNSLRAEDTAMYYCAADFCWVDDFYEYNYWGQGTLVTVSS (AS20594VH8 sdAb amino acid sequence; CDRs are underlined)
                                                SEQ ID NO: 293
EVQLVESGGGLVQPGGSLRLSCAASGYTISSYCMGWFRQAPGKEREGVAAIDSDGSTSYADSVK

GRFTISRDNSKNTLYLQMNSLRAEDTAMYYCAADFCWVDDFYEYNYWGQGTLVTVSS (AS20594VH9 sdAb amino acid sequence; CDRs are underlined)
                                                SEQ ID NO: 294
EVQLVESGGGLVQPGGSLRLSCAASGYTISSYCMGWFRQAPGKEREGVAAIDSDGSTSYADSVK

GRFTISKDNSKNTLYLQMNSLRAEDTAMYYCAADFCWVDDFYEYNYWGQGTLVTVSS (AS20594VH10 sdAb amino acid sequence; CDRs are underlined)
                                                SEQ ID NO: 295
EVQLVESGGGLVQPGGSLRLSCAASGYTISSYCMGWFRQAPGKGLEGVAAIDSDGSTSYADSVK

GRFTISKDNSKNTLYLQMNSLRAEDTAVYYCAADFCWVDDFYEYNYWGQGTLVTVSS (AS20594VH10M1 sdAb amino acid sequence; CDRs are underlined)
                                                SEQ ID NO: 296
EVQLVESGGGLVQPGGSLRLSCAASGYTISSYCMGWFRQAPGKGLEGVAAIDSSGSTSYADSVK

GRFTISKDNSKNTLYLQMNSLRAEDTAVYYCAADFCWVDDFYEYNYWGQGTLVTVSS (AS20846VH4 sdAb amino acid sequence; CDRs are underlined)
                                                SEQ ID NO: 297
EVQLVESGGGLVQPGGSLRLSCAASGYTVSSYCMGWFRQAPGKGLEGVSAIDSDGSVSYADSV
```

-continued

KGRFTISRDNSKNTLYLQMNSLRAEDTAVYYCAA<u>DLCWVDQDQGEYNTW</u>GQGTLVTVSS (AS20846VH5 sdAb amino acid sequence; CDRs are underlined)
SEQ ID NO: 298
EVQLVESGGGLVQPGGSLRLSCAAS<u>GYTVSSYCMG</u>WFRQAPGKGLEGVS<u>AIDSDGSVSYADSV</u>

<u>KGRFTISRDNSKNTLYLQMNSLRAEDTAVYFCAA</u><u>DLCWVDQDQGEYNTW</u>GQGTLVTVSS (AS20846VH6 sdAb amino acid sequence; CDRs are underlined)
SEQ ID NO: 299
EVQLVESGGGLVQPGGSLRLSCAAS<u>GYTVSSYCMG</u>WFRQAPGKGLEGVA<u>AIDSDGSVSYADSV</u>

<u>KGRFTISRDNSKNTLYLQMNSLRAEDTAVYFCAA</u><u>DLCWVDQDQGEYNTW</u>GQGTLVTVSS (AS20846VH7 sdAb amino acid sequence; CDRs are underlined)
SEQ ID NO: 300
EVQLVESGGGLVQPGGSLRLSCAAS<u>GYTVSSYCMG</u>WFRQAPGKGLEGVA<u>AIDSDGSVSYADSV</u>

<u>KGRFTISRDNSKNTLYLQMNSLRAEDTAMYFCAA</u><u>DLCWVDQDQGEYNTW</u>GQGTLVTVSS (AS20846VH8 sdAb amino acid sequence; CDRs are underlined)
SEQ ID NO: 301
EVQLVESGGGLVQPGGSLRLSCAAS<u>GYTVSSYCMG</u>WFRQAPGKGREGVA<u>AIDSDGSVSYADSV</u>

<u>KGRFTISRDNSKNTLYLQMNSLRAEDTAMYFCAA</u><u>DLCWVDQDQGEYNTW</u>GQGTLVTVSS (AS20846VH9 sdAb amino acid sequence; CDRs are underlined)
SEQ ID NO: 302
EVQLVESGGGLVQPGGSLRLSCAAS<u>GYTVSSYCMG</u>WFRQAPGKEREGVA<u>AIDSDGSVSYADSV</u>

<u>KGRFTISRDNSKNTLYLQMNSLRAEDTAMYFCAA</u><u>DLCWVDQDQGEYNTW</u>GQGTLVTVSS (AS20846VH10 sdAb amino acid sequence; CDRs are underlined)
SEQ ID NO: 303
EVQLVESGGGLVQPGGSLRLSCAAS<u>GYTVSSYCMG</u>WFRQAPGKEREGVA<u>AIDSDGSVSYADSV</u>

KGRFTISKDNSKNTLYLQMNSLRAEDTAMYFCAA<u>DLCWVDQDQGEYNTW</u>GQGTLVTVSS (AS20846VH12 sdAb amino acid sequence; CDRs are underlined)
SEQ ID NO: 304
EVQLVESGGGLVQPGGSLRLSCAAS<u>GYTVSSYCMG</u>WFRQAPGKGREGVS<u>AIDSDGSVSYADSV</u>

<u>KGRFTISKDNSKNTLYLQMNSLRAEDTAVYFCAA</u><u>DLCWVDQDQGEYNTW</u>GQGTLVTVSS (AS20846VH12M1 sdAb amino acid sequence; CDRs are underlined)
SEQ ID NO: 305
EVQLVESGGGLVQPGGSLRLSCAAS<u>GYTVSSYCMG</u>WFRQAPGKGREGVS<u>AIDSSGSVSYADSV</u>

<u>KGRFTISKDNSKNTLYLQMNSLRAEDTAVYFCAA</u><u>DLCWVDQDQGEYNTW</u>GQGTLVTVSS (AS20601VH4 sdAb amino acid sequence; CDRs are underlined)
SEQ ID NO: 306
EVQLVESGGGLVQPGGSLRLSCAAS<u>GYTYGGYCMG</u>WFRQAPGKGLEGVS<u>TINSDGSTNYADSV</u>

<u>KGRFTISRDNSKNTLYLQMNSLRAEDTAVYYCAV</u><u>DLAPCWVAGPIEAADFGYW</u>GQGTLVTVSS (AS20601VH4.M6 sdAb amino acid sequence; CDRs are underlined)
SEQ ID NO: 307
EVQLVESGGGLVQPGGSLRLSCAAS<u>GYTYGGYCMG</u>WFRQAPGKGLEGVS<u>TIASEGSTNYADSV</u>

<u>KGRFTISRDNSKNTLYLQMNSLRAEDTAVYYCAV</u><u>DLAPCWVAGPIEAADFGYW</u>GQGTLVTVSS (AS20601VH4.M7 sdAb amino acid sequence; CDRs are underlined)
SEQ ID NO: 308
EVQLVESGGGLVQPGGSLRLSCAAS<u>GYTYGGYCMG</u>WFRQAPGKGLEGVS<u>TIASSGSTNYADSV</u>

<u>KGRFTISRDNSKNTLYLQMNSLRAEDTAVYYCAV</u><u>DLAPCWVAGPIEAADFGYW</u>GQGTLVTVSS (AS20601VH11 sdAb amino acid sequence; CDRs are underlined)
SEQ ID NO: 309
EVQLVESGGGLVQPGGSLRLSCAAS<u>GYTYGGYCMG</u>WFRQAPGKGREGVS<u>TINSDGSTNYADSV</u>

KGRFTISRDNAKNTLYLQMNSLRPEDTAVYYCAV<u>DLAPCWVAGPIEAADFGYW</u>GQGTLVTVSS (AS20601VH11.M6 sdAb amino acid sequence; CDRs are underlined)
SEQ ID NO: 310
EVQLVESGGGLVQPGGSLRLSCAAS<u>GYTYGGYCMG</u>WFRQAPGKGREGVS<u>TIASEGSTNYADSV</u>

KGRFTISRDNAKNTLYLQMNSLRPEDTAVYYCAV<u>DLAPCWVAGPIEAADFGYW</u>GQGTLVTVSS (AS20601VH11.M7 sdAb amino acid sequence; CDRs are underlined)

-continued

SEQ ID NO: 311
EVQLVESGGGLVQPGGSLRLSCAASGYTYGGYCMGWFRQAPGKGREGVSTIASSGSTNYADSV
KGRFTISRDNAKNTLYLQMNSLRPEDTAVYYCAVDLAPCWVAGPIEAADFGYWGQGTLVTVSS (AS20410 HCAb dimeric form amino acid sequence)
SEQ ID NO: 312
QVQLAESGGGSVHAGGSLRLSCVVSEYTFSSDSMGWFRQAPGKEREGVAAIDSDGSTSYAGSVK
GRFTISKDNAENTLYLQMNSLKPEDTAMYYCATSPLWLLSRLDPADFEYWGQGTQVTVSSESK
YGPPCPPCPAPEFLGGPSVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDSDGSFFLYSRLTVDKS
RWQEGNVFSCSVMHEALHNHYTQKSLSLSLGK (AS20592 HCAb dimeric form amino acid sequence)
SEQ ID NO: 313
EVQLVESGGGSVQAGGSLRLSCAASGYIISSYCMGWFRQAPGKEREGVAAIDSDGGTSYADSVK
GRFTISKDNAKNTLYLQMDSLKPEDTAMYYCAADFCWVDEDRHLYEYNSWGQGTQVTVSSES
KYGPPCPPCPAPEFLGGPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLDSDGSFFLYSRLTVDK
SRWQEGNVFSCSVMHEALHNHYTQKSLSLSLGK (AS20594 HCAb dimeric form amino acid sequence)
SEQ ID NO: 314
QVQLAESGGGSVQAGGSLRLSCAASGYTISSYCMGWFRQAPGKEREGVAAIDSDGSTSYADSVK
GRFTISKDNAKNTLYLQMNSLKPEDTAMYYCAADFCWVDDFYEYNYWGQGTQVTVSSESKYG
PPCPPCPAPEFLGGPSVFLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTISKAKGQPREPQVYTLPP
SQEEMTKNQVSLTCLVKGFYPSDIAVEWESNGQPENNYKTTPPVLDSDGSFFLYSRLTVDKSRW
QEGNVFSCSVMHEALHNHYTQKSLSLSLGK (AS20601 HCAb dimeric form amino acid sequence)
SEQ ID NO: 315
EVQLAESGGGSVQAGGSLRLSCAASGYTYGGYCMGWFRQAPGKEREGVATINSDGSTNYADSV
KGRFTISKDNAKNTLYLQMNSLSPEDTAMYYCAVDLAPCWVAGPIEAADFGYWGQGTQVTVSS
ESKYGPPCPPCPAPEFLGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIEKTISKAKGQPREPQ
VYTLPPSQEEMTKNQVSLTCLVKGFYPSDIAVEWESNGQPENNYKTTPPVLDSDGSFFLYSRLTV
DKSRWQEGNVFSCSVMHEALHNHYTQKSLSLSLGK (AS20846 HCAb dimeric form amino acid sequence)
SEQ ID NO: 316
QVHLMESGGGSVQVGGSLRLSCAASGYTVSSYCMGWFRQAPGKEREGVAAIDSDGSVSYADSV
KGRFTISKDNAKNTLYLQMNSLKPEDTAMYFCAADLCWVDQDQGEYNTWGQGTQVTVSSESK
YGPPCPPCPAPEFLGGPSVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDSDGSFFLYSRLTVDKS
RWQEGNVFSCSVMHEALHNHYTQKSLSLSLGK (AS20916 HCAb dimeric form amino acid sequence)
SEQ ID NO: 317
EVQLVESGGGLVQAGGSLRLSCTASGLTFDDYAMGWFRQAPGKEREGVSCISWSGGSTYYTDS
VKGRFTISRDNAKNTLYLQMNSLKPEDTAMYYCAADLFCPPPDDTTGWGMDPPEHNYWGQGT

QVTVSSESKYGPPCPPCPAPEFLGGPSVFLFPPKPKDTLMISRTPEVTCVVVDVSQEDPEVQFNWY

VDGVEVHNAKTKPREEQFNSTYRVVSVLTVLHQDWLNGKEYKCKVSNKGLPSSIEKTISKAKG

QPREPQVYTLPPSQEEMTKNQVSLTCLVKGFYPSDIAVEWESNGQPENNYKTTPPVLDSDGSFFL

YSRLTVDKSRWQEGNVFSCSVMHEALHNHYTQKSLSLSLGK (AS21317 HCAb dimeric form amino acid sequence)
SEQ ID NO: 318

QVQLVESGGGSVQAGGSLRLSCAAS<u>GYTLSSYCMG</u>WFRQAPGKEREGVA<u>AIDSDGSTSYADSV</u>

<u>KG</u>RFTISKDNAKNTLFLQMNGLKPEDTAVYYCAP<u>LCWVDYPLPSGPYW</u>GQGTQVTVSSESKYG

PPCPPCPAPEFLGGPSVFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSFFLYSRLTVDKSRW

QEGNVFSCSVMHEALHNHYTQKSLSLSLGK (AS20592M6 HCAb dimeric form amino acid sequence)
SEQ ID NO: 319

EVQLVESGGGSVQAGGSLRLSCAAS<u>GYIISSYCMG</u>WFRQAPGKEREGVA<u>AIDSSGGTSYADSVK</u>

<u>G</u>RFTISKDNAKNTLYLQMDSLKPEDTAMYYCAAD<u>FCWVDEDRHLYEYQSW</u>GQGTQVTVSSES

KYGPPCPPCPAPEFLGGPSVFLFPPKPKDTLMISRTPEVTCVVVDVSQEDPEVQFNWYVDGVEVH

NAKTKPREEQFNSTYRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLDSDGSFFLYSRLTVDK

SRWQEGNVFSCSVMHEALHNHYTQKSLSLSLGK (AS20592VH4 HCAb dimeric form amino acid sequence)
SEQ ID NO: 320

EVQLVESGGGLVQPGGSLRLSCAAS<u>GYIISSYCMG</u>WFRQAPGKGLEGVS<u>AIDSDGGTSYADSVK</u>

<u>G</u>RFTISRDNSKNTLYLQMNSLRAEDTAVYYCAAD<u>FCWVDEDRHLYEYNSW</u>GQGTLVTVSSESK

YGPPCPPCPAPEFLGGPSVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVDKS

RWQEGNVFSCSVMHEALHNHYTQKSLSLSLGK (AS20592VH5 HCAb dimeric form amino acid sequence)
SEQ ID NO: 321

EVQLVESGGGLVQPGGSLRLSCAAS<u>GYIISSYCMG</u>WFRQAPGKGLEGVA<u>AIDSDGGTSYADSVK</u>

<u>G</u>RFTISRDNSKNTLYLQMNSLRAEDTAVYYCAAD<u>FCWVDEDRHLYEYNSW</u>GQGTLVTVSSESK

YGPPCPPCPAPEFLGGPSVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVDKS

RWQEGNVFSCSVMHEALHNHYTQKSLSLSLGK (AS20592VH6 HCAb dimeric form amino acid sequence)
SEQ ID NO: 322

EVQLVESGGGLVQPGGSLRLSCAAS<u>GYIISSYCMG</u>WFRQAPGKGLEGV<u>AAIDSDGGTSYADSVK</u>

GRFTISRDNSKNTLYLQMNSLRAEDTAMYYCAAD<u>FCWVDEDRHLYEYNSW</u>GQGTLVTVSSESK

YGPPCPPCPAPEFLGGPSVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVDKS

RWQEGNVFSCSVMHEALHNHYTQKSLSLSLGK (AS20592VH7 HCAb dimeric form amino acid sequence)
SEQ ID NO: 323

EVQLVESGGGLVQPGGSLRLSCAAS<u>GYIISSYCMG</u>WFRQAPGKGREGVA<u>AIDSDGGTSYADSVK</u>

-continued

GRFTISRDNSKNTLYLQMNSLRAEDTAMYYCAADFCWVDEDRHLYEYNSWGQGTLVTVSSESK

YGPPCPPCPAPEFLGGPSVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVDKS

RWQEGNVFSCSVMHEALHNHYTQKSLSLSLGK (AS20592VH8 HCAb dimeric form amino acid sequence)
SEQ ID NO: 324
EVQLVESGGGLVQPGGSLRLSCAASGYIISSYCMGWFRQAPGKEREGVAAIDSDGGTSYADSVK

GRFTISRDNSKNTLYLQMNSLRAEDTAMYYCAADFCWVDEDRHLYEYNSWGQGTLVTVSSESK

YGPPCPPCPAPEFLGGPSVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVDKS

RWQEGNVFSCSVMHEALHNHYTQKSLSLSLGK (AS20592VH9 HCAb dimeric form amino acid sequence)
SEQ ID NO: 325
EVQLVESGGGLVQPGGSLRLSCAASGYIISSYCMGWFRQAPGKEREGVAAIDSDGGTSYADSVK

GRFTISKDNSKNTLYLQMNSLRAEDTAMYYCAADFCWVDEDRHLYEYNSWGQGTLVTVSSES

KYGPPCPPCPAPEFLGGPSVFLFPPKPKDTLMISRTPEVTCVVVDVSQEDPEVQFNWYVDGVEVH

NAKTKPREEQFNSTYRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLDSDGSFFLYSRLTVDK

SRWQEGNVFSCSVMHEALHNHYTQKSLSLSLGK (AS20592VH10 HCAb dimeric form amino acid sequence)
SEQ ID NO: 326
EVQLVESGGGLVQPGGSLRLSCAASGYIISSYCMGWFRQAPGKGLEGVAAIDSDGGTSYADSVK

GRFTISKDNSKNTLYLQMNSLRAEDTAMYYCAADFCWVDEDRHLYEYNSWGQGTLVTVSSES

KYGPPCPPCPAPEFLGGPSVFLFPPKPKDTLMISRTPEVTCVVVDVSQEDPEVQFNWYVDGVEVH

NAKTKPREEQFNSTYRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLDSDGSFFLYSRLTVDK

SRWQEGNVFSCSVMHEALHNHYTQKSLSLSLGK (AS20592VH10M1 HCAb dimeric form amino acid sequence)
SEQ ID NO: 327
EVQLVESGGGLVQPGGSLRLSCAASGYIISSYCMGWFRQAPGKGLEGVAAIDSSGGTSYADSVK

GRFTISKDNSKNTLYLQMNSLRAEDTAMYYCAADFCWVDEDRHLYEYNSWGQGTLVTVSSES

KYGPPCPPCPAPEFLGGPSVFLFPPKPKDTLMISRTPEVTCVVVDVSQEDPEVQFNWYVDGVEVH

NAKTKPREEQFNSTYRVVSVLTVLHQDWLNGKEYKCKVSNKGLPSSIEKTISKAKGQPREPQVY

TLPPSQEEMTKNQVSLTCLVKGFYPSDIAVEWESNGQPENNYKTTPPVLDSDGSFFLYSRLTVDK

SRWQEGNVFSCSVMHEALHNHYTQKSLSLSLGK (AS20594VH5 HCAb dimeric form amino acid sequence)
SEQ ID NO: 328
EVQLVESGGGLVQPGGSLRLSCAASGYTISSYCMGWFRQAPGKGLEGVAAIDSDGSTSYADSVK

GRFTISRDNSKNTLYLQMNSLRAEDTAVYYCAADFCWVDDFYEYNYWGQGTLVTVSSESKYGP

PCPPCPAPEFLGGPSVFLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSFFLYSRLTVDKSRWQ

EGNVFSCSVMHEALHNHYTQKSLSLSLGK

-continued (AS20594VH6 HCAb dimeric form amino acid sequence)
SEQ ID NO: 329
EVQLVESGGGLVQPGGSLRLSCAASGYTISSYCMGWFRQAPGKGLEGVAAIDSDGSTSYADSVK

GRFTISRDNSKNTLYLQMNSLRAEDTAMYYCAADFCWVDDFYEYNYWGQGTLVTVSSESKYG

PPCPPCPAPEFLGGPSVFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSFFLYSRLTVDKSRW

QEGNVFSCSVMHEALHNHYTQKSLSLSLGK (AS20594VH7 HCAb dimeric form amino acid sequence)
SEQ ID NO: 330
EVQLVESGGGLVQPGGSLRLSCAASGYTISSYCMGWFRQAPGKGREGVAAIDSDGSTSYADSVK

GRFTISRDNSKNTLYLQMNSLRAEDTAMYYCAADFCWVDDFYEYNYWGQGTLVTVSSESKYG

PPCPPCPAPEFLGGPSVFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSFFLYSRLTVDKSRW

QEGNVFSCSVMHEALHNHYTQKSLSLSLGK (AS20594VH8 HCAb dimeric form amino acid sequence)
SEQ ID NO: 331
EVQLVESGGGLVQPGGSLRLSCAASGYTISSYCMGWFRQAPGKEREGVAAIDSDGSTSYADSVK

GRFTISRDNSKNTLYLQMNSLRAEDTAMYYCAADFCWVDDFYEYNYWGQGTLVTVSSESKYG

PPCPPCPAPEFLGGPSVFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSFFLYSRLTVDKSRW

QEGNVFSCSVMHEALHNHYTQKSLSLSLGK (AS20594VH9 HCAb dimeric form amino acid sequence)
SEQ ID NO: 332
EVQLVESGGGLVQPGGSLRLSCAASGYTISSYCMGWFRQAPGKEREGVAAIDSDGSTSYADSVK

GRFTISKDNSKNTLYLQMNSLRAEDTAMYYCAADFCWVDDFYEYNYWGQGTLVTVSSESKYG

PPCPPCPAPEFLGGPSVFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSFFLYSRLTVDKSRW

QEGNVFSCSVMHEALHNHYTQKSLSLSLGK (AS20594VH10 HCAb dimeric form amino acid sequence)
SEQ ID NO: 333
EVQLVESGGGLVQPGGSLRLSCAASGYTISSYCMGWFRQAPGKGLEGVAAIDSDGSTSYADSVK

GRFTISKDNSKNTLYLQMNSLRAEDTAVYYCAADFCWVDDFYEYNYWGQGTLVTVSSESKYGP

PCPPCPAPEFLGGPSVFLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSFFLYSRLTVDKSRWQ

EGNVFSCSVMHEALHNHYTQKSLSLSLGK (AS20594VH10M1 HCAb dimeric form amino acid sequence)
SEQ ID NO: 334
EVQLVESGGGLVQPGGSLRLSCAASGYTISSYCMGWFRQAPGKGLEGVAAIDSSGSTSYADSVK

GRFTISKDNSKNTLYLQMNSLRAEDTAVYYCAADFCWVDDFYEYNYWGQGTLVTVSSESKYGP

PCPPCPAPEFLGGPSVFLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSFFLYSRLTVDKSRWQ

EGNVFSCSVMHEALHNHYTQKSLSLSLGK (AS20846VH4 HCAb dimeric form amino acid sequence)
SEQ ID NO: 335
EVQLVESGGGLVQPGGSLRLSCAASGYTVSSYCMGWFRQAPGKGLEGVSAIDSDGSVSYADSV
KGRFTISRDNSKNTLYLQMNSLRAEDTAVYYCAADLCWVDQDQGEYNTWGQGTLVTVSSESK
YGPPCPPCPAPEFLGGPSVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDSDGSFFLYSRLTVDKS
RWQEGNVFSCSVMHEALHNHYTQKSLSLSLGK (AS20846VH5 HCAb dimeric form amino acid sequence)
SEQ ID NO: 336
EVQLVESGGGLVQPGGSLRLSCAASGYTVSSYCMGWFRQAPGKGLEGVSAIDSDGSVSYADSV
KGRFTISRDNSKNTLYLQMNSLRAEDTAVYFCAADLCWVDQDQGEYNTWGQGTLVTVSSESK
YGPPCPPCPAPEFLGGPSVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDSDGSFFLYSRLTVDKS
RWQEGNVFSCSVMHEALHNHYTQKSLSLSLGK (AS20846VH6 HCAb dimeric form amino acid sequence)
SEQ ID NO: 337
EVQLVESGGGLVQPGGSLRLSCAASGYTVSSYCMGWFRQAPGKGLEGVAAIDSDGSVSYADSV
KGRFTISRDNSKNTLYLQMNSLRAEDTAVYFCAADLCWVDQDQGEYNTWGQGTLVTVSSESK
YGPPCPPCPAPEFLGGPSVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDSDGSFFLYSRLTVDKS
RWQEGNVFSCSVMHEALHNHYTQKSLSLSLGK (AS20846VH7 HCAb dimeric form amino acid sequence)
SEQ ID NO: 338
EVQLVESGGGLVQPGGSLRLSCAASGYTVSSYCMGWFRQAPGKGLEGVAAIDSDGSVSYADSV
KGRFTISRDNSKNTLYLQMNSLRAEDTAMYFCAADLCWVDQDQGEYNTWGQGTLVTVSSESK
YGPPCPPCPAPEFLGGPSVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDSDGSFFLYSRLTVDKS
RWQEGNVFSCSVMHEALHNHYTQKSLSLSLGK (AS20846VH8 HCAb dimeric form amino acid sequence)
SEQ ID NO: 339
EVQLVESGGGLVQPGGSLRLSCAASGYTVSSYCMGWFRQAPGKGREGVAAIDSDGSVSYADSV
KGRFTISRDNSKNTLYLQMNSLRAEDTAMYFCAADLCWVDQDQGEYNTWGQGTLVTVSSESK
YGPPCPPCPAPEFLGGPSVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDSDGSFFLYSRLTVDKS
RWQEGNVFSCSVMHEALHNHYTQKSLSLSLGK (AS20846VH9 HCAb dimeric form amino acid sequence)
SEQ ID NO: 340
EVQLVESGGGLVQPGGSLRLSCAASGYTVSSYCMGWFRQAPGKEREGVAAIDSDGSVSYADSV
KGRFTISRDNSKNTLYLQMNSLRAEDTAMYFCAADLCWVDQDQGEYNTWGQGTLVTVSSESK
YGPPCPPCPAPEFLGGPSVFLFPPKPKDTLMISRTPEVTCVVVDVSQEDPEVQFNWYVDGVEVHN -continued

AKTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVDKS

RWQEGNVFSCSVMHEALHNHYTQKSLSLSLGK (AS20846VH10 HCAb dimeric form amino acid sequence)
                          SEQ ID NO: 341

EVQLVESGGGLVQPGGSLRLSCAASGYTVSSYCMGWFRQAPGKEREGVAAIDSDGSVSYADSV

KGRFTISKDNSKNTLYLQMNSLRAEDTAMYFCAADLCWVDQDQGEYNTWGQGTLVTVSSESK

YGPPCPPCPAPEFLGGPSVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVDKS

RWQEGNVFSCSVMHEALHNHYTQKSLSLSLGK (AS20846VH12 HCAb dimeric form amino acid sequence)
                          SEQ ID NO: 342

EVQLVESGGGLVQPGGSLRLSCAASGYTVSSYCMGWFRQAPGKGREGVSAIDSDGSVSYADSV

KGRFTISKDNSKNTLYLQMNSLRAEDTAVYFCAADLCWVDQDQGEYNTWGQGTLVTVSSESK

YGPPCPPCPAPEFLGGPSVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVDKS

RWQEGNVFSCSVMHEALHNHYTQKSLSLSLGK (AS20846VH12M1 HCAb dimeric form amino acid sequence)
                          SEQ ID NO: 343

EVQLVESGGGLVQPGGSLRLSCAASGYTVSSYCMGWFRQAPGKGREGVSAIDSSGSVSYADSV

KGRFTISKDNSKNTLYLQMNSLRAEDTAVYFCAADLCWVDQDQGEYNTWGQGTLVTVSSESK

YGPPCPPCPAPEFLGGPSVFLFPPKPKDTLMISRTPEVTCVVVDVSQEDPEVQFNWYVDGVEVHN

AKTKPREEQFNSTYRVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDSDGSFFLYSRLTVDKS

RWQEGNVFSCSVMHEALHNHYTQKSLSLSLGK (AS20601VH4 HCAb dimeric form amino acid sequence)
                          SEQ ID NO: 344

EVQLVESGGGLVQPGGSLRLSCAASGYTYGGYCMGWFRQAPGKGLEGVSTINSDGSTNYADSV

KGRFTISRDNSKNTLYLQMNSLRAEDTAVYYCAVDLAPCWVAGPIEAADFGYWGQGTLVTVSS

ESKYGPPCPPCPAPEFLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPVLDSDGSFFLYSRLTV

DKSRWQEGNVFSCSVMHEALHNHYTQKSLSLSLGK (AS20601VH4.M6 HCAb dimeric form amino acid sequence)
                          SEQ ID NO: 345

EVQLVESGGGLVQPGGSLRLSCAASGYTYGGYCMGWFRQAPGKGLEGVSTIASEGSTNYADSV

KGRFTISRDNSKNTLYLQMNSLRAEDTAVYYCAVDLAPCWVAGPIEAADFGYWGQGTLVTVSS

ESKYGPPCPPCPAPEFLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPVLDSDGSFFLYSRLTV

DKSRWQEGNVFSCSVMHEALHNHYTQKSLSLSLGK (AS20601VH4.M7 HCAb dimeric form amino acid sequence)
                          SEQ ID NO: 346

EVQLVESGGGLVQPGGSLRLSCAASGYTYGGYCMGWFRQAPGKGLEGVSTIASSGSTNYADSV

KGRFTISRDNSKNTLYLQMNSLRAEDTAVYYCAVDLAPCWVAGPIEAADFGYWGQGTLVTVSS

ESKYGPPCPPCPAPEFLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPVLDSDGSFFLYSRLTV

DKSRWQEGNVFSCSVMHEALHNHYTQKSLSLSLGK (AS20601VH11 HCAb dimeric form amino acid sequence)

SEQ ID NO: 347

EVQLVESGGGLVQPGGSLRLSCAASGYTYGGYCMGWFRQAPGKGREGVSTINSDGSTNYADSV

KGRFTISRDNAKNTLYLQMNSLRPEDTAVYYCAVDLAPCWVAGPIEAADFGYWGQGTLVTVSS

ESKYGPPCPPCPAPEFLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPVLDSDGSFFLYSRLTV

DKSRWQEGNVFSCSVMHEALHNHYTQKSLSLSLGK (AS20601VH11.M6 HCAb dimeric form amino acid sequence)

SEQ ID NO: 348

EVQLVESGGGLVQPGGSLRLSCAASGYTYGGYCMGWFRQAPGKGREGVSTIASEGSTNYADSV

KGRFTISRDNAKNTLYLQMNSLRPEDTAVYYCAVDLAPCWVAGPIEAADFGYWGQGTLVTVSS

ESKYGPPCPPCPAPEFLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPVLDSDGSFFLYSRLTV

DKSRWQEGNVFSCSVMHEALHNHYTQKSLSLSLGK (AS20601VH11.M7 HCAb dimeric form amino acid sequence)

SEQ ID NO: 349

EVQLVESGGGLVQPGGSLRLSCAASGYTYGGYCMGWFRQAPGKGREGVSTIASSGSTNYADSV

KGRFTISRDNAKNTLYLQMNSLRPEDTAVYYCAVDLAPCWVAGPIEAADFGYWGQGTLVTVSS

ESKYGPPCPPCPAPEFLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPVLDSDGSFFLYSRLTV

DKSRWQEGNVFSCSVMHEALHNHYTQKSLSLSLGK (Human LAG-3 full length amino acid sequence)

SEQ ID NO: 350

VPVVWAQEGAPAQLPCSPTIPLQDLSLLRRAGVTWQHQPDSGPPAAAPGHPLAPGPHPAAPSSW

GPRPRRYTVLSVGPGGLRSGRLPLQPRVQLDERGRQRGDFSLWLRPARRADAGEYRAAVHLRD

RALSCRLRLRLGQASMTASPPGSLRASDWVILNCSFSRPDRPASVHWFRNRGQGRVPVRESPHH

HLAESFLFLPQVSPMDSGPWGCILTYRDGFNVSIMYNLTVLGLEPPTPLTVYAGAGSRVGLPCRL

PAGVGTRSFLTAKWTPPGGGPDLLVTGDNGDFTLRLEDVSQAQAGTYTCHIHLQEQQLNATVTL

AIITVTPKSFGSPGSLGKLLCEVTPVSGQERFVWSSLDTPSQRSFSGPWLEAQEAQLLSQPWQCQL

YQGERLLGAAVYFTELSSPGAQRSGRAPGALPAGHLLLFLILGVLSLLLLVTGAFGFHLWRRQW

RPRRFSALEQGIHPPQAQSKIEELEQEPEPEPEPEPEPEPEPEPEQL (Human LAG-3 extracellular domain amino acid sequence)

SEQ ID NO: 351

VPVVWAQEGAPAQLPCSPTIPLQDLSLLRRAGVTWQHQPDSGPPAAAPGHPLAPGPHPAAPSSW

GPRPRRYTVLSVGPGGLRSGRLPLQPRVQLDERGRQRGDFSLWLRPARRADAGEYRAAVHLRD

RALSCRLRLRLGQASMTASPPGSLRASDWVILNCSFSRPDRPASVHWFRNRGQGRVPVRESPHH

HLAESFLFLPQVSPMDSGPWGCILTYRDGFNVSIMYNLTVLGLEPPTPLTVYAGAGSRVGLPCRL

PAGVGTRSFLTAKWTPPGGGPDLLVTGDNGDFTLRLEDVSQAQAGTYTCHIHLQEQQLNATVTL

-continued

AIITVTPKSFGSPGSLGKLLCEVTPVSGQERFVWSSLDTPSQRSFSGPWLEAQEAQLLSQPWQCQL

YQGERLLGAAVYFTELSSPGAQRSGRAPGALPAGHL (Human IgG1 hinge amino acid sequence)
SEQ ID NO: 352
EPKSSDKTHTCPPCP (Mutated human IgG1 hinge amino acid sequence)
SEQ ID NO: 353
EPKSSDKTHTSPPSP (BMS-986016 Heavy chain amino acid sequence)
SEQ ID NO: 354
QVQLQQWGAGLLKPSETLSLTCAVYGGSFSDYYWNWIRQPPGKGLEWIGEINHRGSTNSNPSLK

SRVTLSLDTSKNQFSLKLRSVTAADTAVYYCAFGYSDYEYNWFDPWGQGTLVTVSSASTKGPS

VFPLAPCSRSTSESTAALGCLVKDYFPEPVTVSWNSGALTSGVHTFPAVLQSSGLYSLSSVVTVPS

SSLGTKTYTCNVDHKPSNTKVDKRVESKYGPPCPPCPAPEFLGGPSVFLFPPKPKDTLMISRTPEV

TCVVVDVSQEDPEVQFNWYVDGVEVHNAKTKPREEQFNSTYRVVSVLTVLHQDWLNGKEYKC

KVSNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSLSLSLGK (BMS-986016 Light chain amino acid sequence)
SEQ ID NO: 355
EIVLTQSPATLSLSPGERATLSCRASQSISSYLAWYQQKPGQAPRLLIYDASNRATGIPARFSGSGS

GTDFTLTISSLEPEDFAVYYCQQRSNWPLTFGQGTNLEIKRTVAAPSVFIFPPSDEQLKSGTASVV

CLLNNFYPREAKVQWKVDNALQSGNSQESVTEQDSKDSTYSLSSTLTLSKADYEKHKVYACEV

THQGLSSPVTKSFNRGEC (pembrolizumab Heavy chain amino acid sequence)
SEQ ID NO: 356
QVQLVQSGVEVKKPGASVKVSCKASGYTFTNYYMYWVRQAPGQGLEWMGGINPSNGGTNFNE

KFKNRVTLTTDSSTTTAYMELKSLQFDDTAVYYCARRDYRFDMGFDYWGQGTTVTVSSASTKG

PSVFPLAPCSRSTSESTAALGCLVKDYFPEPVTVSWNSGALTSGVHTFPAVLQSSGLYSLSSVVTV

PSSSLGTKTYTCNVDHKPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLVKGFYPSDIAVEWESN

GQPENNYKTTPPVLDSDGSFFLYSRLTVDKSRWQEGNVFSCSVMHEALHNHYTQKSLSLSLGK (pembrolizumab Light chain amino acid sequence)
SEQ ID NO: 357
EIVLTQSPATLSLSPGERATLSCRASKGVSTSGYSYLHWYQQKPGQAPRLLIYLASYLESGVPARF

SGSGSGTDFTLTISSLEPEDFAVYYCQHSRDLPLTFGGGTKVEIKRTVAAPSVFIFPPSDEQLKSGT

ASVVCLLNNFYPREAKVQWKVDNALQSGNSQESVTEQDSKDSTYSLSSTLTLSKADYEKHKVY

ACEVTHQGLSSPVTKSFNRGEC (BLP-21 Heavy chain amino acid sequence)
SEQ ID NO: 358
EVQLVESGGGLVQPGGSLRLSCAASGYTVSSYCMGWFRQAPGKGREGVSAIDSDGSVSYADSV

KGRFTISKDNSKNTLYLQMNSLRAEDTAVYFCAADLCWVDQDQGEYNTWGQGTLVTVSSEPKS

SDKTHTSPPSPQVQLVQSGVEVKKPGASVKVSCKASGYTFTNYYMYWVRQAPGQGLEWMGGI

NPSNGGTNFNEKFKNRVTLTTDSSTTTAYMELKSLQFDDTAVYYCARRDYRFDMGFDYWGQG

TTVTVSSASTKGPSVFPLAPCSRSTSESTAALGCLVKDYFPEPVTVSWNSGALTSGVHTFPAVLQS

SGLYSLSSVVTVPSSSLGTKTYTCNVDHKPSNTKVDKRVESKYGPPCPPCPAPEFLGGPSVFLFPP

KPKDTLMISRTPEVTCVVVDVSQEDPEVQFNWYVDGVEVHNAKTKPREEQFNSTYRVVSVLTV

LHQDWLNGKEYKCKVSNKGLPSSIEKTISKAKGQPREPQVYTLPPSQEEMTKNQVSLTCLVKGF

```
YPSDIAVEWESNGQPENNYKTTPPVLDSDGSFFLYSRLTVDKSRWQEGNVFSCSVMHEALHNHY

TQKSLSLSLGK (BLP-21 Light chain amino acid sequence)
                                                   SEQ ID NO: 359
EIVLTQSPATLSLSPGERATLSCRASKGVSTSGYSYLHWYQQKPGQAPRLLIYLASYLESGVPARF

SGSGSGTDFTLTISSLEPEDFAVYYCQHSRDLPLTFGGGTKVEIKRTVAAPSVFIFPPSDEQLKSGT

ASVVCLLNNFYPREAKVQWKVDNALQSGNSQESVTEQDSKDSTYSLSSTLTLSKADYEKHKVY

ACEVTHQGLSSPVTKSFNRGEC (BLP-22 Heavy chain amino acid sequence)
                                                   SEQ ID NO: 360
QVQLVQSGVEVKKPGASVKVSCKASGYTFTNYYMYWVRQAPGQGLEWMGGINPSNGGTNFNE

KFKNRVTLTTDSSTTTAYMELKSLQFDDTAVYYCARRDYRFDMGFDYWGQGTTVTVSSASTKG

PSVFPLAPCSRSTSESTAALGCLVKDYFPEPVTVSWNSGALTSGVHTFPAVLQSSGLYSLSSVVTV

PSSSLGTKTYTCNVDHKPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLVKGFYPSDIAVEWESN

GQPENNYKTTPPVLDSDGSFFLYSRLTVDKSRWQEGNVFSCSVMHEALHNHYTQKSLSLSLGK (BLP-22 Light chain amino acid sequence)
                                                   SEQ ID NO: 361
EVQLVESGGGLVQPGGSLRLSCAASGYTVSSYCMGWFRQAPGKGREGVSAIDSDGSVSYADSV

KGRFTISKDNSKNTLYLQMNSLRAEDTAVYFCAADLCWVDQDQGEYNTWGQGTLVTVSSEPKS

SDKTHTSPPSPEIVLTQSPATLSLSPGERATLSCRASKGVSTSGYSYLHWYQQKPGQAPRLLIYLA

SYLESGVPARFSGSGSGTDFTLTISSLEPEDFAVYYCQHSRDLPLTFGGGTKVEIKRTVAAPSVFIF

PPSDEQLKSGTASVVCLLNNFYPREAKVQWKVDNALQSGNSQESVTEQDSKDSTYSLSSTLTLS

KADYEKHKVYACEVTHQGLSSPVTKSFNRGEC (BLP-23 Heavy chain amino acid sequence)
                                                   SEQ ID NO: 362
EVQLVESGGGLVQPGGSLRLSCAASGYTYGGYCMGWFRQAPGKGLEGVSTINSDGSTNYADSV

KGRFTISRDNSKNTLYLQMNSLRAEDTAVYYCAVDLAPCWVAGPIEAADFGYWGQGTLVTVSS

EPKSSDKTHTSPPSPQVQLVQSGVEVKKPGASVKVSCKASGYTFTNYYMYWVRQAPGQGLEW

MGGINPSNGGTNFNEKFKNRVTLTTDSSTTTAYMELKSLQFDDTAVYYCARRDYRFDMGFDYW

GQGTTVTVSSASTKGPSVFPLAPCSRSTSESTAALGCLVKDYFPEPVTVSWNSGALTSGVHTFPA

VLQSSGLYSLSSVVTVPSSSLGTKTYTCNVDHKPSNTKVDKRVESKYGPPCPPCPAPEFLGGPSVF

LFPPKPKDTLMISRTPEVTCVVVDVSQEDPEVQFNWYVDGVEVHNAKTKPREEQFNSTYRVVSV

LTVLHQDWLNGKEYKCKVSNKGLPSSIEKTISKAKGQPREPQVYTLPPSQEEMTKNQVSLTCLV

KGFYPSDIAVEWESNGQPENNYKTTPPVLDSDGSFFLYSRLTVDKSRWQEGNVFSCSVMHEALH

NHYTQKSLSLSLGK (BLP-23 Light chain amino acid sequence)
                                                   SEQ ID NO: 363
EIVLTQSPATLSLSPGERATLSCRASKGVSTSGYSYLHWYQQKPGQAPRLLIYLASYLESGVPARF

SGSGSGTDFTLTISSLEPEDFAVYYCQHSRDLPLTFGGGTKVEIKRTVAAPSVFIFPPSDEQLKSGT

ASVVCLLNNFYPREAKVQWKVDNALQSGNSQESVTEQDSKDSTYSLSSTLTLSKADYEKHKVY

ACEVTHQGLSSPVTKSFNRGEC (BLP-24 Heavy chain amino acid sequence)
                                                   SEQ ID NO: 364
QVQLVQSGVEVKKPGASVKVSCKASGYTFTNYYMYWVRQAPGQGLEWMGGINPSNGGTNFNE
```

KFKNRVTLTTDSSTTTAYMELKSLQFDDTAVYYCARRDYRFDMGFDYWGQGTTVTVSSASTKG

PSVFPLAPCSRSTSESTAALGCLVKDYFPEPVTVSWNSGALTSGVHTFPAVLQSSGLYSLSSVVTV

PSSSLGTKTYTCNVDHKPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLVKGFYPSDIAVEWESN

GQPENNYKTTPPVLDSDGSFFLYSRLTVDKSRWQEGNVFSCSVMHEALHNHYTQKSLSLSLGK (BLP-24 Light chain amino acid sequence)
SEQ ID NO: 365
EVQLVESGGGLVQPGGSLRLSCAASGYTYGGYCMGWFRQAPGKGLEGVSTINSDGSTNYADSV

KGRFTISRDNSKNTLYLQMNSLRAEDTAVYYCAVDLAPCWVAGPIEAADFGYWGQGTLVTVSS

EPKSSDKTHTSPPSPEIVLTQSPATLSLSPGERATLSCRASKGVSTSGYSYLHWYQQKPGQAPRLLI

YLASYLESGVPARFSGSGSGTDFTLTISSLEPEDFAVYYCQHSRDLPLTFGGGTKVEIKRTVAAPS

VFIFPPSDEQLKSGTASVVCLLNNFYPREAKVQWKVDNALQSGNSQESVTEQDSKDSTYSLSSTL

TLSKADYEKHKVYACEVTHQGLSSPVTKSFNRGEC (Linker peptide (9GS) amino acid sequence)
SEQ ID NO: 366
GGGGSGGGS (Linker peptide amino acid sequence)
SEQ ID NO: 367
GGGGSGGGGSGGGGS (Linker peptide amino acid sequence, n is an integer of at least one)
SEQ ID NO: 368
(G)$_n$ (Linker peptide amino acid sequence, n is an integer of at least one)
SEQ ID NO: 369
(GS)$_n$ (Linker peptide amino acid sequence, n is an integer of at least one)
SEQ ID NO: 370
(GSGGS)$_n$ (Linker peptide amino acid sequence, n is an integer of at least one)
SEQ ID NO: 371
(GGGS)$_n$ (Linker peptide amino acid sequence, n is an integer of at least one)
SEQ ID NO: 372
(GGGGS)$_n$ (PD1-BM-min Heavy chain amino acid sequence)
SEQ ID NO: 373
EVQLVESGGGLVQPGGSLRLSCAASGFVFSRYDMAWVRQAPGKGLEWVSFISGGGSNTYYPDTVKG

RFTISRDNSKNTLYLQMNSLRAEDTAVYYCISPYYYAMEYWGQGTTVTVSSASTKGPSVFPLAPCSRS

TSESTAALGCLVKDYFPEPVTVSWNSGALTSGVHTFPAVLQSSGLYSLSSVVTVPSSSLGTKTYTCNV

DHKPSNTKVDKRVESKYGPPCPPCPAPEFLGGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDSDGSFFLYS

RLTVDKSRWQEGNVFSCSVMHEALHNHYTQKSLSLSLGK (PD1-BM-min Light chain amino acid sequence)
SEQ ID NO: 374
DIQMTQSPSSVSASVGDRVTITCKASQDVDTAVAWYQQKPGKAPKLLIYWASTRHTGVPSRFSGSGS

GTDFTLTISSLQPEDFATYYCQQYSTFPWTFGGGTKVEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSSP

VTKSFNRGEC (BLP-1 Heavy chain amino acid sequence)

```
                                                    SEQ ID NO: 375
EVQLVESGGGSVQAGGSLRLSCAASGYIISSYCMGWFRQAPGKEREGVAAIDSDGGTSYADSVKGRF

TISKDNAKNTLYLQMDSLKPEDTAMYYCAADFCWVDEDRHLYEYNSWGQGTQVTVSSEPKSSDKT

HTSPPSPEVQLVESGGGLVQPGGSLRLSCAASGFVFSRYDMAWVRQAPGKGLEWVSFISGGGSNTYY

PDTVKGRFTISRDNSKNTLYLQMNSLRAEDTAVYYCISPYYYAMEYWGQGTTVTVSSASTKGPSVFP

LAPCSRSTSESTAALGCLVKDYFPEPVTVSWNSGALTSGVHTFPAVLQSSGLYSLSSVVTVPSSSLGTK

TYTCNVDHKPSNTKVDKRVESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNGKEYKCKVSNKGLPSSIE

KTISKAKGQPREPQVYTLPPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK (BLP-1 Light chain amino acid sequence)
                                                    SEQ ID NO: 376
DIQMTQSPSSVSASVGDRVTITCKASQDVDTAVAWYQQKPGKAPKLLIYWASTRHTGVPSRFSGSGS

GTDFTLTISSLQPEDFATYYCQQYSTFPWTFGGGTKVEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSSP

VTKSFNRGEC (BLP-2 Heavy chain amino acid sequence)
                                                    SEQ ID NO: 377
QVQLAESGGGSVQAGGSLRLSCAASGYTISSYCMGWFRQAPGKEREGVAAIDSDGSTSYADSVKGRF

TISKDNAKNTLYLQMNSLKPEDTAMYYCAADFCWVDDFYEYNYWGQGTQVTVSSEPKSSDKTHTSP

PSPEVQLVESGGGLVQPGGSLRLSCAASGFVFSRYDMAWVRQAPGKGLEWVSFISGGGSNTYYPDTV

KGRFTISRDNSKNTLYLQMNSLRAEDTAVYYCISPYYYAMEYWGQGTTVTVSSASTKGPSVFPLAPC

SRSTSESTAALGCLVKDYFPEPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLMISRTPEVTCVVVDVSQEDPE

VQFNWYVDGVEVHNAKTKPREEQFNSTYRVVSVLTVLHQDWLNGKEYKCKVSNKGLPSSIEKTISK

AKGQPREPQVYTLPPSQEEMTKNQVSLTCLVKGFYPSDIAVEWESNGQPENNYKTTPPVLDSDGSFFL

YSRLTVDKSRWQEGNVFSCSVMHEALHNHYTQKSLSLSLGK (BLP-2 Light chain amino acid sequence)
                                                    SEQ ID NO: 378
DIQMTQSPSSVSASVGDRVTITCKASQDVDTAVAWYQQKPGKAPKLLIYWASTRHTGVPSRFSGSGS

GTDFTLTISSLQPEDFATYYCQQYSTFPWTFGGGTKVEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSSP

VTKSFNRGEC (BLP-3 Heavy chain amino acid sequence)
                                                    SEQ ID NO: 379
EVQLAESGGGSVQAGGSLRLSCAASGYTYGGYCMGWFRQAPGKEREGVATINSDGSTNYADSVKGR

FTISKDNAKNTLYLQMNSLSPEDTAMYYCAVDLAPCWVAGPIEAADFGYWGQGTQVTVSSEPKSSD

KTHTSPPSPEVQLVESGGGLVQPGGSLRLSCAASGFVFSRYDMAWVRQAPGKGLEWVSFISGGGSNT

YYPDTVKGRFTISRDNSKNTLYLQMNSLRAEDTAVYYCISPYYYAMEYWGQGTTVTVSSASTKGPSV

FPLAPCSRSTSESTAALGCLVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKPKDTLMISRTPEVTCVVVD

VSQEDPEVQFNWYVDGVEVHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK (BLP-3 Light chain amino acid sequence)
                                                    SEQ ID NO: 380
```

```
DIQMTQSPSSVSASVGDRVTITCKASQDVDTAVAWYQQKPGKAPKLLIYWASTRHTGVPSRFSGSGS

GTDFTLTISSLQPEDFATYYCQQYSTFPWTFGGGTKVEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSSP

VTKSFNRGEC (BLP-4 Heavy chain amino acid sequence)
                                               SEQ ID NO: 381
QVHLMESGGGSVQVGGSLRLSCAASGYTVSSYCMGWFRQAPGKEREGVAAIDSDGSVSYADSVKGR

FTISKDNAKNTLYLQMNSLKPEDTAMYFCAADLCWVDQDQGEYNTWGQGTQVTVSSEPKSSDKTH

TSPPSPEVQLVESGGGLVQPGGSLRLSCAASGFVFSRYDMAWVRQAPGKGLEWVSFISGGGSNTYYP

DTVKGRFTISRDNSKNTLYLQMNSLRAEDTAVYYCISPYYYAMEYWGQGTTVTVSSASTKGPSVFPL

APCSRSTSESTAALGCLVKDYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKEYKCKVSNKGLPSSIEK

TISKAKGQPREPQVYTLPPSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK (BLP-4 Light chain amino acid sequence)
                                               SEQ ID NO: 382
DIQMTQSPSSVSASVGDRVTITCKASQDVDTAVAWYQQKPGKAPKLLIYWASTRHTGVPSRFSGSGS

GTDFTLTISSLQPEDFATYYCQQYSTFPWTFGGGTKVEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSSP

VTKSFNRGEC (BLP-5 Heavy chain amino acid sequence)
                                               SEQ ID NO: 383
EVQLVESGGGLVQPGGSLRLSCAASGYIISSYCMGWFRQAPGKGLEGVAAIDSDGGTSYADSVKGRF

TISKDNSKNTLYLQMNSLRAEDTAMYYCAADFCWVDEDRHLYEYNSWGQGTLVTVSSEPKSSDKTH

TSPPSPEVQLVESGGGLVQPGGSLRLSCAASGFVFSRYDMAWVRQAPGKGLEWVSFISGGGSNTYYP

DTVKGRFTISRDNSKNTLYLQMNSLRAEDTAVYYCISPYYYAMEYWGQGTTVTVSSASTKGPSVFPL

APCSRSTSESTAALGCLVKDYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKEYKCKVSNKGLPSSIEK

TISKAKGQPREPQVYTLPPSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK (BLP-5 Light chain amino acid sequence)
                                               SEQ ID NO: 384
DIQMTQSPSSVSASVGDRVTITCKASQDVDTAVAWYQQKPGKAPKLLIYWASTRHTGVPSRFSGSGS

GTDFTLTISSLQPEDFATYYCQQYSTFPWTFGGGTKVEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSSP

VTKSFNRGEC (BLP-6 Heavy chain amino acid sequence)
                                               SEQ ID NO: 385
EVQLVESGGGLVQPGGSLRLSCAASGFVFSRYDMAWVRQAPGKGLEWVSFISGGGSNTYYPDTVKG

RFTISRDNSKNTLYLQMNSLRAEDTAVYYCISPYYYAMEYWGQGTTVTVSSASTKGPSVFPLAPCSRS

TSESTAALGCLVKDYFPEPVTVSWNSGALTSGVHTFPAVLQSSGLYSLSSVVTVPSSSLGTKTYTCNV

DHKPSNTKVDKRVESKYGPPCPPCPAPEFLGGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDSDGSFFLYS
```

```
RLTVDKSRWQEGNVFSCSVMHEALHNHYTQKSLSLSLGKEPKSSDKTHTSPPSPEVQLVESGGGLVQ

PGGSLRLSCAASGYIISSYCMGWFRQAPGKGLEGVAAIDSDGGTSYADSVKGRFTISKDNSKNTLYLQ

MNSLRAEDTAMYYCAADFCWVDEDRHLYEYNSWGQGTLVTVSS (BLP-6 Light chain amino acid sequence)
                                          SEQ ID NO: 386
DIQMTQSPSSVSASVGDRVTITCKASQDVDTAVAWYQQKPGKAPKLLIYWASTRHTGVPSRFSGSGS

GTDFTLTISSLQPEDFATYYCQQYSTFPWTFGGGTKVEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSSP

VTKSFNRGEC (BLP-7 Heavy chain amino acid sequence)
                                          SEQ ID NO: 387
EVQLVESGGGLVQPGGSLRLSCAASGFVFSRYDMAWVRQAPGKGLEWVSFISGGGSNTYYPDTVKG

RFTISRDNSKNTLYLQMNSLRAEDTAVYYCISPYYYAMEYWGQGTTVTVSSASTKGPSVFPLAPCSRS

TSESTAALGCLVKDYFPEPVTVSWNSGALTSGVHTFPAVLQSSGLYSLSSVVTVPSSSLGTKTYTCNV

DHKPSNTKVDKRVESKYGPPCPPCPAPEFLGGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDSDGSFFLYS

RLTVDKSRWQEGNVFSCSVMHEALHNHYTQKSLSLSLGK (BLP-7 Light chain amino acid sequence)
                                          SEQ ID NO: 388
EVQLVESGGGLVQPGGSLRLSCAASGYIISSYCMGWFRQAPGKGLEGVAAIDSDGGTSYADSVKGRF

TISKDNSKNTLYLQMNSLRAEDTAMYYCAADFCWVDEDRHLYEYNSWGQGTLVTVSSEPKSSDKTH

TSPPSPDIQMTQSPSSVSASVGDRVTITCKASQDVDTAVAWYQQKPGKAPKWYWASTRHTGVPSRF

SGSGSGTDFTLTISSLQPEDFATYYCQQYSTFPWTFGGGTKVEIKRTVAAPSVFIFPPSDEQLKSGTASV

VCLLNNFYPREAKVQWKVDNALQSGNSQESVTEQDSKDSTYSLSSTLTLSKADYEKHKVYACEVTH

QGLSSPVTKSFNRGEC (BLP-8 Heavy chain amino acid sequence)
                                          SEQ ID NO: 389
EVQLVESGGGLVQPGGSLRLSCAASGFVFSRYDMAWVRQAPGKGLEWVSFISGGGSNTYYPDTVKG

RFTISRDNSKNTLYLQMNSLRAEDTAVYYCISPYYYAMEYWGQGTTVTVSSASTKGPSVFPLAPCSRS

TSESTAALGCLVKDYFPEPVTVSWNSGALTSGVHTFPAVLQSSGLYSLSSVVTVPSSSLGTKTYTCNV

DHKPSNTKVDKRVESKYGPPCPPCPAPEFLGGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDSDGSFFLYS

RLTVDKSRWQEGNVFSCSVMHEALHNHYTQKSLSLSLGK (BLP-8 Light chain amino acid sequence)
                                          SEQ ID NO: 390
DIQMTQSPSSVSASVGDRVTITCKASQDVDTAVAWYQQKPGKAPKLLIYWASTRHTGVPSRFSGSGS

GTDFTLTISSLQPEDFATYYCQQYSTFPWTFGGGTKVEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSSP

VTKSFNRGECEPKSSDKTHTSPPSPEVQLVESGGGLVQPGGSLRLSCAASGYIISSYCMGWFRQAPGK

GLEGVAAIDSDGGTSYADSVKGRFTISKDNSKNTLYLQMNSLRAEDTAMYYCAADFCWVDEDRHLY

EYNSWGQGTLVTVSS (BLP-9 Heavy chain amino acid sequence)
                                          SEQ ID NO: 391
EVQLVESGGGLVQPGGSLRLSCAASGYTISSYCMGWFRQAPGKGLEGVAAIDSDGSTSYADSVKGRF
```

```
TISKDNSKNTLYLQMNSLRAEDTAVYYCAADFCWVDDFYEYNYWGQGTLVTVSSEPKSSDKTHTSP

PSPEVQLVESGGGLVQPGGSLRLSCAASGFVFSRYDMAWVRQAPGKGLEWVSFISGGGSNTYYPDTV

KGRFTISRDNSKNTLYLQMNSLRAEDTAVYYCISPYYYAMEYWGQGTTVTVSSASTKGPSVFPLAPC

SRSTSESTAALGCLVKDYFPEPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLMISRTPEVTCVVVDVSQEDPE

VQFNWYVDGVEVHNAKTKPREEQFNSTYRVVSVLTVLHQDWLNGKEYKCKVSNKGLPSSIEKTISK

AKGQPREPQVYTLPPSQEEMTKNQVSLTCLVKGFYPSDIAVEWESNGQPENNYKTTPPVLDSDGSFFL

YSRLTVDKSRWQEGNVFSCSVMHEALHNHYTQKSLSLSLGK (BLP-9 Light chain amino acid sequence)
                                                         SEQ ID NO: 392
DIQMTQSPSSVSASVGDRVTITCKASQDVDTAVAWYQQKPGKAPKLLIYWASTRHTGVPSRFSGSGS

GTDFTLTISSLQPEDFATYYCQQYSTFPWTFGGGTKVEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSSP

VTKSFNRGEC (BLP-10 Heavy chain amino acid sequence)
                                                         SEQ ID NO: 393
EVQLVESGGGLVQPGGSLRLSCAASGFVFSRYDMAWVRQAPGKGLEWVSFISGGGSNTYYPDTVKG

RFTISRDNSKNTLYLQMNSLRAEDTAVYYCISPYYYAMEYWGQGTTVTVSSASTKGPSVFPLAPCSRS

TSESTAALGCLVKDYFPEPVTVSWNSGALTSGVHTFPAVLQSSGLYSLSSVVTVPSSSLGTKTYTCNV

DHKPSNTKVDKRVESKYGPPCPPCPAPEFLGGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDSDGSFFLYS

RLTVDKSRWQEGNVFSCSVMHEALHNHYTQKSLSLSLGKEPKSSDKTHTSPPSPEVQLVESGGGLVQ

PGGSLRLSCAASGYTISSYCMGWFRQAPGKGLEVAAIDSDGSTSYADSVKGRFTISKDNSKNTLYLQ

MNSLRAEDTAVYYCAADFCWVDDFYEYNYWGQGTLVTVSS (BLP-10 Light chain amino acid sequence)
                                                         SEQ ID NO: 394
DIQMTQSPSSVSASVGDRVTITCKASQDVDTAVAWYQQKPGKAPKLLIYWASTRHTGVPSRFSGSGS

GTDFTLTISSLQPEDFATYYCQQYSTFPWTFGGGTKVEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSSP

VTKSFNRGEC (BLP-11 Heavy chain amino acid sequence)
                                                         SEQ ID NO: 395
EVQLVESGGGLVQPGGSLRLSCAASGFVFSRYDMAWVRQAPGKGLEWVSFISGGGSNTYYPDTVKG

RFTISRDNSKNTLYLQMNSLRAEDTAVYYCISPYYYAMEYWGQGTTVTVSSASTKGPSVFPLAPCSRS

TSESTAALGCLVKDYFPEPVTVSWNSGALTSGVHTFPAVLQSSGLYSLSSVVTVPSSSLGTKTYTCNV

DHKPSNTKVDKRVESKYGPPCPPCPAPEFLGGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDSDGSFFLYS

RLTVDKSRWQEGNVFSCSVMHEALHNHYTQKSLSLSLGK (BLP-11 Light chain amino acid sequence)
                                                         SEQ ID NO: 396
EVQLVESGGGLVQPGGSLRLSCAASGYTISSYCMGWFRQAPGKGLEVAAIDSDGSTSYADSVKGRF

TISKDNSKNTLYLQMNSLRAEDTAVYYCAADFCWVDDFYEYNYWGQGTLVTVSSEPKSSDKTHTSP

PSPDIQMTQSPSSVSASVGDRVTITCKASQDVDTAVAWYQQKPGKAPKLLIYWASTRHTGVPSRFSGS

GSGTDFTLTISSLQPEDFATYYCQQYSTFPWTFGGGTKVEIKRTVAAPSVFIFPPSDEQLKSGTASVVCL
```

LNNFYPREAKVQWKVDNALQSGNSQESVTEQDSKDSTYSLSSTLTLSKADYEKHKVYACEVTHQGL
SSPVTKSFNRGEC (BLP-12 Heavy chain amino acid sequence)
SEQ ID NO: 397
EVQLVESGGGLVQPGGSLRLSCAASGFVFSRYDMAWVRQAPGKGLEWVSFISGGGSNTYYPDTVKG
RFTISRDNSKNTLYLQMNSLRAEDTAVYYCISPYYYAMEYWGQGTTVTVSSASTKGPSVFPLAPCSRS
TSESTAALGCLVKDYFPEPVTVSWNSGALTSGVHTFPAVLQSSGLYSLSSVVTVPSSSLGTKTYTCNV
DHKPSNTKVDKRVESKYGPPCPPCPAPEFLGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYKTTPPVLDSDGSFFLYS
RLTVDKSRWQEGNVFSCSVMHEALHNHYTQKSLSLSLGK (BLP-12 Light chain amino acid sequence)
SEQ ID NO: 398
DIQMTQSPSSVSASVGDRVTITCKASQDVDTAVAWYQQKPGKAPKLLIYWASTRHTGVPSRFSGSGS
GTDFTLTISSLQPEDFATYYCQQYSTFPWTFGGGTKVEIKRTVAAPSVFIFPPSDEQLKSGTASVVCLLN
NFYPREAKVQWKVDNALQSGNSQESVTEQDSKDSTYSLSSTLTLSKADYEKHKVYACEVTHQGLSSP
VTKSFNRGECEPKSSDKTHTSPPSPEVQLVESGGGLVQPGGSLRLSCAASGYTISSYCMGWFRQAPGK
GLEGVAAIDSDGSTSYADSVKGRFTISKDNSKNTLYLQMNSLRAEDTAVYYCAADFCWVDDFYEYN
YWGQGTLVTVSS (BLP-13 Heavy chain amino acid sequence)
SEQ ID NO: 399
EVQLVESGGGLVQPGGSLRLSCAASGYTVSSYCMGWFRQAPGKGREGVSAIDSDGSVSYADSVKGR
FTISKDNSKNTLYLQMNSLRAEDTAVYFCAADLCWVDQDQGEYNTWGQGTLVTVSSEPKSSDKTHT
SPPSPEVQLVESGGGLVQPGGSLRLSCAASGFVFSRYDMAWVRQAPGKGLEWVSFISGGGSNTYYPD
TVKGRFTISRDNSKNTLYLQMNSLRAEDTAVYYCISPYYYAMEYWGQGTTVTVSSASTKGPSVFPLA
PCSRSTSESTAALGCLVKDYFPEPVTVSWNSGALTSGVHTFPAVLQSSGLYSLSSVVTVPSSSLGTKTY
TCNVDHKPSNTKVDKRVESKYGPPCPPCPAPEFLGGPSVFLFPPKPKDTLMISRTPEVTCVVVDVSQE
DPEVQFNWYVDGVEVHNAKTKPREEQFNSTYRVVSVLTVLHQDWLNGKEYKCKVSNKGLPSSIEKT
ISKAKGQPREPQVYTLPPSQEEMTKNQVSLTCLVKGFYPSDIAVEWESNGQPENNYKTTPPVLDSDGS
FFLYSRLTVDKSRWQEGNVFSCSVMHEALHNHYTQKSLSLSLGK (BLP-13 Light chain amino acid sequence)
SEQ ID NO: 400
DIQMTQSPSSVSASVGDRVTITCKASQDVDTAVAWYQQKPGKAPKLLIYWASTRHTGVPSRFSGSGS
GTDFTLTISSLQPEDFATYYCQQYSTFPWTFGGGTKVEIKRTVAAPSVFIFPPSDEQLKSGTASVVCLLN
NFYPREAKVQWKVDNALQSGNSQESVTEQDSKDSTYSLSSTLTLSKADYEKHKVYACEVTHQGLSSP
VTKSFNRGEC (BLP-14 Heavy chain amino acid sequence)
SEQ ID NO: 401
EVQLVESGGGLVQPGGSLRLSCAASGFVFSRYDMAWVRQAPGKGLEWVSFISGGGSNTYYPDTVKG
RFTISRDNSKNTLYLQMNSLRAEDTAVYYCISPYYYAMEYWGQGTTVTVSSASTKGPSVFPLAPCSRS
TSESTAALGCLVKDYFPEPVTVSWNSGALTSGVHTFPAVLQSSGLYSLSSVVTVPSSSLGTKTYTCNV
DHKPSNTKVDKRVESKYGPPCPPCPAPEFLGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYKTTPPVLDSDGSFFLYS
RLTVDKSRWQEGNVFSCSVMHEALHNHYTQKSLSLSLGKEPKSSDKTHTSPPSPEVQLVESGGGLVQ -continued

PGGSLRLSCAASGYTVSSYCMGWFRQAPGKGREGVSAIDSDGSVSYADSVKGRFTISKDNSKNTLYL

QMNSLRAEDTAVYFCAADLCWVDQDQGEYNTWGQGTLVTVSS (BLP-14 Light chain amino acid sequence)
SEQ ID NO: 402
DIQMTQSPSSVSASVGDRVTITCKASQDVDTAVAWYQQKPGKAPKLLIYWASTRHTGVPSRFSGSGS

GTDFTLTISSLQPEDFATYYCQQYSTFPWTFGGGTKVEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSSP

VTKSFNRGEC (BLP-15 Heavy chain amino acid sequence)
SEQ ID NO: 403
EVQLVESGGGLVQPGGSLRLSCAASGFVFSRYDMAWVRQAPGKGLEWVSFISGGGSNTYYPDTVKG

RFTISRDNSKNTLYLQMNSLRAEDTAVYYCISPYYYAMEYWGQGTTVTVSSASTKGPSVFPLAPCSRS

TSESTAALGCLVKDYFPEPVTVSWNSGALTSGVHTFPAVLQSSGLYSLSSVVTVPSSSLGTKTYTCNV

DHKPSNTKVDKRVESKYGPPCPPCPAPEFLGGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDSDGSFFLYS

RLTVDKSRWQEGNVFSCSVMHEALHNHYTQKSLSLSLGK (BLP-15 Light chain amino acid sequence)
SEQ ID NO: 404
EVQLVESGGGLVQPGGSLRLSCAASGYTVSSYCMGWFRQAPGKGREGVSAIDSDGSVSYADSVKGR

FTISKDNSKNTLYLQMNSLRAEDTAVYFCAADLCWVDQDQGEYNTWGQGTLVTVSSEPKSSDKTHT

SPPSPDIQMTQSPSSVSASVGDRVTITCKASQDVDTAVAWYQQKPGKAPKLLIYWASTRHTGVPSRFS

GSGSGTDFTLTISSLQPEDFATYYCQQYSTFPWTFGGGTKVEIKRTVAAPSVFIFPPSDEQLKSGTASVV

CLLNNFYPREAKVQWKVDNALQSGNSQESVTEQDSKDSTYSLSSTLTLSKADYEKHKVYACEVTHQ

GLSSPVTKSFNRGEC (BLP-16 Heavy chain amino acid sequence)
SEQ ID NO: 405
EVQLVESGGGLVQPGGSLRLSCAASGFVFSRYDMAWVRQAPGKGLEWVSFISGGGSNTYYPDTVKG

RFTISRDNSKNTLYLQMNSLRAEDTAVYYCISPYYYAMEYWGQGTTVTVSSASTKGPSVFPLAPCSRS

TSESTAALGCLVKDYFPEPVTVSWNSGALTSGVHTFPAVLQSSGLYSLSSVVTVPSSSLGTKTYTCNV

DHKPSNTKVDKRVESKYGPPCPPCPAPEFLGGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDSDGSFFLYS

RLTVDKSRWQEGNVFSCSVMHEALHNHYTQKSLSLSLGK (BLP-16 Light chain amino acid sequence)
SEQ ID NO: 406
DIQMTQSPSSVSASVGDRVTITCKASQDVDTAVAWYQQKPGKAPKLLIYWASTRHTGVPSRFSGSGS

GTDFTLTISSLQPEDFATYYCQQYSTFPWTFGGGTKVEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSSP

VTKSFNRGECEPKSSDKTHTSPPSPEVQLVESGGGLVQPGGSLRLSCAASGYTVSSYCMGWFRQAPG

KGREGVSAIDSDGSVSYADSVKGRFTISKDNSKNTLYLQMNSLRAEDTAVYFCAADLCWVDQDQGE

YNTWGQGTLVTVSS (BLP-17 Heavy chain amino acid sequence)
SEQ ID NO: 407
EVQLVESGGGLVQPGGSLRLSCAASGYTYGGYCMGWFRQAPGKGLEGVSTINSDGSTNYADSVKGR

FTISRDNSKNTLYLQMNSLRAEDTAVYYCAVDLAPCWVAGPIEAADFGYWGQGTLVTVSSEPKSSDK

THTSPPSPEVQLVESGGGLVQPGGSLRLSCAASGFVFSRYDMAWVRQAPGKGLEWVSFISGGGSNTY

YPDTVKGRFTISRDNSKNTLYLQMNSLRAEDTAVYYCISPYYYAMEYWGQGTTVTVSSASTKGPSVF

PLAPCSRSTSESTAALGCLVKDYFPEPVTVSWNSGALTSGVHTFPAVLQSSGLYSLSSVVTVPSSSLGT

KTYTCNVDHKPSNTKVDKRVESKYGPPCPPCPAPEFLGGPSVFLFPPKPKDTLMISRTPEVTCVVVDV

SQEDPEVQFNWYVDGVEVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK (BLP-17 Light chain amino acid sequence)
                                                      SEQ ID NO: 408
DIQMTQSPSSVSASVGDRVTITCKASQDVDTAVAWYQQKPGKAPKLLIYWASTRHTGVPSRFSGSGS

GTDFTLTISSLQPEDFATYYCQQYSTFPWTFGGGTKVEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSSP

VTKSFNRGEC (BLP-18 Heavy chain amino acid sequence)
                                                      SEQ ID NO: 409
EVQLVESGGGLVQPGGSLRLSCAASGFVFSRYDMAWVRQAPGKGLEWVSFISGGGSNTYYPDTVKG

RFTISRDNSKNTLYLQMNSLRAEDTAVYYCISPYYYAMEYWGQGTTVTVSSASTKGPSVFPLAPCSRS

TSESTAALGCLVKDYFPEPVTVSWNSGALTSGVHTFPAVLQSSGLYSLSSVVTVPSSSLGTKTYTCNV

DHKPSNTKVDKRVESKYGPPCPPCPAPEFLGGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDSDGSFFLYS

RLTVDKSRWQEGNVFSCSVMHEALHNHYTQKSLSLSLGKEPKSSDKTHTSPPSPEVQLVESGGGLVQ

PGGSLRLSCAASGYTYGGYCMGWFRQAPGKGLEGVSTINSDGSTNYADSVKGRFTISRDNSKNTLYL

QMNSLRAEDTAVYYCAVDLAPCWVAGPIEAADFGYWGQGTLVTVSS (BLP-18 Light chain amino acid sequence)
                                                      SEQ ID NO: 410
DIQMTQSPSSVSASVGDRVTITCKASQDVDTAVAWYQQKPGKAPKLLIYWASTRHTGVPSRFSGSGS

GTDFTLTISSLQPEDFATYYCQQYSTFPWTFGGGTKVEIKRTVAAPSVFIFPPSDEQLKSGTASVVCLLN

NFYPREAKVQWKVDNALQSGNSQESVTEQDSKDSTYSLSSTLTLSKADYEKHKVYACEVTHQGLSSP

VTKSFNRGEC (BLP-19 Heavy chain amino acid sequence)
                                                      SEQ ID NO: 411
EVQLVESGGGLVQPGGSLRLSCAASGFVFSRYDMAWVRQAPGKGLEWVSFISGGGSNTYYPDTVKG

RFTISRDNSKNTLYLQMNSLRAEDTAVYYCISPYYYAMEYWGQGTTVTVSSASTKGPSVFPLAPCSRS

TSESTAALGCLVKDYFPEPVTVSWNSGALTSGVHTFPAVLQSSGLYSLSSVVTVPSSSLGTKTYTCNV

DHKPSNTKVDKRVESKYGPPCPPCPAPEFLGGPSVFLFPPKPKDTLMISRTPEVTCVVVDVSQEDPEVQ

FNWYVDGVEVHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPVLDSDGSFFLYS

RLTVDKSRWQEGNVFSCSVMHEALHNHYTQKSLSLSLGK (BLP-19 Light chain amino acid sequence)
                                                      SEQ ID NO: 412
EVQLVESGGGLVQPGGSLRLSCAASGYTYGGYCMGWFRQAPGKGLEGVSTINSDGSTNYADSVKGR

FTISRDNSKNTLYLQMNSLRAEDTAVYYCAVDLAPCWVAGPIEAADFGYWGQGTLVTVSSEPKSSDK

THTSPPSPDIQMTQSPSSVSASVGDRVTITCKASQDVDTAVAWYQQKPGKAPKLLIYWASTRHTGVPS

RFSGSGSGTDFTLTISSLQPEDFATYYCQQYSTFPWTFGGGTKVEIKRTVAAPSVFIFPPSDEQLKSGTA

SVVCLLNNFYPREAKVQWKVDNALQSGNSQESVTEQDSKDSTYSLSSTLTLSKADYEKHKVYACEV

THQGLSSPVTKSFNRGEC (BLP-20 Heavy chain amino acid sequence)
SEQ ID NO: 413
EVQLVESGGGLVQPGGSLRLSCAASGFVFSRYDMAWVRQAPGKGLEWVSFISGGGSNTYYPDTVKG
RFTISRDNSKNTLYLQMNSLRAEDTAVYYCISPYYYAMEYWGQGTTVTVSSASTKGPSVFPLAPCSRS
TSESTAALGCLVKDYFPEPVTVSWNSGALTSGVHTFPAVLQSSGLYSLSSVVTVPSSSLGTKTYTCNV
DHKPSNTKVDKRVESKYGPPCPPCPAPEFLGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYKTTPPVLDSDGSFFLYS
RLTVDKSRWQEGNVFSCSVMHEALHNHYTQKSLSLSLGK (BLP-20 Light chain amino acid sequence)
SEQ ID NO: 414
DIQMTQSPSSVSASVGDRVTITCKASQDVDTAVAWYQQKPGKAPKLLIYWASTRHTGVPSRFSGSGS
GTDFTLTISSLQPEDFATYYCQQYSTFPWTFGGGTKVEIKRTVAAPSVFIFPPSDEQLKSGTASVVCLLN
NFYPREAKVQWKVDNALQSGNSQESVTEQDSKDSTYSLSSTLTLSKADYEKHKVYACEVTHQGLSSP
VTKSFNRGECEPKSSDKTHTSPPSPEVQLVESGGGLVQPGGSLRLSCAASGYTYGGYCMGWFRQAPG
KGLEGVSTINSDGSTNYADSVKGRFTISRDNSKNTLYLQMNSLRAEDTAVYYCAVDLAPCWVAGPIE
AADFGYWGQGTLVTVSS (BLP-25 heavy chain amino acid sequence)
SEQ ID NO: 415
EVQLVESGGGLVQPGGSLRLSCAASGYIISSYCMGWFRQAPGKGLEGVAAIDSDGGTSYADSVKGRFTIS
KDNSKNTLYLQMNSLRAEDTAMYYCAADFCWVDEDRHLYEYNSWGQGTLVTVSSEVQLVESGGGLVQPGG
SLRLSCAASGFVFSRYDMAWVRQAPGKGLEWVSFISGGGSNTYYPDTVKGRFTISRDNSKNTLYLQMNSL
RAEDTAVYYCISPYYYAMEYWGQGTTVTVSSASTKGPSVFPLAPCSRSTSESTAALGCLVKDYFPEPVTV
SWNSGALTSGVHTFPAVLQSSGLYSLSSVVTVPSSSLGTKTYTCNVDHKPSNTKVDKRVESKYGPPCPPC
PAPEFLGGPSVFLFPPKPKDTLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSRWQEGNVFSCSVMHEALHNHYTQK
SLSLSLGK (BLP-25 light chain amino acid sequence)
SEQ ID NO: 416
DIQMTQSPSSVSASVGDRVTITCKASQDVDTAVAWYQQKPGKAPKLLIYWASTRHTGVPSRFSGSGSGTD
FTLTISSLQPEDFATYYCQQYSTFPWTFGGGTKVEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSFN
RGEC (BLP-26 heavy chain amino acid sequence)
SEQ ID NO: 417
EVQLVESGGGLVQPGGSLRLSCAASGFVFSRYDMAWVRQAPGKGLEWVSFISGGGSNTYYPDTVKGRFTI
SRDNSKNTLYLQMNSLRAEDTAVYYCISPYYYAMEYWGQGTTVTVSSASTKGPSVFPLAPCSRSTSESTA
ALGCLVKDYFPEPVTVSWNSGALTSGVHTFPAVLQSSGLYSLSSVVTVPSSSLGTKTYTCNVDHKPSNTK
VDKRVESKYGPPCPPCPAPEFLGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIEKTISKAKGQPREPQVYTLPP
SQEEMTKNQVSLTCLVKGFYPSDIAVEWESNGQPENNYKTTPPVLDSDGSFFLYSRLTVDKSRWQEGNVF
SCSVMHEALHNHYTQKSLSLSLGK (BLP-26 light chain amino acid sequence)
SEQ ID NO: 418
EVQLVESGGGLVQPGGSLRLSCAASGYIISSYCMGWFRQAPGKGLEGVAAIDSDGGTSYADSVKGRFTIS

KDNSKNTLYLQMNSLRAEDTAMYYCAADFCWVDEDRHLYEYNSWGQGTLVTVSSDIQMTQSPSSVSASVG

DRVTITCKASQDVDTAVAWYQQKPGKAPKLLIYWASTRHTGVPSRFSGSGSGTDFTLTISSLQPEDFATY

YCQQYSTFPWTFGGGTKVEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC (BLP-27 heavy chain amino acid sequence)
SEQ ID NO: 419
EVQLVESGGGLVQPGGSLRLSCAASGYTISSYCMGWFRQAPGKGLEGVAAIDSDGSTSYADSVKGRFTIS

KDNSKNTLYLQMNSLRAEDTAVYYCAADFCWVDDFYEYNYWGQGTLVTVSSEVQLVESGGGLVQPGGSLR

LSCAASGFVFSRYDMAWVRQAPGKGLEWVSFISGGGSNTYYPDTVKGRFTISRDNSKNTLYLQMNSLRAE

DTAVYYCISPYYYAMEYWGQGTTVTVSSASTKGPSVFPLAPCSRSTSESTAALGCLVKDYFPEPVTVSWN

SGALTSGVHTFPAVLQSSGLYSLSSVVTVPSSSLGTKTYTCNVDHKPSNTKVDKRVESKYGPPCPPCPAP

EFLGGPSVFLFPPKPKDTLMISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLPPSQEEMTKNQVSLTCLVKGF

YPSDIAVEWESNGQPENNYKTTPPVLDSDGSFFLYSRLTVDKSRWQEGNVFSCSVMHEALHNHYTQKSLS

LSLGK (BLP-27 light chain amino acid sequence)
SEQ ID NO: 420
DIQMTQSPSSVSASVGDRVTITCKASQDVDTAVAWYQQKPGKAPKLLIYWASTRHTGVPSRFSGSGSGTD

FTLTISSLQPEDFATYYCQQYSTFPWTFGGGTKVEIKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSPVTKSFN

RGEC (BLP-28 heavy chain amino acid sequence)
SEQ ID NO: 421
EVQLVESGGGLVQPGGSLRLSCAASGFVFSRYDMAWVRQAPGKGLEWVSFISGGGSNTYYPDTVKGRFTI

SRDNSKNTLYLQMNSLRAEDTAVYYCISPYYYAMEYWGQGTTVTVSSASTKGPSVFPLAPCSRSTSESTA

ALGCLVKDYFPEPVTVSWNSGALTSGVHTFPAVLQSSGLYSLSSVVTVPSSSLGTKTYTCNVDHKPSNTK

VDKRVESKYGPPCPPCPAPEFLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSFFLYSRLTVDKSRWQEGNVF

SCSVMHEALHNHYTQKSLSLSLGK (BLP-28 light chain amino acid sequence)
SEQ ID NO: 422
EVQLVESGGGLVQPGGSLRLSCAASGYTISSYCMGWFRQAPGKGLEGVAAIDSDGSTSYADSVKGRFTIS

KDNSKNTLYLQMNSLRAEDTAVYYCAADFCWVDDFYEYNYWGQGTLVTVSSDIQMTQSPSSVSASVGDRV

TITCKASQDVDTAVAWYQQKPGKAPKLLIYWASTRHTGVPSRFSGSGSGTDFTLTISSLQPEDFATYYCQ

QYSTFPWTFGGGTKVEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC (BLP-29 heavy chain amino acid sequence)
SEQ ID NO: 423
EVQLVESGGGLVQPGGSLRLSCAASGYTVSSYCMGWFRQAPGKGREGVSAIDSDGSVSYADSVKGRFTIS

KDNSKNTLYLQMNSLRAEDTAVYFCAADLCWVDQDQGEYNTWGQGTLVTVSSEVQLVESGGGLVQPGGSL

RLSCAASGFVFSRYDMAWVRQAPGKGLEWVSFISGGGSNTYYPDTVKGRFTISRDNSKNTLYLQMNSLRA

EDTAVYYCISPYYYAMEYWGQGTTVTVSSASTKGPSVFPLAPCSRSTSESTAALGCLVKDYFPEPVTVSW

NSGALTSGVHTFPAVLQSSGLYSLSSVVTVPSSSLGTKTYTCNVDHKPSNTKVDKRVESKYGPPCPPCPA

PEFLGGPSVFLFPPKPKDTLMISRTPEVTCVVVDVSQEDPEVQFNWYVDGVEVHNAKTKPREEQFNSTYR

```
VVSVLTVLHQDWLNGKEYKCKVSNKGLPSSIEKTISKAKGQPREPQVYTLPPSQEEMTKNQVSLTCLVKG

FYPSDIAVEWESNGQPENNYKTTPPVLDSDGSFFLYSRLTVDKSRWQEGNVFSCSVMHEALHNHYTQKSL

SLSLGK
```

(BLP-29 light chain amino acid sequence)
SEQ ID NO: 424
```
DIQMTQSPSSVSASVGDRVTITCKASQDVDTAVAWYQQKPGKAPKLLIYWASTRHTGVPSRFSGSGSGTD

FTLTISSLQPEDFATYYCQQYSTFPWTFGGGTKVEIKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSPVTKSFN

RGEC
```

(BLP-30 heavy chain amino acid sequence)
SEQ ID NO: 425
```
EVQLVESGGGLVQPGGSLRLSCAASGFVFSRYDMAWVRQAPGKGLEWVSFISGGGSNTYYPDTVKGRFTI

SRDNSKNTLYLQMNSLRAEDTAVYYCISPYYYAMEYWGQGTTVTVSSASTKGPSVFPLAPCSRSTSESTA

ALGCLVKDYFPEPVTVSWNSGALTSGVHTFPAVLQSSGLYSLSSVVTVPSSSLGTKTYTCNVDHKPSNTK

VDKRVESKYGPPCPPCPAPEFLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSFFLYSRLTVDKSRWQEGNVF

SCSVMHEALHNHYTQKSLSLSLGK
```

(BLP-30 light chain amino acid sequence)
SEQ ID NO: 426
```
EVQLVESGGGLVQPGGSLRLSCAASGYTVSSYCMGWFRQAPGKGREGVSAIDSDGSVSYADSVKGRFTIS

KDNSKNTLYLQMNSLRAEDTAVYFCAADLCWVDQDQGEYNTWGQGTLVTVSSDIQMTQSPSSVSASVGDR

VTITCKASQDVDTAVAWYQQKPGKAPKLLIYWASTRHTGVPSRFSGSGSGTDFTLTISSLQPEDFATYYC

QQYSTFPWTFGGGTKVEIKRTVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKSFNRGEC
```

(BLP-31 heavy chain amino acid sequence)
SEQ ID NO: 427
```
EVQLVESGGGLVQPGGSLRLSCAASGYTYGGYCMGWFRQAPGKGLEGVSTINSDGSTNYADSVKGRFTIS

RDNSKNTLYLQMNSLRAEDTAVYYCAVDLAPCWVAGPIEAADFGYWGQGTLVTVSSEVQLVESGGGLVQP

GGSLRLSCAASGFVFSRYDMAWVRQAPGKGLEWVSFISGGGSNTYYPDTVKGRFTISRDNSKNTLYLQMN

SLRAEDTAVYYCISPYYYAMEYWGQGTTVTVSSASTKGPSVFPLAPCSRSTSESTAALGCLVKDYFPEPV

TVSWNSGALTSGVHTFPAVLQSSGLYSLSSVVTVPSSSLGTKTYTCNVDHKPSNTKVDKRVESKYGPPCP

PCPAPEFLGGPSVFLFPPKPKDTLMISRTPEVTCVVVDVSQEDPEVQFNWYVDGVEVHNAKTKPREEQFN

STYRVVSVLTVLHQDWLNGKEYKCKVSNKGLPSSIEKTISKAKGQPREPQVYTLPPSQEEMTKNQVSLTC

LVKGFYPSDIAVEWESNGQPENNYKTTPPVLDSDGSFFLYSRLTVDKSRWQEGNVFSCSVMHEALHNHYT

QKSLSLSLGK
```

(BLP-31 light chain amino acid sequence)
SEQ ID NO: 428
```
DIQMTQSPSSVSASVGDRVTITCKASQDVDTAVAWYQQKPGKAPKLLIYWASTRHTGVPSRFSGSGSGTD

FTLTISSLQPEDFATYYCQQYSTFPWTFGGGTKVEIKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSPVTKSFN

RGEC
```

(BLP-32 heavy chain amino acid sequence)
SEQ ID NO: 429
```
EVQLVESGGGLVQPGGSLRLSCAASGFVFSRYDMAWVRQAPGKGLEWVSFISGGGSNTYYPDTVKGRFTI

SRDNSKNTLYLQMNSLRAEDTAVYYCISPYYYAMEYWGQGTTVTVSSASTKGPSVFPLAPCSRSTSESTA

ALGCLVKDYFPEPVTVSWNSGALTSGVHTFPAVLQSSGLYSLSSVVTVPSSSLGTKTYTCNVDHKPSNTK
```

VDKRVESKYGPPCPPCPAPEFLGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIEKTISKAKGQPREPQVYTLPP
SQEEMTKNQVSLTCLVKGFYPSDIAVEWESNGQPENNYKTTPPVLDSDGSFFLYSRLTVDKSRWQEGNVF
SCSVMHEALHNHYTQKSLSLSLGK (BLP-32 light chain amino acid sequence)
SEQ ID NO: 430
EVQLVESGGGLVQPGGSLRLSCAASGYTYGGYCMGWFRQAPGKGLEGVSTINSDGSTNYADSVKGRFTIS
RDNSKNTLYLQMNSLRAEDTAVYYCAVDLAPCWVAGPIEAADFGYWGQGTLVTVSSDIQMTQSPSSVSAS
VGDRVTITCKASQDVDTAVAWYQQKPGKAPKLLIYWASTRHTGVPSRFSGSGSGTDFTLTISSLQPEDFA
TYYCQQYSTFPWTFGGGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (BLP-33 heavy chain amino acid sequence)
SEQ ID NO: 431
EPKSSDKTHTSPPSPEVQLVESGGGLVQPGGSLRLSCAASGYIISSYCMGWFRQAPGKGLEGVAAIDSDG
GTSYADSVKGRFTISKDNSKNTLYLQMNSLRAEDTAMYYCAADFCWVDEDRHLYEYNSWGQGTLVTVSSE
VQLVESGGGLVQPGGSLRLSCAASGFVFSRYDMAWVRQAPGKGLEWVSFISGGGSNTYYPDTVKGRFTIS
RDNSKNTLYLQMNSLRAEDTAVYYCISPYYYAMEYWGQGTTVTVSSASTKGPSVFPLAPCSRSTSESTAA
LGCLVKDYFPEPVTVSWNSGALTSGVHTFPAVLQSSGLYSLSSVVTVPSSSLGTKTYTCNVDHKPSNTKV
DKRVESKYGPPCPPCPAPEFLGGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSFFLYSRLTVDKSRWQEGNVFS
CSVMHEALHNHYTQKSLSLSLGK (BLP-33 light chain amino acid sequence)
SEQ ID NO: 432
DIQMTQSPSSVSASVGDRVTITCKASQDVDTAVAWYQQKPGKAPKLLIYWASTRHTGVPSRFSGSGSGTD
FTLTISSLQPEDFATYYCQQYSTFPWTFGGGTKVEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSFN
RGEC (BLP-34 heavy chain amino acid sequence)
SEQ ID NO: 433
EVQLVESGGGLVQPGGSLRLSCAASGFVFSRYDMAWVRQAPGKGLEWVSFISGGGSNTYYPDTVKGRFTI
SRDNSKNTLYLQMNSLRAEDTAVYYCISPYYYAMEYWGQGTTVTVSSASTKGPSVFPLAPCSRSTSESTA
ALGCLVKDYFPEPVTVSWNSGALTSGVHTFPAVLQSSGLYSLSSVVTVPSSSLGTKTYTCNVDHKPSNTK
VDKRVESKYGPPCPPCPAPEFLGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIEKTISKAKGQPREPQVYTLPP
SQEEMTKNQVSLTCLVKGFYPSDIAVEWESNGQPENNYKTTPPVLDSDGSFFLYSRLTVDKSRWQEGNVF
SCSVMHEALHNHYTQKSLSLSLGK (BLP-34 light chain amino acid sequence)
SEQ ID NO: 434
EPKSSDKTHTSPPSPEVQLVESGGGLVQPGGSLRLSCAASGYIISSYCMGWFRQAPGKGLEGVAAIDSDG
GTSYADSVKGRFTISKDNSKNTLYLQMNSLRAEDTAMYYCAADFCWVDEDRHLYEYNSWGQGTLVTVSSD
IQMTQSPSSVSASVGDRVTITCKASQDVDTAVAWYQQKPGKAPKLLIYWASTRHTGVPSRFSGSGSGTDF
TLTISSLQPEDFATYYCQQYSTFPWTFGGGTKVEIKRTVAAPSVFIFPPSDEQLKSGTASVVCLLNNFYP
REAKVQWKVDNALQSGNSQESVTEQDSKDSTYSLSSTLTLSKADYEKHKVYACEVTHQGLSSPVTKSFNR
GEC (BLP-35 heavy chain amino acid sequence)
SEQ ID NO: 435
EPKSSDKTHTSPPSPEVQLVESGGGLVQPGGSLRLSCAASGYTISSYCMGWFRQAPGKGLEGVAAIDSDG
STSYADSVKGRFTISKDNSKNTLYLQMNSLRAEDTAVYYCAADFCWVDDFYEYNYWGQGTLVTVSSEVQL
VESGGGLVQPGGSLRLSCAASGFVFSRYDMAWVRQAPGKGLEWVSFISGGGSNTYYPDTVKGRFTISRDN
SKNTLYLQMNSLRAEDTAVYYCISPYYYAMEYWGQGTTVTVSSASTKGPSVFPLAPCSRSTSESTAALGC
LVKDYFPEPVTVSWNSGALTSGVHTFPAVLQSSGLYSLSSVVTVPSSSLGTKTYTCNVDHKPSNTKVDKR
VESKYGPPCPPCPAPEFLGGPSVFLFPPKPKDTLMISRTPEVTCVVVDVSQEDPEVQFNWYVDGVEVHNA
KTKPREEQFNSTYRVVSVLTVLHQDWLNGKEYKCKVSNKGLPSSIEKTISKAKGQPREPQVYTLPPSQEE
MTKNQVSLTCLVKGFYPSDIAVEWESNGQPENNYKTTPPVLDSDGSFFLYSRLTVDKSRWQEGNVFSCSV
MHEALHNHYTQKSLSLSLGK (BLP-35 light chain amino acid sequence)
SEQ ID NO: 436
DIQMTQSPSSVSASVGDRVTITCKASQDVDTAVAWYQQKPGKAPKLLIYWASTRHTGVPSRFSGSGSGTD
FTLTISSLQPEDFATYYCQQYSTFPWTFGGGTKVEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSFN
RGEC (BLP-36 heavy chain amino acid sequence)
SEQ ID NO: 437
EVQLVESGGGLVQPGGSLRLSCAASGFVFSRYDMAWVRQAPGKGLEWVSFISGGGSNTYYPDTVKGRFTI
SRDNSKNTLYLQMNSLRAEDTAVYYCISPYYYAMEYWGQGTTVTVSSASTKGPSVFPLAPCSRSTSESTA
ALGCLVKDYFPEPVTVSWNSGALTSGVHTFPAVLQSSGLYSLSSVVTVPSSSLGTKTYTCNVDHKPSNTK
VDKRVESKYGPPCPPCPAPEFLGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIEKTISKAKGQPREPQVYTLPP
SQEEMTKNQVSLTCLVKGFYPSDIAVEWESNGQPENNYKTTPPVLDSDGSFFLYSRLTVDKSRWQEGNVF
SCSVMHEALHNHYTQKSLSLSLGK (BLP-36 light chain amino acid sequence)
SEQ ID NO: 438
EPKSSDKTHTSPPSPEVQLVESGGGLVQPGGSLRLSCAASGYTISSYCMGWERQAPGRGLEGVAAIDSDG
STSYADSVKGRFTISKDNSKNTLYLQMNSLRAEDTAVYYCAADFCWVDDFYEYNYWGQGTLVTVSSDIQM
TQSPSSVSASVGDRVTITCKASQDVDTAVAWYQQKPGKAPKLLIYWASTRHTGVPSRFSGSGSGTDFTLT
ISSLQPEDFATYYCQQYSTFPWTFGGGTKVEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC (BLP-37 heavy chain amino acid sequence)
SEQ ID NO: 439
EPKSSDKTHTSPPSPEVQLVESGGGLVQPGGSLRLSCAASGYTVSSYCMGWFRQAPGKGREGVSAIDSDG
SVSYADSVKGRFTISKDNSKNTLYLQMNSLRAEDTAVYFCAADLCWVDQDQGEYNTWGQGTLVTVSSEVQ
LVESGGGLVQPGGSLRLSCAASGFVFSRYDMAWVRQAPGKGLEWVSFISGGGSNTYYPDTVKGRFTISRD
NSKNTLYLQMNSLRAEDTAVYYCISPYYYAMEYWGQGTTVTVSSASTKGPSVFPLAPCSRSTSESTAALG
CLVKDYFPEPVTVSWNSGALTSGVHTFPAVLQSSGLYSLSSVVTVPSSSLGTKTYTCNVDHKPSNTKVDK
RVESKYGPPCPPCPAPEFLGGPSVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKSRWQEGNVFSCS
VMHEALHNHYTQKSLSLSLGK (BLP-37 light chain amino acid sequence)
SEQ ID NO: 440
DIQMTQSPSSVSASVGDRVTITCKASQDVDTAVAWYQQKPGKAPKLLIYWASTRHTGVPSRFSGSGSGTD

```
FTLTISSLQPEDFATYYCQQYSTFPWTFGGGTKVEIKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSPVTKSFN

RGEC (BLP-38 heavy chain amino acid sequence)
                                                      SEQ ID NO: 441
EVQLVESGGGLVQPGGSLRLSCAASGFVFSRYDMAWVRQAPGKGLEWVSFISGGGSNTYYPDTVKGRFTI

SRDNSKNTLYLQMNSLRAEDTAVYYCISPYYYAMEYWGQGTTVTVSSASTKGPSVFPLAPCSRSTSESTA

ALGCLVKDYFPEPVTVSWNSGALTSGVHTFPAVLQSSGLYSLSSVVTVPSSSLGTKTYTCNVDHKPSNTK

VDKRVESKYGPPCPPCPAPEFLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSFFLYSRLTVDKSRWQEGNVF

SCSVMHEALHNHYTQKSLSLSLGK (BLP-38 light chain amino acid sequence)
                                                      SEQ ID NO: 442
EPKSSDKTHTSPPSPEVQLVESGGGLVQPGGSLRLSCAASGYTVSSYCMGWFRQAPGKGREGVSAIDSDG

SVSYADSVKGRFTISKDNSKNTLYLQMNSLRAEDTAVYFCAADLCWVDQDQGEYNTWGQGTLVTVSSDIQ

MTQSPSSVSASVGDRVTITCKASQDVDTAVAWYQQKPGKAPKLLIYWASTRHTGVPSRFSGSGSGTDFTL

TISSLQPEDFATYYCQQYSTFPWTFGGGTKVEIKRTVAAPSVFIFPPSDEQLKSGTASVVCLLNNFYPRE

AKVQWKVDNALQSGNSQESVTEQDSKDSTYSLSSTLTLSKADYEKHKVYACEVTHQGLSSPVTKSFNRGE

C (BLP-39 heavy chain amino acid sequence)
                                                      SEQ ID NO: 443
EPKSSDKTHTSPPSPEVQLVESGGGLVQPGGSLRLSCAASGYTYGGYCMGWFRQAPGKGLEGVSTINSDG

STNYADSVKGRFTISRDNSKNTLYLQMNSLRAEDTAVYYCAVDLAPCWVAGPIEAADFGYWGQGTLVTVS

SEVQLVESGGGLVQPGGSLRLSCAASGFVFSRYDMAWVRQAPGKGLEWVSFISGGGSNTYYPDTVKGRFT

ISRDNSKNTLYLQMNSLRAEDTAVYYCISPYYYAMEYWGQGTTVTVSSASTKGPSVFPLAPCSRSTSEST

AALGCLVKDYFPEPVTVSWNSGALTSGVHTFPAVLQSSGLYSLSSVVTVPSSSLGTKTYTCNVDHKPSNT

KVDKRVESKYGPPCPPCPAPEFLGGPSVFLFPPKPKDTLMISRTPEVTCVVVDVSQEDPEVQFNWYVDGV

EVHNAKTKPREEQFNSTYRVVSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDGSFFLYSRLTVDKSRWQEGNV

FSCSVMHEALHNHYTQKSLSLSLGK (BLP-39 light chain amino acid sequence)
                                                      SEQ ID NO: 444
DIQMTQSPSSVSASVGDRVTITCKASQDVDTAVAWYQQKPGKAPKLLIYWASTRHTGVPSRFSGSGSGTD

FTLTISSLQPEDFATYYCQQYSTFPWTFGGGTKVEIKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSPVTKSFN

RGEC (BLP-40 heavy chain amino acid sequence)
                                                      SEQ ID NO: 445
EVQLVESGGGLVQPGGSLRLSCAASGFVFSRYDMAWVRQAPGKGLEWVSFISGGGSNTYYPDTVKGRFTI

SRDNSKNTLYLQMNSLRAEDTAVYYCISPYYYAMEYWGQGTTVTVSSASTKGPSVFPLAPCSRSTSESTA

ALGCLVKDYFPEPVTVSWNSGALTSGVHTFPAVLQSSGLYSLSSVVTVPSSSLGTKTYTCNVDHKPSNTK

VDKRVESKYGPPCPPCPAPEFLGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSFFLYSRLTVDKSRWQEGNVF
```

-continued

SCSVMHEALHNHYTQKSLSLSLGK (BLP-40 light chain amino acid sequence)

SEQ ID NO: 446

EPKSSDKTHTSPPSPEVQLVESGGGLVQPGGSLRLSCAAS<u>GYTYGGYCMG</u>WFRQAPGKGLEGVS<u>TINSDG</u>

<u>STNYADSVKG</u>RFTISRDNSKNTLYLQMNSLRAEDTAVYYCAV<u>DLAPCWVAGPIEAADFGY</u>WGQGTLVTVS

SDIQMTQSPSSVSASVGDRVTITC<u>KASQDVDTAVAW</u>YQQKPGKAPKLLIY<u>WASTRH</u>TGVPSRFSGSGSGT

DFTLTISSLQPEDFATYYC<u>QQYSTFPWT</u>EGGGTKVEIKRTVAAPSVFIFPPSDEQLKSGTASVVCLLNNF

YPREAKVQWKVDNALQSGNSQESVTEQDSKDSTYSLSSTLTLSKADYEKHKVYACEVTHQGLSSPVTKSF

NRGEC

What is claimed is:

1. An anti-lymphocyte activation gene-3 (anti-LAG-3) construct comprising a single-domain antibody (sdAb) specifically recognizing LAG-3, wherein the sdAb comprises any one of the following:
   (a) a complimentary-determining region 1 (CDR1) CDR1 comprising the amino acid sequence of SEQ ID NO: 43; a CDR2 comprising the amino acid sequence of SEQ ID NO: 119; and a CDR3 comprising the amino acid sequence of SEQ ID NO: 195;
   (b) a CDR1 comprising the amino acid sequence of SEQ ID NO: 70; a CDR2 comprising the amino acid sequence of SEQ ID NO: 146; and a CDR3 comprising the amino acid sequence of SEQ ID NO: 222;
   (c) a CDR1 comprising the amino acid sequence of SEQ ID NO: 40; a CDR2 comprising the amino acid sequence of SEQ ID NO: 116; and a CDR3 comprising the amino acid sequence of SEQ ID NO: 192;
   (d) a CDR1 comprising the amino acid sequence of SEQ ID NO: 46; a CDR2 comprising the amino acid sequence of SEQ ID NO: 122; and a CDR3 comprising the amino acid sequence of SEQ ID NO: 198;
   (e) a CDR1 comprising the amino acid sequence of SEQ ID NO: 54; a CDR2 comprising the amino acid sequence of SEQ ID NO: 130; and a CDR3 comprising the amino acid sequence of SEQ ID NO: 206;
   (f) a CDR1 comprising the amino acid sequence of SEQ ID NO: 41; a CDR2 comprising the amino acid sequence of SEQ ID NO: 117; and a CDR3 comprising the amino acid sequence of SEQ ID NO: 193;
   (g) a CDR1 comprising the amino acid sequence of SEQ ID NO: 61; a CDR2 comprising the amino acid sequence of SEQ ID NO: 137; and a CDR3 comprising the amino acid sequence of SEQ ID NO: 213;
   (h) a CDR1 comprising the amino acid sequence of SEQ ID NO: 42; a CDR2 comprising the amino acid sequence of SEQ ID NO: 118; and a CDR3 comprising the amino acid sequence of SEQ ID NO: 194;
   (i) a CDR1 comprising the amino acid sequence of SEQ ID NO: 72; a CDR2 comprising the amino acid sequence of SEQ ID NO: 148; and a CDR3 comprising the amino acid sequence of SEQ ID NO: 224;
   (j) a CDR1 comprising the amino acid sequence of SEQ ID NO: 73; a CDR2 comprising the amino acid sequence of SEQ ID NO: 149; and a CDR3 comprising the amino acid sequence of SEQ ID NO: 225;
   (k) a CDR1 comprising the amino acid sequence of SEQ ID NO: 39; a CDR2 comprising the amino acid sequence of SEQ ID NO: 115; and a CDR3 comprising the amino acid sequence of SEQ ID NO: 191;
   (l) a CDR1 comprising the amino acid sequence of SEQ ID NO: 44; a CDR2 comprising the amino acid sequence of SEQ ID NO: 120; and a CDR3 comprising the amino acid sequence of SEQ ID NO: 196; or
   (m) a CDR1 comprising the amino acid sequence of SEQ ID NO: 45; a CDR2 comprising the amino acid sequence of SEQ ID NO: 121; and a CDR3 comprising the amino acid sequence of SEQ ID NO: 197.

2. The anti-LAG-3 construct of claim 1, wherein the sdAb comprises: a CDR1 comprising the amino acid sequence of SEQ ID NO: 40; a CDR2 comprising the amino acid sequence of SEQ ID NO: 116; and a CDR3 comprising the amino acid sequence of SEQ ID NO: 192.

3. The anti-LAG-3 construct of claim 1, wherein the sdAb comprises: a CDR1 comprising the amino acid sequence of SEQ ID NO: 41; a CDR2 comprising the amino acid sequence of SEQ ID NO: 117; and a CDR3 comprising the amino acid sequence of SEQ ID NO: 193.

4. The anti-LAG-3 construct of claim 1, wherein the sdAb comprises: a CDR1 comprising the amino acid sequence of SEQ ID NO: 42; a CDR2 comprising the amino acid sequence of SEQ ID NO: 118; and a CDR3 comprising the amino acid sequence of SEQ ID NO: 194.

5. The anti-LAG-3 construct of claim 1, wherein the sdAb comprises: a CDR1 comprising the amino acid sequence of SEQ ID NO: 43; a CDR2 comprising the amino acid sequence of SEQ ID NO: 119; and a CDR3 comprising the amino acid sequence of SEQ ID NO: 195.

6. The anti-LAG-3 construct of claim 1, wherein the sdAb comprises a variable domain of the heavy chain of heavy chain antibody ($V_HH$ domain) comprising the amino acid sequence of any one of SEQ ID NOs: 274-311, or a variant thereof having at least about 95% sequence identity to any one of SEQ ID NOs: 274-311.

7. The anti-LAG-3 construct of claim 1, wherein the sdAb specifically recognizing LAG-3 is camelid, chimeric, human, partially humanized, or fully humanized.

8. The anti-LAG-3 construct of claim 1, wherein the $K_D$ of the binding between the sdAb and LAG-3 is $10^{-7}$ M to $10^{-12}$ M.

9. The anti-LAG-3 construct of claim 1, wherein the anti-LAG-3 construct is a heavy chain-only antibody (HCAb) comprising the sdAb specifically recognizing LAG-3 fused to an Fc fragment.

10. The anti-LAG-3 construct of claim 9, wherein the sdAb is fused to the Fc fragment via a peptide linker comprising the amino acid sequence of any one of SEQ ID NOs: 352-353 and 366-372.

11. The anti-LAG-3 construct of claim 10, wherein the HCAb comprises the amino acid sequence of any one of SEQ ID NOs: 312-349.

12. The anti-LAG-3 construct of claim 1, comprising: (a) a first antigen binding portion comprising the sdAb specifically recognizing LAG-3; and (b) a second antigen binding portion that specifically recognizes a second epitope.

13. The anti-LAG-3 construct of claim 12, wherein the second antigen binding portion comprises a full-length antibody, a Fab, a Fab', a (Fab')2, an Fv, a single chain Fv (scFv), an scFv-scFv, a minibody, a diabody, or a second sdAb.

14. The anti-LAG-3 construct of claim 12, wherein the first antigen binding portion and the second antigen binding portion are fused to each other via a peptide linker comprising the amino acid sequence of any one of SEQ ID NOs: 352-353 and 366-372.

15. The anti-LAG-3 construct of claim 12, wherein the second antigen binding portion specifically recognizes an immune checkpoint molecule selected from the group consisting of programmed cell death receptor 1 (PD-1), tumor necrosis factor receptor superfamily member 9 (4-1BB), programmed cell death 1 ligand 1 (PD-L1), T cell membrane protein 3 (TIM-3), T cell immunoreceptor with Ig and ITIM domains (TIGIT), cytotoxic T-lymphocyte antigen 4 (CTLA-4), V-domain immunoglobulin (Ig)-containing suppressor of T-cell activation (VISTA), B7-1, B7-H3, cluster of differentiation 47 (CD47), tumor necrosis factor receptor superfamily member 4 (OX40) and glucocorticoid-induced tumor necrosis factor receptor (GITR).

16. The anti-LAG-3 construct of claim 15, wherein the second antigen binding portion specifically recognizes PD-1.

17. The anti-LAG-3 construct of claim 16, wherein the second antigen binding portion comprises:
(a) HC-CDR1, HC-CDR2, and HC-CDR3 of a heavy chain comprising the amino acid sequence of SEQ ID NO: 356, and LC-CDR1, LC-CDR2, and LC-CDR3 of a light chain comprising the amino acid sequence of SEQ ID NO: 357; or
(b) HC-CDR1, HC-CDR2, and HC-CDR3 of a heavy chain comprising the amino acid sequence of SEQ ID NO: 373, and LC-CDR1, LC-CDR2, and LC-CDR3 of a light chain comprising the amino acid sequence of SEQ ID NO: 374.

18. The anti-LAG-3 construct of claim 17, comprising:
(a) a heavy chain comprising the amino acid sequence of SEQ ID NO: 356, and a light chain comprising the amino acid sequence of SEQ ID NO: 357; or
(b) a heavy chain comprising the amino acid sequence of SEQ ID NO: 373, and a light chain comprising the amino acid sequence of SEQ ID NO: 374.

19. The anti-LAG-3 construct of claim 18, wherein
(a) the N-terminus of the sdAb specifically recognizing LAG-3 is fused to the C-terminus of the heavy chain of the second antigen binding portion,
(b) the C-terminus of the sdAb specifically recognizing LAG-3 is fused to the N-terminus of the heavy chain of the second antigen binding portion,
(c) the N-terminus of the sdAb specifically recognizing LAG-3 is fused to the C-terminus of the light chain of the second antigen binding portion, or
(d) the C-terminus of the sdAb specifically recognizing LAG-3 is fused to the N-terminus of the light chain of the second antigen binding portion.

20. The anti-LAG-3 construct of claim 12, comprising
(a) a first polypeptide having the amino acid of SEQ ID NO: 441, and a second polypeptide having the amino acids of SEQ ID NO: 442;
(b) a first polypeptide having the amino acid of SEQ ID NO: 433, and a second polypeptide having the amino acids of SEQ ID NO: 434;
(c) a first polypeptide having the amino acid of SEQ ID NO: 403, and a second polypeptide having the amino acids of SEQ ID NO: 404;
(d) a first polypeptide having the amino acid of SEQ ID NO: 411, and a second polypeptide having the amino acids of SEQ ID NO: 412;
(e) a first polypeptide having the amino acid of SEQ ID NO: 381, and a second polypeptide having the amino acids of SEQ ID NO: 382;
(f) a first polypeptide having the amino acid of SEQ ID NO: 377, and a second polypeptide having the amino acids of SEQ ID NO: 378;
(g) a first polypeptide having the amino acid of SEQ ID NO: 379, and a second polypeptide having the amino acids of SEQ ID NO: 380;
(h) a first polypeptide having the amino acid of SEQ ID NO: 375, and a second polypeptide having the amino acids of SEQ ID NO: 376;
(i) a first polypeptide having the amino acid of SEQ ID NO: 383, and a second polypeptide having the amino acids of SEQ ID NO: 384;
(j) a first polypeptide having the amino acid of SEQ ID NO: 385, and a second polypeptide having the amino acids of SEQ ID NO: 386;

(k) a first polypeptide having the amino acid of SEQ ID NO: 387, and a second polypeptide having the amino acids of SEQ ID NO: 388;
(l) a first polypeptide having the amino acid of SEQ ID NO: 389, and a second polypeptide having the amino acids of SEQ ID NO: 390;
(m) a first polypeptide having the amino acid of SEQ ID NO:391, and a second polypeptide having the amino acids of SEQ ID NO: 392;
(n) a first polypeptide having the amino acid of SEQ ID NO: 393, and a second polypeptide having the amino acids of SEQ ID NO: 394;
(o) a first polypeptide comprising the amino acid sequence of SEQ ID NO: 395, and a second polypeptide comprising the amino acid sequence of SEQ ID NO: 396;
(p) a first polypeptide comprising the amino acid sequence of SEQ ID NO: 397, and a second polypeptide comprising the amino acid sequence of SEQ ID NO: 398;
(q) a first polypeptide comprising the amino acid sequence of SEQ ID NO: 399, and a second polypeptide comprising the amino acid sequence of SEQ ID NO: 400;
(r) a first polypeptide comprising the amino acid sequence of SEQ ID NO: 401, and a second polypeptide comprising the amino acid sequence of SEQ ID NO: 402;
(s) a first polypeptide comprising the amino acid sequence of SEQ ID NO: 405, and a second polypeptide comprising the amino acid sequence of SEQ ID NO: 406;
(t) a first polypeptide comprising the amino acid sequence of SEQ ID NO: 407, and a second polypeptide comprising the amino acid sequence of SEQ ID NO: 408;
(u) a first polypeptide comprising the amino acid sequence of SEQ ID NO: 409, and a second polypeptide comprising the amino acid sequence of SEQ ID NO: 410;
(v) a first polypeptide comprising the amino acid sequence of SEQ ID NO: 413, and a second polypeptide comprising the amino acid sequence of SEQ ID NO: 414;
(w) a first polypeptide comprising the amino acid sequence of SEQ ID NO: 415, and a second polypeptide comprising the amino acid sequence of SEQ ID NO: 416;
(x) a first polypeptide comprising the amino acid sequence of SEQ ID NO: 417, and a second polypeptide comprising the amino acid sequence of SEQ ID NO: 418;
(y) a first polypeptide comprising the amino acid sequence of SEQ ID NO: 419, and a second polypeptide comprising the amino acid sequence of SEQ ID NO: 420;
(z) a first polypeptide comprising the amino acid sequence of SEQ ID NO: 421, and a second polypeptide comprising the amino acid sequence of SEQ ID NO: 422;
(aa) a first polypeptide comprising the amino acid sequence of SEQ ID NO: 423, and a second polypeptide comprising the amino acid sequence of SEQ ID NO: 424;
(bb) a first polypeptide comprising the amino acid sequence of SEQ ID NO: 425, and a second polypeptide comprising the amino acid sequence of SEQ ID NO: 426;
(cc) a first polypeptide comprising the amino acid sequence of SEQ ID NO: 427, and a second polypeptide comprising the amino acid sequence of SEQ ID NO: 428;
(dd) a first polypeptide comprising the amino acid sequence of SEQ ID NO: 429, and a second polypeptide comprising the amino acid sequence of SEQ ID NO: 430;
(ee) a first polypeptide comprising the amino acid sequence of SEQ ID NO: 431, and a second polypeptide comprising the amino acid sequence of SEQ ID NO: 432;
(ff) a first polypeptide comprising the amino acid sequence of SEQ ID NO: 435, and a second polypeptide comprising the amino acid sequence of SEQ ID NO: 436;
(gg) a first polypeptide comprising the amino acid sequence of SEQ ID NO: 437, and a second polypeptide comprising the amino acid sequence of SEQ ID NO: 438;
(hh) a first polypeptide comprising the amino acid sequence of SEQ ID NO: 439, and a second polypeptide comprising the amino acid sequence of SEQ ID NO: 440;
(ii) a first polypeptide comprising the amino acid sequence of SEQ ID NO: 443, and a second polypeptide comprising the amino acid sequence of SEQ ID NO: 444; or
(jj) a first polypeptide comprising the amino acid sequence of SEQ ID NO: 445, and a second polypeptide comprising the amino acid sequence of SEQ ID NO: 446.

21. A pharmaceutical composition comprising an effective amount of the anti-LAG-3 construct of claim 1, and a pharmaceutically acceptable carrier.

22. A method of treating an individual having a cancer, comprising administering to the individual the pharmaceutical composition of claim 21.

23. The method of claim 22, wherein the cancer is colon cancer.

* * * * *

UNITED STATES PATENT AND TRADEMARK OFFICE
CERTIFICATE OF CORRECTION

PATENT NO.      : 11,958,903 B2
APPLICATION NO. : 17/043054
DATED           : April 16, 2024
INVENTOR(S)     : Wang Zhang et al.

It is certified that error appears in the above-identified patent and that said Letters Patent is hereby corrected as shown below:

On the Title Page

Column 1, item (65), Prior Publication Data, After Jan. 21, 2021, please add -- (30) Foreign Priority Data Mar. 30, 2018 (CN) PCT/CN2018/081356 --;

Column 2, Other Publications, Line 14, please delete "specificity.J" and insert therefor -- specificity. J --; and In the Claims Column 575, Claim 1, Line 43, after "(CDR1)", please delete -- CDR1 --.

Signed and Sealed this
Eleventh Day of June, 2024

Katherine Kelly Vidal
*Director of the United States Patent and Trademark Office*

SEQUENCE LISTING

<160> NUMBER OF SEQ ID NOS: 446

<210> SEQ ID NO 1
<211> LENGTH: 25
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Ala Glu Ser Gly Gly Gly Ser Val His Ala Gly Gly
1               5                   10                  15

Ser Leu Arg Leu Ser Cys Val Val Ser
            20                  25

<210> SEQ ID NO 2
<211> LENGTH: 25
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Ser Val Gln Ala Gly Gly
1               5                   10                  15

Ser Leu Arg Leu Ser Cys Ala Ala Ser
            20                  25

<210> SEQ ID NO 3
<211> LENGTH: 25
<212> TYPE: PRT
<213> ORGANISM: Artificial Sequence
<220> FEATURE:
<223> OTHER INFORMATION: Synthetic Construct

<400> SEQUENCE: 3

Gln Val Gln Leu Ala Glu Ser Gly Gly Gly Ser Val Gln Ala Gly Gly
1               5                   10                  15

Ser Leu Arg Leu Ser Cys Ala Ala Ser
            20                  25

<210> SEQ ID NO 4
<211> LENGTH: 25
<212> TYPE: PRT
<213> ORGANISM: Artificial Sequence
<220> FEATURE:
<223> OTHER INFORMATION: Synthetic Construct

<400> SEQUENCE: 4

```
Glu Val Gln Leu Ala Glu Ser Gly Gly Gly Ser Val Gln Ala Gly Gly
1               5                   10                  15

Ser Leu Arg Leu Ser Cys Ala Ala Ser
            20                  25

<210> SEQ ID NO 5
<211> LENGTH: 25
<212> TYPE: PRT
<213> ORGANISM: Artificial Sequence
<220> FEATURE:
<223> OTHER INFORMATION: Synthetic Construct

<400> SEQUENCE: 5

Gln Val His Leu Met Glu Ser Gly Gly Gly Ser Val Gln Val Gly Gly
1               5                   10                  15

Ser Leu Arg Leu Ser Cys Ala Ala Ser
            20                  25

<210> SEQ ID NO 6
<211> LENGTH: 25
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Ala Gly Gly
1               5                   10                  15

Ser Leu Arg Leu Ser Cys Thr Ala Ser
            20                  25

<210> SEQ ID NO 7
<211> LENGTH: 25
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Val Glu Ser Gly Gly Gly Ser Val Gln Ala Gly Gly
1               5                   10                  15

Ser Leu Arg Leu Ser Cys Ala Ala Ser
            20                  25

<210> SEQ ID NO 8
<211> LENGTH: 25
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Glu Ser Gly Gly Gly Ser Val Gln Ala Gly Gly
1               5                   10                  15

Ser Leu Arg Leu Ser Cys Ala Ala Ser
            20                  25

<210> SEQ ID NO 9
<211> LENGTH: 25
<212> TYPE: PRT
<213> ORGANISM: Artificial Sequence
<220> FEATURE:
<223> OTHER INFORMATION: Synthetic Construct

<400> SEQUENCE: 9
```

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 10
<211> LENGTH: 25
<212> TYPE: PRT
<213> ORGANISM: Artificial Sequence
<220> FEATURE:
<223> OTHER INFORMATION: Synthetic Construct

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 11
<211> LENGTH: 25
<212> TYPE: PRT
<213> ORGANISM: Artificial Sequence
<220> FEATURE:
<223> OTHER INFORMATION: Synthetic Construct

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 12
<211> LENGTH: 25
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 13
<211> LENGTH: 25
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 14
<211> LENGTH: 25
<212> TYPE: PRT
<213> ORGANISM: Artificial Sequence
<220> FEATURE:
<223> OTHER INFORMATION: Synthetic Construct

```
<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 15
<211> LENGTH: 25
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 16
<211> LENGTH: 25
<212> TYPE: PRT
<213> ORGANISM: Artificial Sequence
<220> FEATURE:
<223> OTHER INFORMATION: Synthetic Construct

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 17
<211> LENGTH: 25
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 18
<211> LENGTH: 25
<212> TYPE: PRT
<213> ORGANISM: Artificial Sequence
<220> FEATURE:
<223> OTHER INFORMATION: Synthetic Construct

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 19
<211> LENGTH: 25
<212> TYPE: PRT
<213> ORGANISM: Artificial Sequence
<220> FEATURE:
<223> OTHER INFORMATION: Synthetic Construct
```

-continued

```
<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 20
<211> LENGTH: 25
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 21
<211> LENGTH: 25
<212> TYPE: PRT
<213> ORGANISM: Artificial Sequence
<220> FEATURE:
<223> OTHER INFORMATION: Synthetic Construct

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 22
<211> LENGTH: 25
<212> TYPE: PRT
<213> ORGANISM: Artificial Sequence
<220> FEATURE:
<223> OTHER INFORMATION: Synthetic Construct

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 23
<211> LENGTH: 25
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 24
<211> LENGTH: 25
<212> TYPE: PRT
<213> ORGANISM: Artificial Sequence
<220> FEATURE:
```

<223> OTHER INFORMATION: Synthetic Construct

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 25
<211> LENGTH: 25
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 26
<211> LENGTH: 25
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 27
<211> LENGTH: 25
<212> TYPE: PRT
<213> ORGANISM: Artificial Sequence
<220> FEATURE:
<223> OTHER INFORMATION: Synthetic Construct

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 28
<211> LENGTH: 25
<212> TYPE: PRT
<213> ORGANISM: Artificial Sequence
<220> FEATURE:
<223> OTHER INFORMATION: Synthetic Construct

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 29
<211> LENGTH: 25
<212> TYPE: PRT
<213> ORGANISM: Artificial Sequence

```
<220> FEATURE:
<223> OTHER INFORMATION: Synthetic Construct

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 30
<211> LENGTH: 25
<212> TYPE: PRT
<213> ORGANISM: Artificial Sequence
<220> FEATURE:
<223> OTHER INFORMATION: Synthetic Construct

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 31
<211> LENGTH: 25
<212> TYPE: PRT
<213> ORGANISM: Artificial Sequence
<220> FEATURE:
<223> OTHER INFORMATION: Synthetic Construct

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 32
<211> LENGTH: 25
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 33
<211> LENGTH: 25
<212> TYPE: PRT
<213> ORGANISM: Artificial Sequence
<220> FEATURE:
<223> OTHER INFORMATION: Synthetic Construct

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 34
<211> LENGTH: 25
<212> TYPE: PRT
```

```
<213> ORGANISM: Artificial Sequence
<220> FEATURE:
<223> OTHER INFORMATION: Synthetic Construct

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 35
<211> LENGTH: 25
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 36
<211> LENGTH: 25
<212> TYPE: PRT
<213> ORGANISM: Artificial Sequence
<220> FEATURE:
<223> OTHER INFORMATION: Synthetic Construct

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 37
<211> LENGTH: 25
<212> TYPE: PRT
<213> ORGANISM: Artificial Sequence
<220> FEATURE:
<223> OTHER INFORMATION: Synthetic Construct

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 38
<211> LENGTH: 25
<212> TYPE: PRT
<213> ORGANISM: Artificial Sequence
<220> FEATURE:
<223> OTHER INFORMATION: Synthetic Construct

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 39
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 39

Glu Tyr Thr Phe Ser Ser Asp Ser Met Gly
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic Construct

<400> SEQUENCE: 40

Gly Tyr Ile Ile Ser Ser Tyr Cys Met Gly
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Gly Tyr Thr Ile Ser Ser Tyr Cys Met Gly
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Gly Tyr Thr Tyr Gly Gly Tyr Cys Met Gly
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

Gly Tyr Thr Val Ser Ser Tyr Cys Met Gly
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic Construct

<400> SEQUENCE: 44

Gly Leu Thr Phe Asp Asp Tyr Ala Met Gly
1               5                   10

<210> SEQ ID NO 45
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 45

Gly Tyr Thr Leu Ser Ser Tyr Cys Met Gly
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic Construct

<400> SEQUENCE: 46

Gly Tyr Ile Ile Ser Ser Tyr Cys Met Gly
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic Construct

<400> SEQUENCE: 47

Gly Tyr Ile Ile Ser Ser Tyr Cys Met Gly
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic Construct

<400> SEQUENCE: 48

Gly Tyr Ile Ile Ser Ser Tyr Cys Met Gly
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic Construct

<400> SEQUENCE: 49

Gly Tyr Ile Ile Ser Ser Tyr Cys Met Gly
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic Construct

<400> SEQUENCE: 50

Gly Tyr Ile Ile Ser Ser Tyr Cys Met Gly
1               5                   10

<210> SEQ ID NO 51
<211> LENGTH: 10
<212> TYPE: PRT
<213> ORGANISM: Artificial Sequence
```

```
<220> FEATURE:
<223> OTHER INFORMATION: Synthetic Construct

<400> SEQUENCE: 51

Gly Tyr Ile Ile Ser Ser Tyr Cys Met Gly
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic Construct

<400> SEQUENCE: 52

Gly Tyr Ile Ile Ser Ser Tyr Cys Met Gly
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic Construct

<400> SEQUENCE: 53

Gly Tyr Ile Ile Ser Ser Tyr Cys Met Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic Construct

<400> SEQUENCE: 54

Gly Tyr Ile Ile Ser Ser Tyr Cys Met Gly
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic Construct

<400> SEQUENCE: 55

Gly Tyr Thr Ile Ser Ser Tyr Cys Met Gly
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic Construct

<400> SEQUENCE: 56

Gly Tyr Thr Ile Ser Ser Tyr Cys Met Gly
1               5                   10

<210> SEQ ID NO 57
<211> LENGTH: 10
<212> TYPE: PRT
<213> ORGANISM: Artificial Sequence
<220> FEATURE:
```

```
<223> OTHER INFORMATION: Synthetic Construct

<400> SEQUENCE: 57

Gly Tyr Thr Ile Ser Ser Tyr Cys Met Gly
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic Construct

<400> SEQUENCE: 58

Gly Tyr Thr Ile Ser Ser Tyr Cys Met Gly
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic Construct

<400> SEQUENCE: 59

Gly Tyr Thr Ile Ser Ser Tyr Cys Met Gly
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic Construct

<400> SEQUENCE: 60

Gly Tyr Thr Ile Ser Ser Tyr Cys Met Gly
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic Construct

<400> SEQUENCE: 61

Gly Tyr Thr Ile Ser Ser Tyr Cys Met Gly
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic Construct

<400> SEQUENCE: 62

Gly Tyr Thr Val Ser Ser Tyr Cys Met Gly
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 63

Gly Tyr Thr Val Ser Ser Tyr Cys Met Gly
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic Construct

<400> SEQUENCE: 64

Gly Tyr Thr Val Ser Ser Tyr Cys Met Gly
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic Construct

<400> SEQUENCE: 65

Gly Tyr Thr Val Ser Ser Tyr Cys Met Gly
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic Construct

<400> SEQUENCE: 66

Gly Tyr Thr Val Ser Ser Tyr Cys Met Gly
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic Construct

<400> SEQUENCE: 67

Gly Tyr Thr Val Ser Ser Tyr Cys Met Gly
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic Construct

<400> SEQUENCE: 68

Gly Tyr Thr Val Ser Ser Tyr Cys Met Gly
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 69

Gly Tyr Thr Val Ser Ser Tyr Cys Met Gly
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthetic Construct

<400> SEQUENCE: 70

Gly Tyr Thr Val Ser Ser Tyr Cys Met Gly
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic Construct

<400> SEQUENCE: 71

Gly Tyr Thr Tyr Gly Gly Tyr Cys Met Gly
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic Construct

<400> SEQUENCE: 72

Gly Tyr Thr Tyr Gly Gly Tyr Cys Met Gly
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic Construct

<400> SEQUENCE: 73

Gly Tyr Thr Tyr Gly Gly Tyr Cys Met Gly
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic Construct

<400> SEQUENCE: 74

Gly Tyr Thr Tyr Gly Gly Tyr Cys Met Gly
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic Construct

<400> SEQUENCE: 75
```

```
Gly Tyr Thr Tyr Gly Gly Tyr Cys Met Gly
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthetic Construct

<400> SEQUENCE: 76

Gly Tyr Thr Tyr Gly Gly Tyr Cys Met Gly
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Synthetic Construct

<400> SEQUENCE: 77

Trp Phe Arg Gln Ala Pro Gly Lys Glu Arg Glu Gly Val Ala
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Synthetic Construct

<400> SEQUENCE: 78

Trp Phe Arg Gln Ala Pro Gly Lys Glu Arg Glu Gly Val Ala
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Synthetic Construct

<400> SEQUENCE: 79

Trp Phe Arg Gln Ala Pro Gly Lys Glu Arg Glu Gly Val Ala
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Synthetic Construct

<400> SEQUENCE: 80

Trp Phe Arg Gln Ala Pro Gly Lys Glu Arg Glu Gly Val Ala
1               5                   10

<210> SEQ ID NO 81
<211> LENGTH: 14
<212> TYPE: PRT
<213> ORGANISM: Artificial Sequence
<220> FEATURE:
<223> OTHER INFORMATION: Synthetic Construct

<400> SEQUENCE: 81
```

-continued

Trp Phe Arg Gln Ala Pro Gly Lys Glu Arg Glu Gly Val Ala
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Synthetic Construct

<400> SEQUENCE: 82

Trp Phe Arg Gln Ala Pro Gly Lys Glu Arg Glu Gly Val Ser
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Synthetic Construct

<400> SEQUENCE: 83

Trp Phe Arg Gln Ala Pro Gly Lys Glu Arg Glu Gly Val Ala
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Synthetic Construct

<400> SEQUENCE: 84

Trp Phe Arg Gln Ala Pro Gly Lys Glu Arg Glu Gly Val Ala
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Synthetic Construct

<400> SEQUENCE: 85

Trp Phe Arg Gln Ala Pro Gly Lys Gly Leu Glu Gly Val Ser
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Synthetic Construct

<400> SEQUENCE: 86

Trp Phe Arg Gln Ala Pro Gly Lys Gly Leu Glu Gly Val Ala
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Synthetic Construct

<400> SEQUENCE: 87

Trp Phe Arg Gln Ala Pro Gly Lys Gly Leu Glu Gly Val Ala

```
1               5                  10
```

<210> SEQ ID NO 88
<211> LENGTH: 14
<212> TYPE: PRT
<213> ORGANISM: Artificial Sequence
<220> FEATURE:
<223> OTHER INFORMATION: Synthetic Construct

<400> SEQUENCE: 88

```
Trp Phe Arg Gln Ala Pro Gly Lys Gly Arg Glu Gly Val Ala
1               5                  10
```

<210> SEQ ID NO 89
<211> LENGTH: 14
<212> TYPE: PRT
<213> ORGANISM: Artificial Sequence
<220> FEATURE:
<223> OTHER INFORMATION: Synthetic Construct

<400> SEQUENCE: 89

```
Trp Phe Arg Gln Ala Pro Gly Lys Glu Arg Glu Gly Val Ala
1               5                  10
```

<210> SEQ ID NO 90
<211> LENGTH: 14
<212> TYPE: PRT
<213> ORGANISM: Artificial Sequence
<220> FEATURE:
<223> OTHER INFORMATION: Synthetic Construct

<400> SEQUENCE: 90

```
Trp Phe Arg Gln Ala Pro Gly Lys Glu Arg Glu Gly Val Ala
1               5                  10
```

<210> SEQ ID NO 91
<211> LENGTH: 14
<212> TYPE: PRT
<213> ORGANISM: Artificial Sequence
<220> FEATURE:
<223> OTHER INFORMATION: Synthetic Construct

<400> SEQUENCE: 91

```
Trp Phe Arg Gln Ala Pro Gly Lys Gly Leu Glu Gly Val Ala
1               5                  10
```

<210> SEQ ID NO 92
<211> LENGTH: 14
<212> TYPE: PRT
<213> ORGANISM: Artificial Sequence
<220> FEATURE:
<223> OTHER INFORMATION: Synthetic Construct

<400> SEQUENCE: 92

```
Trp Phe Arg Gln Ala Pro Gly Lys Gly Leu Glu Gly Val Ala
1               5                  10
```

<210> SEQ ID NO 93
<211> LENGTH: 14
<212> TYPE: PRT
<213> ORGANISM: Artificial Sequence
<220> FEATURE:
<223> OTHER INFORMATION: Synthetic Construct

<400> SEQUENCE: 93

```
Trp Phe Arg Gln Ala Pro Gly Lys Gly Leu Glu Gly Val Ala
1               5                  10
```

```
<210> SEQ ID NO 94
<211> LENGTH: 14
<212> TYPE: PRT
<213> ORGANISM: Artificial Sequence
<220> FEATURE:
<223> OTHER INFORMATION: Synthetic Construct

<400> SEQUENCE: 94

Trp Phe Arg Gln Ala Pro Gly Lys Gly Leu Glu Gly Val Ala
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Synthetic Construct

<400> SEQUENCE: 95

Trp Phe Arg Gln Ala Pro Gly Lys Gly Arg Glu Gly Val Ala
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Synthetic Construct

<400> SEQUENCE: 96

Trp Phe Arg Gln Ala Pro Gly Lys Glu Arg Glu Gly Val Ala
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Synthetic Construct

<400> SEQUENCE: 97

Trp Phe Arg Gln Ala Pro Gly Lys Glu Arg Glu Gly Val Ala
1               5                   10

<210> SEQ ID NO 98
<211> LENGTH: 14
<212> TYPE: PRT
<213> ORGANISM: Artificial Sequence
<220> FEATURE:
<223> OTHER INFORMATION: Synthetic Construct

<400> SEQUENCE: 98

Trp Phe Arg Gln Ala Pro Gly Lys Gly Leu Glu Gly Val Ala
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Synthetic Construct

<400> SEQUENCE: 99

Trp Phe Arg Gln Ala Pro Gly Lys Gly Leu Glu Gly Val Ala
1               5                   10
```

<210> SEQ ID NO 100
<211> LENGTH: 14
<212> TYPE: PRT
<213> ORGANISM: Artificial Sequence
<220> FEATURE:
<223> OTHER INFORMATION: Synthetic Construct

<400> SEQUENCE: 100

Trp Phe Arg Gln Ala Pro Gly Lys Gly Leu Glu Gly Val Ser
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Synthetic Construct

<400> SEQUENCE: 101

Trp Phe Arg Gln Ala Pro Gly Lys Gly Leu Glu Gly Val Ser
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Synthetic Construct

<400> SEQUENCE: 102

Trp Phe Arg Gln Ala Pro Gly Lys Gly Leu Glu Gly Val Ala
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetic Construct

<400> SEQUENCE: 103

Trp Phe Arg Gln Ala Pro Gly Lys Gly Leu Glu Gly Val Ala
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Synthetic Construct

<400> SEQUENCE: 104

Trp Phe Arg Gln Ala Pro Gly Lys Gly Arg Glu Gly Val Ala
1               5                   10

<210> SEQ ID NO 105
<211> LENGTH: 14
<212> TYPE: PRT
<213> ORGANISM: Artificial Sequence
<220> FEATURE:
<223> OTHER INFORMATION: Synthetic Construct

<400> SEQUENCE: 105

Trp Phe Arg Gln Ala Pro Gly Lys Glu Arg Glu Gly Val Ala
1               5                   10

-continued

```
<210> SEQ ID NO 106
<211> LENGTH: 14
<212> TYPE: PRT
<213> ORGANISM: Artificial Sequence
<220> FEATURE:
<223> OTHER INFORMATION: Synthetic Construct

<400> SEQUENCE: 106

Trp Phe Arg Gln Ala Pro Gly Lys Glu Arg Glu Gly Val Ala
1               5                   10

<210> SEQ ID NO 107
<211> LENGTH: 14
<212> TYPE: PRT
<213> ORGANISM: Artificial Sequence
<220> FEATURE:
<223> OTHER INFORMATION: Synthetic Construct

<400> SEQUENCE: 107

Trp Phe Arg Gln Ala Pro Gly Lys Gly Arg Glu Gly Val Ser
1               5                   10

<210> SEQ ID NO 108
<211> LENGTH: 14
<212> TYPE: PRT
<213> ORGANISM: Artificial Sequence
<220> FEATURE:
<223> OTHER INFORMATION: Synthetic Construct

<400> SEQUENCE: 108

Trp Phe Arg Gln Ala Pro Gly Lys Gly Arg Glu Gly Val Ser
1               5                   10

<210> SEQ ID NO 109
<211> LENGTH: 14
<212> TYPE: PRT
<213> ORGANISM: Artificial Sequence
<220> FEATURE:
<223> OTHER INFORMATION: Synthetic Construct

<400> SEQUENCE: 109

Trp Phe Arg Gln Ala Pro Gly Lys Gly Leu Glu Gly Val Ser
1               5                   10

<210> SEQ ID NO 110
<211> LENGTH: 14
<212> TYPE: PRT
<213> ORGANISM: Artificial Sequence
<220> FEATURE:
<223> OTHER INFORMATION: Synthetic Construct

<400> SEQUENCE: 110

Trp Phe Arg Gln Ala Pro Gly Lys Gly Leu Glu Gly Val Ser
1               5                   10

<210> SEQ ID NO 111
<211> LENGTH: 14
<212> TYPE: PRT
<213> ORGANISM: Artificial Sequence
<220> FEATURE:
<223> OTHER INFORMATION: Synthetic Construct

<400> SEQUENCE: 111

Trp Phe Arg Gln Ala Pro Gly Lys Gly Leu Glu Gly Val Ser
1               5                   10

<210> SEQ ID NO 112
```

```
<211> LENGTH: 14
<212> TYPE: PRT
<213> ORGANISM: Artificial Sequence
<220> FEATURE:
<223> OTHER INFORMATION: Synthetic Construct

<400> SEQUENCE: 112

Trp Phe Arg Gln Ala Pro Gly Lys Gly Arg Glu Gly Val Ser
1               5                   10

<210> SEQ ID NO 113
<211> LENGTH: 14
<212> TYPE: PRT
<213> ORGANISM: Artificial Sequence
<220> FEATURE:
<223> OTHER INFORMATION: Synthetic Construct

<400> SEQUENCE: 113

Trp Phe Arg Gln Ala Pro Gly Lys Gly Arg Glu Gly Val Ser
1               5                   10

<210> SEQ ID NO 114
<211> LENGTH: 14
<212> TYPE: PRT
<213> ORGANISM: Artificial Sequence
<220> FEATURE:
<223> OTHER INFORMATION: Synthetic Construct

<400> SEQUENCE: 114

Trp Phe Arg Gln Ala Pro Gly Lys Gly Arg Glu Gly Val Ser
1               5                   10

<210> SEQ ID NO 115
<211> LENGTH: 16
<212> TYPE: PRT
<213> ORGANISM: Artificial Sequence
<220> FEATURE:
<223> OTHER INFORMATION: Synthetic Construct

<400> SEQUENCE: 115

Ala Ile Asp Ser Asp Gly Ser Thr Ser Tyr Ala Gly Ser Val Lys Gly
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Synthetic Construct

<400> SEQUENCE: 116

Ala Ile Asp Ser Asp Gly Gly Thr Ser Tyr Ala Asp Ser Val Lys Gly
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Synthetic Construct

<400> SEQUENCE: 117

Ala Ile Asp Ser Asp Gly Ser Thr Ser Tyr Ala Asp Ser Val Lys Gly
1               5                   10                  15

<210> SEQ ID NO 118
<211> LENGTH: 16
```

```
<212> TYPE: PRT
<213> ORGANISM: Artificial Sequence
<220> FEATURE:
<223> OTHER INFORMATION: Synthetic Construct

<400> SEQUENCE: 118

Thr Ile Asn Ser Asp Gly Ser Thr Asn Tyr Ala Asp Ser Val Lys Gly
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Synthetic Construct

<400> SEQUENCE: 119

Ala Ile Asp Ser Asp Gly Ser Val Ser Tyr Ala Asp Ser Val Lys Gly
1               5                   10                  15

<210> SEQ ID NO 120
<211> LENGTH: 17
<212> TYPE: PRT
<213> ORGANISM: Artificial Sequence
<220> FEATURE:
<223> OTHER INFORMATION: Synthetic Construct

<400> SEQUENCE: 120

Cys Ile Ser Trp Ser Gly Gly Ser Thr Tyr Tyr Thr Asp Ser Val Lys
1               5                   10                  15

Gly

<210> SEQ ID NO 121
<211> LENGTH: 16
<212> TYPE: PRT
<213> ORGANISM: Artificial Sequence
<220> FEATURE:
<223> OTHER INFORMATION: Synthetic Construct

<400> SEQUENCE: 121

Ala Ile Asp Ser Asp Gly Ser Thr Ser Tyr Ala Asp Ser Val Lys Gly
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: Synthetic Construct

<400> SEQUENCE: 122

Ala Ile Asp Ser Ser Gly Gly Thr Ser Tyr Ala Asp Ser Val Lys Gly
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: Synthetic Construct

<400> SEQUENCE: 123

Ala Ile Asp Ser Asp Gly Gly Thr Ser Tyr Ala Asp Ser Val Lys Gly
1               5                   10                  15

<210> SEQ ID NO 124
```

```
<211> LENGTH: 16
<212> TYPE: PRT
<213> ORGANISM: Artificial Sequence
<220> FEATURE:
<223> OTHER INFORMATION: Synthetic Construct

<400> SEQUENCE: 124

Ala Ile Asp Ser Asp Gly Gly Thr Ser Tyr Ala Asp Ser Val Lys Gly
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Synthetic Construct

<400> SEQUENCE: 125

Ala Ile Asp Ser Asp Gly Gly Thr Ser Tyr Ala Asp Ser Val Lys Gly
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Synthetic Construct

<400> SEQUENCE: 126

Ala Ile Asp Ser Asp Gly Gly Thr Ser Tyr Ala Asp Ser Val Lys Gly
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Synthetic Construct

<400> SEQUENCE: 127

Ala Ile Asp Ser Asp Gly Gly Thr Ser Tyr Ala Asp Ser Val Lys Gly
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Synthetic Construct

<400> SEQUENCE: 128

Ala Ile Asp Ser Asp Gly Gly Thr Ser Tyr Ala Asp Ser Val Lys Gly
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Synthetic Construct

<400> SEQUENCE: 129

Ala Ile Asp Ser Asp Gly Gly Thr Ser Tyr Ala Asp Ser Val Lys Gly
1               5                   10                  15

<210> SEQ ID NO 130
<211> LENGTH: 16
```

```
<212> TYPE: PRT
<213> ORGANISM: Artificial Sequence
<220> FEATURE:
<223> OTHER INFORMATION: Synthetic Construct

<400> SEQUENCE: 130

Ala Ile Asp Ser Ser Gly Gly Thr Ser Tyr Ala Asp Ser Val Lys Gly
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Synthetic Construct

<400> SEQUENCE: 131

Ala Ile Asp Ser Asp Gly Ser Thr Ser Tyr Ala Asp Ser Val Lys Gly
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Synthetic Construct

<400> SEQUENCE: 132

Ala Ile Asp Ser Asp Gly Ser Thr Ser Tyr Ala Asp Ser Val Lys Gly
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Synthetic Construct

<400> SEQUENCE: 133

Ala Ile Asp Ser Asp Gly Ser Thr Ser Tyr Ala Asp Ser Val Lys Gly
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Synthetic Construct

<400> SEQUENCE: 134

Ala Ile Asp Ser Asp Gly Ser Thr Ser Tyr Ala Asp Ser Val Lys Gly
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Synthetic Construct

<400> SEQUENCE: 135

Ala Ile Asp Ser Asp Gly Ser Thr Ser Tyr Ala Asp Ser Val Lys Gly
1               5                   10                  15

<210> SEQ ID NO 136
<211> LENGTH: 16
<212> TYPE: PRT
```

```
<213> ORGANISM: Artificial Sequence
<220> FEATURE:
<223> OTHER INFORMATION: Synthetic Construct

<400> SEQUENCE: 136

Ala Ile Asp Ser Asp Gly Ser Thr Ser Tyr Ala Asp Ser Val Lys Gly
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Synthetic Construct

<400> SEQUENCE: 137

Ala Ile Asp Ser Ser Gly Ser Thr Ser Tyr Ala Asp Ser Val Lys Gly
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: Synthetic Construct

<400> SEQUENCE: 138

Ala Ile Asp Ser Asp Gly Ser Val Ser Tyr Ala Asp Ser Val Lys Gly
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Synthetic Construct

<400> SEQUENCE: 139

Ala Ile Asp Ser Asp Gly Ser Val Ser Tyr Ala Asp Ser Val Lys Gly
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Synthetic Construct

<400> SEQUENCE: 140

Ala Ile Asp Ser Asp Gly Ser Val Ser Tyr Ala Asp Ser Val Lys Gly
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Synthetic Construct

<400> SEQUENCE: 141

Ala Ile Asp Ser Asp Gly Ser Val Ser Tyr Ala Asp Ser Val Lys Gly
1               5                   10                  15

<210> SEQ ID NO 142
<211> LENGTH: 16
<212> TYPE: PRT
<213> ORGANISM: Artificial Sequence
```

```
<220> FEATURE:
<223> OTHER INFORMATION: Synthetic Construct

<400> SEQUENCE: 142

Ala Ile Asp Ser Asp Gly Ser Val Ser Tyr Ala Asp Ser Val Lys Gly
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Synthetic Construct

<400> SEQUENCE: 143

Ala Ile Asp Ser Asp Gly Ser Val Ser Tyr Ala Asp Ser Val Lys Gly
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Synthetic Construct

<400> SEQUENCE: 144

Ala Ile Asp Ser Asp Gly Ser Val Ser Tyr Ala Asp Ser Val Lys Gly
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Synthetic Construct

<400> SEQUENCE: 145

Ala Ile Asp Ser Asp Gly Ser Val Ser Tyr Ala Asp Ser Val Lys Gly
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Synthetic Construct

<400> SEQUENCE: 146

Ala Ile Asp Ser Ser Gly Ser Val Ser Tyr Ala Asp Ser Val Lys Gly
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Synthetic Construct

<400> SEQUENCE: 147

Thr Ile Asn Ser Asp Gly Ser Thr Asn Tyr Ala Asp Ser Val Lys Gly
1               5                   10                  15

<210> SEQ ID NO 148
<211> LENGTH: 16
<212> TYPE: PRT
<213> ORGANISM: Artificial Sequence
<220> FEATURE:
```

```
<223> OTHER INFORMATION: Synthetic Construct

<400> SEQUENCE: 148

Thr Ile Ala Ser Glu Gly Ser Thr Asn Tyr Ala Asp Ser Val Lys Gly
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Synthetic Construct

<400> SEQUENCE: 149

Thr Ile Ala Ser Ser Gly Ser Thr Asn Tyr Ala Asp Ser Val Lys Gly
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Synthetic Construct

<400> SEQUENCE: 150

Thr Ile Asn Ser Asp Gly Ser Thr Asn Tyr Ala Asp Ser Val Lys Gly
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Synthetic Construct

<400> SEQUENCE: 151

Thr Ile Ala Ser Glu Gly Ser Thr Asn Tyr Ala Asp Ser Val Lys Gly
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Synthetic Construct

<400> SEQUENCE: 152

Thr Ile Ala Ser Ser Gly Ser Thr Asn Tyr Ala Asp Ser Val Lys Gly
1               5                   10                  15

<210> SEQ ID NO 153
<211> LENGTH: 32
<212> TYPE: PRT
<213> ORGANISM: Artificial Sequence
<220> FEATURE:
<223> OTHER INFORMATION: Synthetic Construct

<400> SEQUENCE: 153

Arg Phe Thr Ile Ser Lys Asp Asn Ala Glu Asn Thr Leu Tyr Leu Gln
1               5                   10                  15

Met Asn Ser Leu Lys Pro Glu Asp Thr Ala Met Tyr Tyr Cys Ala Thr
                20                  25                  30

<210> SEQ ID NO 154
<211> LENGTH: 32
<212> TYPE: PRT
```

```
<213> ORGANISM: Artificial Sequence
<220> FEATURE:
<223> OTHER INFORMATION: Synthetic Construct

<400> SEQUENCE: 154

Arg Phe Thr Ile Ser Lys Asp Asn Ala Lys Asn Thr Leu Tyr Leu Gln
1               5                   10                  15

Met Asp Ser Leu Lys Pro Glu Asp Thr Ala Met Tyr Tyr Cys Ala Ala
            20                  25                  30

<210> SEQ ID NO 155
<211> LENGTH: 32
<212> TYPE: PRT
<213> ORGANISM: Artificial Sequence
<220> FEATURE:
<223> OTHER INFORMATION: Synthetic Construct

<400> SEQUENCE: 155

Arg Phe Thr Ile Ser Lys Asp Asn Ala Lys Asn Thr Leu Tyr Leu Gln
1               5                   10                  15

Met Asn Ser Leu Lys Pro Glu Asp Thr Ala Met Tyr Tyr Cys Ala Ala
            20                  25                  30

<210> SEQ ID NO 156
<211> LENGTH: 32
<212> TYPE: PRT
<213> ORGANISM: Artificial Sequence
<220> FEATURE:
<223> OTHER INFORMATION: Synthetic Construct

<400> SEQUENCE: 156

Arg Phe Thr Ile Ser Lys Asp Asn Ala Lys Asn Thr Leu Tyr Leu Gln
1               5                   10                  15

Met Asn Ser Leu Ser Pro Glu Asp Thr Ala Met Tyr Tyr Cys Ala Val
            20                  25                  30

<210> SEQ ID NO 157
<211> LENGTH: 32
<212> TYPE: PRT
<213> ORGANISM: Artificial Sequence
<220> FEATURE:
<223> OTHER INFORMATION: Synthetic Construct

<400> SEQUENCE: 157

Arg Phe Thr Ile Ser Lys Asp Asn Ala Lys Asn Thr Leu Tyr Leu Gln
1               5                   10                  15

Met Asn Ser Leu Lys Pro Glu Asp Thr Ala Met Tyr Phe Cys Ala Ala
            20                  25                  30

<210> SEQ ID NO 158
<211> LENGTH: 32
<212> TYPE: PRT
<213> ORGANISM: Artificial Sequence
<220> FEATURE:
<223> OTHER INFORMATION: Synthetic Construct

<400> SEQUENCE: 158

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Met Tyr Tyr Cys Ala Ala
            20                  25                  30

<210> SEQ ID NO 159
<211> LENGTH: 32
```

```
<212> TYPE: PRT
<213> ORGANISM: Artificial Sequence
<220> FEATURE:
<223> OTHER INFORMATION: Synthetic Construct

<400> SEQUENCE: 159

Arg Phe Thr Ile Ser Lys Asp Asn Ala Lys Asn Thr Leu Phe Leu Gln
1               5                   10                  15

Met Asn Gly Leu Lys Pro Glu Asp Thr Ala Val Tyr Tyr Cys Ala Pro
            20                  25                  30

<210> SEQ ID NO 160
<211> LENGTH: 32
<212> TYPE: PRT
<213> ORGANISM: Artificial Sequence
<220> FEATURE:
<223> OTHER INFORMATION: Synthetic Construct

<400> SEQUENCE: 160

Arg Phe Thr Ile Ser Lys Asp Asn Ala Lys Asn Thr Leu Tyr Leu Gln
1               5                   10                  15

Met Asp Ser Leu Lys Pro Glu Asp Thr Ala Met Tyr Tyr Cys Ala Ala
            20                  25                  30

<210> SEQ ID NO 161
<211> LENGTH: 32
<212> TYPE: PRT
<213> ORGANISM: Artificial Sequence
<220> FEATURE:
<223> OTHER INFORMATION: Synthetic Construct

<400> SEQUENCE: 161

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 162
<211> LENGTH: 32
<212> TYPE: PRT
<213> ORGANISM: Artificial Sequence
<220> FEATURE:
<223> OTHER INFORMATION: Synthetic Construct

<400> SEQUENCE: 162

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 163
<211> LENGTH: 32
<212> TYPE: PRT
<213> ORGANISM: Artificial Sequence
<220> FEATURE:
<223> OTHER INFORMATION: Synthetic Construct

<400> SEQUENCE: 163

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Met Tyr Tyr Cys Ala Ala
            20                  25                  30

<210> SEQ ID NO 164
```

```
<211> LENGTH: 32
<212> TYPE: PRT
<213> ORGANISM: Artificial Sequence
<220> FEATURE:
<223> OTHER INFORMATION: Synthetic Construct

<400> SEQUENCE: 164

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Met Tyr Tyr Cys Ala Ala
            20                  25                  30

<210> SEQ ID NO 165
<211> LENGTH: 32
<212> TYPE: PRT
<213> ORGANISM: Artificial Sequence
<220> FEATURE:
<223> OTHER INFORMATION: Synthetic Construct

<400> SEQUENCE: 165

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Met Tyr Tyr Cys Ala Ala
            20                  25                  30

<210> SEQ ID NO 166
<211> LENGTH: 32
<212> TYPE: PRT
<213> ORGANISM: Artificial Sequence
<220> FEATURE:
<223> OTHER INFORMATION: Synthetic Construct

<400> SEQUENCE: 166

Arg Phe Thr Ile Ser Lys Asp Asn Ser Lys Asn Thr Leu Tyr Leu Gln
1               5                   10                  15

Met Asn Ser Leu Arg Ala Glu Asp Thr Ala Met Tyr Tyr Cys Ala Ala
            20                  25                  30

<210> SEQ ID NO 167
<211> LENGTH: 32
<212> TYPE: PRT
<213> ORGANISM: Artificial Sequence
<220> FEATURE:
<223> OTHER INFORMATION: Synthetic Construct

<400> SEQUENCE: 167

Arg Phe Thr Ile Ser Lys Asp Asn Ser Lys Asn Thr Leu Tyr Leu Gln
1               5                   10                  15

Met Asn Ser Leu Arg Ala Glu Asp Thr Ala Met Tyr Tyr Cys Ala Ala
            20                  25                  30

<210> SEQ ID NO 168
<211> LENGTH: 32
<212> TYPE: PRT
<213> ORGANISM: Artificial Sequence
<220> FEATURE:
<223> OTHER INFORMATION: Synthetic Construct

<400> SEQUENCE: 168

Arg Phe Thr Ile Ser Lys Asp Asn Ser Lys Asn Thr Leu Tyr Leu Gln
1               5                   10                  15

Met Asn Ser Leu Arg Ala Glu Asp Thr Ala Met Tyr Tyr Cys Ala Ala
            20                  25                  30
```

-continued

```
<210> SEQ ID NO 169
<211> LENGTH: 32
<212> TYPE: PRT
<213> ORGANISM: Artificial Sequence
<220> FEATURE:
<223> OTHER INFORMATION: Synthetic Construct

<400> SEQUENCE: 169

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 170
<211> LENGTH: 32
<212> TYPE: PRT
<213> ORGANISM: Artificial Sequence
<220> FEATURE:
<223> OTHER INFORMATION: Synthetic Construct

<400> SEQUENCE: 170

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Met Tyr Tyr Cys Ala Ala
            20                  25                  30

<210> SEQ ID NO 171
<211> LENGTH: 32
<212> TYPE: PRT
<213> ORGANISM: Artificial Sequence
<220> FEATURE:
<223> OTHER INFORMATION: Synthetic Construct

<400> SEQUENCE: 171

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Met Tyr Tyr Cys Ala Ala
            20                  25                  30

<210> SEQ ID NO 172
<211> LENGTH: 32
<212> TYPE: PRT
<213> ORGANISM: Artificial Sequence
<220> FEATURE:
<223> OTHER INFORMATION: Synthetic Construct

<400> SEQUENCE: 172

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Met Tyr Tyr Cys Ala Ala
            20                  25                  30

<210> SEQ ID NO 173
<211> LENGTH: 32
<212> TYPE: PRT
<213> ORGANISM: Artificial Sequence
<220> FEATURE:
<223> OTHER INFORMATION: Synthetic Construct

<400> SEQUENCE: 173

Arg Phe Thr Ile Ser Lys Asp Asn Ser Lys Asn Thr Leu Tyr Leu Gln
1               5                   10                  15

Met Asn Ser Leu Arg Ala Glu Asp Thr Ala Met Tyr Tyr Cys Ala Ala
            20                  25                  30
```

<210> SEQ ID NO 174
<211> LENGTH: 32
<212> TYPE: PRT
<213> ORGANISM: Artificial Sequence
<220> FEATURE:
<223> OTHER INFORMATION: Synthetic Construct

<400> SEQUENCE: 174

Arg Phe Thr Ile Ser Lys Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 175
<211> LENGTH: 32
<212> TYPE: PRT
<213> ORGANISM: Artificial Sequence
<220> FEATURE:
<223> OTHER INFORMATION: Synthetic Construct

<400> SEQUENCE: 175

Arg Phe Thr Ile Ser Lys Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 176
<211> LENGTH: 32
<212> TYPE: PRT
<213> ORGANISM: Artificial Sequence
<220> FEATURE:
<223> OTHER INFORMATION: Synthetic Construct

<400> SEQUENCE: 176

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 177
<211> LENGTH: 32
<212> TYPE: PRT
<213> ORGANISM: Artificial Sequence
<220> FEATURE:
<223> OTHER INFORMATION: Synthetic Construct

<400> SEQUENCE: 177

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Phe Cys Ala Ala
            20                  25                  30

<210> SEQ ID NO 178
<211> LENGTH: 32
<212> TYPE: PRT
<213> ORGANISM: Artificial Sequence
<220> FEATURE:
<223> OTHER INFORMATION: Synthetic Construct

<400> SEQUENCE: 178

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Phe Cys Ala Ala
            20                  25                  30

<210> SEQ ID NO 179
<211> LENGTH: 32
<212> TYPE: PRT
<213> ORGANISM: Artificial Sequence
<220> FEATURE:
<223> OTHER INFORMATION: Synthetic Construct

<400> SEQUENCE: 179

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Met Tyr Phe Cys Ala Ala
            20                  25                  30

<210> SEQ ID NO 180
<211> LENGTH: 32
<212> TYPE: PRT
<213> ORGANISM: Artificial Sequence
<220> FEATURE:
<223> OTHER INFORMATION: Synthetic Construct

<400> SEQUENCE: 180

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Met Tyr Phe Cys Ala Ala
            20                  25                  30

<210> SEQ ID NO 181
<211> LENGTH: 32
<212> TYPE: PRT
<213> ORGANISM: Artificial Sequence
<220> FEATURE:
<223> OTHER INFORMATION: Synthetic Construct

<400> SEQUENCE: 181

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Met Tyr Phe Cys Ala Ala
            20                  25                  30

<210> SEQ ID NO 182
<211> LENGTH: 32
<212> TYPE: PRT
<213> ORGANISM: Artificial Sequence
<220> FEATURE:
<223> OTHER INFORMATION: Synthetic Construct

<400> SEQUENCE: 182

Arg Phe Thr Ile Ser Lys Asp Asn Ser Lys Asn Thr Leu Tyr Leu Gln
1               5                   10                  15

Met Asn Ser Leu Arg Ala Glu Asp Thr Ala Met Tyr Phe Cys Ala Ala
            20                  25                  30

<210> SEQ ID NO 183
<211> LENGTH: 32
<212> TYPE: PRT
<213> ORGANISM: Artificial Sequence
<220> FEATURE:
<223> OTHER INFORMATION: Synthetic Construct

<400> SEQUENCE: 183

Arg Phe Thr Ile Ser Lys Asp Asn Ser Lys Asn Thr Leu Tyr Leu Gln
1               5                   10                  15

Met Asn Ser Leu Arg Ala Glu Asp Thr Ala Val Tyr Phe Cys Ala Ala

```
                    20                  25                  30
```

<210> SEQ ID NO 184
<211> LENGTH: 32
<212> TYPE: PRT
<213> ORGANISM: Artificial Sequence
<220> FEATURE:
<223> OTHER INFORMATION: Synthetic Construct

<400> SEQUENCE: 184

```
Arg Phe Thr Ile Ser Lys Asp Asn Ser Lys Asn Thr Leu Tyr Leu Gln
1               5                   10                  15

Met Asn Ser Leu Arg Ala Glu Asp Thr Ala Val Tyr Phe Cys Ala Ala
            20                  25                  30
```

<210> SEQ ID NO 185
<211> LENGTH: 32
<212> TYPE: PRT
<213> ORGANISM: Artificial Sequence
<220> FEATURE:
<223> OTHER INFORMATION: Synthetic Construct

<400> SEQUENCE: 185

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Val
            20                  25                  30
```

<210> SEQ ID NO 186
<211> LENGTH: 32
<212> TYPE: PRT
<213> ORGANISM: Artificial Sequence
<220> FEATURE:
<223> OTHER INFORMATION: Synthetic Construct

<400> SEQUENCE: 186

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Val
            20                  25                  30
```

<210> SEQ ID NO 187
<211> LENGTH: 32
<212> TYPE: PRT
<213> ORGANISM: Artificial Sequence
<220> FEATURE:
<223> OTHER INFORMATION: Synthetic Construct

<400> SEQUENCE: 187

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Val
            20                  25                  30
```

<210> SEQ ID NO 188
<211> LENGTH: 32
<212> TYPE: PRT
<213> ORGANISM: Artificial Sequence
<220> FEATURE:
<223> OTHER INFORMATION: Synthetic Construct

<400> SEQUENCE: 188

```
Arg Phe Thr Ile Ser Arg Asp Asn Ala Lys Asn Thr Leu Tyr Leu Gln
1               5                   10                  15
```

Met Asn Ser Leu Arg Pro Glu Asp Thr Ala Val Tyr Tyr Cys Ala Val
            20                  25                  30

<210> SEQ ID NO 189
<211> LENGTH: 32
<212> TYPE: PRT
<213> ORGANISM: Artificial Sequence
<220> FEATURE:
<223> OTHER INFORMATION: Synthetic Construct

<400> SEQUENCE: 189

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Ala Val
            20                  25                  30

<210> SEQ ID NO 190
<211> LENGTH: 32
<212> TYPE: PRT
<213> ORGANISM: Artificial Sequence
<220> FEATURE:
<223> OTHER INFORMATION: Synthetic Construct

<400> SEQUENCE: 190

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Ala Val
            20                  25                  30

<210> SEQ ID NO 191
<211> LENGTH: 16
<212> TYPE: PRT
<213> ORGANISM: Artificial Sequence
<220> FEATURE:
<223> OTHER INFORMATION: Synthetic Construct

<400> SEQUENCE: 191

Ser Pro Leu Trp Leu Leu Ser Arg Leu Asp Pro Ala Asp Phe Glu Tyr
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: Synthetic Construct

<400> SEQUENCE: 192

Asp Phe Cys Trp Val Asp Glu Asp Arg His Leu Tyr Glu Tyr Asn Ser
1               5                   10                  15

<210> SEQ ID NO 193
<211> LENGTH: 13
<212> TYPE: PRT
<213> ORGANISM: Artificial Sequence
<220> FEATURE:
<223> OTHER INFORMATION: Synthetic Construct

<400> SEQUENCE: 193

Asp Phe Cys Trp Val Asp Asp Phe Tyr Glu Tyr Asn Tyr
1               5                   10

<210> SEQ ID NO 194
<211> LENGTH: 18
<212> TYPE: PRT
<213> ORGANISM: Artificial Sequence

```
<220> FEATURE:
<223> OTHER INFORMATION: Synthetic Construct

<400> SEQUENCE: 194

Asp Leu Ala Pro Cys Trp Val Ala Gly Pro Ile Glu Ala Ala Asp Phe
1               5                   10                  15

Gly Tyr

<210> SEQ ID NO 195
<211> LENGTH: 14
<212> TYPE: PRT
<213> ORGANISM: Artificial Sequence
<220> FEATURE:
<223> OTHER INFORMATION: Synthetic Construct

<400> SEQUENCE: 195

Asp Leu Cys Trp Val Asp Gln Asp Gln Gly Glu Tyr Asn Thr
1               5                   10

<210> SEQ ID NO 196
<211> LENGTH: 22
<212> TYPE: PRT
<213> ORGANISM: Artificial Sequence
<220> FEATURE:
<223> OTHER INFORMATION: Synthetic Construct

<400> SEQUENCE: 196

Asp Leu Phe Cys Pro Pro Asp Asp Thr Thr Gly Trp Gly Met Asp
1               5                   10                  15

Pro Pro Glu His Asn Tyr
            20

<210> SEQ ID NO 197
<211> LENGTH: 13
<212> TYPE: PRT
<213> ORGANISM: Artificial Sequence
<220> FEATURE:
<223> OTHER INFORMATION: Synthetic Construct

<400> SEQUENCE: 197

Leu Cys Trp Val Asp Tyr Pro Leu Pro Ser Gly Pro Tyr
1               5                   10

<210> SEQ ID NO 198
<211> LENGTH: 16
<212> TYPE: PRT
<213> ORGANISM: Artificial Sequence
<220> FEATURE:
<223> OTHER INFORMATION: Synthetic Construct

<400> SEQUENCE: 198

Asp Phe Cys Trp Val Asp Glu Asp Arg His Leu Tyr Glu Tyr Gln Ser
1               5                   10                  15

<210> SEQ ID NO 199
<211> LENGTH: 16
<212> TYPE: PRT
<213> ORGANISM: Artificial Sequence
<220> FEATURE:
<223> OTHER INFORMATION: Synthetic Construct

<400> SEQUENCE: 199

Asp Phe Cys Trp Val Asp Glu Asp Arg His Leu Tyr Glu Tyr Asn Ser
1               5                   10                  15
```

```
<210> SEQ ID NO 200
<211> LENGTH: 16
<212> TYPE: PRT
<213> ORGANISM: Artificial Sequence
<220> FEATURE:
<223> OTHER INFORMATION: Synthetic Construct

<400> SEQUENCE: 200

Asp Phe Cys Trp Val Asp Glu Asp Arg His Leu Tyr Glu Tyr Asn Ser
1               5                   10                  15

<210> SEQ ID NO 201
<211> LENGTH: 16
<212> TYPE: PRT
<213> ORGANISM: Artificial Sequence
<220> FEATURE:
<223> OTHER INFORMATION: Synthetic Construct

<400> SEQUENCE: 201

Asp Phe Cys Trp Val Asp Glu Asp Arg His Leu Tyr Glu Tyr Asn Ser
1               5                   10                  15

<210> SEQ ID NO 202
<211> LENGTH: 16
<212> TYPE: PRT
<213> ORGANISM: Artificial Sequence
<220> FEATURE:
<223> OTHER INFORMATION: Synthetic Construct

<400> SEQUENCE: 202

Asp Phe Cys Trp Val Asp Glu Asp Arg His Leu Tyr Glu Tyr Asn Ser
1               5                   10                  15

<210> SEQ ID NO 203
<211> LENGTH: 16
<212> TYPE: PRT
<213> ORGANISM: Artificial Sequence
<220> FEATURE:
<223> OTHER INFORMATION: Synthetic Construct

<400> SEQUENCE: 203

Asp Phe Cys Trp Val Asp Glu Asp Arg His Leu Tyr Glu Tyr Asn Ser
1               5                   10                  15

<210> SEQ ID NO 204
<211> LENGTH: 16
<212> TYPE: PRT
<213> ORGANISM: Artificial Sequence
<220> FEATURE:
<223> OTHER INFORMATION: Synthetic Construct

<400> SEQUENCE: 204

Asp Phe Cys Trp Val Asp Glu Asp Arg His Leu Tyr Glu Tyr Asn Ser
1               5                   10                  15

<210> SEQ ID NO 205
<211> LENGTH: 16
<212> TYPE: PRT
<213> ORGANISM: Artificial Sequence
<220> FEATURE:
<223> OTHER INFORMATION: Synthetic Construct

<400> SEQUENCE: 205

Asp Phe Cys Trp Val Asp Glu Asp Arg His Leu Tyr Glu Tyr Asn Ser
1               5                   10                  15

<210> SEQ ID NO 206
```

<211> LENGTH: 16
<212> TYPE: PRT
<213> ORGANISM: Artificial Sequence
<220> FEATURE:
<223> OTHER INFORMATION: Synthetic Construct

<400> SEQUENCE: 206

Asp Phe Cys Trp Val Asp Glu Asp Arg His Leu Tyr Glu Tyr Asn Ser
1               5                   10                  15

<210> SEQ ID NO 207
<211> LENGTH: 13
<212> TYPE: PRT
<213> ORGANISM: Artificial Sequence
<220> FEATURE:
<223> OTHER INFORMATION: Synthetic Construct

<400> SEQUENCE: 207

Asp Phe Cys Trp Val Asp Asp Phe Tyr Glu Tyr Asn Tyr
1               5                   10

<210> SEQ ID NO 208
<211> LENGTH: 13
<212> TYPE: PRT
<213> ORGANISM: Artificial Sequence
<220> FEATURE:
<223> OTHER INFORMATION: Synthetic Construct

<400> SEQUENCE: 208

Asp Phe Cys Trp Val Asp Asp Phe Tyr Glu Tyr Asn Tyr
1               5                   10

<210> SEQ ID NO 209
<211> LENGTH: 13
<212> TYPE: PRT
<213> ORGANISM: Artificial Sequence
<220> FEATURE:
<223> OTHER INFORMATION: Synthetic Construct

<400> SEQUENCE: 209

Asp Phe Cys Trp Val Asp Asp Phe Tyr Glu Tyr Asn Tyr
1               5                   10

<210> SEQ ID NO 210
<211> LENGTH: 13
<212> TYPE: PRT
<213> ORGANISM: Artificial Sequence
<220> FEATURE:
<223> OTHER INFORMATION: Synthetic Construct

<400> SEQUENCE: 210

Asp Phe Cys Trp Val Asp Asp Phe Tyr Glu Tyr Asn Tyr
1               5                   10

<210> SEQ ID NO 211
<211> LENGTH: 13
<212> TYPE: PRT
<213> ORGANISM: Artificial Sequence
<220> FEATURE:
<223> OTHER INFORMATION: Synthetic Construct

<400> SEQUENCE: 211

Asp Phe Cys Trp Val Asp Asp Phe Tyr Glu Tyr Asn Tyr
1               5                   10

<210> SEQ ID NO 212
<211> LENGTH: 13

```
<212> TYPE: PRT
<213> ORGANISM: Artificial Sequence
<220> FEATURE:
<223> OTHER INFORMATION: Synthetic Construct

<400> SEQUENCE: 212

Asp Phe Cys Trp Val Asp Asp Phe Tyr Glu Tyr Asn Tyr
1               5                   10

<210> SEQ ID NO 213
<211> LENGTH: 13
<212> TYPE: PRT
<213> ORGANISM: Artificial Sequence
<220> FEATURE:
<223> OTHER INFORMATION: Synthetic Construct

<400> SEQUENCE: 213

Asp Phe Cys Trp Val Asp Asp Phe Tyr Glu Tyr Asn Tyr
1               5                   10

<210> SEQ ID NO 214
<211> LENGTH: 14
<212> TYPE: PRT
<213> ORGANISM: Artificial Sequence
<220> FEATURE:
<223> OTHER INFORMATION: Synthetic Construct

<400> SEQUENCE: 214

Asp Leu Cys Trp Val Asp Gln Asp Gln Gly Glu Tyr Asn Thr
1               5                   10

<210> SEQ ID NO 215
<211> LENGTH: 14
<212> TYPE: PRT
<213> ORGANISM: Artificial Sequence
<220> FEATURE:
<223> OTHER INFORMATION: Synthetic Construct

<400> SEQUENCE: 215

Asp Leu Cys Trp Val Asp Gln Asp Gln Gly Glu Tyr Asn Thr
1               5                   10

<210> SEQ ID NO 216
<211> LENGTH: 14
<212> TYPE: PRT
<213> ORGANISM: Artificial Sequence
<220> FEATURE:
<223> OTHER INFORMATION: Synthetic Construct

<400> SEQUENCE: 216

Asp Leu Cys Trp Val Asp Gln Asp Gln Gly Glu Tyr Asn Thr
1               5                   10

<210> SEQ ID NO 217
<211> LENGTH: 14
<212> TYPE: PRT
<213> ORGANISM: Artificial Sequence
<220> FEATURE:
<223> OTHER INFORMATION: Synthetic Construct

<400> SEQUENCE: 217

Asp Leu Cys Trp Val Asp Gln Asp Gln Gly Glu Tyr Asn Thr
1               5                   10

<210> SEQ ID NO 218
<211> LENGTH: 14
<212> TYPE: PRT
```

<213> ORGANISM: Artificial Sequence
<220> FEATURE:
<223> OTHER INFORMATION: Synthetic Construct

<400> SEQUENCE: 218

Asp Leu Cys Trp Val Asp Gln Asp Gln Gly Glu Tyr Asn Thr
1               5                   10

<210> SEQ ID NO 219
<211> LENGTH: 14
<212> TYPE: PRT
<213> ORGANISM: Artificial Sequence
<220> FEATURE:
<223> OTHER INFORMATION: Synthetic Construct

<400> SEQUENCE: 219

Asp Leu Cys Trp Val Asp Gln Asp Gln Gly Glu Tyr Asn Thr
1               5                   10

<210> SEQ ID NO 220
<211> LENGTH: 14
<212> TYPE: PRT
<213> ORGANISM: Artificial Sequence
<220> FEATURE:
<223> OTHER INFORMATION: Synthetic Construct

<400> SEQUENCE: 220

Asp Leu Cys Trp Val Asp Gln Asp Gln Gly Glu Tyr Asn Thr
1               5                   10

<210> SEQ ID NO 221
<211> LENGTH: 14
<212> TYPE: PRT
<213> ORGANISM: Artificial Sequence
<220> FEATURE:
<223> OTHER INFORMATION: Synthetic Construct

<400> SEQUENCE: 221

Asp Leu Cys Trp Val Asp Gln Asp Gln Gly Glu Tyr Asn Thr
1               5                   10

<210> SEQ ID NO 222
<211> LENGTH: 14
<212> TYPE: PRT
<213> ORGANISM: Artificial Sequence
<220> FEATURE:
<223> OTHER INFORMATION: Synthetic Construct

<400> SEQUENCE: 222

Asp Leu Cys Trp Val Asp Gln Asp Gln Gly Glu Tyr Asn Thr
1               5                   10

<210> SEQ ID NO 223
<211> LENGTH: 18
<212> TYPE: PRT
<213> ORGANISM: Artificial Sequence
<220> FEATURE:
<223> OTHER INFORMATION: Synthetic Construct

<400> SEQUENCE: 223

Asp Leu Ala Pro Cys Trp Val Ala Gly Pro Ile Glu Ala Ala Asp Phe
1               5                   10                  15

Gly Tyr

<210> SEQ ID NO 224
<211> LENGTH: 18

<212> TYPE: PRT
<213> ORGANISM: Artificial Sequence
<220> FEATURE:
<223> OTHER INFORMATION: Synthetic Construct

<400> SEQUENCE: 224

Asp Leu Ala Pro Cys Trp Val Ala Gly Pro Ile Glu Ala Ala Asp Phe
1               5                   10                  15

Gly Tyr

<210> SEQ ID NO 225
<211> LENGTH: 18
<212> TYPE: PRT
<213> ORGANISM: Artificial Sequence
<220> FEATURE:
<223> OTHER INFORMATION: Synthetic Construct

<400> SEQUENCE: 225

Asp Leu Ala Pro Cys Trp Val Ala Gly Pro Ile Glu Ala Ala Asp Phe
1               5                   10                  15

Gly Tyr

<210> SEQ ID NO 226
<211> LENGTH: 18
<212> TYPE: PRT
<213> ORGANISM: Artificial Sequence
<220> FEATURE:
<223> OTHER INFORMATION: Synthetic Construct

<400> SEQUENCE: 226

Asp Leu Ala Pro Cys Trp Val Ala Gly Pro Ile Glu Ala Ala Asp Phe
1               5                   10                  15

Gly Tyr

<210> SEQ ID NO 227
<211> LENGTH: 18
<212> TYPE: PRT
<213> ORGANISM: Artificial Sequence
<220> FEATURE:
<223> OTHER INFORMATION: Synthetic Construct

<400> SEQUENCE: 227

Asp Leu Ala Pro Cys Trp Val Ala Gly Pro Ile Glu Ala Ala Asp Phe
1               5                   10                  15

Gly Tyr

<210> SEQ ID NO 228
<211> LENGTH: 18
<212> TYPE: PRT
<213> ORGANISM: Artificial Sequence
<220> FEATURE:
<223> OTHER INFORMATION: Synthetic Construct

<400> SEQUENCE: 228

Asp Leu Ala Pro Cys Trp Val Ala Gly Pro Ile Glu Ala Ala Asp Phe
1               5                   10                  15

Gly Tyr

<210> SEQ ID NO 229
<211> LENGTH: 11
<212> TYPE: PRT
<213> ORGANISM: Artificial Sequence
<220> FEATURE:
<223> OTHER INFORMATION: Synthetic Construct

<400> SEQUENCE: 229

Trp Gly Gln Gly Thr Gln Val Thr Val Ser Ser
1               5                   10

<210> SEQ ID NO 230
<211> LENGTH: 11
<212> TYPE: PRT
<213> ORGANISM: Artificial Sequence
<220> FEATURE:
<223> OTHER INFORMATION: Synthetic Construct

<400> SEQUENCE: 230

Trp Gly Gln Gly Thr Gln Val Thr Val Ser Ser
1               5                   10

<210> SEQ ID NO 231
<211> LENGTH: 11
<212> TYPE: PRT
<213> ORGANISM: Artificial Sequence
<220> FEATURE:
<223> OTHER INFORMATION: Synthetic Construct

<400> SEQUENCE: 231

Trp Gly Gln Gly Thr Gln Val Thr Val Ser Ser
1               5                   10

<210> SEQ ID NO 232
<211> LENGTH: 11
<212> TYPE: PRT
<213> ORGANISM: Artificial Sequence
<220> FEATURE:
<223> OTHER INFORMATION: Synthetic Construct

<400> SEQUENCE: 232

Trp Gly Gln Gly Thr Gln Val Thr Val Ser Ser
1               5                   10

<210> SEQ ID NO 233
<211> LENGTH: 11
<212> TYPE: PRT
<213> ORGANISM: Artificial Sequence
<220> FEATURE:
<223> OTHER INFORMATION: Synthetic Construct

<400> SEQUENCE: 233

Trp Gly Gln Gly Thr Gln Val Thr Val Ser Ser
1               5                   10

<210> SEQ ID NO 234
<211> LENGTH: 11
<212> TYPE: PRT
<213> ORGANISM: Artificial Sequence
<220> FEATURE:
<223> OTHER INFORMATION: Synthetic Construct

<400> SEQUENCE: 234

Trp Gly Gln Gly Thr Gln Val Thr Val Ser Ser
1               5                   10

<210> SEQ ID NO 235
<211> LENGTH: 11
<212> TYPE: PRT
<213> ORGANISM: Artificial Sequence
<220> FEATURE:
<223> OTHER INFORMATION: Synthetic Construct

<400> SEQUENCE: 235

Trp Gly Gln Gly Thr Gln Val Thr Val Ser Ser
1               5                   10

<210> SEQ ID NO 236
<211> LENGTH: 11
<212> TYPE: PRT
<213> ORGANISM: Artificial Sequence
<220> FEATURE:
<223> OTHER INFORMATION: Synthetic Construct

<400> SEQUENCE: 236

Trp Gly Gln Gly Thr Gln Val Thr Val Ser Ser
1               5                   10

<210> SEQ ID NO 237
<211> LENGTH: 11
<212> TYPE: PRT
<213> ORGANISM: Artificial Sequence
<220> FEATURE:
<223> OTHER INFORMATION: Synthetic Construct

<400> SEQUENCE: 237

Trp Gly Gln Gly Thr Leu Val Thr Val Ser Ser
1               5                   10

<210> SEQ ID NO 238
<211> LENGTH: 11
<212> TYPE: PRT
<213> ORGANISM: Artificial Sequence
<220> FEATURE:
<223> OTHER INFORMATION: Synthetic Construct

<400> SEQUENCE: 238

Trp Gly Gln Gly Thr Leu Val Thr Val Ser Ser
1               5                   10

<210> SEQ ID NO 239
<211> LENGTH: 11
<212> TYPE: PRT
<213> ORGANISM: Artificial Sequence
<220> FEATURE:
<223> OTHER INFORMATION: Synthetic Construct

<400> SEQUENCE: 239

Trp Gly Gln Gly Thr Leu Val Thr Val Ser Ser
1               5                   10

<210> SEQ ID NO 240
<211> LENGTH: 11
<212> TYPE: PRT
<213> ORGANISM: Artificial Sequence
<220> FEATURE:
<223> OTHER INFORMATION: Synthetic Construct

<400> SEQUENCE: 240

Trp Gly Gln Gly Thr Leu Val Thr Val Ser Ser
1               5                   10

<210> SEQ ID NO 241
<211> LENGTH: 11
<212> TYPE: PRT
<213> ORGANISM: Artificial Sequence
<220> FEATURE:
<223> OTHER INFORMATION: Synthetic Construct

<400> SEQUENCE: 241

Trp Gly Gln Gly Thr Leu Val Thr Val Ser Ser
1               5                   10

<210> SEQ ID NO 242
<211> LENGTH: 11
<212> TYPE: PRT
<213> ORGANISM: Artificial Sequence
<220> FEATURE:
<223> OTHER INFORMATION: Synthetic Construct

<400> SEQUENCE: 242

Trp Gly Gln Gly Thr Leu Val Thr Val Ser Ser
1               5                   10

<210> SEQ ID NO 243
<211> LENGTH: 11
<212> TYPE: PRT
<213> ORGANISM: Artificial Sequence
<220> FEATURE:
<223> OTHER INFORMATION: Synthetic Construct

<400> SEQUENCE: 243

Trp Gly Gln Gly Thr Leu Val Thr Val Ser Ser
1               5                   10

<210> SEQ ID NO 244
<211> LENGTH: 11
<212> TYPE: PRT
<213> ORGANISM: Artificial Sequence
<220> FEATURE:
<223> OTHER INFORMATION: Synthetic Construct

<400> SEQUENCE: 244

Trp Gly Gln Gly Thr Leu Val Thr Val Ser Ser
1               5                   10

<210> SEQ ID NO 245
<211> LENGTH: 11
<212> TYPE: PRT
<213> ORGANISM: Artificial Sequence
<220> FEATURE:
<223> OTHER INFORMATION: Synthetic Construct

<400> SEQUENCE: 245

Trp Gly Gln Gly Thr Leu Val Thr Val Ser Ser
1               5                   10

<210> SEQ ID NO 246
<211> LENGTH: 11
<212> TYPE: PRT
<213> ORGANISM: Artificial Sequence
<220> FEATURE:
<223> OTHER INFORMATION: Synthetic Construct

<400> SEQUENCE: 246

Trp Gly Gln Gly Thr Leu Val Thr Val Ser Ser
1               5                   10

<210> SEQ ID NO 247
<211> LENGTH: 11
<212> TYPE: PRT
<213> ORGANISM: Artificial Sequence
<220> FEATURE:
<223> OTHER INFORMATION: Synthetic Construct

<400> SEQUENCE: 247

Trp Gly Gln Gly Thr Leu Val Thr Val Ser Ser
1               5                   10

<210> SEQ ID NO 248
<211> LENGTH: 11
<212> TYPE: PRT
<213> ORGANISM: Artificial Sequence
<220> FEATURE:
<223> OTHER INFORMATION: Synthetic Construct

<400> SEQUENCE: 248

Trp Gly Gln Gly Thr Leu Val Thr Val Ser Ser
1               5                   10

<210> SEQ ID NO 249
<211> LENGTH: 11
<212> TYPE: PRT
<213> ORGANISM: Artificial Sequence
<220> FEATURE:
<223> OTHER INFORMATION: Synthetic Construct

<400> SEQUENCE: 249

Trp Gly Gln Gly Thr Leu Val Thr Val Ser Ser
1               5                   10

<210> SEQ ID NO 250
<211> LENGTH: 11
<212> TYPE: PRT
<213> ORGANISM: Artificial Sequence
<220> FEATURE:
<223> OTHER INFORMATION: Synthetic Construct

<400> SEQUENCE: 250

Trp Gly Gln Gly Thr Leu Val Thr Val Ser Ser
1               5                   10

<210> SEQ ID NO 251
<211> LENGTH: 11
<212> TYPE: PRT
<213> ORGANISM: Artificial Sequence
<220> FEATURE:
<223> OTHER INFORMATION: Synthetic Construct

<400> SEQUENCE: 251

Trp Gly Gln Gly Thr Leu Val Thr Val Ser Ser
1               5                   10

<210> SEQ ID NO 252
<211> LENGTH: 11
<212> TYPE: PRT
<213> ORGANISM: Artificial Sequence
<220> FEATURE:
<223> OTHER INFORMATION: Synthetic Construct

<400> SEQUENCE: 252

Trp Gly Gln Gly Thr Leu Val Thr Val Ser Ser
1               5                   10

<210> SEQ ID NO 253
<211> LENGTH: 11
<212> TYPE: PRT
<213> ORGANISM: Artificial Sequence
<220> FEATURE:
<223> OTHER INFORMATION: Synthetic Construct

<400> SEQUENCE: 253

Trp Gly Gln Gly Thr Leu Val Thr Val Ser Ser 1               5                   10

<210> SEQ ID NO 254
<211> LENGTH: 11
<212> TYPE: PRT
<213> ORGANISM: Artificial Sequence
<220> FEATURE:
<223> OTHER INFORMATION: Synthetic Construct

<400> SEQUENCE: 254

Trp Gly Gln Gly Thr Leu Val Thr Val Ser Ser
1               5                   10

<210> SEQ ID NO 255
<211> LENGTH: 11
<212> TYPE: PRT
<213> ORGANISM: Artificial Sequence
<220> FEATURE:
<223> OTHER INFORMATION: Synthetic Construct

<400> SEQUENCE: 255

Trp Gly Gln Gly Thr Leu Val Thr Val Ser Ser
1               5                   10

<210> SEQ ID NO 256
<211> LENGTH: 11
<212> TYPE: PRT
<213> ORGANISM: Artificial Sequence
<220> FEATURE:
<223> OTHER INFORMATION: Synthetic Construct

<400> SEQUENCE: 256

Trp Gly Gln Gly Thr Leu Val Thr Val Ser Ser
1               5                   10

<210> SEQ ID NO 257
<211> LENGTH: 11
<212> TYPE: PRT
<213> ORGANISM: Artificial Sequence
<220> FEATURE:
<223> OTHER INFORMATION: Synthetic Construct

<400> SEQUENCE: 257

Trp Gly Gln Gly Thr Leu Val Thr Val Ser Ser
1               5                   10

<210> SEQ ID NO 258
<211> LENGTH: 11
<212> TYPE: PRT
<213> ORGANISM: Artificial Sequence
<220> FEATURE:
<223> OTHER INFORMATION: Synthetic Construct

<400> SEQUENCE: 258

Trp Gly Gln Gly Thr Leu Val Thr Val Ser Ser
1               5                   10

<210> SEQ ID NO 259
<211> LENGTH: 11
<212> TYPE: PRT
<213> ORGANISM: Artificial Sequence
<220> FEATURE:
<223> OTHER INFORMATION: Synthetic Construct

<400> SEQUENCE: 259

Trp Gly Gln Gly Thr Leu Val Thr Val Ser Ser
1               5                   10

```
<210> SEQ ID NO 260
<211> LENGTH: 11
<212> TYPE: PRT
<213> ORGANISM: Artificial Sequence
<220> FEATURE:
<223> OTHER INFORMATION: Synthetic Construct

<400> SEQUENCE: 260

Trp Gly Gln Gly Thr Leu Val Thr Val Ser Ser
1               5                   10

<210> SEQ ID NO 261
<211> LENGTH: 11
<212> TYPE: PRT
<213> ORGANISM: Artificial Sequence
<220> FEATURE:
<223> OTHER INFORMATION: Synthetic Construct

<400> SEQUENCE: 261

Trp Gly Gln Gly Thr Leu Val Thr Val Ser Ser
1               5                   10

<210> SEQ ID NO 262
<211> LENGTH: 11
<212> TYPE: PRT
<213> ORGANISM: Artificial Sequence
<220> FEATURE:
<223> OTHER INFORMATION: Synthetic Construct

<400> SEQUENCE: 262

Trp Gly Gln Gly Thr Leu Val Thr Val Ser Ser
1               5                   10

<210> SEQ ID NO 263
<211> LENGTH: 11
<212> TYPE: PRT
<213> ORGANISM: Artificial Sequence
<220> FEATURE:
<223> OTHER INFORMATION: Synthetic Construct

<400> SEQUENCE: 263

Trp Gly Gln Gly Thr Leu Val Thr Val Ser Ser
1               5                   10

<210> SEQ ID NO 264
<211> LENGTH: 11
<212> TYPE: PRT
<213> ORGANISM: Artificial Sequence
<220> FEATURE:
<223> OTHER INFORMATION: Synthetic Construct

<400> SEQUENCE: 264

Trp Gly Gln Gly Thr Leu Val Thr Val Ser Ser
1               5                   10

<210> SEQ ID NO 265
<211> LENGTH: 11
<212> TYPE: PRT
<213> ORGANISM: Artificial Sequence
<220> FEATURE:
<223> OTHER INFORMATION: Synthetic Construct

<400> SEQUENCE: 265

Trp Gly Gln Gly Thr Leu Val Thr Val Ser Ser
1               5                   10
```

<210> SEQ ID NO 266
<211> LENGTH: 11
<212> TYPE: PRT
<213> ORGANISM: Artificial Sequence
<220> FEATURE:
<223> OTHER INFORMATION: Synthetic Construct

<400> SEQUENCE: 266

Trp Gly Gln Gly Thr Leu Val Thr Val Ser Ser
1               5                   10

<210> SEQ ID NO 267
<211> LENGTH: 372
<212> TYPE: DNA
<213> ORGANISM: Artificial Sequence
<220> FEATURE:
<223> OTHER INFORMATION: Synthetic Construct

<400> SEQUENCE: 267

```
caggtgcaac tggcggagtc tgggggaggc tcggtgcatg ctggagggtc tctgagactc      60
tcctgtgtag tttctgaata taccttcagt agtgattcta tgggctggtt ccgccaggct     120
ccagggaagg agcgcgaggg ggtcgcagct attgatagtg atggtagcac aagctacgca     180
ggctccgtga agggcgatt caccatctcc aaagacaacg ccgagaacac tctgtatctg     240
caaatgaaca gcctgaaacc tgaggacact gccatgtact actgtgcgac aagccctctg     300
tggctgctat ccaggctcga cccagctgac tttgaatact ggggccaggg gacccaggtc     360
accgtctcct ca                                                         372
```

<210> SEQ ID NO 268
<211> LENGTH: 372
<212> TYPE: DNA
<213> ORGANISM: Artificial Sequence
<220> FEATURE:
<223> OTHER INFORMATION: Synthetic Construct

<400> SEQUENCE: 268

```
gaggtgcaac tggtggagtc tgggggaggc tcggtgcagg ctggagggtc tctgagactc      60
tcctgtgcag cctctggata catcatcagt agctactgca tgggctggtt ccgccaggct     120
ccagggaagg agcgcgaggg ggtcgcagct attgatagtg atggtggcac aagctacgca     180
gactccgtga agggccgatt caccatctcc aaagacaacg ccaagaacac tctgtatctg     240
caaatggaca gcctgaaacc tgaggacact gccatgtact actgtgcggc agattttgt      300 tgggtagatg aggatcgcca cctctatgag tataactcct ggggccaggg gacccaggtc     360
accgtctcct ca                                                         372
```

<210> SEQ ID NO 269
<211> LENGTH: 363
<212> TYPE: DNA
<213> ORGANISM: Artificial Sequence
<220> FEATURE:
<223> OTHER INFORMATION: Synthetic Construct

<400> SEQUENCE: 269

```
caggtgcagc tggcggagtc tgggggaggc tcggtgcagg ctggagggtc tctgagactc      60
tcctgtgcag cctctggata caccatcagt agctactgca tgggctggtt ccgccaggct     120
ccagggaagg agcgcgaggg ggtcgcagct attgatagtg atggtagcac aagctacgca     180
gactccgtga agggccgatt caccatctcc aaagacaacg ccaagaacac tctgtatctg     240
```

```
caaatgaaca gcctgaaacc tgaggacact gccatgtact actgtgcggc agattttttgt    300 tgggtggacg acttctatga gtataactac tggggccagg ggacccaggt caccgtctcc    360
tca                                                                  363

<210> SEQ ID NO 270
<211> LENGTH: 378
<212> TYPE: DNA
<213> ORGANISM: Artificial Sequence
<220> FEATURE:
<223> OTHER INFORMATION: Synthetic Construct

<400> SEQUENCE: 270
gaggtgcaac tggcggagtc tgggggaggc tcggtgcagg ctggagggtc tctgagactc    60
tcctgtgcag cctctggata cacctacggt ggctactgca tgggctggtt ccgccaggct    120
ccagggaagg agcgcgaggg ggtcgcaact attaatagtg atggtagcac aaactacgca    180
gactccgtga agggccgatt caccatctcc aaagacaacg ccaagaacac tctgtatctg    240
caaatgaaca gcctgagccc tgaggacact gccatgtact actgcgcggt ggatctcgcc    300
ccatgttggg tagctggtcc catcgaggcc gctgactttg ttactgggg ccaggggacc    360 caggtcaccg tctcctca                                                  378

<210> SEQ ID NO 271
<211> LENGTH: 366
<212> TYPE: DNA
<213> ORGANISM: Artificial Sequence
<220> FEATURE:
<223> OTHER INFORMATION: Synthetic Construct

<400> SEQUENCE: 271
caggtgcacc tgatggagtc tgggggaggc tcggtgcagg ttggagggtc tctgagactc    60
tcctgtgcag cctctggata caccgtcagt agctactgca tgggctggtt ccgccaggct    120
ccagggaagg agcgcgaggg ggtcgcagct attgatagtg atggtagcgt aagttatgca    180
gactccgtga agggccgatt caccatctcc aaagacaacg ccaagaacac tctgtatctg    240
caaatgaaca gcctgaaacc tgaggacact gccatgtact tctgtgcggc agatctttgc    300
tgggtggacc aggaccaggg agaatataac acctggggcc aggggaccca ggtcaccgtc    360
tcctca                                                               366

<210> SEQ ID NO 272
<211> LENGTH: 393
<212> TYPE: DNA
<213> ORGANISM: Artificial Sequence
<220> FEATURE:
<223> OTHER INFORMATION: Synthetic Construct

<400> SEQUENCE: 272
gaggtgcagc tggtggagtc tgggggaggc ttggtgcagg caggggggtc tctgagactc    60
tcctgtacag cctctggatt gacttttgat gattatgcca tgggctggtt ccgccaggct    120
ccagggaagg agcgcgaggg ggtctcatgt attagctgga gtggtggtag cacatactat    180
accgactccg tgaagggccg attcaccatc tccagagaca cgccaagaa cacgctgtat    240 ctgcaaatga acagcctgaa acctgaggac acggccatgt attactgtgc ggcagatttg    300
ttctgtcccc cacctgatga tactacgggt tggggtatgg accctcccga gcataactac    360
tggggccagg ggacccaggt caccgtctcc tca                                 393
```

<210> SEQ ID NO 273
<211> LENGTH: 363
<212> TYPE: DNA
<213> ORGANISM: Artificial Sequence
<220> FEATURE:
<223> OTHER INFORMATION: Synthetic Construct

<400> SEQUENCE: 273

```
caggttcagc tggtggagtc tgggggaggc tcggtgcagg ctggagggtc tctgagactt      60
tcctgtgcag cctctggata caccttgagt agctactgca tgggctggtt ccgccaggct     120
ccagggaagg agcgcgaggg ggtcgcagct attgatagtg atggtagcac aagctacgca     180
gactccgtga agggccgatt caccatctcc aaagacaacg ccaagaacac tctgtttctg     240
caaatgaacg gcctgaaacc tgaggacact gcggtgtact actgtgctcc actatgctgg     300
gttgattacc cattgccgtc gggcccatac tggggccagg ggacccaggt caccgtctcc     360
tca                                                                   363
```

<210> SEQ ID NO 274
<211> LENGTH: 124
<212> TYPE: PRT
<213> ORGANISM: Artificial Sequence
<220> FEATURE:
<223> OTHER INFORMATION: Synthetic Construct

<400> SEQUENCE: 274

Gln Val Gln Leu Ala Glu Ser Gly Gly Gly Ser Val His Ala Gly Gly
1               5                   10                  15

Ser Leu Arg Leu Ser Cys Val Val Ser Glu Tyr Thr Phe Ser Ser Asp
            20                  25                  30

Ser Met Gly Trp Phe Arg Gln Ala Pro Gly Lys Glu Arg Glu Gly Val
        35                  40                  45

Ala Ala Ile Asp Ser Asp Gly Ser Thr Ser Tyr Ala Gly Ser Val Lys
    50                  55                  60

Gly Arg Phe Thr Ile Ser Lys Asp Asn Ala Glu Asn Thr Leu Tyr Leu
65                  70                  75                  80

Gln Met Asn Ser Leu Lys Pro Glu Asp Thr Ala Met Tyr Tyr Cys Ala
                85                  90                  95

Thr Ser Pro Leu Trp Leu Leu Ser Arg Leu Asp Pro Ala Asp Phe Glu
            100                 105                 110

Tyr Trp Gly Gln Gly Thr Gln Val Thr Val Ser Ser
        115                 120

<210> SEQ ID NO 275
<211> LENGTH: 124
<212> TYPE: PRT
<213> ORGANISM: Artificial Sequence
<220> FEATURE:
<223> OTHER INFORMATION: Synthetic Construct

<400> SEQUENCE: 275

Glu Val Gln Leu Val Glu Ser Gly Gly Gly Ser Val Gln Ala Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Gly Thr Ser Tyr Ala Asp Ser Val Lys
    50                  55                  60

```
Gly Arg Phe Thr Ile Ser Lys Asp Asn Ala Lys Asn Thr Leu Tyr Leu
65                  70                  75                  80

Gln Met Asp Ser Leu Lys Pro Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Gln Val Thr Val Ser Ser
        115                 120
```

<210> SEQ ID NO 276
<211> LENGTH: 121
<212> TYPE: PRT
<213> ORGANISM: Artificial Sequence
<220> FEATURE:
<223> OTHER INFORMATION: Synthetic Construct

<400> SEQUENCE: 276

```
Gln Val Gln Leu Ala Glu Ser Gly Gly Gly Ser Val Gln Ala Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Asp Phe Cys Trp Val Asp Asp Phe Tyr Glu Tyr Asn Tyr Trp Gly
            100                 105                 110

Gln Gly Thr Gln Val Thr Val Ser Ser
        115                 120
```

<210> SEQ ID NO 277
<211> LENGTH: 126
<212> TYPE: PRT
<213> ORGANISM: Artificial Sequence
<220> FEATURE:
<223> OTHER INFORMATION: Synthetic Construct

<400> SEQUENCE: 277

```
Glu Val Gln Leu Ala Glu Ser Gly Gly Gly Ser Val Gln Ala Gly Gly
1               5                   10                  15

Ser Leu Arg Leu Ser Cys Ala Ala Ser Gly Tyr Thr Tyr Gly Gly Tyr
            20                  25                  30

Cys Met Gly Trp Phe Arg Gln Ala Pro Gly Lys Glu Arg Glu Gly Val
        35                  40                  45

Ala Thr Ile Asn Ser Asp Gly Ser Thr Asn Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Ser Pro Glu Asp Thr Ala Met Tyr Tyr Cys Ala
                85                  90                  95

Val Asp Leu Ala Pro Cys Trp Val Ala Gly Pro Ile Glu Ala Ala Asp
            100                 105                 110

Phe Gly Tyr Trp Gly Gln Gly Thr Gln Val Thr Val Ser Ser
        115                 120                 125
```

<210> SEQ ID NO 278
<211> LENGTH: 122
<212> TYPE: PRT
<213> ORGANISM: Artificial Sequence
<220> FEATURE:
<223> OTHER INFORMATION: Synthetic Construct

<400> SEQUENCE: 278

Gln Val His Leu Met Glu Ser Gly Gly Gly Ser Val Gln Val Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Ser Val Ser Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Phe Cys Ala
                85                  90                  95

Ala Asp Leu Cys Trp Val Asp Asp Gln Gly Glu Tyr Asn Thr Trp
            100                 105                 110

Gly Gln Gly Thr Gln Val Thr Val Ser Ser
        115                 120

<210> SEQ ID NO 279
<211> LENGTH: 131
<212> TYPE: PRT
<213> ORGANISM: Artificial Sequence
<220> FEATURE:
<223> OTHER INFORMATION: Synthetic Construct

<400> SEQUENCE: 279

Glu Val Gln Leu Val Glu Ser Gly Gly Gly Leu Val Gln Ala Gly Gly
1               5                   10                  15

Ser Leu Arg Leu Ser Cys Thr Ala Ser Gly Leu Thr Phe Asp Asp Tyr
            20                  25                  30

Ala Met Gly Trp Phe Arg Gln Ala Pro Gly Lys Glu Arg Glu Gly Val
        35                  40                  45

Ser Cys Ile Ser Trp Ser Gly Gly Ser Thr Tyr Tyr Thr Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Asp Leu Phe Cys Pro Pro Asp Asp Thr Thr Gly Trp Gly
            100                 105                 110

Met Asp Pro Pro Glu His Asn Tyr Trp Gly Gln Gly Thr Gln Val Thr
        115                 120                 125

Val Ser Ser
    130

<210> SEQ ID NO 280
<211> LENGTH: 121
<212> TYPE: PRT
<213> ORGANISM: Artificial Sequence
<220> FEATURE:
<223> OTHER INFORMATION: Synthetic Construct

<400> SEQUENCE: 280

Gln Val Gln Leu Val Glu Ser Gly Gly Ser Val Gln Ala Gly Gly
1               5                   10                  15

Ser Leu Arg Leu Ser Cys Ala Ala Ser Gly Tyr Thr Leu Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Lys Asp Asn Ala Lys Asn Thr Leu Phe Leu
65                  70                  75                  80

Gln Met Asn Gly Leu Lys Pro Glu Asp Thr Ala Val Tyr Tyr Cys Ala
                85                  90                  95

Pro Leu Cys Trp Val Asp Tyr Pro Leu Pro Ser Gly Pro Tyr Trp Gly
            100                 105                 110

Gln Gly Thr Gln Val Thr Val Ser Ser
        115                 120

<210> SEQ ID NO 281
<211> LENGTH: 124
<212> TYPE: PRT
<213> ORGANISM: Artificial Sequence
<220> FEATURE:
<223> OTHER INFORMATION: Synthetic Construct

<400> SEQUENCE: 281

Glu Val Gln Leu Val Glu Ser Gly Gly Gly Ser Val Gln Ala Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Ser Gly Gly Thr Ser Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asp Ser Leu Lys Pro Glu Asp Thr Ala Met Tyr Tyr Cys Ala
                85                  90                  95

Ala Asp Phe Cys Trp Val Asp Glu Asp Arg His Leu Tyr Glu Tyr Gln
            100                 105                 110

Ser Trp Gly Gln Gly Thr Gln Val Thr Val Ser Ser
        115                 120

<210> SEQ ID NO 282
<211> LENGTH: 124
<212> TYPE: PRT
<213> ORGANISM: Artificial Sequence
<220> FEATURE:
<223> OTHER INFORMATION: Synthetic Construct

<400> SEQUENCE: 282

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Gly Leu Glu Gly Val
        35                  40                  45

-continued

```
Ser Ala Ile Asp Ser Asp Gly Gly Thr Ser Tyr Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser
        115                 120
```

<210> SEQ ID NO 283
<211> LENGTH: 124
<212> TYPE: PRT
<213> ORGANISM: Artificial Sequence
<220> FEATURE:
<223> OTHER INFORMATION: Synthetic Construct

<400> SEQUENCE: 283

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ile Ile Ser Ser Tyr
                20                  25                  30

Cys Met Gly Trp Phe Arg Gln Ala Pro Gly Lys Gly Leu Glu Gly Val
            35                  40                  45

Ala Ala Ile Asp Ser Asp Gly Gly Thr Ser Tyr Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser
        115                 120
```

<210> SEQ ID NO 284
<211> LENGTH: 124
<212> TYPE: PRT
<213> ORGANISM: Artificial Sequence
<220> FEATURE:
<223> OTHER INFORMATION: Synthetic Construct

<400> SEQUENCE: 284

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ile Ile Ser Ser Tyr
                20                  25                  30

Cys Met Gly Trp Phe Arg Gln Ala Pro Gly Lys Gly Leu Glu Gly Val
            35                  40                  45

Ala Ala Ile Asp Ser Asp Gly Gly Thr Ser Tyr Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
```

100                 105                 110

Ser Trp Gly Gln Gly Thr Leu Val Thr Val Ser Ser
            115                 120

<210> SEQ ID NO 285
<211> LENGTH: 124
<212> TYPE: PRT
<213> ORGANISM: Artificial Sequence
<220> FEATURE:
<223> OTHER INFORMATION: Synthetic Construct

<400> SEQUENCE: 285

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Gly Arg Glu Gly Val
        35                  40                  45

Ala Ala Ile Asp Ser Asp Gly Gly Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser
            115                 120

<210> SEQ ID NO 286
<211> LENGTH: 124
<212> TYPE: PRT
<213> ORGANISM: Artificial Sequence
<220> FEATURE:
<223> OTHER INFORMATION: Synthetic Construct

<400> SEQUENCE: 286

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Gly Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser
            115                 120

<210> SEQ ID NO 287
<211> LENGTH: 124
<212> TYPE: PRT
<213> ORGANISM: Artificial Sequence
<220> FEATURE:

<223> OTHER INFORMATION: Synthetic Construct

<400> SEQUENCE: 287

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Gly Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser
        115                 120

<210> SEQ ID NO 288
<211> LENGTH: 124
<212> TYPE: PRT
<213> ORGANISM: Artificial Sequence
<220> FEATURE:
<223> OTHER INFORMATION: Synthetic Construct

<400> SEQUENCE: 288

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Gly Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser
        115                 120

<210> SEQ ID NO 289
<211> LENGTH: 124
<212> TYPE: PRT
<213> ORGANISM: Artificial Sequence
<220> FEATURE:
<223> OTHER INFORMATION: Synthetic Construct

<400> SEQUENCE: 289

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Gly Leu Glu Gly Val

```
                35                  40                  45

Ala Ala Ile Asp Ser Ser Gly Thr Ser Tyr Ala Asp Ser Val Lys
        50                  55                  60

Gly Arg Phe Thr Ile Ser Lys Asp Asn Ser Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
                100                 105                 110

Ser Trp Gly Gln Gly Thr Leu Val Thr Val Ser Ser
        115                 120
```

<210> SEQ ID NO 290
<211> LENGTH: 121
<212> TYPE: PRT
<213> ORGANISM: Artificial Sequence
<220> FEATURE:
<223> OTHER INFORMATION: Synthetic Construct

<400> SEQUENCE: 290

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
                20                  25                  30

Cys Met Gly Trp Phe Arg Gln Ala Pro Gly Lys Gly Leu Glu Gly Val
                35                  40                  45

Ala Ala Ile Asp Ser Asp Gly Ser Thr Ser Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Asp Phe Cys Trp Val Asp Asp Phe Tyr Glu Tyr Asn Tyr Trp Gly
                100                 105                 110

Gln Gly Thr Leu Val Thr Val Ser Ser
        115                 120
```

<210> SEQ ID NO 291
<211> LENGTH: 121
<212> TYPE: PRT
<213> ORGANISM: Artificial Sequence
<220> FEATURE:
<223> OTHER INFORMATION: Synthetic Construct

<400> SEQUENCE: 291

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
                20                  25                  30

Cys Met Gly Trp Phe Arg Gln Ala Pro Gly Lys Gly Leu Glu Gly Val
                35                  40                  45

Ala Ala Ile Asp Ser Asp Gly Ser Thr Ser Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95
```

Ala Asp Phe Cys Trp Val Asp Asp Phe Tyr Glu Tyr Asn Tyr Trp Gly
            100                 105                 110

Gln Gly Thr Leu Val Thr Val Ser Ser
        115                 120

<210> SEQ ID NO 292
<211> LENGTH: 121
<212> TYPE: PRT
<213> ORGANISM: Artificial Sequence
<220> FEATURE:
<223> OTHER INFORMATION: Synthetic Construct

<400> SEQUENCE: 292

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Gly Arg Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Asp Phe Tyr Glu Tyr Asn Tyr Trp Gly
            100                 105                 110

Gln Gly Thr Leu Val Thr Val Ser Ser
        115                 120

<210> SEQ ID NO 293
<211> LENGTH: 121
<212> TYPE: PRT
<213> ORGANISM: Artificial Sequence
<220> FEATURE:
<223> OTHER INFORMATION: Synthetic Construct

<400> SEQUENCE: 293

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Asp Phe Tyr Glu Tyr Asn Tyr Trp Gly
            100                 105                 110

Gln Gly Thr Leu Val Thr Val Ser Ser
        115                 120

<210> SEQ ID NO 294
<211> LENGTH: 121
<212> TYPE: PRT
<213> ORGANISM: Artificial Sequence
<220> FEATURE:
<223> OTHER INFORMATION: Synthetic Construct

<400> SEQUENCE: 294

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Asp Phe Tyr Glu Tyr Asn Tyr Trp Gly
            100                 105                 110

Gln Gly Thr Leu Val Thr Val Ser Ser
        115                 120

<210> SEQ ID NO 295
<211> LENGTH: 121
<212> TYPE: PRT
<213> ORGANISM: Artificial Sequence
<220> FEATURE:
<223> OTHER INFORMATION: Synthetic Construct

<400> SEQUENCE: 295

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Asp Phe Cys Trp Val Asp Asp Phe Tyr Glu Tyr Asn Tyr Trp Gly
            100                 105                 110

Gln Gly Thr Leu Val Thr Val Ser Ser
        115                 120

<210> SEQ ID NO 296
<211> LENGTH: 121
<212> TYPE: PRT
<213> ORGANISM: Artificial Sequence
<220> FEATURE:
<223> OTHER INFORMATION: Synthetic Construct

<400> SEQUENCE: 296

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
            20                  25                  30

```
Cys Met Gly Trp Phe Arg Gln Ala Pro Gly Lys Gly Leu Glu Gly Val
            35                  40                  45

Ala Ala Ile Asp Ser Ser Gly Ser Thr Ser Tyr Ala Asp Ser Val Lys
 50                  55                  60

Gly Arg Phe Thr Ile Ser Lys Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Ala Asp Phe Cys Trp Val Asp Asp Phe Tyr Glu Tyr Asn Tyr Trp Gly
                100                 105                 110

Gln Gly Thr Leu Val Thr Val Ser Ser
            115                 120

<210> SEQ ID NO 297
<211> LENGTH: 122
<212> TYPE: PRT
<213> ORGANISM: Artificial Sequence
<220> FEATURE:
<223> OTHER INFORMATION: Synthetic Construct

<400> SEQUENCE: 297

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Val Ser Ser Tyr
                20                  25                  30

Cys Met Gly Trp Phe Arg Gln Ala Pro Gly Lys Gly Leu Glu Gly Val
            35                  40                  45

Ser Ala Ile Asp Ser Asp Gly Ser Val Ser Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Ala Asp Leu Cys Trp Val Asp Gln Asp Gln Gly Tyr Glu Tyr Asn Thr Trp
                100                 105                 110

Gly Gln Gly Thr Leu Val Thr Val Ser Ser
            115                 120

<210> SEQ ID NO 298
<211> LENGTH: 122
<212> TYPE: PRT
<213> ORGANISM: Artificial Sequence
<220> FEATURE:
<223> OTHER INFORMATION: Synthetic Construct

<400> SEQUENCE: 298

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Val Ser Ser Tyr
                20                  25                  30

Cys Met Gly Trp Phe Arg Gln Ala Pro Gly Lys Gly Leu Glu Gly Val
            35                  40                  45

Ser Ala Ile Asp Ser Asp Gly Ser Val Ser Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Phe Cys Ala
                85                  90                  95
```

```
Ala Asp Leu Cys Trp Val Asp Gln Asp Gln Gly Glu Tyr Asn Thr Trp
            100                 105                 110

Gly Gln Gly Thr Leu Val Thr Val Ser Ser
        115                 120

<210> SEQ ID NO 299
<211> LENGTH: 122
<212> TYPE: PRT
<213> ORGANISM: Artificial Sequence
<220> FEATURE:
<223> OTHER INFORMATION: Synthetic Construct

<400> SEQUENCE: 299

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Ser Val Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Ala
            85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser
        115                 120

<210> SEQ ID NO 300
<211> LENGTH: 122
<212> TYPE: PRT
<213> ORGANISM: Artificial Sequence
<220> FEATURE:
<223> OTHER INFORMATION: Synthetic Construct

<400> SEQUENCE: 300

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Ser Val Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Phe Cys Ala
            85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser
        115                 120

<210> SEQ ID NO 301
<211> LENGTH: 122
<212> TYPE: PRT
```

```
<213> ORGANISM: Artificial Sequence
<220> FEATURE:
<223> OTHER INFORMATION: Synthetic Construct

<400> SEQUENCE: 301

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ala Ala Ile Asp Ser Asp Gly Ser Val Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser
        115                 120

<210> SEQ ID NO 302
<211> LENGTH: 122
<212> TYPE: PRT
<213> ORGANISM: Artificial Sequence
<220> FEATURE:
<223> OTHER INFORMATION: Synthetic Construct

<400> SEQUENCE: 302

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Ser Val Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser
        115                 120

<210> SEQ ID NO 303
<211> LENGTH: 122
<212> TYPE: PRT
<213> ORGANISM: Artificial Sequence
<220> FEATURE:
<223> OTHER INFORMATION: Synthetic Construct

<400> SEQUENCE: 303

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30
```

Cys Met Gly Trp Phe Arg Gln Ala Pro Gly Lys Glu Arg Glu Gly Val
            35                  40                  45

Ala Ala Ile Asp Ser Asp Gly Ser Val Ser Tyr Ala Asp Ser Val Lys
 50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Phe Cys Ala
            85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser
            115                 120

<210> SEQ ID NO 304
<211> LENGTH: 122
<212> TYPE: PRT
<213> ORGANISM: Artificial Sequence
<220> FEATURE:
<223> OTHER INFORMATION: Synthetic Construct

<400> SEQUENCE: 304

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
            35                  40                  45

Ser Ala Ile Asp Ser Asp Gly Ser Val Ser Tyr Ala Asp Ser Val Lys
 50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
            85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser
            115                 120

<210> SEQ ID NO 305
<211> LENGTH: 122
<212> TYPE: PRT
<213> ORGANISM: Artificial Sequence
<220> FEATURE:
<223> OTHER INFORMATION: Synthetic Construct

<400> SEQUENCE: 305

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
            35                  40                  45

Ser Ala Ile Asp Ser Ser Gly Ser Val Ser Tyr Ala Asp Ser Val Lys
 50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala

```
                85                  90                  95
Ala Asp Leu Cys Trp Val Asp Gln Asp Gln Gly Glu Tyr Asn Thr Trp
            100                 105                 110
Gly Gln Gly Thr Leu Val Thr Val Ser Ser
        115                 120

<210> SEQ ID NO 306
<211> LENGTH: 126
<212> TYPE: PRT
<213> ORGANISM: Artificial Sequence
<220> FEATURE:
<223> OTHER INFORMATION: Synthetic Construct

<400> SEQUENCE: 306

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Gly Gly Tyr
            20                  25                  30

Cys Met Gly Trp Phe Arg Gln Ala Pro Gly Lys Gly Leu Glu Gly Val
        35                  40                  45

Ser Thr Ile Asn Ser Asp Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Val Asp Leu Ala Pro Cys Trp Val Ala Gly Pro Ile Glu Ala Ala Asp
            100                 105                 110

Phe Gly Tyr Trp Gly Gln Gly Thr Leu Val Thr Val Ser Ser
        115                 120                 125

<210> SEQ ID NO 307
<211> LENGTH: 126
<212> TYPE: PRT
<213> ORGANISM: Artificial Sequence
<220> FEATURE:
<223> OTHER INFORMATION: Synthetic Construct

<400> SEQUENCE: 307

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Gly Gly Tyr
            20                  25                  30

Cys Met Gly Trp Phe Arg Gln Ala Pro Gly Lys Gly Leu Glu Gly Val
        35                  40                  45

Ser Thr Ile Ala Ser Glu Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Val Asp Leu Ala Pro Cys Trp Val Ala Gly Pro Ile Glu Ala Ala Asp
            100                 105                 110

Phe Gly Tyr Trp Gly Gln Gly Thr Leu Val Thr Val Ser Ser
        115                 120                 125

<210> SEQ ID NO 308
<211> LENGTH: 126
```

```
<212> TYPE: PRT
<213> ORGANISM: Artificial Sequence
<220> FEATURE:
<223> OTHER INFORMATION: Synthetic Construct

<400> SEQUENCE: 308

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Gly Gly Tyr
            20                  25                  30

Cys Met Gly Trp Phe Arg Gln Ala Pro Gly Lys Gly Leu Glu Gly Val
        35                  40                  45

Ser Thr Ile Ala Ser Ser Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Val Asp Leu Ala Pro Cys Trp Val Ala Gly Pro Ile Glu Ala Ala Asp
            100                 105                 110

Phe Gly Tyr Trp Gly Gln Gly Thr Leu Val Thr Val Ser Ser
            115                 120                 125

<210> SEQ ID NO 309
<211> LENGTH: 126
<212> TYPE: PRT
<213> ORGANISM: Artificial Sequence
<220> FEATURE:
<223> OTHER INFORMATION: Synthetic Construct

<400> SEQUENCE: 309

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Gly Gly Tyr
            20                  25                  30

Cys Met Gly Trp Phe Arg Gln Ala Pro Gly Lys Gly Arg Glu Gly Val
        35                  40                  45

Ser Thr Ile Asn Ser Asp Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Val Asp Leu Ala Pro Cys Trp Val Ala Gly Pro Ile Glu Ala Ala Asp
            100                 105                 110

Phe Gly Tyr Trp Gly Gln Gly Thr Leu Val Thr Val Ser Ser
            115                 120                 125

<210> SEQ ID NO 310
<211> LENGTH: 126
<212> TYPE: PRT
<213> ORGANISM: Artificial Sequence
<220> FEATURE:
<223> OTHER INFORMATION: Synthetic Construct

<400> SEQUENCE: 310

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Gly Gly Tyr
```

-continued

```
                20                  25                  30

Cys Met Gly Trp Phe Arg Gln Ala Pro Gly Lys Gly Arg Glu Gly Val
         35                  40                  45

Ser Thr Ile Ala Ser Glu Gly Ser Thr Asn Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Val Asp Leu Ala Pro Cys Trp Val Ala Gly Pro Ile Glu Ala Ala Asp
                100                 105                 110

Phe Gly Tyr Trp Gly Gln Gly Thr Leu Val Thr Val Ser Ser
            115                 120                 125

<210> SEQ ID NO 311
<211> LENGTH: 126
<212> TYPE: PRT
<213> ORGANISM: Artificial Sequence
<220> FEATURE:
<223> OTHER INFORMATION: Synthetic Construct

<400> SEQUENCE: 311

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Tyr Gly Gly Tyr
                 20                  25                  30

Cys Met Gly Trp Phe Arg Gln Ala Pro Gly Lys Gly Arg Glu Gly Val
         35                  40                  45

Ser Thr Ile Ala Ser Ser Gly Ser Thr Asn Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                 85                  90                  95

Val Asp Leu Ala Pro Cys Trp Val Ala Gly Pro Ile Glu Ala Ala Asp
                100                 105                 110

Phe Gly Tyr Trp Gly Gln Gly Thr Leu Val Thr Val Ser Ser
            115                 120                 125

<210> SEQ ID NO 312
<211> LENGTH: 353
<212> TYPE: PRT
<213> ORGANISM: Artificial Sequence
<220> FEATURE:
<223> OTHER INFORMATION: Synthetic Construct

<400> SEQUENCE: 312

Gln Val Gln Leu Ala Glu Ser Gly Gly Gly Ser Val His Ala Gly Gly
 1               5                  10                  15

Ser Leu Arg Leu Ser Cys Val Val Ser Glu Tyr Thr Phe Ser Ser Asp
                 20                  25                  30

Ser Met Gly Trp Phe Arg Gln Ala Pro Gly Lys Glu Arg Glu Gly Val
         35                  40                  45

Ala Ala Ile Asp Ser Asp Gly Ser Thr Ser Tyr Ala Gly Ser Val Lys
 50                  55                  60

Gly Arg Phe Thr Ile Ser Lys Asp Asn Ala Glu Asn Thr Leu Tyr Leu
 65                  70                  75                  80
```

Gln Met Asn Ser Leu Lys Pro Glu Asp Thr Ala Met Tyr Tyr Cys Ala
                85                  90                  95

Thr Ser Pro Leu Trp Leu Leu Ser Arg Leu Asp Pro Ala Asp Phe Glu
            100                 105                 110

Tyr Trp Gly Gln Gly Thr Gln Val Thr Val Ser Ser Glu Ser Lys Tyr
            115                 120                 125

Gly Pro Pro Cys Pro Pro Cys Pro Ala Pro Glu Phe Leu Gly Gly Pro
130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
            195                 200                 205

Val Ser Val Leu Thr Val Leu His Gln Asp Trp Leu Asn Gly Lys Glu
210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
            260                 265                 270

Cys Leu Val Lys Gly Phe Tyr Pro Ser Asp Ile Ala Val Glu Trp Glu
            275                 280                 285

Ser Asn Gly Gln Pro Glu Asn Asn Tyr Lys Thr Thr Pro Pro Val Leu
290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Lys

```
<210> SEQ ID NO 313
<211> LENGTH: 353
<212> TYPE: PRT
<213> ORGANISM: Artificial Sequence
<220> FEATURE:
<223> OTHER INFORMATION: Synthetic Construct

<400> SEQUENCE: 313
```

Glu Val Gln Leu Val Glu Ser Gly Gly Gly Val Gln Ala Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Thr Ser Tyr Ala Asp Ser Val Lys
        50                  55                  60

Gly Arg Phe Thr Ile Ser Lys Asp Asn Ala Lys Asn Thr Leu Tyr Leu
65                  70                  75                  80

Gln Met Asp Ser Leu Lys Pro Glu Asp Thr Ala Met Tyr Tyr Cys Ala

```
                85                  90                  95
Ala Asp Phe Cys Trp Val Asp Glu Asp Arg His Leu Tyr Glu Tyr Asn
            100                 105                 110

Ser Trp Gly Gln Gly Thr Gln Val Thr Val Ser Ser Glu Ser Lys Tyr
            115                 120                 125

Gly Pro Pro Cys Pro Pro Cys Pro Ala Pro Glu Phe Leu Gly Gly Pro
            130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
            195                 200                 205

Val Ser Val Leu Thr Val Leu His Gln Asp Trp Leu Asn Gly Lys Glu
210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
            260                 265                 270

Cys Leu Val Lys Gly Phe Tyr Pro Ser Asp Ile Ala Val Glu Trp Glu
            275                 280                 285

Ser Asn Gly Gln Pro Glu Asn Asn Tyr Lys Thr Thr Pro Pro Val Leu
            290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Lys

<210> SEQ ID NO 314
<211> LENGTH: 350
<212> TYPE: PRT
<213> ORGANISM: Artificial Sequence
<220> FEATURE:
<223> OTHER INFORMATION: Synthetic Construct

<400> SEQUENCE: 314

Gln Val Gln Leu Ala Glu Ser Gly Gly Gly Ser Val Gln Ala Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Glu Arg Glu Gly Val
            35                  40                  45

Ala Ala Ile Asp Ser Asp Gly Thr Ser Tyr Ala Asp Ser Val Lys
            50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95
```

```
Ala Asp Phe Cys Trp Val Asp Phe Tyr Glu Tyr Asn Tyr Trp Gly
            100                 105                 110

Gln Gly Thr Gln Val Thr Val Ser Ser Glu Ser Lys Tyr Gly Pro Pro
115                 120                 125

Cys Pro Pro Cys Pro Ala Pro Glu Phe Leu Gly Gly Pro Ser Val Phe
            130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser Gln Glu Asp Pro Glu Val
                165                 170                 175

Gln Phe Asn Trp Tyr Val Asp Gly Val Glu Val His Asn Ala Lys Thr
            180                 185                 190

Lys Pro Arg Glu Glu Gln Phe Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Gly Leu Pro Ser Ser Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Gln Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Arg Leu Thr Val Asp Lys Ser Arg Trp
305                 310                 315                 320

Gln Glu Gly Asn Val Phe Ser Cys Ser Val Met His Glu Ala Leu His
                325                 330                 335

Asn His Tyr Thr Gln Lys Ser Leu Ser Leu Ser Leu Gly Lys
            340                 345                 350

<210> SEQ ID NO 315
<211> LENGTH: 355
<212> TYPE: PRT
<213> ORGANISM: Artificial Sequence
<220> FEATURE:
<223> OTHER INFORMATION: Synthetic Construct

<400> SEQUENCE: 315

Glu Val Gln Leu Ala Glu Ser Gly Gly Gly Ser Val Gln Ala Gly Gly
1               5                   10                  15

Ser Leu Arg Leu Ser Cys Ala Ala Ser Gly Tyr Thr Tyr Gly Gly Tyr
            20                  25                  30

Cys Met Gly Trp Phe Arg Gln Ala Pro Gly Lys Glu Arg Glu Gly Val
        35                  40                  45

Ala Thr Ile Asn Ser Asp Gly Ser Thr Asn Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Ser Pro Glu Asp Thr Ala Met Tyr Tyr Cys Ala
                85                  90                  95

Val Asp Leu Ala Pro Cys Trp Val Ala Gly Pro Ile Glu Ala Ala Asp
            100                 105                 110
```

```
Phe Gly Tyr Trp Gly Gln Gly Thr Gln Val Thr Val Ser Ser Glu Ser
        115                 120                 125

Lys Tyr Gly Pro Pro Cys Pro Pro Cys Pro Ala Pro Glu Phe Leu Gly
        130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser Gln
                165                 170                 175

Glu Asp Pro Glu Val Gln Phe Asn Trp Tyr Val Asp Gly Val Glu Val
                180                 185                 190

His Asn Ala Lys Thr Lys Pro Arg Glu Glu Gln Phe Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Gly Leu Pro Ser Ser Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Gln Glu Glu Met Thr Lys Asn Gln Val Ser
        260                 265                 270

Leu Thr Cys Leu Val Lys Gly Phe Tyr Pro Ser Asp Ile Ala Val Glu
    275                 280                 285

Trp Glu Ser Asn Gly Gln Pro Glu Asn Asn Tyr Lys Thr Thr Pro Pro
        290                 295                 300

Val Leu Asp Ser Asp Gly Ser Phe Phe Leu Tyr Ser Arg Leu Thr Val
305                 310                 315                 320

Asp Lys Ser Arg Trp Gln Glu Gly Asn Val Phe Ser Cys Ser Val Met
                325                 330                 335

His Glu Ala Leu His Asn His Tyr Thr Gln Lys Ser Leu Ser Leu Ser
        340                 345                 350

Leu Gly Lys
        355

<210> SEQ ID NO 316
<211> LENGTH: 351
<212> TYPE: PRT
<213> ORGANISM: Artificial Sequence
<220> FEATURE:
<223> OTHER INFORMATION: Synthetic Construct

<400> SEQUENCE: 316

Gln Val His Leu Met Glu Ser Gly Gly Gly Ser Val Gln Val Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Ser Val Ser Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Phe Cys Ala
                85                  90                  95

Ala Asp Leu Cys Trp Val Asp Gln Asp Gln Gly Glu Tyr Asn Thr Trp
            100                 105                 110
```

Gly Gln Gly Thr Gln Val Thr Val Ser Ser Glu Ser Lys Tyr Gly Pro
            115                 120                 125

Pro Cys Pro Pro Cys Pro Ala Pro Glu Phe Leu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly Lys
            340                 345                 350

<210> SEQ ID NO 317
<211> LENGTH: 360
<212> TYPE: PRT
<213> ORGANISM: Artificial Sequence
<220> FEATURE:
<223> OTHER INFORMATION: Synthetic Construct

<400> SEQUENCE: 317

Glu Val Gln Leu Val Glu Ser Gly Gly Gly Leu Val Gln Ala Gly Gly
1               5                   10                  15

Ser Leu Arg Leu Ser Cys Thr Ala Ser Gly Leu Thr Phe Asp Asp Tyr
            20                  25                  30

Ala Met Gly Trp Phe Arg Gln Ala Pro Gly Lys Glu Arg Glu Gly Val
        35                  40                  45

Ser Cys Ile Ser Trp Ser Gly Gly Ser Thr Tyr Tyr Thr Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Asp Leu Phe Cys Pro Pro Asp Asp Thr Thr Gly Trp Gly Gly
            100                 105                 110

Met Asp Pro Pro Glu His Asn Tyr Trp Gly Gln Gly Thr Gln Val Thr
        115                 120                 125

```
Val Ser Ser Glu Ser Lys Tyr Gly Pro Pro Cys Pro Pro Cys Pro Ala
    130                 135                 140

Pro Glu Phe Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser Gln Glu Asp Pro Glu Val Gln Phe Asn Trp Tyr Val
            180                 185                 190

Asp Gly Val Glu Val His Asn Ala Lys Thr Lys Pro Arg Glu Glu Gln
        195                 200                 205

Phe Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Gly
225                 230                 235                 240

Leu Pro Ser Ser Ile Glu Lys Thr Ile Ser Lys Ala Lys Gly Gln Pro
                245                 250                 255

Arg Glu Pro Gln Val Tyr Thr Leu Pro Pro Ser Gln Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Arg Leu Thr Val Asp Lys Ser Arg Trp Gln Glu Gly Asn Val Phe
                325                 330                 335

Ser Cys Ser Val Met His Glu Ala Leu His Asn His Tyr Thr Gln Lys
            340                 345                 350

Ser Leu Ser Leu Ser Leu Gly Lys
        355                 360

<210> SEQ ID NO 318
<211> LENGTH: 350
<212> TYPE: PRT
<213> ORGANISM: Artificial Sequence
<220> FEATURE:
<223> OTHER INFORMATION: Synthetic Construct

<400> SEQUENCE: 318

Gln Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Leu Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Lys Asp Asn Ala Lys Asn Thr Leu Phe Leu
65                  70                  75                  80

Gln Met Asn Gly Leu Lys Pro Glu Asp Thr Ala Val Tyr Tyr Cys Ala
                85                  90                  95

Pro Leu Cys Trp Val Asp Tyr Pro Leu Pro Ser Gly Pro Tyr Trp Gly
            100                 105                 110

Gln Gly Thr Gln Val Thr Val Ser Ser Glu Ser Lys Tyr Gly Pro Pro
        115                 120                 125
```

```
Cys Pro Pro Cys Pro Ala Pro Glu Phe Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser Gln Glu Asp Pro Glu Val
                165                 170                 175

Gln Phe Asn Trp Tyr Val Asp Gly Val Glu Val His Asn Ala Lys Thr
            180                 185                 190

Lys Pro Arg Glu Glu Gln Phe Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Gly Leu Pro Ser Ser Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Gln Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Arg Leu Thr Val Asp Lys Ser Arg Trp
305                 310                 315                 320

Gln Glu Gly Asn Val Phe Ser Cys Ser Val Met His Glu Ala Leu His
                325                 330                 335

Asn His Tyr Thr Gln Lys Ser Leu Ser Leu Ser Leu Gly Lys
            340                 345                 350

<210> SEQ ID NO 319
<211> LENGTH: 353
<212> TYPE: PRT
<213> ORGANISM: Artificial Sequence
<220> FEATURE:
<223> OTHER INFORMATION: Synthetic Construct

<400> SEQUENCE: 319

Glu Val Gln Leu Val Glu Ser Gly Gly Gly Ser Val Gln Ala Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Ser Gly Gly Thr Ser Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asp Ser Leu Lys Pro Glu Asp Thr Ala Met Tyr Tyr Cys Ala
                85                  90                  95

Ala Asp Phe Cys Trp Val Asp Glu Asp Arg His Leu Tyr Glu Tyr Gln
            100                 105                 110

Ser Trp Gly Gln Gly Thr Gln Val Thr Val Ser Ser Glu Ser Lys Tyr
        115                 120                 125

Gly Pro Pro Cys Pro Pro Cys Pro Ala Pro Glu Phe Leu Gly Gly Pro
    130                 135                 140
```

-continued

Ser Val Phe Leu Phe Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Lys

<210> SEQ ID NO 320
<211> LENGTH: 353
<212> TYPE: PRT
<213> ORGANISM: Artificial Sequence
<220> FEATURE:
<223> OTHER INFORMATION: Synthetic Construct

<400> SEQUENCE: 320

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Gly Leu Glu Gly Val
        35                  40                  45

Ser Ala Ile Asp Ser Asp Gly Gly Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Leu Gly Gly Pro
    130                 135                 140

```
Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Lys

<210> SEQ ID NO 321
<211> LENGTH: 353
<212> TYPE: PRT
<213> ORGANISM: Artificial Sequence
<220> FEATURE:
<223> OTHER INFORMATION: Synthetic Construct

<400> SEQUENCE: 321

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
                20                  25                  30

Cys Met Gly Trp Phe Arg Gln Ala Pro Gly Lys Gly Leu Glu Gly Val
            35                  40                  45

Ala Ala Ile Asp Ser Asp Gly Gly Thr Ser Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Leu Gly Gly Pro
    130                 135                 140

Ser Val Phe Leu Phe Pro Pro Lys Pro Lys Asp Thr Leu Met Ile Ser
```

```
145                 150                 155                 160

Arg Thr Pro Glu Val Thr Cys Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Lys

<210> SEQ ID NO 322
<211> LENGTH: 353
<212> TYPE: PRT
<213> ORGANISM: Artificial Sequence
<220> FEATURE:
<223> OTHER INFORMATION: Synthetic Construct

<400> SEQUENCE: 322

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Gly Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Leu Gly Gly Pro
    130                 135                 140

Ser Val Phe Leu Phe Pro Pro Lys Pro Lys Asp Thr Leu Met Ile Ser
145                 150                 155                 160
```

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
            180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Lys

<210> SEQ ID NO 323
<211> LENGTH: 353
<212> TYPE: PRT
<213> ORGANISM: Artificial Sequence
<220> FEATURE:
<223> OTHER INFORMATION: Synthetic Construct

<400> SEQUENCE: 323

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Gly Arg Glu Gly Val
        35                  40                  45

Ala Ala Ile Asp Ser Asp Gly Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
            165                 170                 175

Pro Glu Val Gln Phe Asn Trp Tyr Val Asp Gly Val Glu Val His Asn
        180                 185                 190

Ala Lys Thr Lys Pro Arg Glu Glu Gln Phe Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Lys

<210> SEQ ID NO 324
<211> LENGTH: 353
<212> TYPE: PRT
<213> ORGANISM: Artificial Sequence
<220> FEATURE:
<223> OTHER INFORMATION: Synthetic Construct

<400> SEQUENCE: 324

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Gly Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp

```
                    165                 170                 175

Pro Glu Val Gln Phe Asn Trp Tyr Val Asp Gly Val Glu Val His Asn
                180                 185                 190

Ala Lys Thr Lys Pro Arg Glu Glu Gln Phe Asn Ser Thr Tyr Arg Val
            195                 200                 205

Val Ser Val Leu Thr Val Leu His Gln Asp Trp Leu Asn Gly Lys Glu
        210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Lys

<210> SEQ ID NO 325
<211> LENGTH: 353
<212> TYPE: PRT
<213> ORGANISM: Artificial Sequence
<220> FEATURE:
<223> OTHER INFORMATION: Synthetic Construct

<400> SEQUENCE: 325

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175
```

```
Pro Glu Val Gln Phe Asn Trp Tyr Val Asp Gly Val Glu Val His Asn
                180                 185                 190

Ala Lys Thr Lys Pro Arg Glu Gln Phe Asn Ser Thr Tyr Arg Val
            195                 200                 205

Val Ser Val Leu Thr Val Leu His Gln Asp Trp Leu Asn Gly Lys Glu
210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
                260                 265                 270

Cys Leu Val Lys Gly Phe Tyr Pro Ser Asp Ile Ala Val Glu Trp Glu
            275                 280                 285

Ser Asn Gly Gln Pro Glu Asn Asn Tyr Lys Thr Thr Pro Pro Val Leu
            290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
                340                 345                 350

Lys

<210> SEQ ID NO 326
<211> LENGTH: 353
<212> TYPE: PRT
<213> ORGANISM: Artificial Sequence
<220> FEATURE:
<223> OTHER INFORMATION: Synthetic Construct

<400> SEQUENCE: 326

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175
```

```
Pro Glu Val Gln Phe Asn Trp Tyr Val Asp Gly Val Glu Val His Asn
                180                 185                 190

Ala Lys Thr Lys Pro Arg Glu Glu Gln Phe Asn Ser Thr Tyr Arg Val
            195                 200                 205

Val Ser Val Leu Thr Val Leu His Gln Asp Trp Leu Asn Gly Lys Glu
        210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Lys

<210> SEQ ID NO 327
<211> LENGTH: 353
<212> TYPE: PRT
<213> ORGANISM: Artificial Sequence
<220> FEATURE:
<223> OTHER INFORMATION: Synthetic Construct

<400> SEQUENCE: 327

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Ser Gly Gly Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser Glu Ser Lys Tyr
        115                 120                 125

Gly Pro Pro Cys Pro Pro Cys Pro Ala Pro Glu Phe Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser Gln Glu Asp
                165                 170                 175

Pro Glu Val Gln Phe Asn Trp Tyr Val Asp Gly Val Glu Val His Asn
```

```
                180                 185                 190
Ala Lys Thr Lys Pro Arg Glu Glu Gln Phe Asn Ser Thr Tyr Arg Val
            195                 200                 205

Val Ser Val Leu Thr Val Leu His Gln Asp Trp Leu Asn Gly Lys Glu
        210                 215                 220

Tyr Lys Cys Lys Val Ser Asn Lys Gly Leu Pro Ser Ser Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Gln Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Arg Leu Thr Val Asp Lys
305                 310                 315                 320

Ser Arg Trp Gln Glu Gly Asn Val Phe Ser Cys Ser Val Met His Glu
                325                 330                 335

Ala Leu His Asn His Tyr Thr Gln Lys Ser Leu Ser Leu Ser Leu Gly
            340                 345                 350

Lys

<210> SEQ ID NO 328
<211> LENGTH: 350
<212> TYPE: PRT
<213> ORGANISM: Artificial Sequence
<220> FEATURE:
<223> OTHER INFORMATION: Synthetic Construct

<400> SEQUENCE: 328

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Asp Phe Cys Trp Val Asp Asp Phe Tyr Glu Tyr Asn Tyr Trp Gly
            100                 105                 110

Gln Gly Thr Leu Val Thr Val Ser Ser Glu Ser Lys Tyr Gly Pro Pro
        115                 120                 125

Cys Pro Pro Cys Pro Ala Pro Glu Phe Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser Gln Glu Asp Pro Glu Val
                165                 170                 175

Gln Phe Asn Trp Tyr Val Asp Gly Val Glu Val His Asn Ala Lys Thr
            180                 185                 190
```

```
Lys Pro Arg Glu Glu Gln Phe Asn Ser Thr Tyr Arg Val Val Ser Val
            195                 200                 205

Leu Thr Val Leu His Gln Asp Trp Leu Asn Gly Lys Glu Tyr Lys Cys
210                 215                 220

Lys Val Ser Asn Lys Gly Leu Pro Ser Ser Ile Glu Lys Thr Ile Ser
225                 230                 235                 240

Lys Ala Lys Gly Gln Pro Arg Glu Pro Gln Val Tyr Thr Leu Pro Pro
            245                 250                 255

Ser Gln Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
            275                 280                 285

Gln Pro Glu Asn Asn Tyr Lys Thr Thr Pro Pro Val Leu Asp Ser Asp
            290                 295                 300

Gly Ser Phe Phe Leu Tyr Ser Arg Leu Thr Val Asp Lys Ser Arg Trp
305                 310                 315                 320

Gln Glu Gly Asn Val Phe Ser Cys Ser Val Met His Glu Ala Leu His
            325                 330                 335

Asn His Tyr Thr Gln Lys Ser Leu Ser Leu Ser Leu Gly Lys
            340                 345                 350

<210> SEQ ID NO 329
<211> LENGTH: 350
<212> TYPE: PRT
<213> ORGANISM: Artificial Sequence
<220> FEATURE:
<223> OTHER INFORMATION: Synthetic Construct

<400> SEQUENCE: 329

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
            85                  90                  95

Ala Asp Phe Cys Trp Val Asp Asp Phe Tyr Glu Tyr Asn Tyr Trp Gly
            100                 105                 110

Gln Gly Thr Leu Val Thr Val Ser Ser Glu Ser Lys Tyr Gly Pro Pro
        115                 120                 125

Cys Pro Pro Cys Pro Ala Pro Glu Phe Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser Gln Glu Asp Pro Glu Val
            165                 170                 175

Gln Phe Asn Trp Tyr Val Asp Gly Val Glu Val His Asn Ala Lys Thr
            180                 185                 190

Lys Pro Arg Glu Glu Gln Phe Asn Ser Thr Tyr Arg Val Val Ser Val
            195                 200                 205
```

```
Leu Thr Val Leu His Gln Asp Trp Leu Asn Gly Lys Glu Tyr Lys Cys
            210                 215                 220

Lys Val Ser Asn Lys Gly Leu Pro Ser Ser Ile Glu Lys Thr Ile Ser
225                 230                 235                 240

Lys Ala Lys Gly Gln Pro Arg Glu Pro Gln Val Tyr Thr Leu Pro Pro
            245                 250                 255

Ser Gln Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
            275                 280                 285

Gln Pro Glu Asn Asn Tyr Lys Thr Thr Pro Pro Val Leu Asp Ser Asp
            290                 295                 300

Gly Ser Phe Phe Leu Tyr Ser Arg Leu Thr Val Asp Lys Ser Arg Trp
305                 310                 315                 320

Gln Glu Gly Asn Val Phe Ser Cys Ser Val Met His Glu Ala Leu His
            325                 330                 335

Asn His Tyr Thr Gln Lys Ser Leu Ser Leu Ser Leu Gly Lys
            340                 345                 350

<210> SEQ ID NO 330
<211> LENGTH: 350
<212> TYPE: PRT
<213> ORGANISM: Artificial Sequence
<220> FEATURE:
<223> OTHER INFORMATION: Synthetic Construct

<400> SEQUENCE: 330

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Gly Arg Glu Gly Val
            35                  40                  45

Ala Ala Ile Asp Ser Asp Gly Ser Thr Ser Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
            85                  90                  95

Ala Asp Phe Cys Trp Val Asp Asp Phe Tyr Glu Tyr Asn Tyr Trp Gly
            100                 105                 110

Gln Gly Thr Leu Val Thr Val Ser Ser Glu Ser Lys Tyr Gly Pro Pro
            115                 120                 125

Cys Pro Pro Cys Pro Ala Pro Glu Phe Leu Gly Gly Pro Ser Val Phe
            130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser Gln Glu Asp Pro Glu Val
            165                 170                 175

Gln Phe Asn Trp Tyr Val Asp Gly Val Glu Val His Asn Ala Lys Thr
            180                 185                 190

Lys Pro Arg Glu Glu Gln Phe Asn Ser Thr Tyr Arg Val Val Ser Val
            195                 200                 205

Leu Thr Val Leu His Gln Asp Trp Leu Asn Gly Lys Glu Tyr Lys Cys
            210                 215                 220
```

```
Lys Val Ser Asn Lys Gly Leu Pro Ser Ser Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Gln Glu Glu Met Thr Lys Asn Gln Val Ser Leu Thr Cys Leu Val
                260                 265                 270

Lys Gly Phe Tyr Pro Ser Asp Ile Ala Val Glu Trp Glu Ser Asn Gly
            275                 280                 285

Gln Pro Glu Asn Asn Tyr Lys Thr Thr Pro Pro Val Leu Asp Ser Asp
            290                 295                 300

Gly Ser Phe Phe Leu Tyr Ser Arg Leu Thr Val Asp Lys Ser Arg Trp
305                 310                 315                 320

Gln Glu Gly Asn Val Phe Ser Cys Ser Val Met His Glu Ala Leu His
                325                 330                 335

Asn His Tyr Thr Gln Lys Ser Leu Ser Leu Ser Leu Gly Lys
                340                 345                 350

<210> SEQ ID NO 331
<211> LENGTH: 350
<212> TYPE: PRT
<213> ORGANISM: Artificial Sequence
<220> FEATURE:
<223> OTHER INFORMATION: Synthetic Construct

<400> SEQUENCE: 331

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
                20                  25                  30

Cys Met Gly Trp Phe Arg Gln Ala Pro Gly Lys Glu Arg Glu Gly Val
            35                  40                  45

Ala Ala Ile Asp Ser Asp Gly Ser Thr Ser Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Asp Phe Tyr Glu Tyr Asn Tyr Trp Gly
            100                 105                 110

Gln Gly Thr Leu Val Thr Val Ser Ser Glu Ser Lys Tyr Gly Pro Pro
        115                 120                 125

Cys Pro Pro Cys Pro Ala Pro Glu Phe Leu Gly Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser Gln Glu Asp Pro Glu Val
                165                 170                 175

Gln Phe Asn Trp Tyr Val Asp Gly Val Glu Val His Asn Ala Lys Thr
            180                 185                 190

Lys Pro Arg Glu Glu Gln Phe Asn Ser Thr Tyr Arg Val Val Ser Val
        195                 200                 205

Leu Thr Val Leu His Gln Asp Trp Leu Asn Gly Lys Glu Tyr Lys Cys
210                 215                 220

Lys Val Ser Asn Lys Gly Leu Pro Ser Ser Ile Glu Lys Thr Ile Ser
225                 230                 235                 240
```

```
Lys Ala Lys Gly Gln Pro Arg Glu Pro Gln Val Tyr Thr Leu Pro Pro
            245                 250                 255

Ser Gln Glu Glu Met Thr Lys Asn Gln Val Ser Leu Thr Cys Leu Val
        260                 265                 270

Lys Gly Phe Tyr Pro Ser Asp Ile Ala Val Glu Trp Glu Ser Asn Gly
    275                 280                 285

Gln Pro Glu Asn Asn Tyr Lys Thr Thr Pro Pro Val Leu Asp Ser Asp
290                 295                 300

Gly Ser Phe Phe Leu Tyr Ser Arg Leu Thr Val Asp Lys Ser Arg Trp
305                 310                 315                 320

Gln Glu Gly Asn Val Phe Ser Cys Ser Val Met His Glu Ala Leu His
            325                 330                 335

Asn His Tyr Thr Gln Lys Ser Leu Ser Leu Ser Leu Gly Lys
            340                 345                 350

<210> SEQ ID NO 332
<211> LENGTH: 350
<212> TYPE: PRT
<213> ORGANISM: Artificial Sequence
<220> FEATURE:
<223> OTHER INFORMATION: Synthetic Construct

<400> SEQUENCE: 332

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Tyr Cys Ala
            85                  90                  95

Ala Asp Phe Cys Trp Val Asp Asp Phe Tyr Glu Tyr Asn Tyr Trp Gly
        100                 105                 110

Gln Gly Thr Leu Val Thr Val Ser Ser Glu Ser Lys Tyr Gly Pro Pro
    115                 120                 125

Cys Pro Pro Cys Pro Ala Pro Glu Phe Leu Gly Gly Pro Ser Val Phe
130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser Gln Glu Asp Pro Glu Val
            165                 170                 175

Gln Phe Asn Trp Tyr Val Asp Gly Val Glu Val His Asn Ala Lys Thr
        180                 185                 190

Lys Pro Arg Glu Glu Gln Phe Asn Ser Thr Tyr Arg Val Val Ser Val
    195                 200                 205

Leu Thr Val Leu His Gln Asp Trp Leu Asn Gly Lys Glu Tyr Lys Cys
210                 215                 220

Lys Val Ser Asn Lys Gly Leu Pro Ser Ser Ile Glu Lys Thr Ile Ser
225                 230                 235                 240

Lys Ala Lys Gly Gln Pro Arg Glu Pro Gln Val Tyr Thr Leu Pro Pro
            245                 250                 255
```

```
Ser Gln Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
290                 295                 300

Gly Ser Phe Phe Leu Tyr Ser Arg Leu Thr Val Asp Lys Ser Arg Trp
305                 310                 315                 320

Gln Glu Gly Asn Val Phe Ser Cys Ser Val Met His Glu Ala Leu His
                325                 330                 335

Asn His Tyr Thr Gln Lys Ser Leu Ser Leu Ser Leu Gly Lys
            340                 345                 350

<210> SEQ ID NO 333
<211> LENGTH: 350
<212> TYPE: PRT
<213> ORGANISM: Artificial Sequence
<220> FEATURE:
<223> OTHER INFORMATION: Synthetic Construct

<400> SEQUENCE: 333

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Asp Phe Cys Trp Val Asp Asp Phe Tyr Glu Tyr Asn Tyr Trp Gly
            100                 105                 110

Gln Gly Thr Leu Val Thr Val Ser Ser Glu Ser Lys Tyr Gly Pro Pro
        115                 120                 125

Cys Pro Pro Cys Pro Ala Pro Glu Phe Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser Gln Glu Asp Pro Glu Val
                165                 170                 175

Gln Phe Asn Trp Tyr Val Asp Gly Val Glu Val His Asn Ala Lys Thr
            180                 185                 190

Lys Pro Arg Glu Glu Gln Phe Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Gly Leu Pro Ser Ser Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Gln Glu Glu Met Thr Lys Asn Gln Val Ser Leu Thr Cys Leu Val
            260                 265                 270
```

-continued

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Arg Leu Thr Val Asp Lys Ser Arg Trp
305                 310                 315                 320

Gln Glu Gly Asn Val Phe Ser Cys Ser Val Met His Glu Ala Leu His
                325                 330                 335

Asn His Tyr Thr Gln Lys Ser Leu Ser Leu Ser Leu Gly Lys
            340                 345                 350

<210> SEQ ID NO 334
<211> LENGTH: 350
<212> TYPE: PRT
<213> ORGANISM: Artificial Sequence
<220> FEATURE:
<223> OTHER INFORMATION: Synthetic Construct

<400> SEQUENCE: 334

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Ser Gly Ser Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Asp Phe Cys Trp Val Asp Asp Phe Tyr Glu Tyr Asn Tyr Trp Gly
            100                 105                 110

Gln Gly Thr Leu Val Thr Val Ser Ser Glu Ser Lys Tyr Gly Pro Pro
        115                 120                 125

Cys Pro Pro Cys Pro Ala Pro Glu Phe Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser Gln Glu Asp Pro Glu Val
                165                 170                 175

Gln Phe Asn Trp Tyr Val Asp Gly Val Glu Val His Asn Ala Lys Thr
            180                 185                 190

Lys Pro Arg Glu Glu Gln Phe Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Gly Leu Pro Ser Ser Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Gln Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

```
Gln Pro Glu Asn Asn Tyr Lys Thr Thr Pro Val Leu Asp Ser Asp
        290                 295                 300

Gly Ser Phe Phe Leu Tyr Ser Arg Leu Thr Val Asp Lys Ser Arg Trp
305                 310                 315                 320

Gln Glu Gly Asn Val Phe Ser Cys Ser Val Met His Glu Ala Leu His
                325                 330                 335

Asn His Tyr Thr Gln Lys Ser Leu Ser Leu Ser Leu Gly Lys
            340                 345                 350

<210> SEQ ID NO 335
<211> LENGTH: 351
<212> TYPE: PRT
<213> ORGANISM: Artificial Sequence
<220> FEATURE:
<223> OTHER INFORMATION: Synthetic Construct

<400> SEQUENCE: 335

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Leu Glu Gly Val
        35                  40                  45

Ser Ala Ile Asp Ser Asp Gly Ser Val Ser Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Ser Lys Tyr Gly Pro
        115                 120                 125

Pro Cys Pro Pro Cys Pro Ala Pro Glu Phe Leu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Val Leu Asp Ser
    290                 295                 300
```

```
Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
            325                 330                 335

His Asn His Tyr Thr Gln Lys Ser Leu Ser Leu Ser Leu Gly Lys
        340                 345                 350

<210> SEQ ID NO 336
<211> LENGTH: 351
<212> TYPE: PRT
<213> ORGANISM: Artificial Sequence
<220> FEATURE:
<223> OTHER INFORMATION: Synthetic Construct

<400> SEQUENCE: 336

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Leu Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Ser Lys Tyr Gly Pro
        115                 120                 125

Pro Cys Pro Pro Cys Pro Ala Pro Glu Phe Leu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320
```

Trp Gln Glu Gly Asn Val Phe Ser Cys Ser Val Met His Glu Ala Leu
            325                 330                 335

His Asn His Tyr Thr Gln Lys Ser Leu Ser Leu Ser Leu Gly Lys
            340                 345                 350

<210> SEQ ID NO 337
<211> LENGTH: 351
<212> TYPE: PRT
<213> ORGANISM: Artificial Sequence
<220> FEATURE:
<223> OTHER INFORMATION: Synthetic Construct

<400> SEQUENCE: 337

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Ser Val Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Ser Lys Tyr Gly Pro
        115                 120                 125

Pro Cys Pro Pro Cys Pro Ala Pro Glu Phe Leu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

```
His Asn His Tyr Thr Gln Lys Ser Leu Ser Leu Ser Leu Gly Lys
            340                 345                 350
```

<210> SEQ ID NO 338
<211> LENGTH: 351
<212> TYPE: PRT
<213> ORGANISM: Artificial Sequence
<220> FEATURE:
<223> OTHER INFORMATION: Synthetic Construct

<400> SEQUENCE: 338

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Ser Val Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Ser Lys Tyr Gly Pro
        115                 120                 125

Pro Cys Pro Pro Cys Pro Ala Pro Glu Phe Leu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly Lys
            340                 345                 350
```

<210> SEQ ID NO 339
<211> LENGTH: 351
<212> TYPE: PRT
<213> ORGANISM: Artificial Sequence
<220> FEATURE:
<223> OTHER INFORMATION: Synthetic Construct

<400> SEQUENCE: 339

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ala Ala Ile Asp Ser Asp Gly Ser Val Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Ser Lys Tyr Gly Pro
        115                 120                 125

Pro Cys Pro Pro Cys Pro Ala Pro Glu Phe Leu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly Lys
            340                 345                 350

<210> SEQ ID NO 340

```
<211> LENGTH: 351
<212> TYPE: PRT
<213> ORGANISM: Artificial Sequence
<220> FEATURE:
<223> OTHER INFORMATION: Synthetic Construct

<400> SEQUENCE: 340

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Ser Val Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Ser Lys Tyr Gly Pro
        115                 120                 125

Pro Cys Pro Pro Cys Pro Ala Pro Glu Phe Leu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly Lys
            340                 345                 350

<210> SEQ ID NO 341
<211> LENGTH: 351
<212> TYPE: PRT
<213> ORGANISM: Artificial Sequence
```

<220> FEATURE:
<223> OTHER INFORMATION: Synthetic Construct

<400> SEQUENCE: 341

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Ser Lys Tyr Gly Pro
        115                 120                 125

Pro Cys Pro Pro Cys Pro Ala Pro Glu Phe Leu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly Lys
            340                 345                 350
```

<210> SEQ ID NO 342
<211> LENGTH: 351
<212> TYPE: PRT
<213> ORGANISM: Artificial Sequence
<220> FEATURE:
<223> OTHER INFORMATION: Synthetic Construct -continued

<400> SEQUENCE: 342

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Ser Lys Tyr Gly Pro
        115                 120                 125

Pro Cys Pro Pro Cys Pro Ala Pro Glu Phe Leu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly Lys
            340                 345                 350

<210> SEQ ID NO 343
<211> LENGTH: 351
<212> TYPE: PRT
<213> ORGANISM: Artificial Sequence
<220> FEATURE:
<223> OTHER INFORMATION: Synthetic Construct

<400> SEQUENCE: 343

Glu Val Gln Leu Val Glu Ser Gly Gly Gly Leu Val Gln Pro Gly Gly

```
              1               5                  10                 15
        Ser Leu Arg Leu Ser Cys Ala Ala Ser Gly Tyr Thr Val Ser Ser Tyr
                         20                  25                 30
        Cys Met Gly Trp Phe Arg Gln Ala Pro Gly Lys Gly Arg Glu Gly Val
                         35                  40                 45
        Ser Ala Ile Asp Ser Ser Gly Ser Val Ser Tyr Ala Asp Ser Val Lys
                         50                  55                 60
        Gly Arg Phe Thr Ile Ser Lys Asp Asn Ser Lys Asn Thr Leu Tyr Leu
        65                       70                  75                 80
        Gln Met Asn Ser Leu Arg Ala Glu Asp Thr Ala Val Tyr Phe Cys Ala
                         85                  90                 95
        Ala Asp Leu Cys Trp Val Asp Gln Asp Gln Gly Glu Tyr Asn Thr Trp
                         100                 105                110
        Gly Gln Gly Thr Leu Val Thr Val Ser Glu Ser Lys Tyr Gly Pro Pro
                         115                 120                125
        Pro Cys Pro Pro Cys Pro Ala Pro Glu Phe Leu Gly Gly Pro Ser Val
                         130                 135                140
        Phe Leu Phe Pro Pro Lys Pro Lys Asp Thr Leu Met Ile Ser Arg Thr
        145                      150                 155                160
        Pro Glu Val Thr Cys Val Val Val Asp Val Ser Gln Glu Asp Pro Glu
                         165                 170                175
        Val Gln Phe Asn Trp Tyr Val Asp Gly Val Glu Val His Asn Ala Lys
                         180                 185                190
        Thr Lys Pro Arg Glu Glu Gln Phe Asn Ser Thr Tyr Arg Val Val Ser
                         195                 200                205
        Val Leu Thr Val Leu His Gln Asp Trp Leu Asn Gly Lys Glu Tyr Lys
                         210                 215                220
        Cys Lys Val Ser Asn Lys Gly Leu Pro Ser Ser Ile Glu Lys Thr Ile
        225                      230                 235                240
        Ser Lys Ala Lys Gly Gln Pro Arg Glu Pro Gln Val Tyr Thr Leu Pro
                         245                 250                255
        Pro Ser Gln Glu Glu Met Thr Lys Asn Gln Val Ser Leu Thr Cys Leu
                         260                 265                270
        Val Lys Gly Phe Tyr Pro Ser Asp Ile Ala Val Glu Trp Glu Ser Asn
                         275                 280                285
        Gly Gln Pro Glu Asn Asn Tyr Lys Thr Thr Pro Pro Val Leu Asp Ser
                         290                 295                300
        Asp Gly Ser Phe Phe Leu Tyr Ser Arg Leu Thr Val Asp Lys Ser Arg
        305                      310                 315                320
        Trp Gln Glu Gly Asn Val Phe Ser Cys Ser Val Met His Glu Ala Leu
                         325                 330                335
        His Asn His Tyr Thr Gln Lys Ser Leu Ser Leu Ser Leu Gly Lys
                         340                 345                350

<210> SEQ ID NO 344
<211> LENGTH: 355
<212> TYPE: PRT
<213> ORGANISM: Artificial Sequence
<220> FEATURE:
<223> OTHER INFORMATION: Synthetic Construct

<400> SEQUENCE: 344

Glu Val Gln Leu Val Glu Ser Gly Gly Gly Leu Val Gln Pro Gly Gly
        1               5                   10                 15

Ser Leu Arg Leu Ser Cys Ala Ala Ser Gly Tyr Thr Tyr Gly Gly Tyr
```

20                  25                  30
    Cys Met Gly Trp Phe Arg Gln Ala Pro Gly Lys Gly Leu Glu Gly Val
             35                  40                  45

Ser Thr Ile Asn Ser Asp Gly Ser Thr Asn Tyr Ala Asp Ser Val Lys
     50                  55                  60

Gly Arg Phe Thr Ile Ser Arg Asp Asn Ser Lys Asn Thr Leu Tyr Leu
     65                  70                  75                  80

Gln Met Asn Ser Leu Arg Ala Glu Asp Thr Ala Val Tyr Tyr Cys Ala
                     85                  90                  95

Val Asp Leu Ala Pro Cys Trp Val Ala Gly Pro Ile Glu Ala Ala Asp
                100                 105                 110

Phe Gly Tyr Trp Gly Gln Gly Thr Leu Val Thr Val Ser Ser Glu Ser
                115                 120                 125

Lys Tyr Gly Pro Pro Cys Pro Pro Cys Pro Ala Pro Glu Phe Leu Gly
                130                 135                 140

Gly Pro Ser Val Phe Leu Phe Pro Pro Lys Pro Lys Asp Thr Leu Met
    145                 150                 155                 160

Ile Ser Arg Thr Pro Glu Val Thr Cys Val Val Val Asp Val Ser Gln
                    165                 170                 175

Glu Asp Pro Glu Val Gln Phe Asn Trp Tyr Val Asp Gly Val Glu Val
                180                 185                 190

His Asn Ala Lys Thr Lys Pro Arg Glu Glu Gln Phe Asn Ser Thr Tyr
                195                 200                 205

Arg Val Val Ser Val Leu Thr Val Leu His Gln Asp Trp Leu Asn Gly
                210                 215                 220

Lys Glu Tyr Lys Cys Lys Val Ser Asn Lys Gly Leu Pro Ser Ser Ile
    225                 230                 235                 240

Glu Lys Thr Ile Ser Lys Ala Lys Gly Gln Pro Arg Glu Pro Gln Val
                    245                 250                 255

Tyr Thr Leu Pro Pro Ser Gln Glu Glu Met Thr Lys Asn Gln Val Ser
                260                 265                 270

Leu Thr Cys Leu Val Lys Gly Phe Tyr Pro Ser Asp Ile Ala Val Glu
                275                 280                 285

Trp Glu Ser Asn Gly Gln Pro Glu Asn Asn Tyr Lys Thr Thr Pro Pro
                290                 295                 300

Val Leu Asp Ser Asp Gly Ser Phe Phe Leu Tyr Ser Arg Leu Thr Val
    305                 310                 315                 320

Asp Lys Ser Arg Trp Gln Glu Gly Asn Val Phe Ser Cys Ser Val Met
                    325                 330                 335

His Glu Ala Leu His Asn His Tyr Thr Gln Lys Ser Leu Ser Leu Ser
                340                 345                 350

Leu Gly Lys
            355

<210> SEQ ID NO 345
    <211> LENGTH: 355
    <212> TYPE: PRT
    <213> ORGANISM: Artificial Sequence
    <220> FEATURE:
    <223> OTHER INFORMATION: Synthetic Construct

<400> SEQUENCE: 345

Glu Val Gln Leu Val Glu Ser Gly Gly Gly Leu Val Gln Pro Gly Gly
    1               5                   10                  15

Ser Leu Arg Leu Ser Cys Ala Ala Ser Gly Tyr Thr Tyr Gly Gly Tyr

```
            20                  25                  30
Cys Met Gly Trp Phe Arg Gln Ala Pro Gly Lys Gly Leu Glu Gly Val
        35                  40                  45

Ser Thr Ile Ala Ser Glu Gly Ser Thr Asn Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Val Asp Leu Ala Pro Cys Trp Val Ala Gly Pro Ile Glu Ala Ala Asp
            100                 105                 110

Phe Gly Tyr Trp Gly Gln Gly Thr Leu Val Thr Val Ser Ser Glu Ser
        115                 120                 125

Lys Tyr Gly Pro Pro Cys Pro Pro Cys Pro Ala Pro Glu Phe Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser Gln
                165                 170                 175

Glu Asp Pro Glu Val Gln Phe Asn Trp Tyr Val Asp Gly Val Glu Val
            180                 185                 190

His Asn Ala Lys Thr Lys Pro Arg Glu Glu Gln Phe Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Gly Leu Pro Ser Ser Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Gln Glu Glu Met Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Arg Leu Thr Val
305                 310                 315                 320

Asp Lys Ser Arg Trp Gln Glu Gly Asn Val Phe Ser Cys Ser Val Met
                325                 330                 335

His Glu Ala Leu His Asn His Tyr Thr Gln Lys Ser Leu Ser Leu Ser
            340                 345                 350

Leu Gly Lys
    355

<210> SEQ ID NO 346
<211> LENGTH: 355
<212> TYPE: PRT
<213> ORGANISM: Artificial Sequence
<220> FEATURE:
<223> OTHER INFORMATION: Synthetic Construct

<400> SEQUENCE: 346

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Gly Gly Tyr
```

```
                20                  25                  30
Cys Met Gly Trp Phe Arg Gln Ala Pro Gly Lys Gly Leu Glu Gly Val
         35                  40                  45

Ser Thr Ile Ala Ser Ser Gly Ser Thr Asn Tyr Ala Asp Ser Val Lys
 50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
             85                  90                  95

Val Asp Leu Ala Pro Cys Trp Val Ala Gly Pro Ile Glu Ala Ala Asp
            100                 105                 110

Phe Gly Tyr Trp Gly Gln Gly Thr Leu Val Thr Val Ser Ser Glu Ser
            115                 120                 125

Lys Tyr Gly Pro Pro Cys Pro Pro Cys Pro Ala Pro Glu Phe Leu Gly
            130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser Gln
            165                 170                 175

Glu Asp Pro Glu Val Gln Phe Asn Trp Tyr Val Asp Gly Val Glu Val
            180                 185                 190

His Asn Ala Lys Thr Lys Pro Arg Glu Glu Gln Phe Asn Ser Thr Tyr
            195                 200                 205

Arg Val Val Ser Val Leu Thr Val Leu His Gln Asp Trp Leu Asn Gly
            210                 215                 220

Lys Glu Tyr Lys Cys Lys Val Ser Asn Lys Gly Leu Pro Ser Ser Ile
225                 230                 235                 240

Glu Lys Thr Ile Ser Lys Ala Lys Gly Gln Pro Arg Glu Pro Gln Val
            245                 250                 255

Tyr Thr Leu Pro Pro Ser Gln Glu Glu Met Thr Lys Asn Gln Val Ser
            260                 265                 270

Leu Thr Cys Leu Val Lys Gly Phe Tyr Pro Ser Asp Ile Ala Val Glu
            275                 280                 285

Trp Glu Ser Asn Gly Gln Pro Glu Asn Asn Tyr Lys Thr Thr Pro Pro
            290                 295                 300

Val Leu Asp Ser Asp Gly Ser Phe Phe Leu Tyr Ser Arg Leu Thr Val
305                 310                 315                 320

Asp Lys Ser Arg Trp Gln Glu Gly Asn Val Phe Ser Cys Ser Val Met
            325                 330                 335

His Glu Ala Leu His Asn His Tyr Thr Gln Lys Ser Leu Ser Leu Ser
            340                 345                 350

Leu Gly Lys
        355

<210> SEQ ID NO 347
<211> LENGTH: 355
<212> TYPE: PRT
<213> ORGANISM: Artificial Sequence
<220> FEATURE:
<223> OTHER INFORMATION: Synthetic Construct

<400> SEQUENCE: 347

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Gly Gly Tyr
```

```
            20                  25                  30
Cys Met Gly Trp Phe Arg Gln Ala Pro Gly Lys Gly Arg Glu Gly Val
        35                  40                  45

Ser Thr Ile Asn Ser Asp Gly Ser Thr Asn Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                85                  90                  95

Val Asp Leu Ala Pro Cys Trp Val Ala Gly Pro Ile Glu Ala Ala Asp
               100                 105                 110

Phe Gly Tyr Trp Gly Gln Gly Thr Leu Val Thr Val Ser Ser Glu Ser
           115                 120                 125

Lys Tyr Gly Pro Pro Cys Pro Pro Cys Pro Ala Pro Glu Phe Leu Gly
       130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser Gln
               165                 170                 175

Glu Asp Pro Glu Val Gln Phe Asn Trp Tyr Val Asp Gly Val Glu Val
               180                 185                 190

His Asn Ala Lys Thr Lys Pro Arg Glu Glu Gln Phe Asn Ser Thr Tyr
           195                 200                 205

Arg Val Val Ser Val Leu Thr Val Leu His Gln Asp Trp Leu Asn Gly
       210                 215                 220

Lys Glu Tyr Lys Cys Lys Val Ser Asn Lys Gly Leu Pro Ser Ser Ile
225                 230                 235                 240

Glu Lys Thr Ile Ser Lys Ala Lys Gly Gln Pro Arg Glu Pro Gln Val
               245                 250                 255

Tyr Thr Leu Pro Pro Ser Gln Glu Glu Met Thr Lys Asn Gln Val Ser
               260                 265                 270

Leu Thr Cys Leu Val Lys Gly Phe Tyr Pro Ser Asp Ile Ala Val Glu
           275                 280                 285

Trp Glu Ser Asn Gly Gln Pro Glu Asn Asn Tyr Lys Thr Thr Pro Pro
       290                 295                 300

Val Leu Asp Ser Asp Gly Ser Phe Phe Leu Tyr Ser Arg Leu Thr Val
305                 310                 315                 320

Asp Lys Ser Arg Trp Gln Glu Gly Asn Val Phe Ser Cys Ser Val Met
               325                 330                 335

His Glu Ala Leu His Asn His Tyr Thr Gln Lys Ser Leu Ser Leu Ser
               340                 345                 350

Leu Gly Lys
        355

<210> SEQ ID NO 348
<211> LENGTH: 355
<212> TYPE: PRT
<213> ORGANISM: Artificial Sequence
<220> FEATURE:
<223> OTHER INFORMATION: Synthetic Construct

<400> SEQUENCE: 348

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Gly Gly Tyr
```

```
            20                  25                  30
Cys Met Gly Trp Phe Arg Gln Ala Pro Gly Lys Gly Arg Glu Gly Val
        35                  40                  45

Ser Thr Ile Ala Ser Glu Gly Ser Thr Asn Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Pro Glu Asp Thr Ala Val Tyr Tyr Cys Ala
                85                  90                  95

Val Asp Leu Ala Pro Cys Trp Val Ala Gly Pro Ile Glu Ala Ala Asp
            100                 105                 110

Phe Gly Tyr Trp Gly Gln Gly Thr Leu Val Thr Val Ser Ser Glu Ser
            115                 120                 125

Lys Tyr Gly Pro Pro Cys Pro Pro Cys Pro Ala Pro Glu Phe Leu Gly
        130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser Gln
                165                 170                 175

Glu Asp Pro Glu Val Gln Phe Asn Trp Tyr Val Asp Gly Val Glu Val
            180                 185                 190

His Asn Ala Lys Thr Lys Pro Arg Glu Glu Gln Phe Asn Ser Thr Tyr
            195                 200                 205

Arg Val Val Ser Val Leu Thr Val Leu His Gln Asp Trp Leu Asn Gly
        210                 215                 220

Lys Glu Tyr Lys Cys Lys Val Ser Asn Lys Gly Leu Pro Ser Ser Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Gln Glu Glu Met Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Arg Leu Thr Val
305                 310                 315                 320

Asp Lys Ser Arg Trp Gln Glu Gly Asn Val Phe Ser Cys Ser Val Met
                325                 330                 335

His Glu Ala Leu His Asn His Tyr Thr Gln Lys Ser Leu Ser Leu Ser
            340                 345                 350

Leu Gly Lys
        355

<210> SEQ ID NO 349
<211> LENGTH: 355
<212> TYPE: PRT
<213> ORGANISM: Artificial Sequence
<220> FEATURE:
<223> OTHER INFORMATION: Synthetic Construct

<400> SEQUENCE: 349

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Gly Gly Tyr
```

```
                20                  25                  30
Cys Met Gly Trp Phe Arg Gln Ala Pro Gly Lys Gly Arg Glu Gly Val
        35                  40                  45

Ser Thr Ile Ala Ser Ser Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Val Asp Leu Ala Pro Cys Trp Val Ala Gly Pro Ile Glu Ala Ala Asp
            100                 105                 110

Phe Gly Tyr Trp Gly Gln Gly Thr Leu Val Thr Val Ser Ser Glu Ser
        115                 120                 125

Lys Tyr Gly Pro Pro Cys Pro Pro Cys Pro Ala Pro Glu Phe Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser Gln
                165                 170                 175

Glu Asp Pro Glu Val Gln Phe Asn Trp Tyr Val Asp Gly Val Glu Val
            180                 185                 190

His Asn Ala Lys Thr Lys Pro Arg Glu Glu Gln Phe Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Gly Leu Pro Ser Ser Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Gln Glu Glu Met Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Arg Leu Thr Val
305                 310                 315                 320

Asp Lys Ser Arg Trp Gln Glu Gly Asn Val Phe Ser Cys Ser Val Met
                325                 330                 335

His Glu Ala Leu His Asn His Tyr Thr Gln Lys Ser Leu Ser Leu Ser
            340                 345                 350

Leu Gly Lys
        355

<210> SEQ ID NO 350
<211> LENGTH: 497
<212> TYPE: PRT
<213> ORGANISM: Artificial Sequence
<220> FEATURE:
<223> OTHER INFORMATION: Synthetic Construct

<400> SEQUENCE: 350

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
```

-continued

```
                20                  25                  30
Val Thr Trp Gln His Gln Pro Asp Ser Gly Pro Pro Ala Ala Pro
             35                  40                  45

Gly His Pro Leu Ala Pro Gly Pro His Pro Ala Ala Pro Ser Ser Trp
 50                  55                  60

Gly Pro Arg Pro Arg Arg Tyr Thr Val Leu Ser Val Gly Pro Gly Gly
 65                  70                  75                  80

Leu Arg Ser Gly Arg Leu Pro Leu Gln Pro Arg Val Gln Leu Asp Glu
                 85                  90                  95

Arg Gly Arg Gln Arg Gly Asp Phe Ser Leu Trp Leu Arg Pro Ala Arg
                100                 105                 110

Arg Ala Asp Ala Gly Glu Tyr Arg Ala Ala Val His Leu Arg Asp Arg
                115                 120                 125

Ala Leu Ser Cys Arg Leu Arg Leu Gly Gln Ala Ser Met Thr
                130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
                180                 185                 190

Leu Ala Glu Ser Phe Leu Phe Leu Pro Gln Val Ser Pro Met Asp Ser
                195                 200                 205

Gly Pro Trp Gly Cys Ile Leu Thr Tyr Arg Asp Gly Phe Asn Val Ser
                210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
                260                 265                 270

Pro Gly Gly Gly Pro Asp Leu Leu Val Thr Gly Asp Asn Gly Asp Phe
                275                 280                 285

Thr Leu Arg Leu Glu Asp Val Ser Gln Ala Gln Ala Gly Thr Tyr Thr
                290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
                340                 345                 350

Val Trp Ser Ser Leu Asp Thr Pro Ser Gln Arg Ser Phe Ser Gly Pro
                355                 360                 365

Trp Leu Glu Ala Gln Glu Ala Gln Leu Leu Ser Gln Pro Trp Gln Cys
                370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
                405                 410                 415

Leu Pro Ala Gly His Leu Leu Phe Leu Ile Leu Gly Val Leu Ser
                420                 425                 430

Leu Leu Leu Leu Val Thr Gly Ala Phe Gly Phe His Leu Trp Arg Arg
                435                 440                 445
```

-continued

Gln Trp Arg Pro Arg Arg Phe Ser Ala Leu Glu Gln Gly Ile His Pro
            450                 455                 460

Pro Gln Ala Gln Ser Lys Ile Glu Glu Leu Glu Gln Pro Glu Pro
465                 470                 475                 480

Glu Pro Glu Pro Glu Pro Glu Pro Glu Pro Glu Pro Glu Gln
                485                 490                 495

Leu

<210> SEQ ID NO 351
<211> LENGTH: 422
<212> TYPE: PRT
<213> ORGANISM: Artificial Sequence
<220> FEATURE:
<223> OTHER INFORMATION: Synthetic Construct

<400> SEQUENCE: 351

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
                20                  25                  30

Val Thr Trp Gln His Gln Pro Asp Ser Gly Pro Pro Ala Ala Ala Pro
            35                  40                  45

Gly His Pro Leu Ala Pro Gly Pro His Pro Ala Ala Pro Ser Ser Trp
        50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly Gln Ala Ser Met Thr
130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
            260                 265                 270

Pro Gly Gly Gly Pro Asp Leu Leu Val Thr Gly Asp Asn Gly Asp Phe
        275                 280                 285

Thr Leu Arg Leu Glu Asp Val Ser Gln Ala Gln Ala Gly Thr Tyr Thr
290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
        355                 360                 365

Trp Leu Glu Ala Gln Glu Ala Gln Leu Leu Ser Gln Pro Trp Gln Cys
    370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
                405                 410                 415

Leu Pro Ala Gly His Leu
            420

<210> SEQ ID NO 352
<211> LENGTH: 15
<212> TYPE: PRT
<213> ORGANISM: Artificial Sequence
<220> FEATURE:
<223> OTHER INFORMATION: Synthetic Construct

<400> SEQUENCE: 352

Glu Pro Lys Ser Ser Asp Lys Thr His Thr Cys Pro Pro Cys Pro
1               5                   10                  15

<210> SEQ ID NO 353
<211> LENGTH: 15
<212> TYPE: PRT
<213> ORGANISM: Artificial Sequence
<220> FEATURE:
<223> OTHER INFORMATION: Synthetic Construct

<400> SEQUENCE: 353

Glu Pro Lys Ser Ser Asp Lys Thr His Thr Ser Pro Pro Ser Pro
1               5                   10                  15

<210> SEQ ID NO 354
<211> LENGTH: 447
<212> TYPE: PRT
<213> ORGANISM: Artificial Sequence
<220> FEATURE:
<223> OTHER INFORMATION: Synthetic Construct

<400> SEQUENCE: 354

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln

```
                    100                 105                 110
Gly Thr Leu Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 355
<211> LENGTH: 214
<212> TYPE: PRT
<213> ORGANISM: Artificial Sequence
<220> FEATURE:
<223> OTHER INFORMATION: Synthetic Construct

<400> SEQUENCE: 355

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
```

-continued

```
                20                  25                  30
Leu Ala Trp Tyr Gln Gln Lys Pro Gly Gln Ala Pro Arg Leu Leu Ile
            35                  40                  45
Tyr Asp Ala Ser Asn Arg Ala Thr Gly Ile Pro Ala Arg Phe Ser Gly
 50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Asn Trp Pro Leu
                85                  90                  95
Thr Phe Gly Gln Gly Thr Asn Leu Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
    210
```

<210> SEQ ID NO 356
<211> LENGTH: 447
<212> TYPE: PRT
<213> ORGANISM: Artificial Sequence
<220> FEATURE:
<223> OTHER INFORMATION: Synthetic Construct

<400> SEQUENCE: 356

```
Gln Val Gln Leu Val Gln Ser Gly Val Glu Val Lys Lys Pro Gly Ala
 1               5                  10                  15
Ser Val Lys Val Ser Cys Lys Ala Ser Gly Tyr Thr Phe Thr Asn Tyr
            20                  25                  30
Tyr Met Tyr Trp Val Arg Gln Ala Pro Gly Gln Gly Leu Glu Trp Met
            35                  40                  45
Gly Gly Ile Asn Pro Ser Asn Gly Gly Thr Asn Phe Asn Glu Lys Phe
 50                  55                  60
Lys Asn Arg Val Thr Leu Thr Thr Asp Ser Ser Thr Thr Thr Ala Tyr
 65                  70                  75                  80
Met Glu Leu Lys Ser Leu Gln Phe Asp Thr Ala Val Tyr Tyr Cys
                85                  90                  95
Ala Arg Arg Asp Tyr Arg Phe Asp Met Gly Phe Asp Tyr Trp Gly Gln
            100                 105                 110
Gly Thr Thr Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
```

165                 170                 175
Leu Gln Ser Ser Gly Leu Tyr Ser Leu Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly Lys
        435                 440                 445

<210> SEQ ID NO 357
<211> LENGTH: 218
<212> TYPE: PRT
<213> ORGANISM: Artificial Sequence
<220> FEATURE:
<223> OTHER INFORMATION: Synthetic Construct

<400> SEQUENCE: 357

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Lys Gly Val Ser Thr Ser
            20                  25                  30
Gly Tyr Ser Tyr Leu His Trp Tyr Gln Gln Lys Pro Gly Gln Ala Pro
        35                  40                  45
Arg Leu Leu Ile Tyr Leu Ala Ser Tyr Leu Glu Ser Gly Val Pro Ala
    50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Val Tyr Tyr Cys Gln His Ser Arg

```
                    85                  90                  95
Asp Leu Pro Leu Thr Phe Gly Gly Thr Lys Val Glu Ile Lys Arg
            100                 105                 110

Thr Val Ala Ala Pro Ser Val Phe Ile Phe Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 358
<211> LENGTH: 584
<212> TYPE: PRT
<213> ORGANISM: Artificial Sequence
<220> FEATURE:
<223> OTHER INFORMATION: Synthetic Construct

<400> SEQUENCE: 358

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Pro Lys Ser Ser Asp
        115                 120                 125

Lys Thr His Thr Ser Pro Pro Ser Pro Gln Val Gln Leu Val Gln Ser
    130                 135                 140

Gly Val Glu Val Lys Lys Pro Gly Ala Ser Val Lys Val Ser Cys Lys
145                 150                 155                 160

Ala Ser Gly Tyr Thr Phe Thr Asn Tyr Tyr Met Tyr Trp Val Arg Gln
                165                 170                 175

Ala Pro Gly Gln Gly Leu Glu Trp Met Gly Gly Ile Asn Pro Ser Asn
            180                 185                 190

Gly Gly Thr Asn Phe Asn Glu Lys Phe Lys Asn Arg Val Thr Leu Thr
        195                 200                 205

Thr Asp Ser Ser Thr Thr Thr Ala Tyr Met Glu Leu Lys Ser Leu Gln
    210                 215                 220

Phe Asp Asp Thr Ala Val Tyr Tyr Cys Ala Arg Arg Asp Tyr Arg Phe
```

```
            225                 230                 235                 240
Asp Met Gly Phe Asp Tyr Trp Gly Gln Gly Thr Thr Val Thr Val Ser
                245                 250                 255

Ser Ala Ser Thr Lys Gly Pro Ser Val Phe Pro Leu Ala Pro Cys Ser
                260                 265                 270

Arg Ser Thr Ser Glu Ser Thr Ala Ala Leu Gly Cys Leu Val Lys Asp
                275                 280                 285

Tyr Phe Pro Glu Pro Val Thr Val Ser Trp Asn Ser Gly Ala Leu Thr
                290                 295                 300

Ser Gly Val His Thr Phe Pro Ala Val Leu Gln Ser Ser Gly Leu Tyr
305                 310                 315                 320

Ser Leu Ser Ser Val Val Thr Val Pro Ser Ser Ser Leu Gly Thr Lys
                325                 330                 335

Thr Tyr Thr Cys Asn Val Asp His Lys Pro Ser Asn Thr Lys Val Asp
                340                 345                 350

Lys Arg Val Glu Ser Lys Tyr Gly Pro Pro Cys Pro Pro Cys Pro Ala
                355                 360                 365

Pro Glu Phe Leu Gly Gly Pro Ser Val Phe Leu Phe Pro Pro Lys Pro
                370                 375                 380

Lys Asp Thr Leu Met Ile Ser Arg Thr Pro Glu Val Thr Cys Val Val
385                 390                 395                 400

Val Asp Val Ser Gln Glu Asp Pro Glu Val Gln Phe Asn Trp Tyr Val
                405                 410                 415

Asp Gly Val Glu Val His Asn Ala Lys Thr Lys Pro Arg Glu Glu Gln
                420                 425                 430

Phe Asn Ser Thr Tyr Arg Val Val Ser Val Leu Thr Val Leu His Gln
                435                 440                 445

Asp Trp Leu Asn Gly Lys Glu Tyr Lys Cys Lys Val Ser Asn Lys Gly
                450                 455                 460

Leu Pro Ser Ser Ile Glu Lys Thr Ile Ser Lys Ala Lys Gly Gln Pro
465                 470                 475                 480

Arg Glu Pro Gln Val Tyr Thr Leu Pro Pro Ser Gln Glu Glu Met Thr
                485                 490                 495

Lys Asn Gln Val Ser Leu Thr Cys Leu Val Lys Gly Phe Tyr Pro Ser
                500                 505                 510

Asp Ile Ala Val Glu Trp Glu Ser Asn Gly Gln Pro Glu Asn Asn Tyr
                515                 520                 525

Lys Thr Thr Pro Pro Val Leu Asp Ser Asp Gly Ser Phe Phe Leu Tyr
                530                 535                 540

Ser Arg Leu Thr Val Asp Lys Ser Arg Trp Gln Glu Gly Asn Val Phe
545                 550                 555                 560

Ser Cys Ser Val Met His Glu Ala Leu His Asn His Tyr Thr Gln Lys
                565                 570                 575

Ser Leu Ser Leu Ser Leu Gly Lys
                580

<210> SEQ ID NO 359
<211> LENGTH: 218
<212> TYPE: PRT
<213> ORGANISM: Artificial Sequence
<220> FEATURE:
<223> OTHER INFORMATION: Synthetic Construct

<400> SEQUENCE: 359

Glu Ile Val Leu Thr Gln Ser Pro Ala Thr Leu Ser Leu Ser Pro Gly
```

```
              1               5                  10                 15
        Glu Arg Ala Thr Leu Ser Cys Arg Ala Ser Lys Gly Val Ser Thr Ser
                         20                 25                 30
        Gly Tyr Ser Tyr Leu His Trp Tyr Gln Gln Lys Pro Gly Gln Ala Pro
                         35                 40                 45
        Arg Leu Leu Ile Tyr Leu Ala Ser Tyr Leu Glu Ser Gly Val Pro Ala
                50                 55                 60
        Arg Phe Ser Gly Ser Gly Ser Gly Thr Asp Phe Thr Leu Thr Ile Ser
        65                 70                 75                 80
        Ser Leu Glu Pro Glu Asp Phe Ala Val Tyr Tyr Cys Gln His Ser Arg
                         85                 90                 95
        Asp Leu Pro Leu Thr Phe Gly Gly Gly Thr Lys Val Glu Ile Lys Arg
                        100                105                110
        Thr Val Ala Ala Pro Ser Val Phe Ile Phe Pro Pro Ser Asp Glu Gln
                        115                120                125
        Leu Lys Ser Gly Thr Ala Ser Val Val Cys Leu Leu Asn Asn Phe Tyr
                130                135                140
        Pro Arg Glu Ala Lys Val Gln Trp Lys Val Asp Asn Ala Leu Gln Ser
        145                150                155                160
        Gly Asn Ser Gln Glu Ser Val Thr Glu Gln Asp Ser Lys Asp Ser Thr
                        165                170                175
        Tyr Ser Leu Ser Ser Thr Leu Thr Leu Ser Lys Ala Asp Tyr Glu Lys
                        180                185                190
        His Lys Val Tyr Ala Cys Glu Val Thr His Gln Gly Leu Ser Ser Pro
                        195                200                205
        Val Thr Lys Ser Phe Asn Arg Gly Glu Cys
                210                215

<210> SEQ ID NO 360
<211> LENGTH: 447
<212> TYPE: PRT
<213> ORGANISM: Artificial Sequence
<220> FEATURE:
<223> OTHER INFORMATION: Synthetic Construct

<400> SEQUENCE: 360

Gln Val Gln Leu Val Gln Ser Gly Val Glu Val Lys Lys Pro Gly Ala
        1               5                  10                 15
        Ser Val Lys Val Ser Cys Lys Ala Ser Gly Tyr Thr Phe Thr Asn Tyr
                         20                 25                 30
        Tyr Met Tyr Trp Val Arg Gln Ala Pro Gly Gln Gly Leu Glu Trp Met
                         35                 40                 45
        Gly Gly Ile Asn Pro Ser Asn Gly Gly Thr Asn Phe Asn Glu Lys Phe
                50                 55                 60
        Lys Asn Arg Val Thr Leu Thr Thr Asp Ser Ser Thr Thr Thr Ala Tyr
        65                 70                 75                 80
        Met Glu Leu Lys Ser Leu Gln Phe Asp Asp Thr Ala Val Tyr Tyr Cys
                         85                 90                 95
        Ala Arg Arg Asp Tyr Arg Phe Asp Met Gly Phe Asp Tyr Trp Gly Gln
                        100                105                110
        Gly Thr Thr Val Thr Val Ser Ser Ala Ser Thr Lys Gly Pro Ser Val
                        115                120                125
        Phe Pro Leu Ala Pro Cys Ser Arg Ser Thr Ser Glu Ser Thr Ala Ala
                130                135                140
        Leu Gly Cys Leu Val Lys Asp Tyr Phe Pro Glu Pro Val Thr Val Ser
```

```
                145                 150                 155                 160
Trp Asn Ser Gly Ala Leu Thr Ser Gly Val His Thr Phe Pro Ala Val
                    165                 170                 175

Leu Gln Ser Ser Gly Leu Tyr Ser Leu Ser Ser Val Val Thr Val Pro
                    180                 185                 190

Ser Ser Ser Leu Gly Thr Lys Thr Tyr Thr Cys Asn Val Asp His Lys
                    195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                    245                 250                 255

Pro Glu Val Thr Cys Val Val Val Asp Val Ser Gln Glu Asp Pro Glu
                    260                 265                 270

Val Gln Phe Asn Trp Tyr Val Asp Gly Val Glu Val His Asn Ala Lys
                    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                    325                 330                 335

Ser Lys Ala Lys Gly Gln Pro Arg Glu Pro Gln Val Tyr Thr Leu Pro
                    340                 345                 350

Pro Ser Gln Glu Glu Met Thr Lys Asn Gln Val Ser Leu Thr Cys Leu
                    355                 360                 365

Val Lys Gly Phe Tyr Pro Ser Asp Ile Ala Val Glu Trp Glu Ser Asn
                    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                    405                 410                 415

Trp Gln Glu Gly Asn Val Phe Ser Cys Ser Val Met His Glu Ala Leu
                    420                 425                 430

His Asn His Tyr Thr Gln Lys Ser Leu Ser Leu Ser Leu Gly Lys
                    435                 440                 445

<210> SEQ ID NO 361
<211> LENGTH: 355
<212> TYPE: PRT
<213> ORGANISM: Artificial Sequence
<220> FEATURE:
<223> OTHER INFORMATION: Synthetic Construct

<400> SEQUENCE: 361

Glu Val Gln Leu Val Glu Ser Gly Gly Gly Leu Val Gln Pro Gly Gly
1                   5                   10                  15

Ser Leu Arg Leu Ser Cys Ala Ala Ser Gly Tyr Thr Val Ser Ser Tyr
                    20                  25                  30

Cys Met Gly Trp Phe Arg Gln Ala Pro Gly Lys Gly Arg Glu Gly Val
                    35                  40                  45

Ser Ala Ile Asp Ser Asp Gly Ser Val Ser Tyr Ala Asp Ser Val Lys
                    50                  55                  60

Gly Arg Phe Thr Ile Ser Lys Asp Asn Ser Lys Asn Thr Leu Tyr Leu
```

```
                65                  70                  75                  80
        Gln Met Asn Ser Leu Arg Ala Glu Asp Thr Ala Val Tyr Phe Cys Ala
                        85                  90                  95

Ala Asp Leu Cys Trp Val Asp Gln Asp Gln Gly Glu Tyr Asn Thr Trp
                        100                 105                110

Gly Gln Gly Thr Leu Val Thr Val Ser Ser Glu Pro Lys Ser Ser Asp
                        115                 120                125

Lys Thr His Thr Ser Pro Pro Ser Pro Glu Ile Val Leu Thr Gln Ser
        130                 135                 140

Pro Ala Thr Leu Ser Leu Ser Pro Gly Glu Arg Ala Thr Leu Ser Cys
        145                 150                 155                 160

Arg Ala Ser Lys Gly Val Ser Thr Ser Gly Tyr Ser Tyr Leu His Trp
                        165                 170                 175

Tyr Gln Gln Lys Pro Gly Gln Ala Pro Arg Leu Leu Ile Tyr Leu Ala
                        180                 185                 190

Ser Tyr Leu Glu Ser Gly Val Pro Ala Arg Phe Ser Gly Ser Gly Ser
                        195                 200                 205

Gly Thr Asp Phe Thr Leu Thr Ile Ser Ser Leu Glu Pro Glu Asp Phe
                        210                 215                 220

Ala Val Tyr Tyr Cys Gln His Ser Arg Asp Leu Pro Leu Thr Phe Gly
        225                 230                 235                 240

Gly Gly Thr Lys Val Glu Ile Lys Arg Thr Val Ala Ala Pro Ser Val
                        245                 250                 255

Phe Ile Phe Pro Pro Ser Asp Glu Gln Leu Lys Ser Gly Thr Ala Ser
                        260                 265                 270

Val Val Cys Leu Leu Asn Asn Phe Tyr Pro Arg Glu Ala Lys Val Gln
                        275                 280                 285

Trp Lys Val Asp Asn Ala Leu Gln Ser Gly Asn Ser Gln Glu Ser Val
                        290                 295                 300

Thr Glu Gln Asp Ser Lys Asp Ser Thr Tyr Ser Leu Ser Ser Thr Leu
        305                 310                 315                 320

Thr Leu Ser Lys Ala Asp Tyr Glu Lys His Lys Val Tyr Ala Cys Glu
                        325                 330                 335

Val Thr His Gln Gly Leu Ser Ser Pro Val Thr Lys Ser Phe Asn Arg
                        340                 345                 350

Gly Glu Cys
                355

<210> SEQ ID NO 362
<211> LENGTH: 588
<212> TYPE: PRT
<213> ORGANISM: Artificial Sequence
<220> FEATURE:
<223> OTHER INFORMATION: Synthetic Construct

<400> SEQUENCE: 362

Glu Val Gln Leu Val Glu Ser Gly Gly Gly Leu Val Gln Pro Gly Gly
        1               5                   10                  15

Ser Leu Arg Leu Ser Cys Ala Ala Ser Gly Tyr Thr Tyr Gly Gly Tyr
                        20                  25                  30

Cys Met Gly Trp Phe Arg Gln Ala Pro Gly Lys Gly Leu Glu Gly Val
                        35                  40                  45

Ser Thr Ile Asn Ser Asp Gly Ser Thr Asn Tyr Ala Asp Ser Val Lys
                        50                  55                  60

Gly Arg Phe Thr Ile Ser Arg Asp Asn Ser Lys Asn Thr Leu Tyr Leu
```

```
                65                  70                  75                  80
            Gln Met Asn Ser Leu Arg Ala Glu Asp Thr Ala Val Tyr Tyr Cys Ala
                            85                  90                  95

Val Asp Leu Ala Pro Cys Trp Val Ala Gly Pro Ile Glu Ala Ala Asp
                            100                 105                 110

Phe Gly Tyr Trp Gly Gln Gly Thr Leu Val Thr Val Ser Ser Glu Pro
                            115                 120                 125

Lys Ser Ser Asp Lys Thr His Thr Ser Pro Pro Ser Pro Gln Val Gln
            130                 135                 140

Leu Val Gln Ser Gly Val Glu Val Lys Lys Pro Gly Ala Ser Val Lys
            145                 150                 155                 160

Val Ser Cys Lys Ala Ser Gly Tyr Thr Phe Thr Asn Tyr Tyr Met Tyr
                            165                 170                 175

Trp Val Arg Gln Ala Pro Gly Gln Gly Leu Glu Trp Met Gly Gly Ile
                            180                 185                 190

Asn Pro Ser Asn Gly Gly Thr Asn Phe Asn Glu Lys Phe Lys Asn Arg
                            195                 200                 205

Val Thr Leu Thr Thr Asp Ser Ser Thr Thr Ala Tyr Met Glu Leu
                            210                 215                 220

Lys Ser Leu Gln Phe Asp Asp Thr Ala Val Tyr Tyr Cys Ala Arg Arg
            225                 230                 235                 240

Asp Tyr Arg Phe Asp Met Gly Phe Asp Tyr Trp Gly Gln Gly Thr Thr
                            245                 250                 255

Val Thr Val Ser Ser Ala Ser Thr Lys Gly Pro Ser Val Phe Pro Leu
                            260                 265                 270

Ala Pro Cys Ser Arg Ser Thr Ser Glu Ser Thr Ala Ala Leu Gly Cys
                            275                 280                 285

Leu Val Lys Asp Tyr Phe Pro Glu Pro Val Thr Val Ser Trp Asn Ser
            290                 295                 300

Gly Ala Leu Thr Ser Gly Val His Thr Phe Pro Ala Val Leu Gln Ser
            305                 310                 315                 320

Ser Gly Leu Tyr Ser Leu Ser Ser Val Val Thr Val Pro Ser Ser Ser
                            325                 330                 335

Leu Gly Thr Lys Thr Tyr Thr Cys Asn Val Asp His Lys Pro Ser Asn
                            340                 345                 350

Thr Lys Val Asp Lys Arg Val Glu Ser Lys Tyr Gly Pro Pro Cys Pro
                            355                 360                 365

Pro Cys Pro Ala Pro Glu Phe Leu Gly Gly Pro Ser Val Phe Leu Phe
            370                 375                 380

Pro Pro Lys Pro Lys Asp Thr Leu Met Ile Ser Arg Thr Pro Glu Val
            385                 390                 395                 400

Thr Cys Val Val Val Asp Val Ser Gln Glu Asp Pro Glu Val Gln Phe
                            405                 410                 415

Asn Trp Tyr Val Asp Gly Val Glu Val His Asn Ala Lys Thr Lys Pro
                            420                 425                 430

Arg Glu Glu Gln Phe Asn Ser Thr Tyr Arg Val Val Ser Val Leu Thr
                            435                 440                 445

Val Leu His Gln Asp Trp Leu Asn Gly Lys Glu Tyr Lys Cys Lys Val
                            450                 455                 460

Ser Asn Lys Gly Leu Pro Ser Ser Ile Glu Lys Thr Ile Ser Lys Ala
            465                 470                 475                 480

Lys Gly Gln Pro Arg Glu Pro Gln Val Tyr Thr Leu Pro Pro Ser Gln
                            485                 490                 495
```

```
Glu Met Thr Lys Asn Gln Val Ser Leu Thr Cys Leu Val Lys Gly
            500                 505                 510
Phe Tyr Pro Ser Asp Ile Ala Val Glu Trp Glu Ser Asn Gly Gln Pro
        515                 520                 525
Glu Asn Asn Tyr Lys Thr Thr Pro Pro Val Leu Asp Ser Asp Gly Ser
        530                 535                 540
Phe Phe Leu Tyr Ser Arg Leu Thr Val Asp Lys Ser Arg Trp Gln Glu
545                 550                 555                 560
Gly Asn Val Phe Ser Cys Ser Val Met His Glu Ala Leu His Asn His
                565                 570                 575
Tyr Thr Gln Lys Ser Leu Ser Leu Ser Leu Gly Lys
            580                 585

<210> SEQ ID NO 363
<211> LENGTH: 218
<212> TYPE: PRT
<213> ORGANISM: Artificial Sequence
<220> FEATURE:
<223> OTHER INFORMATION: Synthetic Construct

<400> SEQUENCE: 363

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Lys Gly Val Ser Thr Ser
            20                  25                  30
Gly Tyr Ser Tyr Leu His Trp Tyr Gln Gln Lys Pro Gly Gln Ala Pro
        35                  40                  45
Arg Leu Leu Ile Tyr Leu Ala Ser Tyr Leu Glu Ser Gly Val Pro Ala
    50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Val Tyr Tyr Cys Gln His Ser Arg
                85                  90                  95
Asp Leu Pro Leu Thr Phe Gly Gly Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 364
<211> LENGTH: 447
<212> TYPE: PRT
<213> ORGANISM: Artificial Sequence
<220> FEATURE:
<223> OTHER INFORMATION: Synthetic Construct
```

<400> SEQUENCE: 364

| | | | | | | | | | | | | | | |
|---|---|---|---|---|---|---|---|---|---|---|---|---|---|---|
|Gln|Val|Gln|Leu|Val|Gln|Ser|Gly|Val|Glu|Val|Lys|Lys|Pro|Gly|Ala|
|1| | | |5| | | | |10| | | | |15|
|Ser|Val|Lys|Val|Ser|Cys|Lys|Ala|Ser|Gly|Tyr|Thr|Phe|Thr|Asn|Tyr|
| | | |20| | | | |25| | | | |30| |
|Tyr|Met|Tyr|Trp|Val|Arg|Gln|Ala|Pro|Gly|Gln|Gly|Leu|Glu|Trp|Met|
| | |35| | | | |40| | | | |45| | |
|Gly|Gly|Ile|Asn|Pro|Ser|Asn|Gly|Gly|Thr|Asn|Phe|Asn|Glu|Lys|Phe|
| |50| | | | |55| | | | |60| | | |
|Lys|Asn|Arg|Val|Thr|Leu|Thr|Thr|Asp|Ser|Ser|Thr|Thr|Thr|Ala|Tyr|
|65| | | | |70| | | | |75| | | | |80|
|Met|Glu|Leu|Lys|Ser|Leu|Gln|Phe|Asp|Asp|Thr|Ala|Val|Tyr|Tyr|Cys|
| | | | |85| | | | |90| | | | |95| |
|Ala|Arg|Arg|Asp|Tyr|Arg|Phe|Asp|Met|Gly|Phe|Asp|Tyr|Trp|Gly|Gln|
| | | |100| | | | |105| | | | |110| | |
|Gly|Thr|Thr|Val|Thr|Val|Ser|Ser|Ala|Ser|Thr|Lys|Gly|Pro|Ser|Val|
| | |115| | | | |120| | | | |125| | | |
|Phe|Pro|Leu|Ala|Pro|Cys|Ser|Arg|Ser|Thr|Ser|Glu|Ser|Thr|Ala|Ala|
| |130| | | | |135| | | | |140| | | | |
|Leu|Gly|Cys|Leu|Val|Lys|Asp|Tyr|Phe|Pro|Glu|Pro|Val|Thr|Val|Ser|
|145| | | | |150| | | | |155| | | | |160|
|Trp|Asn|Ser|Gly|Ala|Leu|Thr|Ser|Gly|Val|His|Thr|Phe|Pro|Ala|Val|
| | | | |165| | | | |170| | | | |175| |
|Leu|Gln|Ser|Ser|Gly|Leu|Tyr|Ser|Leu|Ser|Ser|Val|Val|Thr|Val|Pro|
| | | |180| | | | |185| | | | |190| | |
|Ser|Ser|Ser|Leu|Gly|Thr|Lys|Thr|Tyr|Thr|Cys|Asn|Val|Asp|His|Lys|
| | |195| | | | |200| | | | |205| | | |
|Pro|Ser|Asn|Thr|Lys|Val|Asp|Lys|Arg|Val|Glu|Ser|Lys|Tyr|Gly|Pro|
| |210| | | | |215| | | | |220| | | | |
|Pro|Cys|Pro|Pro|Cys|Pro|Ala|Pro|Glu|Phe|Leu|Gly|Gly|Pro|Ser|Val|
|225| | | | |230| | | | |235| | | | |240|
|Phe|Leu|Phe|Pro|Pro|Lys|Pro|Lys|Asp|Thr|Leu|Met|Ile|Ser|Arg|Thr|
| | | | |245| | | | |250| | | | |255| |
|Pro|Glu|Val|Thr|Cys|Val|Val|Val|Asp|Val|Ser|Gln|Glu|Asp|Pro|Glu|
| | | |260| | | | |265| | | | |270| | | |
|Val|Gln|Phe|Asn|Trp|Tyr|Val|Asp|Gly|Val|Glu|Val|His|Asn|Ala|Lys|
| | |275| | | | |280| | | | |285| | | |
|Thr|Lys|Pro|Arg|Glu|Glu|Gln|Phe|Asn|Ser|Thr|Tyr|Arg|Val|Val|Ser|
| |290| | | | |295| | | | |300| | | | |
|Val|Leu|Thr|Val|Leu|His|Gln|Asp|Trp|Leu|Asn|Gly|Lys|Glu|Tyr|Lys|
|305| | | | |310| | | | |315| | | | |320|
|Cys|Lys|Val|Ser|Asn|Lys|Gly|Leu|Pro|Ser|Ser|Ile|Glu|Lys|Thr|Ile|
| | | | |325| | | | |330| | | | |335| |
|Ser|Lys|Ala|Lys|Gly|Gln|Pro|Arg|Glu|Pro|Gln|Val|Tyr|Thr|Leu|Pro|
| | | |340| | | | |345| | | | |350| | |
|Pro|Ser|Gln|Glu|Glu|Met|Thr|Lys|Asn|Gln|Val|Ser|Leu|Thr|Cys|Leu|
| | |355| | | | |360| | | | |365| | | |
|Val|Lys|Gly|Phe|Tyr|Pro|Ser|Asp|Ile|Ala|Val|Glu|Trp|Glu|Ser|Asn|
| |370| | | | |375| | | | |380| | | | |
|Gly|Gln|Pro|Glu|Asn|Asn|Tyr|Lys|Thr|Thr|Pro|Pro|Val|Leu|Asp|Ser|
|385| | | | |390| | | | |395| | | | |400|
|Asp|Gly|Ser|Phe|Phe|Leu|Tyr|Ser|Arg|Leu|Thr|Val|Asp|Lys|Ser|Arg|
| | | | |405| | | | |410| | | | |415| |

```
Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445

<210> SEQ ID NO 365
<211> LENGTH: 359
<212> TYPE: PRT
<213> ORGANISM: Artificial Sequence
<220> FEATURE:
<223> OTHER INFORMATION: Synthetic Construct

<400> SEQUENCE: 365

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Gly Gly Tyr
            20                  25                  30

Cys Met Gly Trp Phe Arg Gln Ala Pro Gly Lys Gly Leu Glu Gly Val
        35                  40                  45

Ser Thr Ile Asn Ser Asp Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Val Asp Leu Ala Pro Cys Trp Val Ala Gly Pro Ile Glu Ala Ala Asp
            100                 105                 110

Phe Gly Tyr Trp Gly Gln Gly Thr Leu Val Thr Val Ser Ser Glu Pro
        115                 120                 125

Lys Ser Ser Asp Lys Thr His Thr Ser Pro Pro Ser Pro Glu Ile Val
    130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Lys Gly Val Ser Thr Ser Gly Tyr Ser
                165                 170                 175

Tyr Leu His Trp Tyr Gln Gln Lys Pro Gly Gln Ala Pro Arg Leu Leu
            180                 185                 190

Ile Tyr Leu Ala Ser Tyr Leu Glu Ser Gly Val Pro Ala Arg Phe Ser
        195                 200                 205

Gly Ser Gly Ser Gly Thr Asp Phe Thr Leu Thr Ile Ser Ser Leu Glu
    210                 215                 220

Pro Glu Asp Phe Ala Val Tyr Tyr Cys Gln His Ser Arg Asp Leu Pro
225                 230                 235                 240

Leu Thr Phe Gly Gly Gly Thr Lys Val Glu Ile Lys Arg Thr Val Ala
                245                 250                 255

Ala Pro Ser Val Phe Ile Phe Pro Pro Ser Asp Glu Gln Leu Lys Ser
            260                 265                 270

Gly Thr Ala Ser Val Val Cys Leu Leu Asn Asn Phe Tyr Pro Arg Glu
        275                 280                 285

Ala Lys Val Gln Trp Lys Val Asp Asn Ala Leu Gln Ser Gly Asn Ser
    290                 295                 300

Gln Glu Ser Val Thr Glu Gln Asp Ser Lys Asp Ser Thr Tyr Ser Leu
305                 310                 315                 320

Ser Ser Thr Leu Thr Leu Ser Lys Ala Asp Tyr Glu Lys His Lys Val
                325                 330                 335
```

Tyr Ala Cys Glu Val Thr His Gln Gly Leu Ser Ser Pro Val Thr Lys
            340                 345                 350

Ser Phe Asn Arg Gly Glu Cys
        355

<210> SEQ ID NO 366
<211> LENGTH: 9
<212> TYPE: PRT
<213> ORGANISM: Artificial Sequence
<220> FEATURE:
<223> OTHER INFORMATION: Synthetic Construct

<400> SEQUENCE: 366

Gly Gly Gly Gly Ser Gly Gly Gly Ser
1               5

<210> SEQ ID NO 367
<211> LENGTH: 15
<212> TYPE: PRT
<213> ORGANISM: Artificial Sequence
<220> FEATURE:
<223> OTHER INFORMATION: Synthetic Construct

<400> SEQUENCE: 367

Gly Gly Gly Gly Ser Gly Gly Gly Gly Ser Gly Gly Gly Gly Ser
1               5                   10                  15

<210> SEQ ID NO 368
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: can be present in repeat of at least 1

<400> SEQUENCE: 368

Gly
1

<210> SEQ ID NO 369
<211> LENGTH: 2
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(2)
<223> OTHER INFORMATION: can be present in repeat of at least 1

<400> SEQUENCE: 369

Gly Ser
1

<210> SEQ ID NO 370
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: can be present in repeat of at least 1

```
<400> SEQUENCE: 370

Gly Ser Gly Gly Ser
1               5

<210> SEQ ID NO 371
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: can be present in repeat of at least 1

<400> SEQUENCE: 371

Gly Gly Gly Ser
1

<210> SEQ ID NO 372
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: can be present in repeat of at least 1

<400> SEQUENCE: 372

Gly Gly Gly Gly Ser
1               5

<210> SEQ ID NO 373
<211> LENGTH: 444
<212> TYPE: PRT
<213> ORGANISM: Artificial Sequence
<220> FEATURE:
<223> OTHER INFORMATION: Synthetic Construct

<400> SEQUENCE: 373

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160
```

Gly Ala Leu Thr Ser Gly Val His Thr Phe Pro Ala Val Leu Gln Ser
              165                 170                 175

Ser Gly Leu Tyr Ser Leu Ser Ser Val Val Thr Val Pro Ser Ser Ser
          180                 185                 190

Leu Gly Thr Lys Thr Tyr Thr Cys Asn Val Asp His Lys Pro Ser Asn
          195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
              245                 250                 255

Thr Cys Val Val Val Asp Val Ser Gln Glu Asp Pro Glu Val Gln Phe
          260                 265                 270

Asn Trp Tyr Val Asp Gly Val Glu Val His Asn Ala Lys Thr Lys Pro
          275                 280                 285

Arg Glu Glu Gln Phe Asn Ser Thr Tyr Arg Val Val Ser Val Leu Thr
      290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
              325                 330                 335

Lys Gly Gln Pro Arg Glu Pro Gln Val Tyr Thr Leu Pro Pro Ser Gln
          340                 345                 350

Glu Glu Met Thr Lys Asn Gln Val Ser Leu Thr Cys Leu Val Lys Gly
          355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
              405                 410                 415

Gly Asn Val Phe Ser Cys Ser Val Met His Glu Ala Leu His Asn His
          420                 425                 430

Tyr Thr Gln Lys Ser Leu Ser Leu Ser Leu Gly Lys
          435                 440

<210> SEQ ID NO 374
<211> LENGTH: 214
<212> TYPE: PRT
<213> ORGANISM: Artificial Sequence
<220> FEATURE:
<223> OTHER INFORMATION: Synthetic Construct

<400> SEQUENCE: 374

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
              20                  25                  30

Val Ala Trp Tyr Gln Gln Lys Pro Gly Lys Ala Pro Lys Leu Leu Ile
          35                  40                  45

Tyr Trp Ala Ser Thr Arg His Thr Gly Val Pro Ser Arg Phe Ser Gly
      50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 375
<211> LENGTH: 583
<212> TYPE: PRT
<213> ORGANISM: Artificial Sequence
<220> FEATURE:
<223> OTHER INFORMATION: Synthetic Construct

<400> SEQUENCE: 375

Glu Val Gln Leu Val Glu Ser Gly Gly Gly Ser Val Gln Ala Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Gly Thr Ser Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asp Ser Leu Lys Pro Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Gln Val Thr Val Ser Ser Glu Pro Lys Ser
        115                 120                 125

Ser Asp Lys Thr His Thr Ser Pro Pro Ser Pro Glu Val Gln Leu Val
    130                 135                 140

Glu Ser Gly Gly Gly Leu Val Gln Pro Gly Gly Ser Leu Arg Leu Ser
145                 150                 155                 160

Cys Ala Ala Ser Gly Phe Val Phe Ser Arg Tyr Asp Met Ala Trp Val
                165                 170                 175

Arg Gln Ala Pro Gly Lys Gly Leu Glu Trp Val Ser Phe Ile Ser Gly
            180                 185                 190

Gly Gly Ser Asn Thr Tyr Tyr Pro Asp Thr Val Lys Gly Arg Phe Thr
        195                 200                 205

Ile Ser Arg Asp Asn Ser Lys Asn Thr Leu Tyr Leu Gln Met Asn Ser
    210                 215                 220
```

Leu Arg Ala Glu Asp Thr Ala Val Tyr Tyr Cys Ile Ser Pro Tyr Tyr
225                 230                 235                 240

Tyr Ala Met Glu Tyr Trp Gly Gln Gly Thr Thr Val Thr Val Ser Ser
            245                 250                 255

Ala Ser Thr Lys Gly Pro Ser Val Phe Pro Leu Ala Pro Cys Ser Arg
            260                 265                 270

Ser Thr Ser Glu Ser Thr Ala Ala Leu Gly Cys Leu Val Lys Asp Tyr
        275                 280                 285

Phe Pro Glu Pro Val Thr Val Ser Trp Asn Ser Gly Ala Leu Thr Ser
    290                 295                 300

Gly Val His Thr Phe Pro Ala Val Leu Gln Ser Ser Gly Leu Tyr Ser
305                 310                 315                 320

Leu Ser Ser Val Val Thr Val Pro Ser Ser Ser Leu Gly Thr Lys Thr
                325                 330                 335

Tyr Thr Cys Asn Val Asp His Lys Pro Ser Asn Thr Lys Val Asp Lys
            340                 345                 350

Arg Val Glu Ser Lys Tyr Gly Pro Pro Cys Pro Pro Cys Pro Ala Pro
        355                 360                 365

Glu Phe Leu Gly Gly Pro Ser Val Phe Leu Phe Pro Pro Lys Pro Lys
    370                 375                 380

Asp Thr Leu Met Ile Ser Arg Thr Pro Glu Val Thr Cys Val Val Val
385                 390                 395                 400

Asp Val Ser Gln Glu Asp Pro Glu Val Gln Phe Asn Trp Tyr Val Asp
                405                 410                 415

Gly Val Glu Val His Asn Ala Lys Thr Lys Pro Arg Glu Glu Gln Phe
            420                 425                 430

Asn Ser Thr Tyr Arg Val Val Ser Val Leu Thr Val Leu His Gln Asp
        435                 440                 445

Trp Leu Asn Gly Lys Glu Tyr Lys Cys Lys Val Ser Asn Lys Gly Leu
    450                 455                 460

Pro Ser Ser Ile Glu Lys Thr Ile Ser Lys Ala Lys Gly Gln Pro Arg
465                 470                 475                 480

Glu Pro Gln Val Tyr Thr Leu Pro Pro Ser Gln Glu Glu Met Thr Lys
                485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
        515                 520                 525

Thr Thr Pro Pro Val Leu Asp Ser Asp Gly Ser Phe Phe Leu Tyr Ser
    530                 535                 540

Arg Leu Thr Val Asp Lys Ser Arg Trp Gln Glu Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Leu Gly Lys
            580

<210> SEQ ID NO 376
<211> LENGTH: 214
<212> TYPE: PRT
<213> ORGANISM: Artificial Sequence
<220> FEATURE:
<223> OTHER INFORMATION: Synthetic Construct

<400> SEQUENCE: 376

```
Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50              55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 377
<211> LENGTH: 580
<212> TYPE: PRT
<213> ORGANISM: Artificial Sequence
<220> FEATURE:
<223> OTHER INFORMATION: Synthetic Construct

<400> SEQUENCE: 377

Gln Val Gln Leu Ala Glu Ser Gly Gly Gly Ser Val Gln Ala Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Glu Arg Glu Gly Val
        35                  40                  45

Ala Ala Ile Asp Ser Asp Gly Ser Thr Ser Tyr Ala Asp Ser Val Lys
50              55                  60

Gly Arg Phe Thr Ile Ser Lys Asp Asn Ala Lys Asn Thr Leu Tyr Leu
65              70                  75                  80

Gln Met Asn Ser Leu Lys Pro Glu Asp Thr Ala Met Tyr Tyr Cys Ala
                85                  90                  95

Ala Asp Phe Cys Trp Val Asp Asp Phe Tyr Glu Tyr Asn Tyr Trp Gly
            100                 105                 110

Gln Gly Thr Gln Val Thr Val Ser Ser Glu Pro Lys Ser Ser Asp Lys
        115                 120                 125

Thr His Thr Ser Pro Pro Ser Pro Glu Val Gln Leu Val Glu Ser Gly
    130                 135                 140
```

-continued

Gly Gly Leu Val Gln Pro Gly Gly Ser Leu Arg Leu Ser Cys Ala Ala
145                 150                 155                 160

Ser Gly Phe Val Phe Ser Arg Tyr Asp Met Ala Trp Val Arg Gln Ala
            165                 170                 175

Pro Gly Lys Gly Leu Glu Trp Val Ser Phe Ile Ser Gly Gly Gly Ser
        180                 185                 190

Asn Thr Tyr Tyr Pro Asp Thr Val Lys Gly Arg Phe Thr Ile Ser Arg
    195                 200                 205

Asp Asn Ser Lys Asn Thr Leu Tyr Leu Gln Met Asn Ser Leu Arg Ala
210                 215                 220

Glu Asp Thr Ala Val Tyr Tyr Cys Ile Ser Pro Tyr Tyr Ala Met
225                 230                 235                 240

Glu Tyr Trp Gly Gln Gly Thr Val Thr Val Ser Ala Ser Thr
            245                 250                 255

Lys Gly Pro Ser Val Phe Pro Leu Ala Pro Cys Ser Arg Ser Thr Ser
        260                 265                 270

Glu Ser Thr Ala Ala Leu Gly Cys Leu Val Lys Asp Tyr Phe Pro Glu
    275                 280                 285

Pro Val Thr Val Ser Trp Asn Ser Gly Ala Leu Thr Ser Gly Val His
290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Lys Thr Tyr Thr Cys
            325                 330                 335

Asn Val Asp His Lys Pro Ser Asn Thr Lys Val Asp Lys Arg Val Glu
        340                 345                 350

Ser Lys Tyr Gly Pro Pro Cys Pro Pro Cys Pro Ala Pro Glu Phe Leu
    355                 360                 365

Gly Gly Pro Ser Val Phe Leu Phe Pro Pro Lys Pro Lys Asp Thr Leu
370                 375                 380

Met Ile Ser Arg Thr Pro Glu Val Thr Cys Val Val Val Asp Val Ser
385                 390                 395                 400

Gln Glu Asp Pro Glu Val Gln Phe Asn Trp Tyr Val Asp Gly Val Glu
            405                 410                 415

Val His Asn Ala Lys Thr Lys Pro Arg Glu Glu Gln Phe Asn Ser Thr
        420                 425                 430

Tyr Arg Val Val Ser Val Leu Thr Val Leu His Gln Asp Trp Leu Asn
    435                 440                 445

Gly Lys Glu Tyr Lys Cys Lys Val Ser Asn Lys Gly Leu Pro Ser Ser
450                 455                 460

Ile Glu Lys Thr Ile Ser Lys Ala Lys Gly Gln Pro Arg Glu Pro Gln
465                 470                 475                 480

Val Tyr Thr Leu Pro Pro Ser Gln Glu Glu Met Thr Lys Asn Gln Val
            485                 490                 495

Ser Leu Thr Cys Leu Val Lys Gly Phe Tyr Pro Ser Asp Ile Ala Val
        500                 505                 510

Glu Trp Glu Ser Asn Gly Gln Pro Glu Asn Asn Tyr Lys Thr Thr Pro
    515                 520                 525

Pro Val Leu Asp Ser Asp Gly Ser Phe Phe Leu Tyr Ser Arg Leu Thr
530                 535                 540

Val Asp Lys Ser Arg Trp Gln Glu Gly Asn Val Phe Ser Cys Ser Val
545                 550                 555                 560

Met His Glu Ala Leu His Asn His Tyr Thr Gln Lys Ser Leu Ser Leu

-continued

```
                 565                 570                 575

Ser Leu Gly Lys
            580

<210> SEQ ID NO 378
<211> LENGTH: 214
<212> TYPE: PRT
<213> ORGANISM: Artificial Sequence
<220> FEATURE:
<223> OTHER INFORMATION: Synthetic Construct

<400> SEQUENCE: 378

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 379
<211> LENGTH: 585
<212> TYPE: PRT
<213> ORGANISM: Artificial Sequence
<220> FEATURE:
<223> OTHER INFORMATION: Synthetic Construct

<400> SEQUENCE: 379

Glu Val Gln Leu Ala Glu Ser Gly Gly Gly Ser Val Gln Ala Gly Gly
1               5                   10                  15

Ser Leu Arg Leu Ser Cys Ala Ala Ser Gly Tyr Thr Tyr Gly Gly Tyr
            20                  25                  30

Cys Met Gly Trp Phe Arg Gln Ala Pro Gly Lys Glu Arg Glu Gly Val
        35                  40                  45

Ala Thr Ile Asn Ser Asp Gly Ser Thr Asn Tyr Ala Asp Ser Val Lys
    50                  55                  60
```

```
Gly Arg Phe Thr Ile Ser Lys Asp Asn Ala Lys Asn Thr Leu Tyr Leu
65                  70                  75                  80

Gln Met Asn Ser Leu Ser Pro Glu Asp Thr Ala Met Tyr Tyr Cys Ala
                85                  90                  95

Val Asp Leu Ala Pro Cys Trp Val Ala Gly Pro Ile Glu Ala Ala Asp
            100                 105                 110

Phe Gly Tyr Trp Gly Gln Gly Thr Gln Val Thr Val Ser Ser Glu Pro
        115                 120                 125

Lys Ser Ser Asp Lys Thr His Thr Ser Pro Pro Ser Pro Glu Val Gln
130                 135                 140

Leu Val Glu Ser Gly Gly Gly Leu Val Gln Pro Gly Gly Ser Leu Arg
145                 150                 155                 160

Leu Ser Cys Ala Ala Ser Gly Phe Val Phe Ser Arg Tyr Asp Met Ala
                165                 170                 175

Trp Val Arg Gln Ala Pro Gly Lys Gly Leu Glu Trp Val Ser Phe Ile
            180                 185                 190

Ser Gly Gly Gly Ser Asn Thr Tyr Tyr Pro Asp Thr Val Lys Gly Arg
        195                 200                 205

Phe Thr Ile Ser Arg Asp Asn Ser Lys Asn Thr Leu Tyr Leu Gln Met
210                 215                 220

Asn Ser Leu Arg Ala Glu Asp Thr Ala Val Tyr Tyr Cys Ile Ser Pro
225                 230                 235                 240

Tyr Tyr Tyr Ala Met Glu Tyr Trp Gly Gln Gly Thr Thr Val Thr Val
                245                 250                 255

Ser Ser Ala Ser Thr Lys Gly Pro Ser Val Phe Pro Leu Ala Pro Cys
            260                 265                 270

Ser Arg Ser Thr Ser Glu Ser Thr Ala Ala Leu Gly Cys Leu Val Lys
            275                 280                 285

Asp Tyr Phe Pro Glu Pro Val Thr Val Ser Trp Asn Ser Gly Ala Leu
            290                 295                 300

Thr Ser Gly Val His Thr Phe Pro Ala Val Leu Gln Ser Ser Gly Leu
305                 310                 315                 320

Tyr Ser Leu Ser Ser Val Val Thr Val Pro Ser Ser Ser Leu Gly Thr
                325                 330                 335

Lys Thr Tyr Thr Cys Asn Val Asp His Lys Pro Ser Asn Thr Lys Val
                340                 345                 350

Asp Lys Arg Val Glu Ser Lys Tyr Gly Pro Pro Cys Pro Pro Cys Pro
            355                 360                 365

Ala Pro Glu Phe Leu Gly Gly Pro Ser Val Phe Leu Phe Pro Pro Lys
370                 375                 380

Pro Lys Asp Thr Leu Met Ile Ser Arg Thr Pro Glu Val Thr Cys Val
385                 390                 395                 400

Val Val Asp Val Ser Gln Glu Asp Pro Glu Val Gln Phe Asn Trp Tyr
                405                 410                 415

Val Asp Gly Val Glu Val His Asn Ala Lys Thr Lys Pro Arg Glu Glu
            420                 425                 430

Gln Phe Asn Ser Thr Tyr Arg Val Val Ser Val Leu Thr Val Leu His
            435                 440                 445

Gln Asp Trp Leu Asn Gly Lys Glu Tyr Lys Cys Lys Val Ser Asn Lys
            450                 455                 460

Gly Leu Pro Ser Ser Ile Glu Lys Thr Ile Ser Lys Ala Lys Gly Gln
465                 470                 475                 480

Pro Arg Glu Pro Gln Val Tyr Thr Leu Pro Pro Ser Gln Glu Glu Met
```

-continued

```
                        485                 490                 495
Thr Lys Asn Gln Val Ser Leu Thr Cys Leu Val Lys Gly Phe Tyr Pro
                    500                 505                 510

Ser Asp Ile Ala Val Glu Trp Glu Ser Asn Gly Gln Pro Glu Asn Asn
                515                 520                 525

Tyr Lys Thr Thr Pro Pro Val Leu Asp Ser Asp Gly Ser Phe Phe Leu
            530                 535                 540

Tyr Ser Arg Leu Thr Val Asp Lys Ser Arg Trp Gln Glu Gly Asn Val
545                 550                 555                 560

Phe Ser Cys Ser Val Met His Glu Ala Leu His Asn His Tyr Thr Gln
                565                 570                 575

Lys Ser Leu Ser Leu Ser Leu Gly Lys
                580                 585

<210> SEQ ID NO 380
<211> LENGTH: 214
<212> TYPE: PRT
<213> ORGANISM: Artificial Sequence
<220> FEATURE:
<223> OTHER INFORMATION: Synthetic Construct

<400> SEQUENCE: 380

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 381
<211> LENGTH: 581
<212> TYPE: PRT
<213> ORGANISM: Artificial Sequence
<220> FEATURE:
<223> OTHER INFORMATION: Synthetic Construct
```

<400> SEQUENCE: 381

```
Gln Val His Leu Met Glu Ser Gly Gly Gly Ser Val Gln Val Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Glu Arg Glu Gly Val
            35                  40                  45

Ala Ala Ile Asp Ser Asp Gly Ser Val Ser Tyr Ala Asp Ser Val Lys
        50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Gln Val Thr Val Ser Ser Glu Pro Lys Ser Ser Asp
        115                 120                 125

Lys Thr His Thr Ser Pro Pro Ser Pro Glu Val Gln Leu Val Glu Ser
130                 135                 140

Gly Gly Gly Leu Val Gln Pro Gly Gly Ser Leu Arg Leu Ser Cys Ala
145                 150                 155                 160

Ala Ser Gly Phe Val Phe Ser Arg Tyr Asp Met Ala Trp Val Arg Gln
                165                 170                 175

Ala Pro Gly Lys Gly Leu Glu Trp Val Ser Phe Ile Ser Gly Gly Gly
            180                 185                 190

Ser Asn Thr Tyr Tyr Pro Asp Thr Val Lys Gly Arg Phe Thr Ile Ser
        195                 200                 205

Arg Asp Asn Ser Lys Asn Thr Leu Tyr Leu Gln Met Asn Ser Leu Arg
210                 215                 220

Ala Glu Asp Thr Ala Val Tyr Tyr Cys Ile Ser Pro Tyr Tyr Tyr Ala
225                 230                 235                 240

Met Glu Tyr Trp Gly Gln Gly Thr Thr Val Thr Val Ser Ser Ala Ser
                245                 250                 255

Thr Lys Gly Pro Ser Val Phe Pro Leu Ala Pro Cys Ser Arg Ser Thr
            260                 265                 270

Ser Glu Ser Thr Ala Ala Leu Gly Cys Leu Val Lys Asp Tyr Phe Pro
        275                 280                 285

Glu Pro Val Thr Val Ser Trp Asn Ser Gly Ala Leu Thr Ser Gly Val
    290                 295                 300

His Thr Phe Pro Ala Val Leu Gln Ser Ser Gly Leu Tyr Ser Leu Ser
305                 310                 315                 320

Ser Val Val Thr Val Pro Ser Ser Ser Leu Gly Thr Lys Thr Tyr Thr
                325                 330                 335

Cys Asn Val Asp His Lys Pro Ser Asn Thr Lys Val Asp Lys Arg Val
            340                 345                 350

Glu Ser Lys Tyr Gly Pro Pro Cys Pro Pro Cys Pro Ala Pro Glu Phe
        355                 360                 365

Leu Gly Gly Pro Ser Val Phe Leu Phe Pro Pro Lys Pro Lys Asp Thr
    370                 375                 380

Leu Met Ile Ser Arg Thr Pro Glu Val Thr Cys Val Val Val Asp Val
385                 390                 395                 400

Ser Gln Glu Asp Pro Glu Val Gln Phe Asn Trp Tyr Val Asp Gly Val
```

405                 410                 415
Glu Val His Asn Ala Lys Thr Lys Pro Arg Glu Glu Gln Phe Asn Ser
            420                 425                 430
Thr Tyr Arg Val Val Ser Val Leu Thr Val Leu His Gln Asp Trp Leu
        435                 440                 445
Asn Gly Lys Glu Tyr Lys Cys Lys Val Ser Asn Lys Gly Leu Pro Ser
    450                 455                 460
Ser Ile Glu Lys Thr Ile Ser Lys Ala Lys Gly Gln Pro Arg Glu Pro
465                 470                 475                 480
Gln Val Tyr Thr Leu Pro Pro Ser Gln Glu Glu Met Thr Lys Asn Gln
                485                 490                 495
Val Ser Leu Thr Cys Leu Val Lys Gly Phe Tyr Pro Ser Asp Ile Ala
            500                 505                 510
Val Glu Trp Glu Ser Asn Gly Gln Pro Glu Asn Asn Tyr Lys Thr Thr
        515                 520                 525
Pro Pro Val Leu Asp Ser Asp Gly Ser Phe Phe Leu Tyr Ser Arg Leu
    530                 535                 540
Thr Val Asp Lys Ser Arg Trp Gln Glu Gly Asn Val Phe Ser Cys Ser
545                 550                 555                 560
Val Met His Glu Ala Leu His Asn His Tyr Thr Gln Lys Ser Leu Ser
                565                 570                 575
Leu Ser Leu Gly Lys
            580

<210> SEQ ID NO 382
<211> LENGTH: 214
<212> TYPE: PRT
<213> ORGANISM: Artificial Sequence
<220> FEATURE:
<223> OTHER INFORMATION: Synthetic Construct

<400> SEQUENCE: 382

Asp Ile Gln Met Thr Gln Ser Pro Ser Ser Val Ser Ala Ser Val Gly
1               5                   10                  15
Asp Arg Val Thr Ile Thr Cys Lys Ala Ser Gln Asp Val Asp Thr Ala
            20                  25                  30
Val Ala Trp Tyr Gln Gln Lys Pro Gly Lys Ala Pro Lys Leu Leu Ile
        35                  40                  45
Tyr Trp Ala Ser Thr Arg His Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Thr Phe Pro Trp
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr

```
            180                 185                 190
Ala Cys Glu Val Thr His Gln Gly Leu Ser Ser Pro Val Thr Lys Ser
        195                 200                 205

Phe Asn Arg Gly Glu Cys
    210

<210> SEQ ID NO 383
<211> LENGTH: 583
<212> TYPE: PRT
<213> ORGANISM: Artificial Sequence
<220> FEATURE:
<223> OTHER INFORMATION: Synthetic Construct

<400> SEQUENCE: 383

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser Glu Pro Lys Ser
        115                 120                 125

Ser Asp Lys Thr His Thr Ser Pro Pro Ser Pro Glu Val Gln Leu Val
    130                 135                 140

Glu Ser Gly Gly Gly Leu Val Gln Pro Gly Gly Ser Leu Arg Leu Ser
145                 150                 155                 160

Cys Ala Ala Ser Gly Phe Val Phe Ser Arg Tyr Asp Met Ala Trp Val
                165                 170                 175

Arg Gln Ala Pro Gly Lys Gly Leu Glu Trp Val Ser Phe Ile Ser Gly
            180                 185                 190

Gly Gly Ser Asn Thr Tyr Tyr Pro Asp Thr Val Lys Gly Arg Phe Thr
        195                 200                 205

Ile Ser Arg Asp Asn Ser Lys Asn Thr Leu Tyr Leu Gln Met Asn Ser
    210                 215                 220

Leu Arg Ala Glu Asp Thr Ala Val Tyr Tyr Cys Ile Ser Pro Tyr Tyr
225                 230                 235                 240

Tyr Ala Met Glu Tyr Trp Gly Gln Gly Thr Thr Val Thr Val Ser Ser
                245                 250                 255

Ala Ser Thr Lys Gly Pro Ser Val Phe Pro Leu Ala Pro Cys Ser Arg
            260                 265                 270

Ser Thr Ser Glu Ser Thr Ala Ala Leu Gly Cys Leu Val Lys Asp Tyr
        275                 280                 285

Phe Pro Glu Pro Val Thr Val Ser Trp Asn Ser Gly Ala Leu Thr Ser
    290                 295                 300

Gly Val His Thr Phe Pro Ala Val Leu Gln Ser Ser Gly Leu Tyr Ser
305                 310                 315                 320

Leu Ser Ser Val Val Thr Val Pro Ser Ser Ser Leu Gly Thr Lys Thr
```

```
                    325                 330                 335
Tyr Thr Cys Asn Val Asp His Lys Pro Ser Asn Thr Lys Val Asp Lys
                340                 345                 350

Arg Val Glu Ser Lys Tyr Gly Pro Pro Cys Pro Pro Cys Pro Ala Pro
            355                 360                 365

Glu Phe Leu Gly Gly Pro Ser Val Phe Leu Phe Pro Pro Lys Pro Lys
        370                 375                 380

Asp Thr Leu Met Ile Ser Arg Thr Pro Glu Val Thr Cys Val Val Val
385                 390                 395                 400

Asp Val Ser Gln Glu Asp Pro Glu Val Gln Phe Asn Trp Tyr Val Asp
                405                 410                 415

Gly Val Glu Val His Asn Ala Lys Thr Lys Pro Arg Glu Glu Gln Phe
                420                 425                 430

Asn Ser Thr Tyr Arg Val Val Ser Val Leu Thr Val Leu His Gln Asp
            435                 440                 445

Trp Leu Asn Gly Lys Glu Tyr Lys Cys Lys Val Ser Asn Lys Gly Leu
        450                 455                 460

Pro Ser Ser Ile Glu Lys Thr Ile Ser Lys Ala Lys Gly Gln Pro Arg
465                 470                 475                 480

Glu Pro Gln Val Tyr Thr Leu Pro Pro Ser Gln Glu Glu Met Thr Lys
                485                 490                 495

Asn Gln Val Ser Leu Thr Cys Leu Val Lys Gly Phe Tyr Pro Ser Asp
                500                 505                 510

Ile Ala Val Glu Trp Glu Ser Asn Gly Gln Pro Glu Asn Asn Tyr Lys
            515                 520                 525

Thr Thr Pro Pro Val Leu Asp Ser Asp Gly Ser Phe Phe Leu Tyr Ser
        530                 535                 540

Arg Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Leu Gly Lys
            580

<210> SEQ ID NO 384
<211> LENGTH: 214
<212> TYPE: PRT
<213> ORGANISM: Artificial Sequence
<220> FEATURE:
<223> OTHER INFORMATION: Synthetic Construct

<400> SEQUENCE: 384

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
                20                  25                  30

Val Ala Trp Tyr Gln Gln Lys Pro Gly Lys Ala Pro Lys Leu Leu Ile
            35                  40                  45

Tyr Trp Ala Ser Thr Arg His Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
```

```
                100             105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135             140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 385
<211> LENGTH: 583
<212> TYPE: PRT
<213> ORGANISM: Artificial Sequence
<220> FEATURE:
<223> OTHER INFORMATION: Synthetic Construct

<400> SEQUENCE: 385

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
        210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
```

```
                    245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Glu Pro Lys Ser
        435                 440                 445

Ser Asp Lys Thr His Thr Ser Pro Pro Ser Pro Glu Val Gln Leu Val
    450                 455                 460

Glu Ser Gly Gly Gly Leu Val Gln Pro Gly Gly Ser Leu Arg Leu Ser
465                 470                 475                 480

Cys Ala Ala Ser Gly Tyr Ile Ile Ser Ser Tyr Cys Met Gly Trp Phe
                485                 490                 495

Arg Gln Ala Pro Gly Lys Gly Leu Glu Gly Val Ala Ala Ile Asp Ser
            500                 505                 510

Asp Gly Gly Thr Ser Tyr Ala Asp Ser Val Lys Gly Arg Phe Thr Ile
        515                 520                 525

Ser Lys Asp Asn Ser Lys Asn Thr Leu Tyr Leu Gln Met Asn Ser Leu
    530                 535                 540

Arg Ala Glu Asp Thr Ala Met Tyr Tyr Cys Ala Ala Asp Phe Cys Trp
545                 550                 555                 560

Val Asp Glu Asp Arg His Leu Tyr Glu Tyr Asn Ser Trp Gly Gln Gly
                565                 570                 575

Thr Leu Val Thr Val Ser Ser
            580

<210> SEQ ID NO 386
<211> LENGTH: 214
<212> TYPE: PRT
<213> ORGANISM: Artificial Sequence
<220> FEATURE:
<223> OTHER INFORMATION: Synthetic Construct

<400> SEQUENCE: 386

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
```

```
                20                  25                  30
Val Ala Trp Tyr Gln Gln Lys Pro Gly Lys Ala Pro Lys Leu Leu Ile
             35                  40                  45
Tyr Trp Ala Ser Thr Arg His Thr Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Ser Thr Phe Pro Trp
                 85                  90                  95
Thr Phe Gly Gly Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 387
<211> LENGTH: 444
<212> TYPE: PRT
<213> ORGANISM: Artificial Sequence
<220> FEATURE:
<223> OTHER INFORMATION: Synthetic Construct

<400> SEQUENCE: 387

Glu Val Gln Leu Val Glu Ser Gly Gly Gly Leu Val Gln Pro Gly Gly
1               5                  10                  15
Ser Leu Arg Leu Ser Cys Ala Ala Ser Gly Phe Val Phe Ser Arg Tyr
             20                  25                  30
Asp Met Ala Trp Val Arg Gln Ala Pro Gly Lys Gly Leu Glu Trp Val
             35                  40                  45
Ser Phe Ile Ser Gly Gly Gly Ser Asn Thr Tyr Tyr Pro Asp Thr Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ile Ser Pro Tyr Tyr Tyr Ala Met Glu Tyr Trp Gly Gln Gly Thr Thr
                100                 105                 110
Val Thr Val Ser Ser Ala Ser Thr Lys Gly Pro Ser Val Phe Pro Leu
            115                 120                 125
Ala Pro Cys Ser Arg Ser Thr Ser Glu Ser Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
```

```
                165                 170                 175
Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 388
<211> LENGTH: 353
<212> TYPE: PRT
<213> ORGANISM: Artificial Sequence
<220> FEATURE:
<223> OTHER INFORMATION: Synthetic Construct

<400> SEQUENCE: 388

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Gly Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Tyr Cys Ala
```

```
                         85                   90                   95
Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser Glu Pro Lys Ser
            115                 120                 125

Ser Asp Lys Thr His Thr Ser Pro Pro Ser Pro Asp Ile Gln Met Thr
    130                 135                 140

Gln Ser Pro Ser Ser Val Ser Ala Ser Val Gly Asp Arg Val Thr Ile
145                 150                 155                 160

Thr Cys Lys Ala Ser Gln Asp Val Asp Thr Ala Val Ala Trp Tyr Gln
                165                 170                 175

Gln Lys Pro Gly Lys Ala Pro Lys Leu Leu Ile Tyr Trp Ala Ser Thr
            180                 185                 190

Arg His Thr Gly Val Pro Ser Arg Phe Ser Gly Ser Gly Ser Gly Thr
    195                 200                 205

Asp Phe Thr Leu Thr Ile Ser Ser Leu Gln Pro Glu Asp Phe Ala Thr
    210                 215                 220

Tyr Tyr Cys Gln Gln Tyr Ser Thr Phe Pro Trp Thr Phe Gly Gly Gly
225                 230                 235                 240

Thr Lys Val Glu Ile Lys Arg Thr Val Ala Ala Pro Ser Val Phe Ile
                245                 250                 255

Phe Pro Pro Ser Asp Glu Gln Leu Lys Ser Gly Thr Ala Ser Val Val
            260                 265                 270

Cys Leu Leu Asn Asn Phe Tyr Pro Arg Glu Ala Lys Val Gln Trp Lys
            275                 280                 285

Val Asp Asn Ala Leu Gln Ser Gly Asn Ser Gln Glu Ser Val Thr Glu
    290                 295                 300

Gln Asp Ser Lys Asp Ser Thr Tyr Ser Leu Ser Ser Thr Leu Thr Leu
305                 310                 315                 320

Ser Lys Ala Asp Tyr Glu Lys His Lys Val Tyr Ala Cys Glu Val Thr
                325                 330                 335

His Gln Gly Leu Ser Ser Pro Val Thr Lys Ser Phe Asn Arg Gly Glu
            340                 345                 350

Cys

<210> SEQ ID NO 389
<211> LENGTH: 444
<212> TYPE: PRT
<213> ORGANISM: Artificial Sequence
<220> FEATURE:
<223> OTHER INFORMATION: Synthetic Construct

<400> SEQUENCE: 389

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ile Ser Pro Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 390
<211> LENGTH: 353
<212> TYPE: PRT
<213> ORGANISM: Artificial Sequence
<220> FEATURE:
<223> OTHER INFORMATION: Synthetic Construct

<400> SEQUENCE: 390

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Pro Lys Ser Ser Asp Lys Thr His Thr
    210                 215                 220

Ser Pro Pro Ser Pro Glu Val Gln Leu Val Glu Ser Gly Gly Gly Leu
225                 230                 235                 240

Val Gln Pro Gly Gly Ser Leu Arg Leu Ser Cys Ala Ala Ser Gly Tyr
                245                 250                 255

Ile Ile Ser Ser Tyr Cys Met Gly Trp Phe Arg Gln Ala Pro Gly Lys
            260                 265                 270

Gly Leu Glu Gly Val Ala Ala Ile Asp Ser Asp Gly Thr Ser Tyr
        275                 280                 285

Ala Asp Ser Val Lys Gly Arg Phe Thr Ile Ser Lys Asp Asn Ser Lys
    290                 295                 300

Asn Thr Leu Tyr Leu Gln Met Asn Ser Leu Arg Ala Glu Asp Thr Ala
305                 310                 315                 320

Met Tyr Tyr Cys Ala Ala Asp Phe Cys Trp Val Asp Glu Asp Arg His
                325                 330                 335

Leu Tyr Gly Tyr Asn Ser Trp Gly Gln Gly Thr Leu Val Thr Val Ser
            340                 345                 350

Ser

<210> SEQ ID NO 391
<211> LENGTH: 580
<212> TYPE: PRT
<213> ORGANISM: Artificial Sequence
<220> FEATURE:
<223> OTHER INFORMATION: Synthetic Construct

<400> SEQUENCE: 391

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Tyr Thr Ile Ser Ser Tyr
            20                  25                  30
Cys Met Gly Trp Phe Arg Gln Ala Pro Gly Lys Gly Leu Glu Gly Val
        35                  40                  45
Ala Ala Ile Asp Ser Asp Gly Ser Thr Ser Tyr Ala Asp Ser Val Lys
50                  55                  60
Gly Arg Phe Thr Ile Ser Lys Asp Asn Ser Lys Asn Thr Leu Tyr Leu
65                  70                  75                  80
Gln Met Asn Ser Leu Arg Ala Glu Asp Thr Ala Val Tyr Tyr Cys Ala
            85                  90                  95
Ala Asp Phe Cys Trp Val Asp Asp Phe Tyr Glu Tyr Asn Tyr Trp Gly
        100                 105                 110
Gln Gly Thr Leu Val Thr Val Ser Ser Glu Pro Lys Ser Ser Asp Lys
    115                 120                 125
Thr His Thr Ser Pro Pro Ser Pro Glu Val Gln Leu Val Glu Ser Gly
130                 135                 140
Gly Gly Leu Val Gln Pro Gly Gly Ser Leu Arg Leu Ser Cys Ala Ala
145                 150                 155                 160
Ser Gly Phe Val Phe Ser Arg Tyr Asp Met Ala Trp Val Arg Gln Ala
            165                 170                 175
Pro Gly Lys Gly Leu Glu Trp Val Ser Phe Ile Ser Gly Gly Gly Ser
        180                 185                 190
Asn Thr Tyr Tyr Pro Asp Thr Val Lys Gly Arg Phe Thr Ile Ser Arg
    195                 200                 205
Asp Asn Ser Lys Asn Thr Leu Tyr Leu Gln Met Asn Ser Leu Arg Ala
210                 215                 220
Glu Asp Thr Ala Val Tyr Tyr Cys Ile Ser Pro Tyr Tyr Ala Met
225                 230                 235                 240
Glu Tyr Trp Gly Gln Gly Thr Thr Val Thr Val Ser Ala Ser Thr
            245                 250                 255
Lys Gly Pro Ser Val Phe Pro Leu Ala Pro Cys Ser Arg Ser Thr Ser
        260                 265                 270
Glu Ser Thr Ala Ala Leu Gly Cys Leu Val Lys Asp Tyr Phe Pro Glu
    275                 280                 285
Pro Val Thr Val Ser Trp Asn Ser Gly Ala Leu Thr Ser Gly Val His
290                 295                 300
Thr Phe Pro Ala Val Leu Gln Ser Ser Gly Leu Tyr Ser Leu Ser Ser
305                 310                 315                 320
Val Val Thr Val Pro Ser Ser Ser Leu Gly Thr Lys Thr Tyr Thr Cys
            325                 330                 335
Asn Val Asp His Lys Pro Ser Asn Thr Lys Val Asp Lys Arg Val Glu
        340                 345                 350
Ser Lys Tyr Gly Pro Pro Cys Pro Pro Cys Pro Ala Pro Glu Phe Leu
    355                 360                 365
Gly Gly Pro Ser Val Phe Leu Phe Pro Pro Lys Pro Lys Asp Thr Leu
370                 375                 380
Met Ile Ser Arg Thr Pro Glu Val Thr Cys Val Val Val Asp Val Ser
385                 390                 395                 400
Gln Glu Asp Pro Glu Val Gln Phe Asn Trp Tyr Val Asp Gly Val Glu
            405                 410                 415
Val His Asn Ala Lys Thr Lys Pro Arg Glu Glu Gln Phe Asn Ser Thr
        420                 425                 430
Tyr Arg Val Val Ser Val Leu Thr Val Leu His Gln Asp Trp Leu Asn
```

```
                435                 440                 445
Gly Lys Glu Tyr Lys Cys Lys Val Ser Asn Lys Gly Leu Pro Ser Ser
            450                 455                 460

Ile Glu Lys Thr Ile Ser Lys Ala Lys Gly Gln Pro Arg Glu Pro Gln
465                 470                 475                 480

Val Tyr Thr Leu Pro Pro Ser Gln Glu Glu Met Thr Lys Asn Gln Val
                485                 490                 495

Ser Leu Thr Cys Leu Val Lys Gly Phe Tyr Pro Ser Asp Ile Ala Val
            500                 505                 510

Glu Trp Glu Ser Asn Gly Gln Pro Glu Asn Asn Tyr Lys Thr Thr Pro
            515                 520                 525

Pro Val Leu Asp Ser Asp Gly Ser Phe Phe Leu Tyr Ser Arg Leu Thr
            530                 535                 540

Val Asp Lys Ser Arg Trp Gln Glu Gly Asn Val Phe Ser Cys Ser Val
545                 550                 555                 560

Met His Glu Ala Leu His Asn His Tyr Thr Gln Lys Ser Leu Ser Leu
            565                 570                 575

Ser Leu Gly Lys
            580

<210> SEQ ID NO 392
<211> LENGTH: 214
<212> TYPE: PRT
<213> ORGANISM: Artificial Sequence
<220> FEATURE:
<223> OTHER INFORMATION: Synthetic Construct

<400> SEQUENCE: 392

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
            35                  40                  45

Tyr Trp Ala Ser Thr Arg His Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

<210> SEQ ID NO 393
<211> LENGTH: 580
<212> TYPE: PRT
<213> ORGANISM: Artificial Sequence
<220> FEATURE:
<223> OTHER INFORMATION: Synthetic Construct

<400> SEQUENCE: 393

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
```

```
                    355                 360                 365
Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Glu Pro Lys Ser
                435                 440                 445

Ser Asp Lys Thr His Thr Ser Pro Pro Ser Pro Glu Val Gln Leu Val
    450                 455                 460

Glu Ser Gly Gly Gly Leu Val Gln Pro Gly Gly Ser Leu Arg Leu Ser
465                 470                 475                 480

Cys Ala Ala Ser Gly Tyr Thr Ile Ser Ser Tyr Cys Met Gly Trp Phe
                485                 490                 495

Arg Gln Ala Pro Gly Lys Gly Leu Glu Gly Val Ala Ala Ile Asp Ser
                500                 505                 510

Asp Gly Ser Thr Ser Tyr Ala Asp Ser Val Lys Gly Arg Phe Thr Ile
            515                 520                 525

Ser Lys Asp Asn Ser Lys Asn Thr Leu Tyr Leu Gln Met Asn Ser Leu
    530                 535                 540

Arg Ala Glu Asp Thr Ala Val Tyr Tyr Cys Ala Ala Asp Phe Cys Trp
545                 550                 555                 560

Val Asp Asp Phe Tyr Glu Tyr Asn Tyr Trp Gly Gln Gly Thr Leu Val
                565                 570                 575

Thr Val Ser Ser
            580

<210> SEQ ID NO 394
<211> LENGTH: 214
<212> TYPE: PRT
<213> ORGANISM: Artificial Sequence
<220> FEATURE:
<223> OTHER INFORMATION: Synthetic Construct

<400> SEQUENCE: 394

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
                20                  25                  30

Val Ala Trp Tyr Gln Gln Lys Pro Gly Lys Ala Pro Lys Leu Leu Ile
            35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
```

130               135               140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                    195                 200                 205

Phe Asn Arg Gly Glu Cys
        210

<210> SEQ ID NO 395
<211> LENGTH: 444
<212> TYPE: PRT
<213> ORGANISM: Artificial Sequence
<220> FEATURE:
<223> OTHER INFORMATION: Synthetic Construct

<400> SEQUENCE: 395

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
                20                  25                  30

Asp Met Ala Trp Val Arg Gln Ala Pro Gly Lys Gly Leu Glu Trp Val
            35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro

```
                275                 280                 285
Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
                435                 440
```

<210> SEQ ID NO 396
<211> LENGTH: 350
<212> TYPE: PRT
<213> ORGANISM: Artificial Sequence
<220> FEATURE:
<223> OTHER INFORMATION: Synthetic Construct

<400> SEQUENCE: 396

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
                20                  25                  30

Cys Met Gly Trp Phe Arg Gln Ala Pro Gly Lys Gly Leu Glu Gly Val
                35                  40                  45

Ala Ala Ile Asp Ser Asp Gly Ser Thr Ser Tyr Ala Asp Ser Val Lys
                50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Asp Phe Cys Trp Val Asp Asp Phe Tyr Glu Tyr Asn Tyr Trp Gly
                100                 105                 110

Gln Gly Thr Leu Val Thr Val Ser Ser Glu Pro Lys Ser Ser Asp Lys
                115                 120                 125

Thr His Thr Ser Pro Pro Ser Pro Asp Ile Gln Met Thr Gln Ser Pro
                130                 135                 140

Ser Ser Val Ser Ala Ser Val Gly Asp Arg Val Thr Ile Thr Cys Lys
145                 150                 155                 160

Ala Ser Gln Asp Val Asp Thr Ala Val Ala Trp Tyr Gln Gln Lys Pro
                165                 170                 175

Gly Lys Ala Pro Lys Leu Leu Ile Tyr Trp Ala Ser Thr Arg His Thr
                180                 185                 190

Gly Val Pro Ser Arg Phe Ser Gly Ser Gly Ser Gly Thr Asp Phe Thr
```

```
                195                 200                 205
Leu Thr Ile Ser Ser Leu Gln Pro Glu Asp Phe Ala Thr Tyr Tyr Cys
    210                 215                 220

Gln Gln Tyr Ser Thr Phe Pro Trp Thr Phe Gly Gly Gly Thr Lys Val
225                 230                 235                 240

Glu Ile Lys Arg Thr Val Ala Ala Pro Ser Val Phe Ile Phe Pro Pro
                245                 250                 255

Ser Asp Glu Gln Leu Lys Ser Gly Thr Ala Ser Val Val Cys Leu Leu
            260                 265                 270

Asn Asn Phe Tyr Pro Arg Glu Ala Lys Val Gln Trp Lys Val Asp Asn
        275                 280                 285

Ala Leu Gln Ser Gly Asn Ser Gln Glu Ser Val Thr Glu Gln Asp Ser
    290                 295                 300

Lys Asp Ser Thr Tyr Ser Leu Ser Ser Thr Leu Thr Leu Ser Lys Ala
305                 310                 315                 320

Asp Tyr Glu Lys His Lys Val Tyr Ala Cys Glu Val Thr His Gln Gly
                325                 330                 335

Leu Ser Ser Pro Val Thr Lys Ser Phe Asn Arg Gly Glu Cys
            340                 345                 350

<210> SEQ ID NO 397
<211> LENGTH: 444
<212> TYPE: PRT
<213> ORGANISM: Artificial Sequence
<220> FEATURE:
<223> OTHER INFORMATION: Synthetic Construct

<400> SEQUENCE: 397

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
```

```
                210                 215                 220
Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Tyr Arg Val Val Ser Val Leu Thr
                290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
                435                 440

<210> SEQ ID NO 398
<211> LENGTH: 350
<212> TYPE: PRT
<213> ORGANISM: Artificial Sequence
<220> FEATURE:
<223> OTHER INFORMATION: Synthetic Construct

<400> SEQUENCE: 398

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
                20                  25                  30

Val Ala Trp Tyr Gln Gln Lys Pro Gly Lys Ala Pro Lys Leu Leu Ile
                35                  40                  45

Tyr Trp Ala Ser Thr Arg His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
```

-continued

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Pro Lys Ser Ser Asp Lys Thr His Thr
    210                 215                 220

Ser Pro Pro Ser Pro Glu Val Gln Leu Val Glu Ser Gly Gly Gly Leu
225                 230                 235                 240

Val Gln Pro Gly Gly Ser Leu Arg Leu Ser Cys Ala Ala Ser Gly Tyr
                245                 250                 255

Thr Ile Ser Ser Tyr Cys Met Gly Trp Phe Arg Gln Ala Pro Gly Lys
            260                 265                 270

Gly Leu Glu Gly Val Ala Ala Ile Asp Ser Asp Gly Ser Thr Ser Tyr
        275                 280                 285

Ala Asp Ser Val Lys Gly Arg Phe Thr Ile Ser Lys Asp Asn Ser Lys
    290                 295                 300

Asn Thr Leu Tyr Leu Gln Met Asn Ser Leu Arg Ala Glu Asp Thr Ala
305                 310                 315                 320

Val Tyr Tyr Cys Ala Ala Asp Phe Cys Trp Val Asp Asp Phe Tyr Glu
                325                 330                 335

Tyr Asn Tyr Trp Gly Gln Gly Thr Leu Val Thr Val Ser Ser
            340                 345                 350

<210> SEQ ID NO 399
<211> LENGTH: 581
<212> TYPE: PRT
<213> ORGANISM: Artificial Sequence
<220> FEATURE:
<223> OTHER INFORMATION: Synthetic Construct

<400> SEQUENCE: 399

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Pro Lys Ser Ser Asp
        115                 120                 125

Lys Thr His Thr Ser Pro Pro Ser Pro Glu Val Gln Leu Val Glu Ser
    130                 135                 140

Gly Gly Gly Leu Val Gln Pro Gly Gly Ser Leu Arg Leu Ser Cys Ala
```

```
                145                 150                 155                 160
        Ala Ser Gly Phe Val Phe Ser Arg Tyr Asp Met Ala Trp Val Arg Gln
                        165                 170                 175
        Ala Pro Gly Lys Gly Leu Glu Trp Val Ser Phe Ile Ser Gly Gly Gly
                        180                 185                 190
        Ser Asn Thr Tyr Tyr Pro Asp Thr Val Lys Gly Arg Phe Thr Ile Ser
                        195                 200                 205
        Arg Asp Asn Ser Lys Asn Thr Leu Tyr Leu Gln Met Asn Ser Leu Arg
                        210                 215                 220
        Ala Glu Asp Thr Ala Val Tyr Tyr Cys Ile Ser Pro Tyr Tyr Ala
        225                 230                 235                 240
        Met Glu Tyr Trp Gly Gln Gly Thr Thr Val Thr Val Ser Ser Ala Ser
                        245                 250                 255
        Thr Lys Gly Pro Ser Val Phe Pro Leu Ala Pro Cys Ser Arg Ser Thr
                        260                 265                 270
        Ser Glu Ser Thr Ala Ala Leu Gly Cys Leu Val Lys Asp Tyr Phe Pro
                        275                 280                 285
        Glu Pro Val Thr Val Ser Trp Asn Ser Gly Ala Leu Thr Ser Gly Val
                        290                 295                 300
        His Thr Phe Pro Ala Val Leu Gln Ser Ser Gly Leu Tyr Ser Leu Ser
        305                 310                 315                 320
        Ser Val Val Thr Val Pro Ser Ser Ser Leu Gly Thr Lys Thr Tyr Thr
                        325                 330                 335
        Cys Asn Val Asp His Lys Pro Ser Asn Thr Lys Val Asp Lys Arg Val
                        340                 345                 350
        Glu Ser Lys Tyr Gly Pro Pro Cys Pro Pro Cys Pro Ala Pro Glu Phe
                        355                 360                 365
        Leu Gly Gly Pro Ser Val Phe Leu Phe Pro Pro Lys Pro Lys Asp Thr
                        370                 375                 380
        Leu Met Ile Ser Arg Thr Pro Glu Val Thr Cys Val Val Val Asp Val
        385                 390                 395                 400
        Ser Gln Glu Asp Pro Glu Val Gln Phe Asn Trp Tyr Val Asp Gly Val
                        405                 410                 415
        Glu Val His Asn Ala Lys Thr Lys Pro Arg Glu Glu Gln Phe Asn Ser
                        420                 425                 430
        Thr Tyr Arg Val Val Ser Val Leu Thr Val Leu His Gln Asp Trp Leu
                        435                 440                 445
        Asn Gly Lys Glu Tyr Lys Cys Lys Val Ser Asn Lys Gly Leu Pro Ser
                        450                 455                 460
        Ser Ile Glu Lys Thr Ile Ser Lys Ala Lys Gly Gln Pro Arg Glu Pro
        465                 470                 475                 480
        Gln Val Tyr Thr Leu Pro Pro Ser Gln Glu Glu Met Thr Lys Asn Gln
                        485                 490                 495
        Val Ser Leu Thr Cys Leu Val Lys Gly Phe Tyr Pro Ser Asp Ile Ala
                        500                 505                 510
        Val Glu Trp Glu Ser Asn Gly Gln Pro Glu Asn Asn Tyr Lys Thr Thr
                        515                 520                 525
        Pro Pro Val Leu Asp Ser Asp Gly Ser Phe Phe Leu Tyr Ser Arg Leu
                        530                 535                 540
        Thr Val Asp Lys Ser Arg Trp Gln Glu Gly Asn Val Phe Ser Cys Ser
        545                 550                 555                 560
        Val Met His Glu Ala Leu His Asn His Tyr Thr Gln Lys Ser Leu Ser
                        565                 570                 575
```

Leu Ser Leu Gly Lys
        580

<210> SEQ ID NO 400
<211> LENGTH: 214
<212> TYPE: PRT
<213> ORGANISM: Artificial Sequence
<220> FEATURE:
<223> OTHER INFORMATION: Synthetic Construct

<400> SEQUENCE: 400

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 401
<211> LENGTH: 581
<212> TYPE: PRT
<213> ORGANISM: Artificial Sequence
<220> FEATURE:
<223> OTHER INFORMATION: Synthetic Construct

<400> SEQUENCE: 401

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr

-continued

```
                65                  70                  75                  80
Leu Gln Met Asn Ser Leu Arg Ala Glu Asp Thr Ala Val Tyr Tyr Cys
                    85                  90                  95
Ile Ser Pro Tyr Tyr Ala Met Glu Tyr Trp Gly Gln Gly Thr Thr
                100                 105                 110
Val Thr Val Ser Ser Ala Ser Thr Lys Gly Pro Ser Val Phe Pro Leu
                115                 120                 125
Ala Pro Cys Ser Arg Ser Thr Ser Glu Ser Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Lys Thr Tyr Thr Cys Asn Val Asp His Lys Pro Ser Asn
                195                 200                 205
Thr Lys Val Asp Lys Arg Val Glu Ser Lys Tyr Gly Pro Pro Cys Pro
210                 215                 220
Pro Cys Pro Ala Pro Glu Phe Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
                260                 265                 270
Asn Trp Tyr Val Asp Gly Val Glu Val His Asn Ala Lys Thr Lys Pro
            275                 280                 285
Arg Glu Glu Gln Phe Asn Ser Thr Tyr Arg Val Val Ser Val Leu Thr
            290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
                340                 345                 350
Glu Glu Met Thr Lys Asn Gln Val Ser Leu Thr Cys Leu Val Lys Gly
                355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
                420                 425                 430
Tyr Thr Gln Lys Ser Leu Ser Leu Ser Leu Gly Lys Glu Pro Lys Ser
                435                 440                 445
Ser Asp Lys Thr His Thr Ser Pro Pro Ser Pro Glu Val Gln Leu Val
            450                 455                 460
Glu Ser Gly Gly Gly Leu Val Gln Pro Gly Gly Ser Leu Arg Leu Ser
465                 470                 475                 480
Cys Ala Ala Ser Gly Tyr Thr Val Ser Ser Tyr Cys Met Gly Trp Phe
                485                 490                 495
```

Arg Gln Ala Pro Gly Lys Gly Arg Glu Gly Val Ser Ala Ile Asp Ser
            500                 505                 510

Asp Gly Ser Val Ser Tyr Ala Asp Ser Val Lys Gly Arg Phe Thr Ile
            515                 520                 525

Ser Lys Asp Asn Ser Lys Asn Thr Leu Tyr Leu Gln Met Asn Ser Leu
530                 535                 540

Arg Ala Glu Asp Thr Ala Val Tyr Phe Cys Ala Ala Asp Leu Cys Trp
545                 550                 555                 560

Val Asp Gln Asp Gln Gly Glu Tyr Asn Thr Trp Gly Gln Gly Thr Leu
                565                 570                 575

Val Thr Val Ser Ser
            580

<210> SEQ ID NO 402
<211> LENGTH: 214
<212> TYPE: PRT
<213> ORGANISM: Artificial Sequence
<220> FEATURE:
<223> OTHER INFORMATION: Synthetic Construct

<400> SEQUENCE: 402

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 403
<211> LENGTH: 444
<212> TYPE: PRT
<213> ORGANISM: Artificial Sequence
<220> FEATURE:
<223> OTHER INFORMATION: Synthetic Construct -continued

```
<400> SEQUENCE: 403

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415
```

```
Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440

<210> SEQ ID NO 404
<211> LENGTH: 351
<212> TYPE: PRT
<213> ORGANISM: Artificial Sequence
<220> FEATURE:
<223> OTHER INFORMATION: Synthetic Construct

<400> SEQUENCE: 404

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Pro Lys Ser Ser Asp
        115                 120                 125

Lys Thr His Thr Ser Pro Pro Ser Pro Asp Ile Gln Met Thr Gln Ser
    130                 135                 140

Pro Ser Ser Val Ser Ala Ser Val Gly Asp Arg Val Thr Ile Thr Cys
145                 150                 155                 160

Lys Ala Ser Gln Asp Val Asp Thr Ala Val Ala Trp Tyr Gln Gln Lys
                165                 170                 175

Pro Gly Lys Ala Pro Lys Leu Leu Ile Tyr Trp Ala Ser Thr Arg His
            180                 185                 190

Thr Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Tyr Ser Thr Phe Pro Trp Thr Phe Gly Gly Gly Thr Lys
225                 230                 235                 240

Val Glu Ile Lys Arg Thr Val Ala Ala Pro Ser Val Phe Ile Phe Pro
                245                 250                 255

Pro Ser Asp Glu Gln Leu Lys Ser Gly Thr Ala Ser Val Val Cys Leu
            260                 265                 270

Leu Asn Asn Phe Tyr Pro Arg Glu Ala Lys Val Gln Trp Lys Val Asp
        275                 280                 285

Asn Ala Leu Gln Ser Gly Asn Ser Gln Glu Ser Val Thr Glu Gln Asp
    290                 295                 300

Ser Lys Asp Ser Thr Tyr Ser Leu Ser Ser Thr Leu Thr Leu Ser Lys
305                 310                 315                 320

Ala Asp Tyr Glu Lys His Lys Val Tyr Ala Cys Glu Val Thr His Gln
                325                 330                 335
```

```
Gly Leu Ser Ser Pro Val Thr Lys Ser Phe Asn Arg Gly Glu Cys
                340                 345                 350

<210> SEQ ID NO 405
<211> LENGTH: 444
<212> TYPE: PRT
<213> ORGANISM: Artificial Sequence
<220> FEATURE:
<223> OTHER INFORMATION: Synthetic Construct

<400> SEQUENCE: 405

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350
```

```
Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 406
<211> LENGTH: 351
<212> TYPE: PRT
<213> ORGANISM: Artificial Sequence
<220> FEATURE:
<223> OTHER INFORMATION: Synthetic Construct

<400> SEQUENCE: 406

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Pro Lys Ser Ser Asp Lys Thr His Thr
    210                 215                 220

Ser Pro Pro Ser Pro Glu Val Gln Leu Val Glu Ser Gly Gly Gly Leu
225                 230                 235                 240

Val Gln Pro Gly Gly Ser Leu Arg Leu Ser Cys Ala Ala Ser Gly Tyr
                245                 250                 255

Thr Val Ser Ser Tyr Cys Met Gly Trp Phe Arg Gln Ala Pro Gly Lys
            260                 265                 270
```

```
Gly Arg Glu Gly Val Ser Ala Ile Asp Ser Asp Gly Ser Val Ser Tyr
            275                 280                 285

Ala Asp Ser Val Lys Gly Arg Phe Thr Ile Ser Lys Asp Asn Ser Lys
    290                 295                 300

Asn Thr Leu Tyr Leu Gln Met Asn Ser Leu Arg Ala Glu Asp Thr Ala
305                 310                 315                 320

Val Tyr Phe Cys Ala Ala Asp Leu Cys Trp Val Asp Gln Asp Gln Gly
                325                 330                 335

Glu Tyr Asn Thr Trp Gly Gln Gly Thr Leu Val Thr Val Ser Ser
            340                 345                 350

<210> SEQ ID NO 407
<211> LENGTH: 585
<212> TYPE: PRT
<213> ORGANISM: Artificial Sequence
<220> FEATURE:
<223> OTHER INFORMATION: Synthetic Construct

<400> SEQUENCE: 407

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Gly Gly Tyr
            20                  25                  30

Cys Met Gly Trp Phe Arg Gln Ala Pro Gly Lys Gly Leu Glu Gly Val
        35                  40                  45

Ser Thr Ile Asn Ser Asp Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Val Asp Leu Ala Pro Cys Trp Val Ala Gly Pro Ile Glu Ala Ala Asp
            100                 105                 110

Phe Gly Tyr Trp Gly Gln Gly Thr Leu Val Thr Val Ser Ser Glu Pro
        115                 120                 125

Lys Ser Ser Asp Lys Thr His Thr Ser Pro Pro Ser Pro Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Phe Val Phe Ser Arg Tyr Asp Met Ala
                165                 170                 175

Trp Val Arg Gln Ala Pro Gly Lys Gly Leu Glu Trp Val Ser Phe Ile
            180                 185                 190

Ser Gly Gly Gly Ser Asn Thr Tyr Tyr Pro Asp Thr Val Lys Gly Arg
        195                 200                 205

Phe Thr Ile Ser Arg Asp Asn Ser Lys Asn Thr Leu Tyr Leu Gln Met
    210                 215                 220

Asn Ser Leu Arg Ala Glu Asp Thr Ala Val Tyr Tyr Cys Ile Ser Pro
225                 230                 235                 240

Tyr Tyr Tyr Ala Met Glu Tyr Trp Gly Gln Gly Thr Val Thr Val
                245                 250                 255

Ser Ser Ala Ser Thr Lys Gly Pro Ser Val Phe Pro Leu Ala Pro Cys
            260                 265                 270

Ser Arg Ser Thr Ser Glu Ser Thr Ala Ala Leu Gly Cys Leu Val Lys
        275                 280                 285
```

-continued

Asp Tyr Phe Pro Glu Pro Val Thr Val Ser Trp Asn Ser Gly Ala Leu
            290                 295                 300

Thr Ser Gly Val His Thr Phe Pro Ala Val Leu Gln Ser Ser Gly Leu
305                 310                 315                 320

Tyr Ser Leu Ser Ser Val Val Thr Val Pro Ser Ser Ser Leu Gly Thr
            325                 330                 335

Lys Thr Tyr Thr Cys Asn Val Asp His Lys Pro Ser Asn Thr Lys Val
            340                 345                 350

Asp Lys Arg Val Glu Ser Lys Tyr Gly Pro Pro Cys Pro Pro Cys Pro
            355                 360                 365

Ala Pro Glu Phe Leu Gly Gly Pro Ser Val Phe Leu Phe Pro Pro Lys
            370                 375                 380

Pro Lys Asp Thr Leu Met Ile Ser Arg Thr Pro Glu Val Thr Cys Val
385                 390                 395                 400

Val Val Asp Val Ser Gln Glu Asp Pro Glu Val Gln Phe Asn Trp Tyr
            405                 410                 415

Val Asp Gly Val Glu Val His Asn Ala Lys Thr Lys Pro Arg Glu Glu
            420                 425                 430

Gln Phe Asn Ser Thr Tyr Arg Val Val Ser Val Leu Thr Val Leu His
            435                 440                 445

Gln Asp Trp Leu Asn Gly Lys Glu Tyr Lys Cys Lys Val Ser Asn Lys
450                 455                 460

Gly Leu Pro Ser Ser Ile Glu Lys Thr Ile Ser Lys Ala Lys Gly Gln
465                 470                 475                 480

Pro Arg Glu Pro Gln Val Tyr Thr Leu Pro Pro Ser Gln Glu Glu Met
            485                 490                 495

Thr Lys Asn Gln Val Ser Leu Thr Cys Leu Val Lys Gly Phe Tyr Pro
            500                 505                 510

Ser Asp Ile Ala Val Glu Trp Glu Ser Asn Gly Gln Pro Glu Asn Asn
            515                 520                 525

Tyr Lys Thr Thr Pro Pro Val Leu Asp Ser Asp Gly Ser Phe Phe Leu
            530                 535                 540

Tyr Ser Arg Leu Thr Val Asp Lys Ser Arg Trp Gln Glu Gly Asn Val
545                 550                 555                 560

Phe Ser Cys Ser Val Met His Glu Ala Leu His Asn His Tyr Thr Gln
            565                 570                 575

Lys Ser Leu Ser Leu Ser Leu Gly Lys
            580                 585

<210> SEQ ID NO 408
<211> LENGTH: 214
<212> TYPE: PRT
<213> ORGANISM: Artificial Sequence
<220> FEATURE:
<223> OTHER INFORMATION: Synthetic Construct

<400> SEQUENCE: 408

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 409
<211> LENGTH: 585
<212> TYPE: PRT
<213> ORGANISM: Artificial Sequence
<220> FEATURE:
<223> OTHER INFORMATION: Synthetic Construct

<400> SEQUENCE: 409

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
    275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
        340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
        420                 425                 430

Tyr Thr Gln Lys Ser Leu Ser Leu Ser Leu Gly Lys Glu Pro Lys Ser
    435                 440                 445

Ser Asp Lys Thr His Thr Ser Pro Pro Ser Pro Glu Val Gln Leu Val
450                 455                 460

Glu Ser Gly Gly Gly Leu Val Gln Pro Gly Gly Ser Leu Arg Leu Ser
465                 470                 475                 480

Cys Ala Ala Ser Gly Tyr Thr Tyr Gly Gly Tyr Cys Met Gly Trp Phe
            485                 490                 495

Arg Gln Ala Pro Gly Lys Gly Leu Glu Gly Val Ser Thr Ile Asn Ser
        500                 505                 510

Asp Gly Ser Thr Asn Tyr Ala Asp Ser Val Lys Gly Arg Phe Thr Ile
    515                 520                 525

Ser Arg Asp Asn Ser Lys Asn Thr Leu Tyr Leu Gln Met Asn Ser Leu
530                 535                 540

Arg Ala Glu Asp Thr Ala Val Tyr Tyr Cys Ala Val Asp Leu Ala Pro
545                 550                 555                 560

Cys Trp Val Ala Gly Pro Ile Glu Ala Ala Asp Phe Gly Tyr Trp Gly
            565                 570                 575

Gln Gly Thr Leu Val Thr Val Ser Ser
        580                 585

<210> SEQ ID NO 410
<211> LENGTH: 214
<212> TYPE: PRT
<213> ORGANISM: Artificial Sequence
<220> FEATURE:

<223> OTHER INFORMATION: Synthetic Construct

<400> SEQUENCE: 410

```
Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 411
<211> LENGTH: 444
<212> TYPE: PRT
<213> ORGANISM: Artificial Sequence
<220> FEATURE:
<223> OTHER INFORMATION: Synthetic Construct

<400> SEQUENCE: 411

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125
```

```
Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 412
<211> LENGTH: 355
<212> TYPE: PRT
<213> ORGANISM: Artificial Sequence
<220> FEATURE:
<223> OTHER INFORMATION: Synthetic Construct

<400> SEQUENCE: 412

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Gly Gly Tyr
            20                  25                  30

Cys Met Gly Trp Phe Arg Gln Ala Pro Gly Lys Gly Leu Glu Gly Val
        35                  40                  45
```

```
Ser Thr Ile Asn Ser Asp Gly Ser Thr Asn Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Val Asp Leu Ala Pro Cys Trp Val Ala Gly Pro Ile Glu Ala Ala Asp
             100                 105                 110

Phe Gly Tyr Trp Gly Gln Gly Thr Leu Val Thr Val Ser Ser Glu Pro
         115                 120                 125

Lys Ser Ser Asp Lys Thr His Thr Ser Pro Pro Ser Pro Asp Ile Gln
    130                 135                 140

Met Thr Gln Ser Pro Ser Ser Val Ser Ala Ser Val Gly Asp Arg Val
145                 150                 155                 160

Thr Ile Thr Cys Lys Ala Ser Gln Asp Val Asp Thr Ala Val Ala Trp
                165                 170                 175

Tyr Gln Gln Lys Pro Gly Lys Ala Pro Lys Leu Leu Ile Tyr Trp Ala
            180                 185                 190

Ser Thr Arg His Thr Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Tyr Tyr Cys Gln Gln Tyr Ser Thr Phe Pro Trp Thr Phe Gly Gly
225                 230                 235                 240

Gly Thr Lys Val Glu Ile Lys Arg Thr Val Ala Ala Pro Ser Val
                245                 250                 255

Phe Ile Phe Pro Pro Ser Asp Glu Gln Leu Lys Ser Gly Thr Ala Ser
                260                 265                 270

Val Val Cys Leu Leu Asn Asn Phe Tyr Pro Arg Glu Ala Lys Val Gln
            275                 280                 285

Trp Lys Val Asp Asn Ala Leu Gln Ser Gly Asn Ser Gln Glu Ser Val
        290                 295                 300

Thr Glu Gln Asp Ser Lys Asp Ser Thr Tyr Ser Leu Ser Ser Thr Leu
305                 310                 315                 320

Thr Leu Ser Lys Ala Asp Tyr Glu Lys His Lys Val Tyr Ala Cys Glu
                325                 330                 335

Val Thr His Gln Gly Leu Ser Ser Pro Val Thr Lys Ser Phe Asn Arg
            340                 345                 350

Gly Glu Cys
        355

<210> SEQ ID NO 413
<211> LENGTH: 444
<212> TYPE: PRT
<213> ORGANISM: Artificial Sequence
<220> FEATURE:
<223> OTHER INFORMATION: Synthetic Construct

<400> SEQUENCE: 413

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Val Phe Ser Arg Tyr
                 20                  25                  30

Asp Met Ala Trp Val Arg Gln Ala Pro Gly Lys Gly Leu Glu Trp Val
             35                  40                  45
```

-continued

Ser Phe Ile Ser Gly Gly Ser Asn Thr Tyr Tyr Pro Asp Thr Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 414
<211> LENGTH: 355

```
<212> TYPE: PRT
<213> ORGANISM: Artificial Sequence
<220> FEATURE:
<223> OTHER INFORMATION: Synthetic Construct

<400> SEQUENCE: 414

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Pro Lys Ser Ser Asp Lys Thr His Thr
210                 215                 220

Ser Pro Pro Ser Pro Glu Val Gln Leu Val Glu Ser Gly Gly Gly Leu
225                 230                 235                 240

Val Gln Pro Gly Gly Ser Leu Arg Leu Ser Cys Ala Ala Ser Gly Tyr
                245                 250                 255

Thr Tyr Gly Gly Tyr Cys Met Gly Trp Phe Arg Gln Ala Pro Gly Lys
            260                 265                 270

Gly Leu Glu Gly Val Ser Thr Ile Asn Ser Asp Gly Ser Thr Asn Tyr
        275                 280                 285

Ala Asp Ser Val Lys Gly Arg Phe Thr Ile Ser Arg Asp Asn Ser Lys
290                 295                 300

Asn Thr Leu Tyr Leu Gln Met Asn Ser Leu Arg Ala Glu Asp Thr Ala
305                 310                 315                 320

Val Tyr Tyr Cys Ala Val Asp Leu Ala Pro Cys Trp Val Ala Gly Pro
                325                 330                 335

Ile Glu Ala Ala Asp Phe Gly Tyr Trp Gly Gln Gly Thr Leu Val Thr
            340                 345                 350

Val Ser Ser
        355

<210> SEQ ID NO 415
<211> LENGTH: 568
```

<212> TYPE: PRT
<213> ORGANISM: Artificial Sequence
<220> FEATURE:
<223> OTHER INFORMATION: Synthetic Construct

<400> SEQUENCE: 415

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Gly Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser Glu Val Gln Leu
        115                 120                 125

Val Glu Ser Gly Gly Gly Leu Val Gln Pro Gly Gly Ser Leu Arg Leu
130                 135                 140

Ser Cys Ala Ala Ser Gly Phe Val Phe Ser Arg Tyr Asp Met Ala Trp
145                 150                 155                 160

Val Arg Gln Ala Pro Gly Lys Gly Leu Glu Trp Val Ser Phe Ile Ser
                165                 170                 175

Gly Gly Gly Ser Asn Thr Tyr Tyr Pro Asp Thr Val Lys Gly Arg Phe
            180                 185                 190

Thr Ile Ser Arg Asp Asn Ser Lys Asn Thr Leu Tyr Leu Gln Met Asn
        195                 200                 205

Ser Leu Arg Ala Glu Asp Thr Ala Val Tyr Tyr Cys Ile Ser Pro Tyr
210                 215                 220

Tyr Tyr Ala Met Glu Tyr Trp Gly Gln Gly Thr Thr Val Thr Val Ser
225                 230                 235                 240

Ser Ala Ser Thr Lys Gly Pro Ser Val Phe Pro Leu Ala Pro Cys Ser
                245                 250                 255

Arg Ser Thr Ser Glu Ser Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
290                 295                 300

Ser Leu Ser Ser Val Val Thr Val Pro Ser Ser Ser Leu Gly Thr Lys
305                 310                 315                 320

Thr Tyr Thr Cys Asn Val Asp His Lys Pro Ser Asn Thr Lys Val Asp
                325                 330                 335

Lys Arg Val Glu Ser Lys Tyr Gly Pro Pro Cys Pro Pro Cys Pro Ala
            340                 345                 350

Pro Glu Phe Leu Gly Gly Pro Ser Val Phe Leu Phe Pro Pro Lys Pro
        355                 360                 365

Lys Asp Thr Leu Met Ile Ser Arg Thr Pro Glu Val Thr Cys Val Val
    370                 375                 380

```
Val Asp Val Ser Gln Glu Asp Pro Glu Val Gln Phe Asn Trp Tyr Val
385                 390                 395                 400

Asp Gly Val Glu Val His Asn Ala Lys Thr Lys Pro Arg Glu Glu Gln
            405                 410                 415

Phe Asn Ser Thr Tyr Arg Val Val Ser Val Leu Thr Val Leu His Gln
        420                 425                 430

Asp Trp Leu Asn Gly Lys Glu Tyr Lys Cys Lys Val Ser Asn Lys Gly
    435                 440                 445

Leu Pro Ser Ser Ile Glu Lys Thr Ile Ser Lys Ala Lys Gly Gln Pro
    450                 455                 460

Arg Glu Pro Gln Val Tyr Thr Leu Pro Pro Ser Gln Glu Glu Met Thr
465                 470                 475                 480

Lys Asn Gln Val Ser Leu Thr Cys Leu Val Lys Gly Phe Tyr Pro Ser
                485                 490                 495

Asp Ile Ala Val Glu Trp Glu Ser Asn Gly Gln Pro Glu Asn Asn Tyr
            500                 505                 510

Lys Thr Thr Pro Pro Val Leu Asp Ser Asp Gly Ser Phe Phe Leu Tyr
        515                 520                 525

Ser Arg Leu Thr Val Asp Lys Ser Arg Trp Gln Glu Gly Asn Val Phe
    530                 535                 540

Ser Cys Ser Val Met His Glu Ala Leu His Asn His Tyr Thr Gln Lys
545                 550                 555                 560

Ser Leu Ser Leu Ser Leu Gly Lys
                565

<210> SEQ ID NO 416
<211> LENGTH: 214
<212> TYPE: PRT
<213> ORGANISM: Artificial Sequence
<220> FEATURE:
<223> OTHER INFORMATION: Synthetic Construct

<400> SEQUENCE: 416

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 417
<211> LENGTH: 444
<212> TYPE: PRT
<213> ORGANISM: Artificial Sequence
<220> FEATURE:
<223> OTHER INFORMATION: Synthetic Construct

<400> SEQUENCE: 417

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320
```

```
Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 418
<211> LENGTH: 338
<212> TYPE: PRT
<213> ORGANISM: Artificial Sequence
<220> FEATURE:
<223> OTHER INFORMATION: Synthetic Construct

<400> SEQUENCE: 418

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Met Tyr Tyr Cys Ala
                85                  90                  95

Ala Asp Phe Cys Trp Val Asp Glu Asp Arg His Leu Tyr Glu Tyr Asn
            100                 105                 110

Ser Trp Gly Gln Gly Thr Leu Val Thr Val Ser Ser Asp Ile Gln Met
        115                 120                 125

Thr Gln Ser Pro Ser Ser Val Ser Ala Ser Val Gly Asp Arg Val Thr
    130                 135                 140

Ile Thr Cys Lys Ala Ser Gln Asp Val Asp Thr Ala Val Ala Trp Tyr
145                 150                 155                 160

Gln Gln Lys Pro Gly Lys Ala Pro Lys Leu Leu Ile Tyr Trp Ala Ser
                165                 170                 175

Thr Arg His Thr Gly Val Pro Ser Arg Phe Ser Gly Ser Gly Ser Gly
            180                 185                 190

Thr Asp Phe Thr Leu Thr Ile Ser Ser Leu Gln Pro Glu Asp Phe Ala
        195                 200                 205

Thr Tyr Tyr Cys Gln Gln Tyr Ser Thr Phe Pro Trp Thr Phe Gly Gly
    210                 215                 220

Gly Thr Lys Val Glu Ile Lys Arg Thr Val Ala Ala Pro Ser Val Phe
225                 230                 235                 240
```

-continued

```
Ile Phe Pro Pro Ser Asp Glu Gln Leu Lys Ser Gly Thr Ala Ser Val
                245                 250                 255

Val Cys Leu Leu Asn Asn Phe Tyr Pro Arg Glu Ala Lys Val Gln Trp
            260                 265                 270

Lys Val Asp Asn Ala Leu Gln Ser Gly Asn Ser Gln Glu Ser Val Thr
        275                 280                 285

Glu Gln Asp Ser Lys Asp Ser Thr Tyr Ser Leu Ser Ser Thr Leu Thr
    290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
                325                 330                 335

Glu Cys

<210> SEQ ID NO 419
<211> LENGTH: 565
<212> TYPE: PRT
<213> ORGANISM: Artificial Sequence
<220> FEATURE:
<223> OTHER INFORMATION: Synthetic Construct

<400> SEQUENCE: 419

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Asp Phe Cys Trp Val Asp Asp Phe Tyr Glu Tyr Asn Tyr Trp Gly
            100                 105                 110

Gln Gly Thr Leu Val Thr Val Ser Ser Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Val Phe Ser Arg Tyr Asp Met Ala Trp Val Arg Gln
145                 150                 155                 160

Ala Pro Gly Lys Gly Leu Glu Trp Val Ser Phe Ile Ser Gly Gly Gly
                165                 170                 175

Ser Asn Thr Tyr Tyr Pro Asp Thr Val Lys Gly Arg Phe Thr Ile Ser
            180                 185                 190

Arg Asp Asn Ser Lys Asn Thr Leu Tyr Leu Gln Met Asn Ser Leu Arg
        195                 200                 205

Ala Glu Asp Thr Ala Val Tyr Tyr Cys Ile Ser Pro Tyr Tyr Tyr Ala
    210                 215                 220

Met Glu Tyr Trp Gly Gln Gly Thr Thr Val Thr Val Ser Ser Ala Ser
225                 230                 235                 240

Thr Lys Gly Pro Ser Val Phe Pro Leu Ala Pro Cys Ser Arg Ser Thr
                245                 250                 255

Ser Glu Ser Thr Ala Ala Leu Gly Cys Leu Val Lys Asp Tyr Phe Pro
```

```
                260                 265                 270
Glu Pro Val Thr Val Ser Trp Asn Ser Gly Ala Leu Thr Ser Gly Val
            275                 280                 285

His Thr Phe Pro Ala Val Leu Gln Ser Ser Gly Leu Tyr Ser Leu Ser
        290                 295                 300

Ser Val Val Thr Val Pro Ser Ser Ser Leu Gly Thr Lys Thr Tyr Thr
305                 310                 315                 320

Cys Asn Val Asp His Lys Pro Ser Asn Thr Lys Val Asp Lys Arg Val
                325                 330                 335

Glu Ser Lys Tyr Gly Pro Pro Cys Pro Pro Cys Pro Ala Pro Glu Phe
            340                 345                 350

Leu Gly Gly Pro Ser Val Phe Leu Phe Pro Pro Lys Pro Lys Asp Thr
        355                 360                 365

Leu Met Ile Ser Arg Thr Pro Glu Val Thr Cys Val Val Val Asp Val
    370                 375                 380

Ser Gln Glu Asp Pro Glu Val Gln Phe Asn Trp Tyr Val Asp Gly Val
385                 390                 395                 400

Glu Val His Asn Ala Lys Thr Lys Pro Arg Glu Glu Gln Phe Asn Ser
                405                 410                 415

Thr Tyr Arg Val Val Ser Val Leu Thr Val Leu His Gln Asp Trp Leu
            420                 425                 430

Asn Gly Lys Glu Tyr Lys Cys Lys Val Ser Asn Lys Gly Leu Pro Ser
        435                 440                 445

Ser Ile Glu Lys Thr Ile Ser Lys Ala Lys Gly Gln Pro Arg Glu Pro
    450                 455                 460

Gln Val Tyr Thr Leu Pro Pro Ser Gln Glu Glu Met Thr Lys Asn Gln
465                 470                 475                 480

Val Ser Leu Thr Cys Leu Val Lys Gly Phe Tyr Pro Ser Asp Ile Ala
                485                 490                 495

Val Glu Trp Glu Ser Asn Gly Gln Pro Glu Asn Asn Tyr Lys Thr Thr
            500                 505                 510

Pro Pro Val Leu Asp Ser Asp Gly Ser Phe Phe Leu Tyr Ser Arg Leu
        515                 520                 525

Thr Val Asp Lys Ser Arg Trp Gln Glu Gly Asn Val Phe Ser Cys Ser
    530                 535                 540

Val Met His Glu Ala Leu His Asn His Tyr Thr Gln Lys Ser Leu Ser
545                 550                 555                 560

Leu Ser Leu Gly Lys
                565

<210> SEQ ID NO 420
<211> LENGTH: 214
<212> TYPE: PRT
<213> ORGANISM: Artificial Sequence
<220> FEATURE:
<223> OTHER INFORMATION: Synthetic Construct

<400> SEQUENCE: 420

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
```

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Phe Pro Trp
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 421
<211> LENGTH: 444
<212> TYPE: PRT
<213> ORGANISM: Artificial Sequence
<220> FEATURE:
<223> OTHER INFORMATION: Synthetic Construct

<400> SEQUENCE: 421

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Val Phe Ser Arg Tyr
                 20                  25                  30

Asp Met Ala Trp Val Arg Gln Ala Pro Gly Lys Gly Leu Glu Trp Val
             35                  40                  45

Ser Phe Ile Ser Gly Gly Gly Ser Asn Thr Tyr Tyr Pro Asp Thr Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ile Ser Pro Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
```

-continued

```
                195                 200                 205
Thr Lys Val Asp Lys Arg Val Glu Ser Lys Tyr Gly Pro Pro Cys Pro
210                     215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 422
<211> LENGTH: 335
<212> TYPE: PRT
<213> ORGANISM: Artificial Sequence
<220> FEATURE:
<223> OTHER INFORMATION: Synthetic Construct

<400> SEQUENCE: 422

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Ile Ser Ser Tyr
            20                  25                  30

Cys Met Gly Trp Phe Arg Gln Ala Pro Gly Lys Gly Leu Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Asp Phe Cys Trp Val Asp Asp Phe Tyr Glu Tyr Asn Tyr Trp Gly
            100                 105                 110

Gln Gly Thr Leu Val Thr Val Ser Ser Asp Ile Gln Met Thr Gln Ser
```

```
            115                 120                 125
Pro Ser Ser Val Ser Ala Ser Val Gly Asp Arg Val Thr Ile Thr Cys
130                 135                 140

Lys Ala Ser Gln Asp Val Asp Thr Ala Val Ala Trp Tyr Gln Lys
145                 150                 155                 160

Pro Gly Lys Ala Pro Lys Leu Leu Ile Tyr Trp Ala Ser Thr Arg His
                165                 170                 175

Thr Gly Val Pro Ser Arg Phe Ser Gly Ser Gly Ser Gly Thr Asp Phe
            180                 185                 190

Thr Leu Thr Ile Ser Ser Leu Gln Pro Glu Asp Phe Ala Thr Tyr Tyr
        195                 200                 205

Cys Gln Gln Tyr Ser Thr Phe Pro Trp Thr Phe Gly Gly Gly Thr Lys
    210                 215                 220

Val Glu Ile Lys Arg Thr Val Ala Ala Pro Ser Val Phe Ile Phe Pro
225                 230                 235                 240

Pro Ser Asp Glu Gln Leu Lys Ser Gly Thr Ala Ser Val Val Cys Leu
                245                 250                 255

Leu Asn Asn Phe Tyr Pro Arg Glu Ala Lys Val Gln Trp Lys Val Asp
            260                 265                 270

Asn Ala Leu Gln Ser Gly Asn Ser Gln Glu Ser Val Thr Glu Gln Asp
        275                 280                 285

Ser Lys Asp Ser Thr Tyr Ser Leu Ser Ser Thr Leu Thr Leu Ser Lys
    290                 295                 300

Ala Asp Tyr Glu Lys His Lys Val Tyr Ala Cys Glu Val Thr His Gln
305                 310                 315                 320

Gly Leu Ser Ser Pro Val Thr Lys Ser Phe Asn Arg Gly Glu Cys
                325                 330                 335

<210> SEQ ID NO 423
<211> LENGTH: 566
<212> TYPE: PRT
<213> ORGANISM: Artificial Sequence
<220> FEATURE:
<223> OTHER INFORMATION: Synthetic Construct

<400> SEQUENCE: 423

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Val Phe Ser Arg Tyr Asp Met Ala Trp Val Arg
```

```
            145                 150                 155                 160
        Gln Ala Pro Gly Lys Gly Leu Glu Trp Val Ser Phe Ile Ser Gly Gly
                        165                 170                 175
        Gly Ser Asn Thr Tyr Tyr Pro Asp Thr Val Lys Gly Arg Phe Thr Ile
                        180                 185                 190
        Ser Arg Asp Asn Ser Lys Asn Thr Leu Tyr Leu Gln Met Asn Ser Leu
                        195                 200                 205
        Arg Ala Glu Asp Thr Ala Val Tyr Tyr Cys Ile Ser Pro Tyr Tyr Tyr
                        210                 215                 220
        Ala Met Glu Tyr Trp Gly Gln Gly Thr Thr Val Thr Val Ser Ser Ala
        225                 230                 235                 240
        Ser Thr Lys Gly Pro Ser Val Phe Pro Leu Ala Pro Cys Ser Arg Ser
                        245                 250                 255
        Thr Ser Glu Ser Thr Ala Ala Leu Gly Cys Leu Val Lys Asp Tyr Phe
                        260                 265                 270
        Pro Glu Pro Val Thr Val Ser Trp Asn Ser Gly Ala Leu Thr Ser Gly
                        275                 280                 285
        Val His Thr Phe Pro Ala Val Leu Gln Ser Ser Gly Leu Tyr Ser Leu
                        290                 295                 300
        Ser Ser Val Val Thr Val Pro Ser Ser Ser Leu Gly Thr Lys Thr Tyr
        305                 310                 315                 320
        Thr Cys Asn Val Asp His Lys Pro Ser Asn Thr Lys Val Asp Lys Arg
                        325                 330                 335
        Val Glu Ser Lys Tyr Gly Pro Pro Cys Pro Pro Cys Pro Ala Pro Glu
                        340                 345                 350
        Phe Leu Gly Gly Pro Ser Val Phe Leu Phe Pro Pro Lys Pro Lys Asp
                        355                 360                 365
        Thr Leu Met Ile Ser Arg Thr Pro Glu Val Thr Cys Val Val Val Asp
                        370                 375                 380
        Val Ser Gln Glu Asp Pro Glu Val Gln Phe Asn Trp Tyr Val Asp Gly
        385                 390                 395                 400
        Val Glu Val His Asn Ala Lys Thr Lys Pro Arg Glu Glu Gln Phe Asn
                        405                 410                 415
        Ser Thr Tyr Arg Val Val Ser Val Leu Thr Val Leu His Gln Asp Trp
                        420                 425                 430
        Leu Asn Gly Lys Glu Tyr Lys Cys Lys Val Ser Asn Lys Gly Leu Pro
                        435                 440                 445
        Ser Ser Ile Glu Lys Thr Ile Ser Lys Ala Lys Gly Gln Pro Arg Glu
                        450                 455                 460
        Pro Gln Val Tyr Thr Leu Pro Pro Ser Gln Glu Glu Met Thr Lys Asn
        465                 470                 475                 480
        Gln Val Ser Leu Thr Cys Leu Val Lys Gly Phe Tyr Pro Ser Asp Ile
                        485                 490                 495
        Ala Val Glu Trp Glu Ser Asn Gly Gln Pro Glu Asn Asn Tyr Lys Thr
                        500                 505                 510
        Thr Pro Pro Val Leu Asp Ser Asp Gly Ser Phe Phe Leu Tyr Ser Arg
                        515                 520                 525
        Leu Thr Val Asp Lys Ser Arg Trp Gln Glu Gly Asn Val Phe Ser Cys
                        530                 535                 540
        Ser Val Met His Glu Ala Leu His Asn His Tyr Thr Gln Lys Ser Leu
        545                 550                 555                 560
        Ser Leu Ser Leu Gly Lys
                        565
```

<210> SEQ ID NO 424
<211> LENGTH: 214
<212> TYPE: PRT
<213> ORGANISM: Artificial Sequence
<220> FEATURE:
<223> OTHER INFORMATION: Synthetic Construct

<400> SEQUENCE: 424

```
Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 425
<211> LENGTH: 444
<212> TYPE: PRT
<213> ORGANISM: Artificial Sequence
<220> FEATURE:
<223> OTHER INFORMATION: Synthetic Construct

<400> SEQUENCE: 425

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
            85                  90                  95
Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 426
<211> LENGTH: 336
<212> TYPE: PRT
<213> ORGANISM: Artificial Sequence
<220> FEATURE:
<223> OTHER INFORMATION: Synthetic Construct

<400> SEQUENCE: 426

Glu Val Gln Leu Val Glu Ser Gly Gly Gly Leu Val Gln Pro Gly Gly
```

```
            1               5                  10                  15
         Ser Leu Arg Leu Ser Cys Ala Ala Ser Gly Tyr Thr Val Ser Ser Tyr
                        20                  25                  30

Cys Met Gly Trp Phe Arg Gln Ala Pro Gly Lys Gly Arg Glu Gly Val
                        35                  40                  45

Ser Ala Ile Asp Ser Asp Gly Ser Val Ser Tyr Ala Asp Ser Val Lys
                        50                  55                  60

Gly Arg Phe Thr Ile Ser Lys Asp Asn Ser Lys Asn Thr Leu Tyr Leu
         65                 70                  75                  80

Gln Met Asn Ser Leu Arg Ala Glu Asp Thr Ala Val Tyr Phe Cys Ala
                        85                  90                  95

Ala Asp Leu Cys Trp Val Asp Gln Asp Gln Gly Glu Tyr Asn Thr Trp
                        100                 105                 110

Gly Gln Gly Thr Leu Val Thr Val Ser Ser Asp Ile Gln Met Thr Gln
                        115                 120                 125

Ser Pro Ser Ser Val Ser Ala Ser Val Gly Asp Arg Val Thr Ile Thr
                        130                 135                 140

Cys Lys Ala Ser Gln Asp Val Asp Thr Ala Val Ala Trp Tyr Gln Gln
         145                150                 155                 160

Lys Pro Gly Lys Ala Pro Lys Leu Leu Ile Tyr Trp Ala Ser Thr Arg
                        165                 170                 175

His Thr Gly Val Pro Ser Arg Phe Ser Gly Ser Gly Ser Gly Thr Asp
                        180                 185                 190

Phe Thr Leu Thr Ile Ser Ser Leu Gln Pro Glu Asp Phe Ala Thr Tyr
                        195                 200                 205

Tyr Cys Gln Gln Tyr Ser Thr Phe Pro Trp Thr Phe Gly Gly Gly Thr
                        210                 215                 220

Lys Val Glu Ile Lys Arg Thr Val Ala Ala Pro Ser Val Phe Ile Phe
         225                230                 235                 240

Pro Pro Ser Asp Glu Gln Leu Lys Ser Gly Thr Ala Ser Val Val Cys
                        245                 250                 255

Leu Leu Asn Asn Phe Tyr Pro Arg Glu Ala Lys Val Gln Trp Lys Val
                        260                 265                 270

Asp Asn Ala Leu Gln Ser Gly Asn Ser Gln Glu Ser Val Thr Glu Gln
                        275                 280                 285

Asp Ser Lys Asp Ser Thr Tyr Ser Leu Ser Ser Thr Leu Thr Leu Ser
                        290                 295                 300

Lys Ala Asp Tyr Glu Lys His Lys Val Tyr Ala Cys Glu Val Thr His
         305                310                 315                 320

Gln Gly Leu Ser Ser Pro Val Thr Lys Ser Phe Asn Arg Gly Glu Cys
                        325                 330                 335

<210> SEQ ID NO 427
<211> LENGTH: 570
<212> TYPE: PRT
<213> ORGANISM: Artificial Sequence
<220> FEATURE:
<223> OTHER INFORMATION: Synthetic Construct

<400> SEQUENCE: 427

Glu Val Gln Leu Val Glu Ser Gly Gly Gly Leu Val Gln Pro Gly Gly
         1               5                   10                  15

Ser Leu Arg Leu Ser Cys Ala Ala Ser Gly Tyr Thr Tyr Gly Gly Tyr
                        20                  25                  30

Cys Met Gly Trp Phe Arg Gln Ala Pro Gly Lys Gly Leu Glu Gly Val
```

```
             35                  40                  45
Ser Thr Ile Asn Ser Asp Gly Ser Thr Asn Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Val Asp Leu Ala Pro Cys Trp Val Ala Gly Pro Ile Glu Ala Ala Asp
                100                 105                 110

Phe Gly Tyr Trp Gly Gln Gly Thr Leu Val Thr Val Ser Ser Glu Val
                115                 120                 125

Gln Leu Val Glu Ser Gly Gly Leu Val Gln Pro Gly Gly Ser Leu
130                 135                 140

Arg Leu Ser Cys Ala Ala Ser Gly Phe Val Phe Ser Arg Tyr Asp Met
145                 150                 155                 160

Ala Trp Val Arg Gln Ala Pro Gly Lys Gly Leu Glu Trp Val Ser Phe
                165                 170                 175

Ile Ser Gly Gly Gly Ser Asn Thr Tyr Tyr Pro Asp Thr Val Lys Gly
                180                 185                 190

Arg Phe Thr Ile Ser Arg Asp Asn Ser Lys Asn Thr Leu Tyr Leu Gln
                195                 200                 205

Met Asn Ser Leu Arg Ala Glu Asp Thr Ala Val Tyr Tyr Cys Ile Ser
210                 215                 220

Pro Tyr Tyr Tyr Ala Met Glu Tyr Trp Gly Gln Gly Thr Thr Val Thr
225                 230                 235                 240

Val Ser Ser Ala Ser Thr Lys Gly Pro Ser Val Phe Pro Leu Ala Pro
                245                 250                 255

Cys Ser Arg Ser Thr Ser Glu Ser Thr Ala Ala Leu Gly Cys Leu Val
                260                 265                 270

Lys Asp Tyr Phe Pro Glu Pro Val Thr Val Ser Trp Asn Ser Gly Ala
                275                 280                 285

Leu Thr Ser Gly Val His Thr Phe Pro Ala Val Leu Gln Ser Ser Gly
                290                 295                 300

Leu Tyr Ser Leu Ser Ser Val Val Thr Val Pro Ser Ser Ser Leu Gly
305                 310                 315                 320

Thr Lys Thr Tyr Thr Cys Asn Val Asp His Lys Pro Ser Asn Thr Lys
                325                 330                 335

Val Asp Lys Arg Val Glu Ser Lys Tyr Gly Pro Pro Cys Pro Pro Cys
                340                 345                 350

Pro Ala Pro Glu Phe Leu Gly Gly Pro Ser Val Phe Leu Phe Pro Pro
                355                 360                 365

Lys Pro Lys Asp Thr Leu Met Ile Ser Arg Thr Pro Glu Val Thr Cys
                370                 375                 380

Val Val Val Asp Val Ser Gln Glu Asp Pro Glu Val Gln Phe Asn Trp
385                 390                 395                 400

Tyr Val Asp Gly Val Glu Val His Asn Ala Lys Thr Lys Pro Arg Glu
                405                 410                 415

Glu Gln Phe Asn Ser Thr Tyr Arg Val Val Ser Val Leu Thr Val Leu
                420                 425                 430

His Gln Asp Trp Leu Asn Gly Lys Glu Tyr Lys Cys Lys Val Ser Asn
                435                 440                 445

Lys Gly Leu Pro Ser Ser Ile Glu Lys Thr Ile Ser Lys Ala Lys Gly
                450                 455                 460
```

-continued

Gln Pro Arg Glu Pro Gln Val Tyr Thr Leu Pro Pro Ser Gln Glu Glu
465                 470                 475                 480

Met Thr Lys Asn Gln Val Ser Leu Thr Cys Leu Val Lys Gly Phe Tyr
            485                 490                 495

Pro Ser Asp Ile Ala Val Glu Trp Glu Ser Asn Gly Gln Pro Glu Asn
        500                 505                 510

Asn Tyr Lys Thr Thr Pro Pro Val Leu Asp Ser Asp Gly Ser Phe Phe
    515                 520                 525

Leu Tyr Ser Arg Leu Thr Val Asp Lys Ser Arg Trp Gln Glu Gly Asn
530                 535                 540

Val Phe Ser Cys Ser Val Met His Glu Ala Leu His Asn His Tyr Thr
545                 550                 555                 560

Gln Lys Ser Leu Ser Leu Ser Leu Gly Lys
                565                 570

<210> SEQ ID NO 428
<211> LENGTH: 214
<212> TYPE: PRT
<213> ORGANISM: Artificial Sequence
<220> FEATURE:
<223> OTHER INFORMATION: Synthetic Construct

<400> SEQUENCE: 428

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 429
<211> LENGTH: 444
<212> TYPE: PRT
<213> ORGANISM: Artificial Sequence

```
<220> FEATURE:
<223> OTHER INFORMATION: Synthetic Construct

<400> SEQUENCE: 429

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400
```

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 430
<211> LENGTH: 340
<212> TYPE: PRT
<213> ORGANISM: Artificial Sequence
<220> FEATURE:
<223> OTHER INFORMATION: Synthetic Construct

<400> SEQUENCE: 430

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Gly Gly Tyr
            20                  25                  30

Cys Met Gly Trp Phe Arg Gln Ala Pro Gly Lys Gly Leu Glu Gly Val
        35                  40                  45

Ser Thr Ile Asn Ser Asp Gly Ser Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Val Asp Leu Ala Pro Cys Trp Val Ala Gly Pro Ile Glu Ala Ala Asp
            100                 105                 110

Phe Gly Tyr Trp Gly Gln Gly Thr Leu Val Thr Val Ser Ser Asp Ile
        115                 120                 125

Gln Met Thr Gln Ser Pro Ser Ser Val Ser Ala Ser Val Gly Asp Arg
    130                 135                 140

Val Thr Ile Thr Cys Lys Ala Ser Gln Asp Val Asp Thr Ala Val Ala
145                 150                 155                 160

Trp Tyr Gln Gln Lys Pro Gly Lys Ala Pro Lys Leu Leu Ile Tyr Trp
                165                 170                 175

Ala Ser Thr Arg His Thr Gly Val Pro Ser Arg Phe Ser Gly Ser Gly
            180                 185                 190

Ser Gly Thr Asp Phe Thr Leu Thr Ile Ser Ser Leu Gln Pro Glu Asp
        195                 200                 205

Phe Ala Thr Tyr Tyr Cys Gln Gln Tyr Ser Thr Phe Pro Trp Thr Phe
    210                 215                 220

Gly Gly Gly Thr Lys Val Glu Ile Lys Arg Thr Val Ala Ala Pro Ser
225                 230                 235                 240

Val Phe Ile Phe Pro Pro Ser Asp Glu Gln Leu Lys Ser Gly Thr Ala
                245                 250                 255

Ser Val Val Cys Leu Leu Asn Asn Phe Tyr Pro Arg Glu Ala Lys Val
            260                 265                 270

Gln Trp Lys Val Asp Asn Ala Leu Gln Ser Gly Asn Ser Gln Glu Ser
        275                 280                 285

Val Thr Glu Gln Asp Ser Lys Asp Ser Thr Tyr Ser Leu Ser Ser Thr
    290                 295                 300

Leu Thr Leu Ser Lys Ala Asp Tyr Glu Lys His Lys Val Tyr Ala Cys
305                 310                 315                 320

Glu Val Thr His Gln Gly Leu Ser Ser Pro Val Thr Lys Ser Phe Asn
            325                 330                 335

Arg Gly Glu Cys
            340

<210> SEQ ID NO 431
<211> LENGTH: 583
<212> TYPE: PRT
<213> ORGANISM: Artificial Sequence
<220> FEATURE:
<223> OTHER INFORMATION: Synthetic Construct

<400> SEQUENCE: 431

Glu Pro Lys Ser Ser Asp Lys Thr His Thr Ser Pro Ser Pro Glu
1               5                   10                  15

Val Gln Leu Val Glu Ser Gly Gly Leu Val Gln Pro Gly Gly Ser
            20                  25                  30

Leu Arg Leu Ser Cys Ala Ala Ser Gly Tyr Ile Ile Ser Ser Tyr Cys
            35                  40                  45

Met Gly Trp Phe Arg Gln Ala Pro Gly Lys Gly Leu Glu Gly Val Ala
    50                  55                  60

Ala Ile Asp Ser Asp Gly Gly Thr Ser Tyr Ala Asp Ser Val Lys Gly
65                  70                  75                  80

Arg Phe Thr Ile Ser Lys Asp Asn Ser Lys Asn Thr Leu Tyr Leu Gln
                85                  90                  95

Met Asn Ser Leu Arg Ala Glu Asp Thr Ala Met Tyr Tyr Cys Ala Ala
            100                 105                 110

Asp Phe Cys Trp Val Asp Glu Asp Arg His Leu Tyr Glu Tyr Asn Ser
            115                 120                 125

Trp Gly Gln Gly Thr Leu Val Thr Val Ser Ser Glu Val Gln Leu Val
    130                 135                 140

Glu Ser Gly Gly Gly Leu Val Gln Pro Gly Gly Ser Leu Arg Leu Ser
145                 150                 155                 160

Cys Ala Ala Ser Gly Phe Val Phe Ser Arg Tyr Asp Met Ala Trp Val
                165                 170                 175

Arg Gln Ala Pro Gly Lys Gly Leu Glu Trp Val Ser Phe Ile Ser Gly
            180                 185                 190

Gly Gly Ser Asn Thr Tyr Tyr Pro Asp Thr Val Lys Gly Arg Phe Thr
            195                 200                 205

Ile Ser Arg Asp Asn Ser Lys Asn Thr Leu Tyr Leu Gln Met Asn Ser
    210                 215                 220

Leu Arg Ala Glu Asp Thr Ala Val Tyr Tyr Cys Ile Ser Pro Tyr Tyr
225                 230                 235                 240

Tyr Ala Met Glu Tyr Trp Gly Gln Gly Thr Thr Val Thr Val Ser Ser
                245                 250                 255

Ala Ser Thr Lys Gly Pro Ser Val Phe Pro Leu Ala Pro Cys Ser Arg
            260                 265                 270

Ser Thr Ser Glu Ser Thr Ala Ala Leu Gly Cys Leu Val Lys Asp Tyr
        275                 280                 285

Phe Pro Glu Pro Val Thr Val Ser Trp Asn Ser Gly Ala Leu Thr Ser
    290                 295                 300

Gly Val His Thr Phe Pro Ala Val Leu Gln Ser Ser Gly Leu Tyr Ser
305                 310                 315                 320

Leu Ser Ser Val Val Thr Val Pro Ser Ser Ser Leu Gly Thr Lys Thr
                325                 330                 335

Tyr Thr Cys Asn Val Asp His Lys Pro Ser Asn Thr Lys Val Asp Lys
                340                 345                 350

Arg Val Glu Ser Lys Tyr Gly Pro Pro Cys Pro Pro Cys Pro Ala Pro
                355                 360                 365

Glu Phe Leu Gly Gly Pro Ser Val Phe Leu Phe Pro Pro Lys Pro Lys
370                 375                 380

Asp Thr Leu Met Ile Ser Arg Thr Pro Glu Val Thr Cys Val Val Val
385                 390                 395                 400

Asp Val Ser Gln Glu Asp Pro Glu Val Gln Phe Asn Trp Tyr Val Asp
                405                 410                 415

Gly Val Glu Val His Asn Ala Lys Thr Lys Pro Arg Glu Glu Gln Phe
                420                 425                 430

Asn Ser Thr Tyr Arg Val Val Ser Val Leu Thr Val Leu His Gln Asp
                435                 440                 445

Trp Leu Asn Gly Lys Glu Tyr Lys Cys Lys Val Ser Asn Lys Gly Leu
                450                 455                 460

Pro Ser Ser Ile Glu Lys Thr Ile Ser Lys Ala Lys Gly Gln Pro Arg
465                 470                 475                 480

Glu Pro Gln Val Tyr Thr Leu Pro Pro Ser Gln Glu Glu Met Thr Lys
                485                 490                 495

Asn Gln Val Ser Leu Thr Cys Leu Val Lys Gly Phe Tyr Pro Ser Asp
                500                 505                 510

Ile Ala Val Glu Trp Glu Ser Asn Gly Gln Pro Glu Asn Asn Tyr Lys
                515                 520                 525

Thr Thr Pro Pro Val Leu Asp Ser Asp Gly Ser Phe Phe Leu Tyr Ser
530                 535                 540

Arg Leu Thr Val Asp Lys Ser Arg Trp Gln Glu Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Leu Gly Lys
                580

<210> SEQ ID NO 432
<211> LENGTH: 214
<212> TYPE: PRT
<213> ORGANISM: Artificial Sequence
<220> FEATURE:
<223> OTHER INFORMATION: Synthetic Construct

<400> SEQUENCE: 432

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
                20                  25                  30

Val Ala Trp Tyr Gln Gln Lys Pro Gly Lys Ala Pro Lys Leu Leu Ile
                35                  40                  45

Tyr Trp Ala Ser Thr Arg His Thr Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
                100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 433
<211> LENGTH: 444
<212> TYPE: PRT
<213> ORGANISM: Artificial Sequence
<220> FEATURE:
<223> OTHER INFORMATION: Synthetic Construct

<400> SEQUENCE: 433

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255
```

```
Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 434
<211> LENGTH: 353
<212> TYPE: PRT
<213> ORGANISM: Artificial Sequence
<220> FEATURE:
<223> OTHER INFORMATION: Synthetic Construct

<400> SEQUENCE: 434

Glu Pro Lys Ser Ser Asp Lys Thr His Thr Ser Pro Pro Ser Pro Glu
1               5                   10                  15

Val Gln Leu Val Glu Ser Gly Gly Gly Leu Val Gln Pro Gly Gly Ser
            20                  25                  30

Leu Arg Leu Ser Cys Ala Ala Ser Gly Tyr Ile Ile Ser Ser Tyr Cys
        35                  40                  45

Met Gly Trp Phe Arg Gln Ala Pro Gly Lys Gly Leu Glu Gly Val Ala
    50                  55                  60

Ala Ile Asp Ser Asp Gly Gly Thr Ser Tyr Ala Asp Ser Val Lys Gly
65                  70                  75                  80

Arg Phe Thr Ile Ser Lys Asp Asn Ser Lys Asn Thr Leu Tyr Leu Gln
                85                  90                  95

Met Asn Ser Leu Arg Ala Glu Asp Thr Ala Met Tyr Tyr Cys Ala Ala
            100                 105                 110

Asp Phe Cys Trp Val Asp Glu Asp Arg His Leu Tyr Glu Tyr Asn Ser
        115                 120                 125

Trp Gly Gln Gly Thr Leu Val Thr Val Ser Ser Asp Ile Gln Met Thr
    130                 135                 140

Gln Ser Pro Ser Ser Val Ser Ala Ser Val Gly Asp Arg Val Thr Ile
145                 150                 155                 160

Thr Cys Lys Ala Ser Gln Asp Val Asp Thr Ala Val Ala Trp Tyr Gln
                165                 170                 175
```

```
Gln Lys Pro Gly Lys Ala Pro Lys Leu Leu Ile Tyr Trp Ala Ser Thr
            180                 185                 190

Arg His Thr Gly Val Pro Ser Arg Phe Ser Gly Ser Gly Ser Gly Thr
            195                 200                 205

Asp Phe Thr Leu Thr Ile Ser Ser Leu Gln Pro Glu Asp Phe Ala Thr
            210                 215                 220

Tyr Tyr Cys Gln Gln Tyr Ser Thr Phe Pro Trp Thr Phe Gly Gly Gly
225                 230                 235                 240

Thr Lys Val Glu Ile Lys Arg Thr Val Ala Ala Pro Ser Val Phe Ile
            245                 250                 255

Phe Pro Pro Ser Asp Glu Gln Leu Lys Ser Gly Thr Ala Ser Val Val
            260                 265                 270

Cys Leu Leu Asn Asn Phe Tyr Pro Arg Glu Ala Lys Val Gln Trp Lys
            275                 280                 285

Val Asp Asn Ala Leu Gln Ser Gly Asn Ser Gln Glu Ser Val Thr Glu
            290                 295                 300

Gln Asp Ser Lys Asp Ser Thr Tyr Ser Leu Ser Ser Thr Leu Thr Leu
305                 310                 315                 320

Ser Lys Ala Asp Tyr Glu Lys His Lys Val Tyr Ala Cys Glu Val Thr
            325                 330                 335

His Gln Gly Leu Ser Ser Pro Val Thr Lys Ser Phe Asn Arg Gly Glu
            340                 345                 350

Cys

<210> SEQ ID NO 435
<211> LENGTH: 580
<212> TYPE: PRT
<213> ORGANISM: Artificial Sequence
<220> FEATURE:
<223> OTHER INFORMATION: Synthetic Construct

<400> SEQUENCE: 435

Glu Pro Lys Ser Ser Asp Lys Thr His Thr Ser Pro Ser Pro Glu
1               5                   10                  15

Val Gln Leu Val Glu Ser Gly Gly Leu Val Gln Pro Gly Gly Ser
            20                  25                  30

Leu Arg Leu Ser Cys Ala Ala Ser Gly Tyr Thr Ile Ser Ser Tyr Cys
            35                  40                  45

Met Gly Trp Phe Arg Gln Ala Pro Gly Lys Gly Leu Glu Gly Val Ala
            50                  55                  60

Ala Ile Asp Ser Asp Gly Ser Thr Ser Tyr Ala Asp Ser Val Lys Gly
65                  70                  75                  80

Arg Phe Thr Ile Ser Lys Asp Asn Ser Lys Asn Thr Leu Tyr Leu Gln
            85                  90                  95

Met Asn Ser Leu Arg Ala Glu Asp Thr Ala Val Tyr Tyr Cys Ala Ala
            100                 105                 110

Asp Phe Cys Trp Val Asp Asp Phe Tyr Glu Tyr Asn Tyr Trp Gly Gln
            115                 120                 125

Gly Thr Leu Val Thr Val Ser Ser Glu Val Gln Leu Val Glu Ser Gly
            130                 135                 140

Gly Gly Leu Val Gln Pro Gly Gly Ser Leu Arg Leu Ser Cys Ala Ala
145                 150                 155                 160

Ser Gly Phe Val Phe Ser Arg Tyr Asp Met Ala Trp Val Arg Gln Ala
            165                 170                 175
```

```
Pro Gly Lys Gly Leu Glu Trp Val Ser Phe Ile Ser Gly Gly Ser
            180                 185                 190
Asn Thr Tyr Tyr Pro Asp Thr Val Lys Gly Arg Phe Thr Ile Ser Arg
            195                 200                 205
Asp Asn Ser Lys Asn Thr Leu Tyr Leu Gln Met Asn Ser Leu Arg Ala
210                 215                 220
Glu Asp Thr Ala Val Tyr Tyr Cys Ile Ser Pro Tyr Tyr Ala Met
225                 230                 235                 240
Glu Tyr Trp Gly Gln Gly Thr Thr Val Thr Val Ser Ser Ala Ser Thr
                245                 250                 255
Lys Gly Pro Ser Val Phe Pro Leu Ala Pro Cys Ser Arg Ser Thr Ser
            260                 265                 270
Glu Ser Thr Ala Ala Leu Gly Cys Leu Val Lys Asp Tyr Phe Pro Glu
            275                 280                 285
Pro Val Thr Val Ser Trp Asn Ser Gly Ala Leu Thr Ser Gly Val His
            290                 295                 300
Thr Phe Pro Ala Val Leu Gln Ser Ser Gly Leu Tyr Ser Leu Ser Ser
305                 310                 315                 320
Val Val Thr Val Pro Ser Ser Ser Leu Gly Thr Lys Thr Tyr Thr Cys
                325                 330                 335
Asn Val Asp His Lys Pro Ser Asn Thr Lys Val Asp Lys Arg Val Glu
            340                 345                 350
Ser Lys Tyr Gly Pro Pro Cys Pro Pro Cys Pro Ala Pro Glu Phe Leu
            355                 360                 365
Gly Gly Pro Ser Val Phe Leu Phe Pro Pro Lys Pro Lys Asp Thr Leu
            370                 375                 380
Met Ile Ser Arg Thr Pro Glu Val Thr Cys Val Val Val Asp Val Ser
385                 390                 395                 400
Gln Glu Asp Pro Glu Val Gln Phe Asn Trp Tyr Val Asp Gly Val Glu
                405                 410                 415
Val His Asn Ala Lys Thr Lys Pro Arg Glu Glu Gln Phe Asn Ser Thr
            420                 425                 430
Tyr Arg Val Val Ser Val Leu Thr Val Leu His Gln Asp Trp Leu Asn
            435                 440                 445
Gly Lys Glu Tyr Lys Cys Lys Val Ser Asn Lys Gly Leu Pro Ser Ser
            450                 455                 460
Ile Glu Lys Thr Ile Ser Lys Ala Lys Gly Gln Pro Arg Glu Pro Gln
465                 470                 475                 480
Val Tyr Thr Leu Pro Pro Ser Gln Glu Glu Met Thr Lys Asn Gln Val
                485                 490                 495
Ser Leu Thr Cys Leu Val Lys Gly Phe Tyr Pro Ser Asp Ile Ala Val
            500                 505                 510
Glu Trp Glu Ser Asn Gly Gln Pro Glu Asn Asn Tyr Lys Thr Thr Pro
            515                 520                 525
Pro Val Leu Asp Ser Asp Gly Ser Phe Phe Leu Tyr Ser Arg Leu Thr
            530                 535                 540
Val Asp Lys Ser Arg Trp Gln Glu Gly Asn Val Phe Ser Cys Ser Val
545                 550                 555                 560
Met His Glu Ala Leu His Asn His Tyr Thr Gln Lys Ser Leu Ser Leu
                565                 570                 575
Ser Leu Gly Lys
            580
```

```
<210> SEQ ID NO 436
<211> LENGTH: 214
<212> TYPE: PRT
<213> ORGANISM: Artificial Sequence
<220> FEATURE:
<223> OTHER INFORMATION: Synthetic Construct

<400> SEQUENCE: 436

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 437
<211> LENGTH: 444
<212> TYPE: PRT
<213> ORGANISM: Artificial Sequence
<220> FEATURE:
<223> OTHER INFORMATION: Synthetic Construct

<400> SEQUENCE: 437

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ile Ser Pro Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 438
<211> LENGTH: 350
<212> TYPE: PRT
<213> ORGANISM: Artificial Sequence
<220> FEATURE:
<223> OTHER INFORMATION: Synthetic Construct

<400> SEQUENCE: 438

Glu Pro Lys Ser Ser Asp Lys Thr His Thr Ser Pro Pro Ser Pro Glu
1               5                   10                  15

Val Gln Leu Val Glu Ser Gly Gly Gly Leu Val Gln Pro Gly Gly Ser
            20                  25                  30

Leu Arg Leu Ser Cys Ala Ala Ser Gly Tyr Thr Ile Ser Ser Tyr Cys
        35                  40                  45

Met Gly Trp Phe Arg Gln Ala Pro Gly Lys Gly Leu Glu Gly Val Ala
    50                  55                  60

Ala Ile Asp Ser Asp Gly Ser Thr Ser Tyr Ala Asp Ser Val Lys Gly
65                  70                  75                  80

Arg Phe Thr Ile Ser Lys Asp Asn Ser Lys Asn Thr Leu Tyr Leu Gln
                85                  90                  95

Met Asn Ser Leu Arg Ala Glu Asp Thr Ala Val Tyr Tyr Cys Ala Ala
            100                 105                 110

Asp Phe Cys Trp Val Asp Phe Tyr Glu Tyr Asn Tyr Trp Gly Gln
        115                 120                 125

Gly Thr Leu Val Thr Val Ser Ser Asp Ile Gln Met Thr Gln Ser Pro
    130                 135                 140

Ser Ser Val Ser Ala Ser Val Gly Asp Arg Val Thr Ile Thr Cys Lys
145                 150                 155                 160

Ala Ser Gln Asp Val Asp Thr Ala Val Ala Trp Tyr Gln Gln Lys Pro
                165                 170                 175

Gly Lys Ala Pro Lys Leu Leu Ile Tyr Trp Ala Ser Thr Arg His Thr
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Tyr Ser Thr Phe Pro Trp Thr Phe Gly Gly Gly Thr Lys Val
225                 230                 235                 240

Glu Ile Lys Arg Thr Val Ala Ala Pro Ser Val Phe Ile Phe Pro Pro
                245                 250                 255

Ser Asp Glu Gln Leu Lys Ser Gly Thr Ala Ser Val Val Cys Leu Leu
            260                 265                 270

Asn Asn Phe Tyr Pro Arg Glu Ala Lys Val Gln Trp Lys Val Asp Asn
        275                 280                 285

Ala Leu Gln Ser Gly Asn Ser Gln Glu Ser Val Thr Glu Gln Asp Ser
    290                 295                 300

Lys Asp Ser Thr Tyr Ser Leu Ser Ser Thr Leu Thr Leu Ser Lys Ala
305                 310                 315                 320

Asp Tyr Glu Lys His Lys Val Tyr Ala Cys Glu Val Thr His Gln Gly
                325                 330                 335

Leu Ser Ser Pro Val Thr Lys Ser Phe Asn Arg Gly Glu Cys
            340                 345                 350

<210> SEQ ID NO 439
<211> LENGTH: 581
<212> TYPE: PRT
<213> ORGANISM: Artificial Sequence
<220> FEATURE:
<223> OTHER INFORMATION: Synthetic Construct

<400> SEQUENCE: 439

Glu Pro Lys Ser Ser Asp Lys Thr His Thr Ser Pro Pro Ser Pro Glu
1               5                   10                  15

Val Gln Leu Val Glu Ser Gly Gly Gly Leu Val Gln Pro Gly Gly Ser
            20                  25                  30

```
Leu Arg Leu Ser Cys Ala Ala Ser Gly Tyr Thr Val Ser Tyr Cys
         35                  40                  45

Met Gly Trp Phe Arg Gln Ala Pro Gly Lys Gly Arg Glu Gly Val Ser
 50                  55                  60

Ala Ile Asp Ser Asp Gly Ser Val Ser Tyr Ala Asp Ser Val Lys Gly
 65                  70                  75                  80

Arg Phe Thr Ile Ser Lys Asp Asn Ser Lys Asn Thr Leu Tyr Leu Gln
                 85                  90                  95

Met Asn Ser Leu Arg Ala Glu Asp Thr Ala Val Tyr Phe Cys Ala Ala
             100                 105                 110

Asp Leu Cys Trp Val Asp Gln Asp Gln Gly Glu Tyr Asn Thr Trp Gly
         115                 120                 125

Gln Gly Thr Leu Val Thr Val Ser Ser Glu Val Gln Leu Val Glu Ser
 130                 135                 140

Gly Gly Gly Leu Val Gln Pro Gly Gly Ser Leu Arg Leu Ser Cys Ala
145                 150                 155                 160

Ala Ser Gly Phe Val Phe Ser Arg Tyr Asp Met Ala Trp Val Arg Gln
                 165                 170                 175

Ala Pro Gly Lys Gly Leu Glu Trp Val Ser Phe Ile Ser Gly Gly Gly
             180                 185                 190

Ser Asn Thr Tyr Tyr Pro Asp Thr Val Lys Gly Arg Phe Thr Ile Ser
         195                 200                 205

Arg Asp Asn Ser Lys Asn Thr Leu Tyr Leu Gln Met Asn Ser Leu Arg
     210                 215                 220

Ala Glu Asp Thr Ala Val Tyr Tyr Cys Ile Ser Pro Tyr Tyr Ala
225                 230                 235                 240

Met Glu Tyr Trp Gly Gln Gly Thr Thr Val Thr Val Ser Ser Ala Ser
                 245                 250                 255

Thr Lys Gly Pro Ser Val Phe Pro Leu Ala Pro Cys Ser Arg Ser Thr
             260                 265                 270

Ser Glu Ser Thr Ala Ala Leu Gly Cys Leu Val Lys Asp Tyr Phe Pro
         275                 280                 285

Glu Pro Val Thr Val Ser Trp Asn Ser Gly Ala Leu Thr Ser Gly Val
     290                 295                 300

His Thr Phe Pro Ala Val Leu Gln Ser Ser Gly Leu Tyr Ser Leu Ser
305                 310                 315                 320

Ser Val Val Thr Val Pro Ser Ser Ser Leu Gly Thr Lys Thr Tyr Thr
                 325                 330                 335

Cys Asn Val Asp His Lys Pro Ser Asn Thr Lys Val Asp Lys Arg Val
             340                 345                 350

Glu Ser Lys Tyr Gly Pro Pro Cys Pro Pro Cys Pro Ala Pro Glu Phe
         355                 360                 365

Leu Gly Gly Pro Ser Val Phe Leu Phe Pro Pro Lys Pro Lys Asp Thr
     370                 375                 380

Leu Met Ile Ser Arg Thr Pro Glu Val Thr Cys Val Val Val Asp Val
385                 390                 395                 400

Ser Gln Glu Asp Pro Glu Val Gln Phe Asn Trp Tyr Val Asp Gly Val
                 405                 410                 415

Glu Val His Asn Ala Lys Thr Lys Pro Arg Glu Glu Gln Phe Asn Ser
             420                 425                 430

Thr Tyr Arg Val Val Ser Val Leu Thr Val Leu His Gln Asp Trp Leu
         435                 440                 445

Asn Gly Lys Glu Tyr Lys Cys Lys Val Ser Asn Lys Gly Leu Pro Ser
```

```
                    450                 455                 460
Ser Ile Glu Lys Thr Ile Ser Lys Ala Lys Gly Gln Pro Arg Glu Pro
465                 470                 475                 480

Gln Val Tyr Thr Leu Pro Pro Ser Gln Glu Glu Met Thr Lys Asn Gln
                485                 490                 495

Val Ser Leu Thr Cys Leu Val Lys Gly Phe Tyr Pro Ser Asp Ile Ala
            500                 505                 510

Val Glu Trp Glu Ser Asn Gly Gln Pro Glu Asn Asn Tyr Lys Thr Thr
        515                 520                 525

Pro Pro Val Leu Asp Ser Asp Gly Ser Phe Phe Leu Tyr Ser Arg Leu
    530                 535                 540

Thr Val Asp Lys Ser Arg Trp Gln Glu Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Leu Gly Lys
            580

<210> SEQ ID NO 440
<211> LENGTH: 214
<212> TYPE: PRT
<213> ORGANISM: Artificial Sequence
<220> FEATURE:
<223> OTHER INFORMATION: Synthetic Construct

<400> SEQUENCE: 440

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asp Thr Ala
                20                  25                  30

Val Ala Trp Tyr Gln Gln Lys Pro Gly Lys Ala Pro Lys Leu Leu Ile
            35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Phe Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 441
<211> LENGTH: 444
<212> TYPE: PRT
<213> ORGANISM: Artificial Sequence
<220> FEATURE:
<223> OTHER INFORMATION: Synthetic Construct

<400> SEQUENCE: 441

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Tyr Ala Met Glu Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
```

```
                370               375                380
Glu Asn Asn Tyr Lys Thr Thr Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
                435                 440

<210> SEQ ID NO 442
<211> LENGTH: 351
<212> TYPE: PRT
<213> ORGANISM: Artificial Sequence
<220> FEATURE:
<223> OTHER INFORMATION: Synthetic Construct

<400> SEQUENCE: 442

Glu Pro Lys Ser Ser Asp Lys Thr His Thr Ser Pro Pro Ser Pro Glu
1               5                  10                  15

Val Gln Leu Val Glu Ser Gly Gly Gly Leu Val Gln Pro Gly Gly Ser
                20                  25                  30

Leu Arg Leu Ser Cys Ala Ala Ser Gly Tyr Thr Val Ser Ser Tyr Cys
            35                  40                  45

Met Gly Trp Phe Arg Gln Ala Pro Gly Lys Gly Arg Glu Gly Val Ser
    50                  55                  60

Ala Ile Asp Ser Asp Gly Ser Val Ser Tyr Ala Asp Ser Val Lys Gly
65                  70                  75                  80

Arg Phe Thr Ile Ser Lys Asp Asn Ser Lys Asn Thr Leu Tyr Leu Gln
                85                  90                  95

Met Asn Ser Leu Arg Ala Glu Asp Thr Ala Val Tyr Phe Cys Ala Ala
            100                 105                 110

Asp Leu Cys Trp Val Asp Gln Asp Gln Gly Glu Tyr Asn Thr Trp Gly
        115                 120                 125

Gln Gly Thr Leu Val Thr Val Ser Ser Asp Ile Gln Met Thr Gln Ser
130                 135                 140

Pro Ser Ser Val Ser Ala Ser Val Gly Asp Arg Val Thr Ile Thr Cys
145                 150                 155                 160

Lys Ala Ser Gln Asp Val Asp Thr Ala Val Ala Trp Tyr Gln Gln Lys
                165                 170                 175

Pro Gly Lys Ala Pro Lys Leu Leu Ile Tyr Trp Ala Ser Thr Arg His
            180                 185                 190

Thr Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Tyr Ser Thr Phe Pro Trp Thr Phe Gly Gly Gly Thr Lys
225                 230                 235                 240

Val Glu Ile Lys Arg Thr Val Ala Ala Pro Ser Val Phe Ile Phe Pro
                245                 250                 255

Pro Ser Asp Glu Gln Leu Lys Ser Gly Thr Ala Ser Val Val Cys Leu
            260                 265                 270

Leu Asn Asn Phe Tyr Pro Arg Glu Ala Lys Val Gln Trp Lys Val Asp
        275                 280                 285

Asn Ala Leu Gln Ser Gly Asn Ser Gln Glu Ser Val Thr Glu Gln Asp
```

```
                290             295             300
Ser Lys Asp Ser Thr Tyr Ser Leu Ser Ser Thr Leu Thr Leu Ser Lys
305                 310                 315                 320

Ala Asp Tyr Glu Lys His Lys Val Tyr Ala Cys Glu Val Thr His Gln
                325                 330                 335

Gly Leu Ser Ser Pro Val Thr Lys Ser Phe Asn Arg Gly Glu Cys
                340                 345                 350

<210> SEQ ID NO 443
<211> LENGTH: 585
<212> TYPE: PRT
<213> ORGANISM: Artificial Sequence
<220> FEATURE:
<223> OTHER INFORMATION: Synthetic Construct

<400> SEQUENCE: 443

Glu Pro Lys Ser Ser Asp Lys Thr His Thr Ser Pro Ser Pro Glu
1               5                   10                  15

Val Gln Leu Val Glu Ser Gly Gly Gly Leu Val Gln Pro Gly Gly Ser
                20                  25                  30

Leu Arg Leu Ser Cys Ala Ala Ser Gly Tyr Thr Tyr Gly Gly Tyr Cys
            35                  40                  45

Met Gly Trp Phe Arg Gln Ala Pro Gly Lys Gly Leu Glu Gly Val Ser
50                  55                  60

Thr Ile Asn Ser Asp Gly Ser Thr Asn Tyr Ala Asp Ser Val Lys Gly
65                  70                  75                  80

Arg Phe Thr Ile Ser Arg Asp Asn Ser Lys Asn Thr Leu Tyr Leu Gln
                85                  90                  95

Met Asn Ser Leu Arg Ala Glu Asp Thr Ala Val Tyr Tyr Cys Ala Val
            100                 105                 110

Asp Leu Ala Pro Cys Trp Val Ala Gly Pro Ile Glu Ala Ala Asp Phe
        115                 120                 125

Gly Tyr Trp Gly Gln Gly Thr Leu Val Thr Val Ser Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Phe Val Phe Ser Arg Tyr Asp Met Ala
                165                 170                 175

Trp Val Arg Gln Ala Pro Gly Lys Gly Leu Glu Trp Val Ser Phe Ile
            180                 185                 190

Ser Gly Gly Gly Ser Asn Thr Tyr Tyr Pro Asp Thr Val Lys Gly Arg
        195                 200                 205

Phe Thr Ile Ser Arg Asp Asn Ser Lys Asn Thr Leu Tyr Leu Gln Met
    210                 215                 220

Asn Ser Leu Arg Ala Glu Asp Thr Ala Val Tyr Tyr Cys Ile Ser Pro
225                 230                 235                 240

Tyr Tyr Tyr Ala Met Glu Tyr Trp Gly Gln Gly Thr Val Thr Val
                245                 250                 255

Ser Ser Ala Ser Thr Lys Gly Pro Ser Val Phe Pro Leu Ala Pro Cys
            260                 265                 270

Ser Arg Ser Thr Ser Glu Ser Thr Ala Ala Leu Gly Cys Leu Val Lys
        275                 280                 285

Asp Tyr Phe Pro Glu Pro Val Thr Val Ser Trp Asn Ser Gly Ala Leu
    290                 295                 300

Thr Ser Gly Val His Thr Phe Pro Ala Val Leu Gln Ser Ser Gly Leu
```

-continued

```
                305                 310                 315                 320
Tyr Ser Leu Ser Ser Val Val Thr Val Pro Ser Ser Leu Gly Thr
                325                 330                 335
Lys Thr Tyr Thr Cys Asn Val Asp His Lys Pro Ser Asn Thr Lys Val
                340                 345                 350
Asp Lys Arg Val Glu Ser Lys Tyr Gly Pro Pro Cys Pro Cys Pro
                355                 360                 365
Ala Pro Glu Phe Leu Gly Gly Pro Ser Val Phe Leu Phe Pro Pro Lys
    370                 375                 380
Pro Lys Asp Thr Leu Met Ile Ser Arg Thr Pro Glu Val Thr Cys Val
385                 390                 395                 400
Val Val Asp Val Ser Gln Glu Asp Pro Glu Val Gln Phe Asn Trp Tyr
                405                 410                 415
Val Asp Gly Val Glu Val His Asn Ala Lys Thr Lys Pro Arg Glu Glu
            420                 425                 430
Gln Phe Asn Ser Thr Tyr Arg Val Val Ser Val Leu Thr Val Leu His
            435                 440                 445
Gln Asp Trp Leu Asn Gly Lys Glu Tyr Lys Cys Lys Val Ser Asn Lys
    450                 455                 460
Gly Leu Pro Ser Ser Ile Glu Lys Thr Ile Ser Lys Ala Lys Gly Gln
465                 470                 475                 480
Pro Arg Glu Pro Gln Val Tyr Thr Leu Pro Pro Ser Gln Glu Glu Met
                485                 490                 495
Thr Lys Asn Gln Val Ser Leu Thr Cys Leu Val Lys Gly Phe Tyr Pro
            500                 505                 510
Ser Asp Ile Ala Val Glu Trp Glu Ser Asn Gly Gln Pro Glu Asn Asn
        515                 520                 525
Tyr Lys Thr Thr Pro Pro Val Leu Asp Ser Asp Gly Ser Phe Phe Leu
    530                 535                 540
Tyr Ser Arg Leu Thr Val Asp Lys Ser Arg Trp Gln Glu Gly Asn Val
545                 550                 555                 560
Phe Ser Cys Ser Val Met His Glu Ala Leu His Asn His Tyr Thr Gln
                565                 570                 575
Lys Ser Leu Ser Leu Ser Leu Gly Lys
            580                 585
```

<210> SEQ ID NO 444
<211> LENGTH: 214
<212> TYPE: PRT
<213> ORGANISM: Artificial Sequence
<220> FEATURE:
<223> OTHER INFORMATION: Synthetic Construct

<400> SEQUENCE: 444

```
Asp Ile Gln Met Thr Gln Ser Pro Ser Ser Val Ser Ala Ser Val Gly
1               5                   10                  15
Asp Arg Val Thr Ile Thr Cys Lys Ala Ser Gln Asp Val Asp Thr Ala
            20                  25                  30
Val Ala Trp Tyr Gln Gln Lys Pro Gly Lys Ala Pro Lys Leu Leu Ile
        35                  40                  45
Tyr Trp Ala Ser Thr Arg His Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Thr Phe Pro Trp
```

```
                    85                  90                  95
Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 445
<211> LENGTH: 444
<212> TYPE: PRT
<213> ORGANISM: Artificial Sequence
<220> FEATURE:
<223> OTHER INFORMATION: Synthetic Construct

<400> SEQUENCE: 445

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Arg Tyr
            20                  25                  30

Asp Met Ala Trp Val Arg Gln Ala Pro Gly Lys Gly Leu Glu Trp Val
        35                  40                  45

Ser Phe Ile Ser Gly Gly Gly Ser Asn Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Ser Pro Tyr Tyr Ala Met Glu Tyr Trp Gly Gln Gly Thr Thr
                100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
```

```
                    225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 446
<211> LENGTH: 355
<212> TYPE: PRT
<213> ORGANISM: Artificial Sequence
<220> FEATURE:
<223> OTHER INFORMATION: Synthetic Construct

<400> SEQUENCE: 446

Glu Pro Lys Ser Ser Asp Lys Thr His Thr Ser Pro Ser Pro Glu
1               5                   10                  15

Val Gln Leu Val Glu Ser Gly Gly Gly Leu Val Gln Pro Gly Gly Ser
                20                  25                  30

Leu Arg Leu Ser Cys Ala Ala Ser Gly Tyr Thr Tyr Gly Gly Tyr Cys
            35                  40                  45

Met Gly Trp Phe Arg Gln Ala Pro Gly Lys Gly Leu Glu Gly Val Ser
        50                  55                  60

Thr Ile Asn Ser Asp Gly Ser Thr Asn Tyr Ala Asp Ser Val Lys Gly
65                  70                  75                  80

Arg Phe Thr Ile Ser Arg Asp Asn Ser Lys Asn Thr Leu Tyr Leu Gln
                85                  90                  95

Met Asn Ser Leu Arg Ala Glu Asp Thr Ala Val Tyr Tyr Cys Ala Val
            100                 105                 110

Asp Leu Ala Pro Cys Trp Val Ala Gly Pro Ile Glu Ala Ala Asp Phe
        115                 120                 125

Gly Tyr Trp Gly Gln Gly Thr Leu Val Thr Val Ser Ser Asp Ile Gln
    130                 135                 140

Met Thr Gln Ser Pro Ser Ser Val Ser Ala Ser Val Gly Asp Arg Val
```

```
145                 150                 155                 160
Thr Ile Thr Cys Lys Ala Ser Gln Asp Val Asp Thr Ala Val Ala Trp
                165                 170                 175

Tyr Gln Gln Lys Pro Gly Lys Ala Pro Lys Leu Leu Ile Tyr Trp Ala
                180                 185                 190

Ser Thr Arg His Thr Gly Val Pro Ser Arg Phe Ser Gly Ser Gly Ser
            195                 200                 205

Gly Thr Asp Phe Thr Leu Thr Ile Ser Ser Leu Gln Pro Glu Asp Phe
        210                 215                 220

Ala Thr Tyr Tyr Cys Gln Gln Tyr Ser Thr Phe Pro Trp Thr Phe Gly
225                 230                 235                 240

Gly Gly Thr Lys Val Glu Ile Lys Arg Thr Val Ala Ala Pro Ser Val
                245                 250                 255

Phe Ile Phe Pro Pro Ser Asp Glu Gln Leu Lys Ser Gly Thr Ala Ser
                260                 265                 270

Val Val Cys Leu Leu Asn Asn Phe Tyr Pro Arg Glu Ala Lys Val Gln
                275                 280                 285

Trp Lys Val Asp Asn Ala Leu Gln Ser Gly Asn Ser Gln Glu Ser Val
        290                 295                 300

Thr Glu Gln Asp Ser Lys Asp Ser Thr Tyr Ser Leu Ser Ser Thr Leu
305                 310                 315                 320

Thr Leu Ser Lys Ala Asp Tyr Glu Lys His Lys Val Tyr Ala Cys Glu
                325                 330                 335

Val Thr His Gln Gly Leu Ser Ser Pro Val Thr Lys Ser Phe Asn Arg
            340                 345                 350

Gly Glu Cys
        355
```